US012594347B2

(12) United States Patent
Yousefpour et al.

(10) Patent No.: US 12,594,347 B2
(45) Date of Patent: Apr. 7, 2026

(54) NANOPARTICULATE DRUG DELIVERY SYSTEMS

(71) Applicant: Duke University, Durham, NC (US)

(72) Inventors: Parisa Yousefpour, Durham, NC (US); Ashutosh Chilkoti, Durham, NC (US)

(73) Assignee: Duke University, Durham, NC (US)

( * ) Notice: Subject to any disclaimer, the term of this patent is extended or adjusted under 35 U.S.C. 154(b) by 960 days.

(21) Appl. No.: 17/272,887

(22) PCT Filed: Sep. 6, 2019

(86) PCT No.: PCT/US2019/050077

§ 371 (c)(1),
(2) Date: Mar. 2, 2021

(87) PCT Pub. No.: WO2020/051541

PCT Pub. Date: Mar. 12, 2020

(65) Prior Publication Data

US 2021/0316007 A1 Oct. 14, 2021

Related U.S. Application Data

(60) Provisional application No. 62/728,582, filed on Sep. 7, 2018.

(51) Int. Cl.
*A61K 47/64* (2017.01)
*A61K 47/69* (2017.01)
*A61P 35/00* (2006.01)

(52) U.S. Cl.
CPC .......... *A61K 47/6907* (2017.08); *A61K 47/64* (2017.08); *A61P 35/00* (2018.01)

(58) Field of Classification Search
CPC ................ A61K 47/6907; A61K 47/64; A61K 49/0041; A61K 49/0056; A61K 49/0082; A61P 35/00; C07K 2319/00; C07K 14/315
See application file for complete search history.

(56) References Cited

U.S. PATENT DOCUMENTS

| | | | |
|---|---|---|---|
| 4,415,732 | A | 11/1983 | Caruthers et al. |
| 4,458,066 | A | 7/1984 | Caruthers et al. |
| 4,500,707 | A | 2/1985 | Caruthers et al. |
| 4,554,101 | A | 11/1985 | Hopp |
| 4,668,777 | A | 5/1987 | Caruthers et al. |
| 4,973,679 | A | 11/1990 | Caruthers et al. |
| 4,976,734 | A | 12/1990 | Urry et al. |
| 5,153,319 | A | 10/1992 | Caruthers et al. |
| 5,250,516 | A | 10/1993 | Urry |
| 5,278,302 | A | 1/1994 | Caruthers et al. |
| 5,336,256 | A | 8/1994 | Urry |
| 5,453,496 | A | 9/1995 | Caruthers et al. |
| 5,534,408 | A | 7/1996 | Green et al. |
| 5,578,577 | A | 11/1996 | Ching et al. |
| 5,580,859 | A | 12/1996 | Felgner et al. |
| 5,602,244 | A | 2/1997 | Caruthers et al. |
| 5,676,646 | A | 10/1997 | Hofmann et al. |
| 5,679,647 | A | 10/1997 | Carson et al. |
| 5,702,359 | A | 12/1997 | Hofmann et al. |
| 5,703,055 | A | 12/1997 | Felgner et al. |
| 5,935,776 | A | 8/1999 | Green et al. |
| 6,013,763 | A | 1/2000 | Braisted et al. |
| 6,068,650 | A | 5/2000 | Hofmann et al. |
| 6,096,020 | A | 8/2000 | Hofmann |
| 6,120,493 | A | 9/2000 | Hofmann |
| 6,150,148 | A | 11/2000 | Nanda et al. |
| 6,181,964 | B1 | 1/2001 | Hofmann et al. |
| 6,192,270 | B1 | 2/2001 | Hofmann et al. |
| 6,207,749 | B1 | 3/2001 | Mayes et al. |
| 6,208,893 | B1 | 3/2001 | Hofmann |
| 6,216,034 | B1 | 4/2001 | Hofmann et al. |
| 6,233,482 | B1 | 5/2001 | Hofmann et al. |
| 6,241,701 | B1 | 6/2001 | Hofmann |
| 6,245,515 | B1 | 6/2001 | Vogelstein et al. |
| 6,296,831 | B1 | 10/2001 | Weller et al. |
| 6,302,874 | B1 | 10/2001 | Zhang et al. |
| 6,413,587 | B1 | 7/2002 | Hawker et al. |
| 6,512,060 | B1 | 1/2003 | Matyjaszewski et al. |

(Continued)

FOREIGN PATENT DOCUMENTS

| | | | |
|---|---|---|---|
| AU | 2007265628 | B2 | 12/2012 |
| CA | 2327325 | A1 | 11/1999 |

(Continued)

OTHER PUBLICATIONS

MacKay (Nature Materials, vol. 8, Dec. 2009, 993-999) (Year: 2009).*

(Continued)

*Primary Examiner* — Sudhakar Katakam

(74) *Attorney, Agent, or Firm* — Michael Best & Friedrich LLP

(57) ABSTRACT

Described herein are compositions that include an assembly of self-assembling conjugates. The self-assembling conjugates may include a polypeptide having a transition temperature (17) above 50° C. when the polypeptide is not attached to the conjugate, an albumin binding domain (ABD) attached to a first end of the polypeptide, and at least one molecule attached to a second end of the polypeptide through a cysteine group, wherein the molecule has an octanol-water distribution coefficient (log D) of greater than or equal to 1.5 at a pH of 7.4 when the molecule is not attached to the conjugate. Also described herein are methods of using the compositions.

16 Claims, 63 Drawing Sheets

Specification includes a Sequence Listing.

(56) References Cited

U.S. PATENT DOCUMENTS

| | | | | |
|---|---|---|---|---|
| 6,541,580 | B1 | 4/2003 | Matyjaszewski et al. | |
| 6,623,950 | B1 | 9/2003 | Osten et al. | |
| 6,649,138 | B2 | 11/2003 | Adams et al. | |
| 6,660,247 | B1 | 12/2003 | Gutowska et al. | |
| 6,841,617 | B2 | 1/2005 | Jeong et al. | |
| 6,852,834 | B2 | 2/2005 | Chilkoti | |
| 6,869,588 | B2 | 3/2005 | Weller et al. | |
| 7,033,571 | B2 | 4/2006 | Gutowska et al. | |
| 7,087,244 | B2 | 8/2006 | Jeong et al. | |
| 7,300,922 | B2 | 11/2007 | Sullenger et al. | |
| 7,429,458 | B2 | 9/2008 | Chilkoti | |
| 7,531,524 | B2 | 5/2009 | Rusconi | |
| 7,664,545 | B2 | 2/2010 | Westersten et al. | |
| 7,674,882 | B2 | 3/2010 | Kaplan et al. | |
| 8,129,330 | B2 | 3/2012 | Martinez et al. | |
| 8,283,125 | B2 | 10/2012 | Cebolla Ramirez et al. | |
| 8,470,967 | B2 | 6/2013 | Chilkoti et al. | |
| 8,497,356 | B2 | 7/2013 | Chilkoti et al. | |
| 8,506,963 | B2 | 8/2013 | Li et al. | |
| 8,586,347 | B2 | 11/2013 | Lochhead et al. | |
| 8,841,414 | B1 | 9/2014 | Raucher et al. | |
| 8,912,310 | B2 | 12/2014 | Chilkoti et al. | |
| 8,937,153 | B2 * | 1/2015 | Abrahmsen ............ | C07K 14/00 530/324 |
| 9,127,047 | B2 | 9/2015 | Chilkoti | |
| 9,132,178 | B2 | 9/2015 | Philip | |
| 9,138,743 | B2 | 9/2015 | Yager et al. | |
| 9,482,664 | B2 | 11/2016 | Chilkoti et al. | |
| 9,592,303 | B2 | 3/2017 | Chilkoti et al. | |
| 9,662,422 | B2 | 5/2017 | Pollock et al. | |
| 9,771,396 | B2 | 9/2017 | Chilkoti et al. | |
| 9,804,170 | B2 | 10/2017 | Krishna et al. | |
| 9,890,420 | B2 | 2/2018 | Chilkoti et al. | |
| 10,064,954 | B2 | 9/2018 | Wu | |
| 10,131,690 | B2 | 11/2018 | Bonny et al. | |
| 10,302,636 | B2 | 5/2019 | Chilkoti et al. | |
| 10,364,451 | B2 | 7/2019 | Chilkoti et al. | |
| 10,385,115 | B2 | 8/2019 | Chilkoti et al. | |
| 10,434,182 | B2 | 10/2019 | Weng et al. | |
| 11,169,150 | B2 | 11/2021 | Chilkoti et al. | |
| 2001/0034050 | A1 | 10/2001 | Chilkoti | |
| 2002/0052443 | A1 | 5/2002 | Greenwald et al. | |
| 2002/0146794 | A1 | 10/2002 | Tomycz | |
| 2003/0008308 | A1 | 1/2003 | Enzelberger et al. | |
| 2003/0138829 | A1 | 7/2003 | Unger et al. | |
| 2003/0161816 | A1 | 8/2003 | Fraser et al. | |
| 2003/0175290 | A1 | 9/2003 | Renner et al. | |
| 2003/0185741 | A1 | 10/2003 | Matyjaszewski et al. | |
| 2003/0225251 | A1 | 12/2003 | Sallberg et al. | |
| 2003/0233675 | A1 | 12/2003 | Cao et al. | |
| 2004/0053976 | A1 | 3/2004 | Martinez et al. | |
| 2004/0101852 | A1 | 5/2004 | Bennett et al. | |
| 2004/0192072 | A1 | 9/2004 | Snow et al. | |
| 2005/0037967 | A1 | 2/2005 | Rosenblum | |
| 2005/0186214 | A1 | 8/2005 | Liu et al. | |
| 2005/0255554 | A1 | 11/2005 | Chilkoti | |
| 2005/0288229 | A1 | 12/2005 | Sindrey et al. | |
| 2006/0025524 | A1 | 2/2006 | Schneider et al. | |
| 2006/0034796 | A1 | 2/2006 | Ashwell et al. | |
| 2006/0051798 | A1 | 3/2006 | Mirkin et al. | |
| 2006/0073101 | A1 | 4/2006 | Oldfield et al. | |
| 2007/0087114 | A1 | 4/2007 | Chilkoti et al. | |
| 2007/0117173 | A1 | 5/2007 | Levison et al. | |
| 2008/0181861 | A1 | 7/2008 | Jiang et al. | |
| 2009/0098652 | A1 | 4/2009 | Stupp et al. | |
| 2009/0215194 | A1 | 8/2009 | Magni et al. | |
| 2009/0247424 | A1 | 10/2009 | Chilkoti et al. | |
| 2010/0015070 | A1 | 1/2010 | Bollschweiler et al. | |
| 2010/0022455 | A1 | 1/2010 | Chilkoti | |
| 2010/0048473 | A1 | 2/2010 | Chaikof et al. | |
| 2010/0120018 | A1 | 5/2010 | Quake et al. | |
| 2010/0241054 | A1 | 9/2010 | Dacey et al. | |
| 2010/0311059 | A1 | 12/2010 | Didion et al. | |
| 2010/0311669 | A1 | 12/2010 | Greene et al. | |
| 2010/0325765 | P1 | 12/2010 | Pait et al. | |
| 2011/0060032 | A1 | 3/2011 | MacLachlan et al. | |
| 2011/0082283 | A1 | 4/2011 | Dagher et al. | |
| 2011/0110866 | A1 | 5/2011 | Chilkoti et al. | |
| 2011/0119778 | A1 | 5/2011 | Liss | |
| 2011/0165557 | A1 | 7/2011 | Ah et al. | |
| 2011/0207673 | A1 | 8/2011 | Chilkoti et al. | |
| 2011/0248698 | A1 | 10/2011 | Kikuchi et al. | |
| 2011/0294189 | A1 | 12/2011 | Chilkoti et al. | |
| 2011/0303303 | A1 | 12/2011 | Proper et al. | |
| 2011/0305718 | A1 | 12/2011 | Mugica et al. | |
| 2012/0172298 | A1 | 7/2012 | Andersen et al. | |
| 2012/0208742 | A1 | 8/2012 | Primiano et al. | |
| 2013/0039927 | A1 | 2/2013 | Dewhurst et al. | |
| 2013/0079277 | A1 | 3/2013 | Chilkoti | |
| 2013/0079280 | A1 | 3/2013 | Baca et al. | |
| 2013/0096058 | A1 | 4/2013 | Baca et al. | |
| 2013/0102993 | A1 | 4/2013 | Kim et al. | |
| 2013/0130384 | A1 | 5/2013 | Okamoto et al. | |
| 2013/0150432 | A1 | 6/2013 | Thodeti et al. | |
| 2013/0157889 | A1 | 6/2013 | Chilkoti et al. | |
| 2013/0165389 | A1 | 6/2013 | Schellenberger et al. | |
| 2013/0172274 | A1 | 7/2013 | Chilkoti | |
| 2013/0197359 | A1 | 8/2013 | Park et al. | |
| 2013/0315823 | A1 | 11/2013 | Trieu | |
| 2013/0330335 | A1 | 12/2013 | Bremel et al. | |
| 2014/0024600 | A1 | 1/2014 | Chilkoti et al. | |
| 2014/0163201 | A1 | 6/2014 | Winter et al. | |
| 2014/0170142 | A1 * | 6/2014 | Lubman ............ | A61K 39/3955 435/69.6 |
| 2014/0275227 | A1 | 9/2014 | Hoge et al. | |
| 2014/0294932 | A1 | 10/2014 | Kim et al. | |
| 2015/0094270 | A1 | 4/2015 | Harris et al. | |
| 2015/0099707 | A1 | 4/2015 | Pastan et al. | |
| 2015/0112022 | A1 | 4/2015 | Chilkoti et al. | |
| 2016/0017278 | A1 | 1/2016 | Montclare et al. | |
| 2016/0114053 | A1 | 4/2016 | Chilkoti | |
| 2016/0120952 | A1 | 5/2016 | Chilkoti | |
| 2016/0200787 | A1 | 7/2016 | Matern et al. | |
| 2016/0209356 | A1 | 7/2016 | Herget et al. | |
| 2016/0220727 | A1 | 8/2016 | Lu et al. | |
| 2016/0250165 | A1 | 9/2016 | Sullenger et al. | |
| 2016/0271262 | A1 | 9/2016 | Lopez et al. | |
| 2016/0303091 | A1 | 10/2016 | Wang | |
| 2016/0348147 | A1 | 12/2016 | Lopez et al. | |
| 2016/0355802 | A1 | 12/2016 | Isaacs et al. | |
| 2017/0020961 | A1 | 1/2017 | Rosenblatt et al. | |
| 2017/0088670 | A1 | 3/2017 | Rowan et al. | |
| 2017/0102357 | A1 | 4/2017 | Liang et al. | |
| 2017/0166621 | A1 | 6/2017 | Boettcher et al. | |
| 2017/0170142 | A1 | 6/2017 | Edelstein et al. | |
| 2017/0189545 | A1 | 7/2017 | Lee et al. | |
| 2017/0209601 | A1 | 7/2017 | Kumar et al. | |
| 2017/0233714 | A1 | 8/2017 | Chilkoti et al. | |
| 2017/0239363 | A1 | 8/2017 | Chilkoti et al. | |
| 2017/0369651 | A1 | 12/2017 | Cheng et al. | |
| 2018/0133401 | A1 | 5/2018 | Schwab et al. | |
| 2018/0135060 | A1 | 5/2018 | Romero Ramos et al. | |
| 2018/0161772 | A1 | 6/2018 | Rammohan et al. | |
| 2018/0171337 | A1 | 6/2018 | O'Neill et al. | |
| 2018/0200196 | A1 | 7/2018 | Fahmy et al. | |
| 2018/0217136 | A1 | 8/2018 | Chilkoti et al. | |
| 2018/0231469 | A1 | 8/2018 | Gibbons et al. | |
| 2018/0238864 | A1 | 8/2018 | Burd et al. | |
| 2018/0258157 | A1 | 9/2018 | Chilkoti et al. | |
| 2018/0326044 | A1 | 11/2018 | Carter | |
| 2018/0327752 | A1 | 11/2018 | Pillay et al. | |
| 2018/0369399 | A1 | 12/2018 | Hershfield et al. | |
| 2019/0016763 | A1 | 1/2019 | Kitazawa et al. | |
| 2019/0204309 | A1 | 7/2019 | Gibbs | |
| 2019/0285623 | A1 | 9/2019 | Chilkoti et al. | |
| 2019/0292549 | A1 | 9/2019 | Zhang et al. | |
| 2019/0345228 | A1 | 11/2019 | Chilkoti et al. | |
| 2020/0030496 | A1 | 1/2020 | Reddy et al. | |
| 2020/0078313 | A1 | 3/2020 | Roy et al. | |
| 2020/0121809 | A1 | 4/2020 | Hope et al. | |
| 2020/0148724 | A1 | 5/2020 | Chilkoti et al. | |
| 2020/0163878 | A1 | 5/2020 | Baumhof et al. | |
| 2020/0181555 | A1 | 6/2020 | Hinojosa et al. | |
| 2021/0046188 | A1 | 2/2021 | Hucknall et al. | |

(56) References Cited

U.S. PATENT DOCUMENTS

| | | | |
|---|---|---|---|
| 2021/0128734 A1 | 5/2021 | Chilkoti et al. |
| 2021/0154143 A1 | 5/2021 | Chilkoti et al. |
| 2021/0346570 A1 | 11/2021 | Wu et al. |
| 2022/0074938 A1 | 3/2022 | Omir et al. |
| 2022/0347489 A1 | 11/2022 | Brachman et al. |
| 2023/0098149 A1 | 3/2023 | Chilkoti et al. |
| 2023/0225998 A1 | 7/2023 | Mansour et al. |
| 2024/0050642 A1 | 2/2024 | Tal et al. |

FOREIGN PATENT DOCUMENTS

| | | | |
|---|---|---|---|
| CA | 2423488 | A1 | 4/2002 |
| CN | 102575229 | A | 7/2012 |
| CN | 104725628 | B | 4/2018 |
| CN | 112946261 | A | 6/2021 |
| CN | 112961065 | A | 6/2021 |
| EP | 1670315 | B1 | 4/2017 |
| EP | 2664340 | B1 | 2/2020 |
| JP | 2014-156428 | A | 8/2014 |
| JP | 2014-534265 | A | 12/2014 |
| WO | WO1991/019813 | A1 | 12/1991 |
| WO | WO2003/040165 | A2 | 10/2002 |
| WO | WO2004/096124 | A2 | 11/2004 |
| WO | WO2006/004778 | A2 | 1/2006 |
| WO | 2006/110292 | A2 | 10/2006 |
| WO | WO2007/073486 | A2 | 6/2007 |
| WO | WO2007/108013 | A2 | 9/2007 |
| WO | WO2007/134245 | A2 | 11/2007 |
| WO | WO2008/012543 | A1 | 1/2008 |
| WO | WO2008/030968 | A2 | 3/2008 |
| WO | WO2009/067584 | A1 | 5/2009 |
| WO | WO2010/054699 | A1 | 5/2010 |
| WO | WO2010/057154 | A1 | 5/2010 |
| WO | WO2010/096422 | A1 | 8/2010 |
| WO | WO2011/025572 | A1 | 3/2011 |
| WO | WO2011/123813 | A2 | 10/2011 |
| WO | 2012/156058 | A1 | 11/2012 |
| WO | 2012/162426 | A1 | 11/2012 |
| WO | WO2013/049234 | A2 | 4/2013 |
| WO | WO2013/065009 | A1 | 5/2013 |
| WO | 2013/106715 | A1 | 7/2013 |
| WO | WO2014/037373 | A1 | 3/2014 |
| WO | WO2014/194244 | A1 | 12/2014 |
| WO | 2015/011231 | A1 | 1/2015 |
| WO | WO2015/130846 | A2 | 9/2015 |
| WO | 2016/065300 | A1 | 4/2016 |
| WO | WO2016/065273 | A1 | 4/2016 |
| WO | WO2016/090103 | A1 | 6/2016 |
| WO | WO2016/154530 | A1 | 9/2016 |
| WO | WO2017/015132 | A1 | 1/2017 |
| WO | WO2017/024182 | A1 | 2/2017 |
| WO | WO2017/112825 | A2 | 6/2017 |
| WO | WO2017/112826 | A2 | 6/2017 |
| WO | WO2017/192449 | A1 | 11/2017 |
| WO | WO2018/115401 | A1 | 6/2018 |
| WO | WO2018/144854 | A1 | 8/2018 |
| WO | 2018/231834 | A1 | 12/2018 |
| WO | 2019/103744 | A1 | 5/2019 |
| WO | WO2019/147954 | A1 | 8/2019 |
| WO | 2020/037100 | A1 | 2/2020 |
| WO | 2020/037214 | A1 | 2/2020 |
| WO | 2020/051223 | A1 | 3/2020 |
| WO | WO2020/051220 | A1 | 3/2020 |
| WO | 2020/160472 | A1 | 8/2020 |
| WO | 2021/178898 | A1 | 9/2021 |
| WO | 2022/016089 | A2 | 1/2022 |
| WO | 2022/178438 | A1 | 8/2022 |
| WO | 2022/216821 | A1 | 10/2022 |
| WO | 2022/066635 | A1 | 3/2023 |

OTHER PUBLICATIONS

Jacobs (Protein Engineering Design & Selection, 2015, vol. 8, No. 10, pp. 385-393) (Year: 2015).*

Ahmed et al., "Preliminary Identification of Potential Vaccine Targets for the COVID-19 Coronavirus (SARS-CoV-2) Based on SARS-CoV Immunological Studies," Viruses, 2020, 12:254, 15 pages.

Amanat et al., "A serological assay to detect SARS-CoV-2 seroconversion in humans," Nat Med, 2020, 26(7): 1033-1036.

American Hospital Association, "AHA Hospital Statistics," 2020 edition. Available at: <https://www.aha.org/statistics/fast-facts-us-hospitals>.

Armbruster et al., "Limit of blank, limit of detection and limit of quantitation," Clin Biochem Rev, 2008, 29 Suppl 1: S49-52.

Arshavsky-Graham et al., "Lab-on-a-Chip Devices for Point-of-Care Medical Diagnostics," Advances in Biochemical Engineering/Biotechnology, 2020, 19 pages.

Atyeo et al., "Distinct Early Serological Signatures Track with SARS-CoV-2 Survival," Immunity, 2020, 53: 524-532.

Baraf et al., "Infusion-related reactions with pegloticase, a recombinant uricase for the treatment of chronic gout refractory to conventional therapy," J Clin Rheumatol, 2014, 20: 427-432.

Benn et al., "Physiology of Hyperuricemia and Urate-Lowering Treatments," Front Med (Lausanne), 2018, 5: 160, 28 pages.

Berry et al., "Development and characterisation of neutralising monoclonal antibody to the SARS-coronavirus," J Virol Methods, 2004, 120: 87-96.

Bryant et al., "Serology for SARS-CoV-2: Apprehensions, opportunities, and the path forward," Sci Immunol, 2020, 5: eabc6347, 4 pages.

Calabrese et al., "Frequency, distribution and immunologic nature of infusion reactions in subjects receiving pegloticase for chronic refractory gout," Arthritis Res Ther, 2017, 19: 191, 7 pages.

Caves et al., "Thermal inactivation of uricase (urate oxidase): mechanism and effects of additives," Biochemistry, 2013, 52: 497-507.

Chae et al., "Pharmacokinetic and pharmacodynamic evaluation of site-specific PEGylated glucagon-like peptide-1 analogs as flexible postprandial-glucose controllers," J Pharm Sci, 2009, 98(4): 1556-1567.

Chen et al., "Real-world patterns of pegloticase use for treatment of gout: descriptive multidatabase cohort study," BMJ Open, 2020, 10: e041167, 6 pages.

Chen et al., "The influence of polymer topology on pharmacokinetics: differences between cyclic and linear PEGylated poly(acrylic acid) comb polymers," J Control Release, 2009, 140: 203-209.

Chu et al., "Molecular Diagnosis of a Novel Coronavirus (2019-nCoV) Causing an Outbreak of Pneumonia," Clin Chem, 2020, 66(4): 549-555.

Cong et al., "Nucleocapsid Protein Recruitment to Replication-Transcription Complexes Plays a Crucial Role in Coronaviral Life Cycle," J Virol, 2020, 94: e01925-19, 21 pages.

Crowther, "The Elisa guidebook," Methods Mol Biol, 2000, 149(III-IV): 1-413.

Dincer et al., "Multiplexed Point-of-Care Testing—xPOCT," Trends Biotechnol, 2017, 35(8): 728-742.

Dong et al., "An interactive web-based dashboard to track COVID-19 in real time," Lancet Infect Dis, 2020, 20: 533-534.

Dutta et al., "The Nucleocapsid Protein of SARS-CoV-2: a Target for Vaccine Development," J Virol, 2020, 94(13): e00647-20, 2 pages.

Ekladious et al., "Polymer-drug conjugate therapeutics: advances, insights and prospects," Nature Reviews Drug Discovery, 2019, 18: 273-294.

Fathallah et al., "Immunogenicity of Subcutaneously Administered Therapeutic Proteins—a Mechanistic Perspective," The AAPS Journal, 2013, 15(4): 897-900.

Fox et al., "Soluble polymer carriers for the treatment of cancer: the importance of molecular architecture," Acc Chem Res, 2009, 42(8): 1141-1151.

Garay et al., "Therapeutic perspectives on uricases for gout," Joint Bone Spine, 2012, 79: 237-242.

Harris et al., "Effect of pegylation on pharmaceuticals," Nature Reviews Drug Discovery, 2003, 2: 214-221.

(56) References Cited

OTHER PUBLICATIONS

Heggestad et al., "In Pursuit of Zero 2.0: Recent Developments in Nonfouling Polymer Brushes for Immunoassays," Adv Mater, 2020, 32: e1903285.
Hermanson et al., "Peginesatide for the treatment of anemia due to chronic kidney disease—an unfulfilled promise," Expert Opin Drug Saf, 2016, 15(10): 1421-1426.
Hershfield et al., "Treating gout with pegloticase, a PEGylated urate oxidase, provides insight into the importance of uric acid as an antioxidant in vivo," Proc Natl Acad Sci U S A, 2010, 107(32): 14351-14356.
Huang et al., "Clinical features of patients infected with 2019 novel coronavirus in Wuhan," China. Lancet, 2020, 395: 497-506.
Hucknall et al., "Simple Fabrication of Antibody Microarrays on Nonfouling Polymer Brushes with Femtomolar Sensitivity for Protein Analytes in Serum and Blood," Adv Mater, 2009, 21(19): 1968-1971.
Jiang et al., "Neutralizing Antibodies against SARS-CoV-2 and Other Human Coronaviruses," Trends Immunol, 2020, 41(5): 355-359.
Joh et al., "Architectural Modification of Conformal PEG-Bottlebrush Coatings Minimizes Anti-PEG Antigenicity While Preserving Stealth Properties," Advanced Healthcare Materials, 2019, 8(8): 1801177, 27 pages.
Joh et al., "Inkjet-printed point-of-care immunoassay on a nanoscale polymer brush enables subpicomolar detection of analytes in blood," Proc Natl Acad Sci U S A, 2017, 114: E7054-E7062.
Kang et al., "Crystal structure of SARS-CoV-2 nucleocapsid protein RNA binding domain reveals potential unique drug targeting sites," Acta Pharm Sin B, 2020, 10(7): 1228-1238.
Khailany et al., "Genomic characterization of a novel SARS-CoV-2," Gene Rep, 2020, 9: 100682, 6 pages.
Kozel et al., "Point-of-care testing for infectious diseases: past, present, and future," J Clin Microbiol, 2017, 55: 2313-2320.
Kozma et al., "Anti-PEG antibodies: Properties, formation, testing and role in adverse immune reactions to PEGylated nano-biopharmaceuticals," Adv Drug Deliv Rev, 2020, 154-155, 163-175.
Krammer et al., "Serology assays to manage COVID-19," Science, 2020, 368: 1060-1061.
Kuo et al., "Global epidemiology of gout: prevalence, incidence and risk factors," Nature Reviews Rheumatology, 2015, 11: 649-662.
Laing et al., "A dynamic COVID-19 immune signature includes associations with poor prognosis," Nat Med, 2020, 26:1623-1635.
Lieberman et al., "Comparison of Commercially Available and Laboratory-Developed Assays for in Vitro Detection of SARS-CoV-2 in Clinical Laboratories," J Clin Microbiol, 2020, 58(8):e00821-20.
Lipsitch et al., "Antibody testing will enhance the power and accuracy of COVID-19-prevention trials," Nat Med, 2020, 26: 818-819.
Lipsky et al., "Pegloticase immunogenicity: the relationship between efficacy and antibody development in patients treated for refractory chronic gout," Arthritis Res Ther, 2014, 16: R60.
Lisboa Bastos et al., "Diagnostic accuracy of serological tests for covid-19: systematic review and meta-analysis," BMJ, 2020, 370: m2516.
Liu et al., "High neutralizing antibody titer in intensive care unit patients with COVID-19," Emerg Microbes Infect, 2020, 9: 1664-1670.
Liu et al., "Semi-permeable coatings fabricated from comb-polymers efficiently protect proteins in vivo," Nature Communications, 2014, 5: 5526.
Liu et al., "The experiences of health-care providers during the COVID-19 crisis in China: a qualitative study," Lancet Glob Health, 2020, 8: e790-e798.
Lu et al., "Genomic characterisation and epidemiology of 2019 novel coronavirus: implications for virus origins and receptor binding," Lancet, 2020, 395: 565-574.
McAndrews et al., "Heterogeneous antibodies against SARS-CoV-2 spike receptor binding domain and nucleocapsid with implications for COVID-19 immunity," JCI Insight, 2020, 5(18):e142386, 14 pages.
McElvaney et al., "A linear prognostic score based on the ratio of interleukin-6 to interleukin-10 predicts outcomes in COVID-19," EBioMedicine, 2020, 61: 103026, 8 pages.
Mejía-Salazar et al., "Microfluidic Point-of-Care Devices: New Trends and Future Prospects for eHealth Diagnostics," Sensors, 2020, 20: 1951, 19 pages.
Miller et al., "Disease and healthcare burden of COVID-19 in the United States," Nat Med, 2020, 26: 1212-1217.
Nalla et al., "Comparative Performance of SARS-CoV-2 Detection Assays Using Seven Different Primer-Probe Sets and One Assay Kit," J Clin Microbiol, 2020, 58: e00557-20, 6 pages.
Norman et al., "Ultrasensitive high-resolution profiling of early seroconversion in patients with COVID-19," Nat Biomed Eng, 2020, 11 pages.
Nunn et al., "Crystal Structure of Tobacco Etch Virus Protease Shows the Protein C Terminus Bound within the Active Site," Journal of Molecular Biology, 2005, 350: 145-155.
Nyborg et al., "A Therapeutic Uricase with Reduced Immunogenicity Risk and Improved Development Properties," PLoS One, 2016, 11(12): e0167935, 23 pages.
Okba et al., "Severe Acute Respiratory Syndrome Coronavirus 2-Specific Antibody Responses in Coronavirus Disease Patients," Emerg Infect Dis, 2020, 26: 1478-1488.
Ozer et al., "Effect of Molecular Architecture on Cell Interactions and Stealth Properties of PEG," Biomacromolecules, 2017, 18: 2699-2710.
Pecoraro et al., "A systematic evaluation of immunoassay point-of-care testing to define impact on patients' outcomes," Ann Clin Biochem, 2017, 54(4): 420-431.
Ponti et al., "Biomarkers associated with COVID-19 disease progression," Crit Rev Clin Lab Sci, 2020, 57, 11 pages.
Posthuma-Trumpie et al., "Lateral flow (immuno)assay: its strengths, weaknesses, opportunities and threats. A literature survey," Anal Bioanal Chem, 2009, 393: 569-582.
Radzicka et al., "Comparing the Polrities of the Amino Acids: Side-Chain Distribution Coefficients between the Vapor Phase, Cyclohexane, 1-Octanol, and Neutral Aqueous Solution," Biochemistry, 1988, 27: 1664-1670.
Ravichandran et al., "Antibody signature induced by SARS-CoV-2 spike protein immunogens in rabbits," Sci Transl Med, 2020, 10.1126/scitranslmed.abc3539, 9 pages.
Rogers et al., "Isolation of potent SARS-CoV-2 neutralizing antibodies and protection from disease in a small animal model," Science, 2020, 369: 956-963.
Rosadas et al., "Testing for responses to the wrong SARS-CoV-2 antigen," Lancet, 2020, 396: e23.
Rothe et al., "Transmission of 2019-nCoV Infection from an Asymptomatic Contact in Germany," N Engl J Med, 2020, 382: 10, 2 pages.
Seow et al., "Longitudinal evaluation and decline of antibody responses in SARS-CoV-2 infection," medRxiv, 2020, 24 pages.
Sundy et al., "Efficacy and tolerability of pegloticase for the treatment of chronic gout in patients refractory to conventional treatment: two randomized controlled trials," Jama, 2011, 306(7): 711-720.
Sundy et al., "Pharmacokinetics and pharmacodynamics of intravenous PEGylated recombinant mammalian urate oxidase in patients with refractory gout," Arthritis Rheum, 2007, 56(3): 1021-1028.
Tang et al., "Laboratory Diagnosis of COVID-19: Current Issues and Challenges," J Clin Microbiol, 2020, 58: e00512-20, 9 pages.
Turner et al., "Challenges and Opportunities for the Subcutaneous Delivery of Therapeutic Proteins," Journal of Pharmaceutical Sciences, 2018, 107(5): 1247-1260.
U.S. FDA—Classify your medical devices. Updated as of: Feb. 7, 2020. Available at: <https://www.fda.gov/medical-devices/overview-device-regulation/classify-your-medical-device>.
U.S. FDA—In Vitro Diagnostics. Updated as of: Oct. 25, 2019. Available at: <https://www.fda.gov/medical-devices/products-and-medical-procedures/vitro-diagnostics>.

(56) References Cited

OTHER PUBLICATIONS

Vaninov, "In the eye of the COVID-19 cytokine storm," Nat Rev Immunol, 2020, 20: 277, 1 page.
Vashist et al., "Emerging Technologies for Next-Generation Point-of-Care Testing," Trends Biotechnol, 2015, 33(11): 692-705.
Verhoef et al., "Potential induction of anti-PEG antibodies and complement activation toward PEGylated therapeutics," Drug Discov Today, 2014, 19(12): 1945-1952.
Vugmeyster et al., "Pharmacokinetics and toxicology of therapeutic proteins: Advances and challenges," World J Biol Chem, 2012, 3(4): 73-92.
Waterboer et al., "Suppression of non-specific binding in serological Luminex assays," J Immunol Methods, 2006, 309: 200-204.
Weinhandl et al., "Relative safety of peginesatide and epoetin alfa," Pharmacoepidemiology and Drug Safety, 2014, 23(10): 1003-1011.
Whitman et al., "Evaluation of SARS-CoV-2 serology assays reveals a range of test performance," Nat Biotechnol, 2020, 38: 1174-1183.
Wiersinga et al., "Pathophysiology, Transmission, Diagnosis, and Treatment of Coronavirus Disease 2019 (COVID-19): A Review," JAMA, 2020, 324(8): 782-793.
Winter et al., "The important role of serology for COVID-19 control," Lancet Infect Dis, 2020, 20: 758-759.
Wölfel et al., "Virological assessment of hospitalized patients with COVID-2019," Nature, 2020, 581: 465-469.
Yang et al., "Analysis of Pre-existing IgG and IgM Antibodies against Polyethylene Glycol (PEG) in the General Population," Analytical Chemistry, 2016, 88(23): 11804-11812.
Yang et al., "Anti-PEG immunity: emergence, characteristics, and unaddressed questions," Wiley Interdiscip Rev Nanomed Nanobiotechnol, 2015, 7(5): 655-677.
Yang et al., "Plasma IP-10 and MCP-3 levels are highly associated with disease severity and predict the progression of COVID-19," J Allergy Clin Immunol, 2020, 146: 119-127.
Yang et al., "Uricases as therapeutic agents to treat refractory gout: Current states and future directions," Drug Dev Res, 2012, 73(2): 66-72.
Yong et al., "Connecting clusters of COVID-19: an epidemiological and serological investigation," Lancet Infect Dis, 2020, 20: 809-815.
Zhang et al., "Anti-PEG antibodies in the clinic: Current issues and beyond PEGylation," J Control Release, 2016, 244(Pt B): 184-193.
Zhang et al., "Impact of Large Aggregated Uricases and PEG Diol on Accelerated Blood Clearance of PEGylated Canine Uricase," PLoS ONE, 2012, 7(6): e39659.
Zhao et al., "Antibody responses to SARS-CoV-2 in patients of novel coronavirus disease 2019," Clin Infect Dis, 2020, 22 pages.
International Search Report and Written Opinion for Application No. PCT/US2021/020591 dated Oct. 7, 2021 (14 pages).
United States Patent Office Action for U.S. Appl. No. 16/614,282 dated Oct. 21, 2021 (14 pages).
United States Patent Office Action for U.S. Appl. No. 15/749,797 dated Nov. 29, 2021 (10 pages).
United States Patent Office Action for U.S. Appl. No. 16/477,229 dated Oct. 26, 2021 (10 pages).
Cereghetti et al., "Reversible, functional amyloids: towards an understanding of their regulation in yeast and humans," Cell Cycle, 2018, 17(13): 1545-1558.
Uversky et al., "Life in Phases: Intra- and Inter-Molecular Phase Transitions in Protein Solutions," Biomolecules, 2019, 9(12): 842.
McPherson, "Product purification by reversible phase transition following *Escherichia coli* expression of genes encoding up to 251 repeats of the elastomeric pentapeptide GVGVP," Protein Expression and Purification, 1996, 7: 51-57.
Cascarina et al., "Generalizable Compositional Features Influencing the Proteostatic Fates of Polar Low-Complexity Domains," International Journal of Molecular Sciences, 2021, 22(16): 8944.
Krainer et al., "Reentrant liquid condensate phase of proteins is stabilized by hydrophobic and non-ionic interactions," Nature Communications, 2021, 12(1): 1085.
United States Patent Office Action for U.S. Appl. No. 17/477,192 dated Jan. 4, 2024 (11 pages).
United States Patent Office Notice of Allowance for U.S. Appl. No. 18/051,487 dated Dec. 11, 2023 (5 pages).
United States Patent Office Action for U.S. Appl. No. 16/964,832 dated Jan. 19, 2024 (9 pages).
United States Patent Office Action for U.S. Appl. No. 17/051,202 dated Jan. 19, 2024 (5 pages).
Nikolic et al., "Structural basis for the recognition of LDL-receptor family members by VSV glycoprotein," Nature Communications, 2018, 9: 1029, 12 pages.
International Search Report and Written Opinion for Application No. PCT/US2021/020589 dated Jul. 15, 2021 (21 pages).
International Search Report and Written Opinion for Application No. PCT/US2021/017809 dated Jul. 22, 2021 (20 pages).
Erbacher et al., "Transfection and Physical Properties of Various Saccharide, Poly(ethylene glycol), and Antibody-Derivatized Polyethylenimines (PEI)," The Journal of Gene Medicine, 1999, 1: 210-222.
Alves et al., "Influence of doxorubicin on model cell membrane properties: insight from in vitro and in silico studies," Sci Rep, 2017, 7(1): 6343.
International Search Report and Written Opinion for Application No. PCT/US2022/078659 dated Feb. 1, 2023 (17 pages).
United States Patent Office Action for U.S. Appl. No. 16/964,832 dated Apr. 17, 2023 (17 pages).
International Search Report and Written Opinion for Application No. PCT/US2021/046833 dated Nov. 8, 2021 (13 pages).
International Search Report and Written Opinion for Application No. PCT/US2021/035823 dated Dec. 8, 2021 (16 pages).
United States Patent Office Action for U.S. Appl. No. 17/265,165 dated Dec. 21, 2021 (11 pages).
United States Patent Office Action for U.S. Appl. No. 16/964,832 dated Jan. 19, 2022 (12 pages).
United States Patent Office Action for U.S. Appl. No. 16/625,899 dated Dec. 15, 2021 (12 pages).
United States Patent Office Action for U.S. Appl. No. 16/927,982 dated Jan. 6, 2022 (6 pages).
Da Pieve Chiara et al., "Modification of Thiol Functionalized Aptamers by Conjugation of Synthetic Polymers," Bioconjugate Chemistry, 2009, 1(1): 169-174.
International Search Report and Written Opinion for Application No. PCT2022/023158 dated Jun. 21, 2022 (7 pages).
International Search Report and Written Opinion for Application No. PCT/US2022/017349 dated Jun. 3, 2022 (20 pages).
United States Patent Office Action for U.S. Appl. No. 16/964,832 dated Jul. 14, 2022 (6 pages).
United States Patent Office Notice of Allowance for U.S. Appl. No. 16/927,982 dated Jul. 15, 2022 (8 pages).
United States Patent Office Notice of Allowance for U.S. Appl. No. 16/614,282 dated Aug. 23, 2022 (7 pages).
United States Patent Office Notice of Allowance for U.S. Appl. No. 17/015,315 dated Apr. 26, 2023 (7 pages).
United States Patent Office Action for U.S. Appl. No. 17/051,202 dated Jun. 21, 2023 (10 pages).
Liu et al., "Stable Evans Blue Derived Exendin-4 Peptide for Type 2 Diabetes Treatment," Bioconjugate Chem, 2016, 27: 54058.
Chan et al., "A randomized, repeat-dose, pharmacodynamic and safety study of an antidote-controlled factor IXa inhibitor," J Thromb Haemost, 2008, 6(5): 789-796.
Chan et al., "Phase 1b randomized study of antidote-controlled modulation of factor IXa activity in patients with stable coronary artery disease," Circulation, 2008, 117(22): 2865-2874.
Chappell et al., "Computational design of small transcription activating RNAs for versatile and dynamic gene regulation," Nat Commun, 2017, 8(1): 1051.
Chappell et al., "Creating small transcription activating RNAs," Nat Chem Biol, 2015, 11(3): 214-220.
Chase et al., "Single-Stranded DNA Binding Proteins Required for DNA Replication," Ann. Rev. Biochem., 1986, 55: 103-136.

(56) References Cited

OTHER PUBLICATIONS

Cohen et al., "First clinical application of an actively reversible direct factor IXa inhibitor as an anticoagulation strategy in patients undergoing percutaneous coronary intervention," Circulation, 2010, 122(6): 614-622.
Dale et al., "Direct covalent mercuration of nucleotides and polynucleotides," Biochemistry, 1975, 14(11): 2447-2457.
Davis et al., "Antibodies and the RNA World: A Role for Low-molecular-weight Effectors in Biochemical Evolution," RNA World, 1993, Chapter 8, p. 185-204.
Dyke et al., "First-in-human experience of an antidote-controlled anticoagulant using RNA aptamer technology: a phase 1a pharmacodynamic evaluation of a drug-antidote pair for the controlled regulation of factor IXa activity," Circulation, 2006, 114(23): 2490-2497.
Eichhorn et al., "Interactions of metal ions with polynucleotides and related compounds. XII. The relative effect of various metal ions on DNA helicity," J. Am. Chem. Soc, 1968, 90: 7323-7328.
Ganesan et al., "Lipid Nanoparticles: Different Preparation Techniques, Characterization, Hurdles, and Strategies for the Production of Solid Lipid Nanoparticles and Nanostructured Lipid Carriers for Oral Drug Delivery," Sustain. Chem. Pharm., 2017, 6: 37-56.
Gold et al., "Aptamers and the RNA World, Past and Present," Cold Spring Harbor Perspect. Biol., 2012, 4: a003582, 9 pages.
Heus, "RNA aptamers," Nat Struct Biol, 1997, 4(8): 597-600.
Hucknall et al., "Simple Fabrication of Antibody Microarrays on Nonfouling Polymer Brushes with Femtomolar Sensitivity for Protein Analytes in Serum and Blood," Adv Mater, 2009, 21: 1968-1971.
Hwang et al., "Inhibition of gene expression in human cells through small molecule-RNA interactions," Proc. Natl. Acad. Sci. USA, 1999, 96(23): 12997-13002.
Keefe et al., "Aptamers as therapeutics," Nature Reviews Drug Discovery, 2010, 9: 537-550.
Korte et al., "Short activated partial thromboplastin times are related to increased thrombin generation and an increased risk for thromboembolism," Am J Clin Pathol, 2000, 113(1): 123-127.
Li et al., "Ferric Chloride-induced Murine Thrombosis Models," J. Vis. Exp., 2016, 115: e54479, 12 pages.
Lincoff et al., "Effect of the REG1 anticoagulation system versus bivalirudin on outcomes after percutaneous coronary intervention (Regulate-PCI): a randomised clinical trial," Lancet, 2016, 387(10016): 349-356.
Lippard et al., "Platinum complexes: probes of polynucleotide structure and antitumor drugs," Acc. Chem. Res., 1978, 11(5): 211-217.
Maier et al., "From selection hits to clinical leads: progress in aptamer discovery," Mol. Ther. Methods Clin. Dev., 2016, 3: 16014, 10 pages.
McManus et al., "Gene silencing in mammals by small interfering RNAs," Nat Rev Genet, 2002, 3(10): 737-747.
Moreno et al., "Anti-PEG Antibodies Inhibit the Anticoagulant Activity of PEGylated Aptamers," Cell Chem Biol, 2019, 26(5): 634-644.e3.
Nimjee et al., "Aptamers as Therapeutics," Annu Rev Pharmacol Toxicol, 2017, 57: 61-79.
Pisal et al., "Delivery of therapeutic proteins," Journal of Pharmaceutical Sciences, 2010, 99(6): 2557-2575.
Povsic et al., "A Phase 2, randomized, partially blinded, active-controlled study assessing the efficacy and safety of variable anticoagulation reversal using the REG1 system in patients with acute coronary syndromes: results of the Radar trial," Eur Heart J, 2013, 34(31): 2481-2489.
Povsic et al., "Pre-existing anti-PEG antibodies are associated with severe immediate allergic reactions to pegnivacogin, a PEGylated aptamer," J Allergy Clin Immunol, 2016, 138(6): 1712-1715.
Purtell et al., "Isoelectric point of albumin: effect on renal handling of albumin," Kidney Int, 1979, 16(3): 366-376.
Richter et al., "Mechanistic determinants of biotherapeutics absorption following SC administration," AAPS J, 2012, 14(3): 559-570.
Rinaldi et al., "Antisense oligonucleotides: the next frontier for treatment of neurological disorders," Nat Rev Neurol, 2018, 14(1): 9-21.
Rusconi et al., "Antidote-mediated control of an anticoagulant aptamer in vivo," Nat Biotechnol, 2004, 22(11): 1423-1428.
Rusconi et al., "RNA aptamers as reversible antagonists of coagulation factor lxa," Nature, 2002, 19(6902): 90-94
Shu et al., "GISAID: Global initiative on sharing all influenza data—from vision to reality," Euro Surveill 22, 2017, 22(13): 30494, 3 pages.
Smith et al., "Coronaviruses lacking exoribonuclease activity are susceptible to lethal mutagenesis: evidence for proofreading and potential therapeutics," PLoS Pathog, 2013, 9: e1003565, 11 pages.
Tuerk et al., "Systematic evolution of ligands by exponential enrichment: RNA ligands to bacteriophage T4 DNA polymerase," Science, 1990, 249(4968): 505-510.
Werstuck et al., "Controlling gene expression in living cells through small molecule-RNA interactions," Science, 1998, 282(5387): 296-298.
Woodruff et al., "Modulation of the Coagulation Cascade Using Aptamers," Arterioscler Thromb Vasc Biol, 2015, 35(10): 2083-2091.
Yamaoka et al., "Distribution and tissue uptake of poly(ethylene glycol) with different molecular weights after intravenous administration to mice," Journal of Pharmaceutical Sciences, 1994, 83(4): 601-606.
Yizhi et al., "A brush-polymer/exendin-4 conjugate reduces blood glucose levels for up to five days and eliminates poly(ethylene glycol) antigenicity," Nature Biomedical Engineering, 2016, 1(1): 0002.
Zhou et al., "Aptamers as targeted therapeutics: current potential and challenges," Nat Rev Drug Discov, 2017, 16(3): 181-202.
Gilroy et al., "Sustained release of a GLP-1 and FGF21 dual agonist from an injectable depot protects mice from obesity and hyperglycemia," Science Advances, 2020, 6(35): eaaz9890, 12 pages.
United States Patent Office Notice of Allowance for U.S. Appl. No. 15/749,797 dated Mar. 16, 2022 (6 pages).
United States Patent Office Action for U.S. Appl. No. 16/477,229 dated Mar. 3, 2022 (10 pages).
Ozer et al., "Injectable non-immunogenic PEG-like conjugate that forms a subcutaneous depot and enables sustained delivery of a peptide drug," Research Square, 2021, 38 pages.
Hu et al., "Site-specific in situ growth of a cyclized protein-polymer conjugate with improved stability and tumor retention," Biomaterials, 2015, 47:13-19.
International Search Report and Written Opinion for Application No. PCT/US2022/041241 dated Oct. 25, 2022 (10 pages).
United States Patent Office Action for U.S. Appl. No. 17/265,165 dated Sep. 2, 2022 (5 pages).
United States Patent Office Action for U.S. Appl. No. 17/015,315 dated Dec. 23, 2022 (10 pages).
United States Patent Office Notice of Allowance for U.S. Appl. No. 16/477,229 dated Jan. 6, 2023 (8 pages).
United States Patent Office Notice of Allowance for U.S. Appl. No. 17/265,165 dated Jan. 10, 2023 (7 pages).
United States Patent Office Notice of Allowance for U.S. Appl. No. 16/625,899 dated Jan. 18, 2023 (8 pages).
AACR, "AACR Cancer Progress Report 2016," Clin Cancer Res, Oct. 2016, vol. 22, Issue 19, 143 pages.
Aaron et al., "Elastin as a Random-Network Elastomer—a Mechanical and Optical Analysis of Single Elastin Fibers," Biopolymers, 1981, 20(6):1247-1260.
Abbaspourrad et al., "Controlling release from pH-responsive microcapsules," Langmuir, 2013, 29: 12697-12702.
Abbaspourrad et al., "Polymer microcapsules with programmable active release," J Am Chem Soc, 2013, 135: 7744-7750.
Abbruzzese et al., "A phase I clinical, plasma, and cellular pharmacology study of gemcitabine," J. Clin. Oncol. 1991, 3, 491-498.
Adams et al., "Safety and utilization of blood components as therapeutic delivery systems," Curr Pharm Biotechnol, 2003, 4(5): 275-82.

(56) References Cited

OTHER PUBLICATIONS

Adams et al., "Sustained release of antibiotics from injectable and thermally responsive polypeptide depots," J Biomed Mater Res B Appl Biomater, Jul. 2009, vol. 90B, Issue 1, pp. 67-74.
Adamska et al., "Pancreatic ductal adenocarcinoma: Current and evolving therapies," J Mol Sci, Jun. 2017, vol. 18, Issue 7, pp. 1338-1380.
Adiseshaiah et al., "Nanomedicine strategies to overcome the pathophysiological barriers of pancreatic cancer," Nat Rev Clin Oncol, Dec. 2016, vol. 13, Issue 12, pp. 750-765.
Agarwal et al., "One-step microfluidic generation of pre-hatching embryo-like core-shell microcapsules for miniaturized 3D culture of pluripotent stem cells," Lab Chip, 2013, 13: 4525-4533.
Aladini et al., "Chemical Synthesis and Characterization of Elastin-Like Polypeptides (ELPs) With Variable Guest Residues," J Pept Sci, May 2016, vol. 22, Issue 5, pp. 334-342.
Alarcon et al., "Exendin 4 controls insulin production in rat islet beta cells predominantly by potentiation of glucose-stimulated proinsulin biosynthesis at the translational level," Diabetologia, 2006, 49(12):2920-2929.
Albanese et al., "The effect of nanoparticle size, shape, and surface chemistry on biological systems," Annu. Rev. Biomed. Eng., Aug. 2012, vol. 14, pp. 1-16.
Alconcel et al., "FDA-approved poly(ethylene glycol)—protein conjugate drugs," Polym. Chem., vol. 2, Apr. 2011, Issue 7, pp. 1442-1448.
Allen et al., "Liposomal drug delivery systems: from concept to clinical applications," Adv Drug Deliv Rev, Elsevier, Jan. 2013, 65(1):36-48.
Alley et al., "Feasibility of drug screening with panels of human tumor cell lines using a microculture tetrazolium assay," Cancer Res., 1988, 48, 589-601.
Aluri et al., "Elastin-like peptide amphiphiles Form nanofibers with tunable length," Biomacromolecules, Sep. 2012, vol. 13, Issue 9, pp. 2645-2654.
American Diabetes Association, Standards of medical care in diabetes—2018. Diabetes Care, Jan. 2018, vol. 41, Supplement 1, pp. S1-S159.
Amiram et al., "A depot-forming glucagon-like peptide-1 fusion protein reduces blood glucose for five days with a single injection," J. Control. Release, Nov. 2013, vol. 172, Issue, pp. 144-151.
Amiram et al., "Evolution of translation machinery in recoded bacteria enables multi-site incorporation of nonstandard amino acids," Nat Biotechnol, 2015, 33: 1272-1279.
Amiram et al., "Injectable protease-operated depots of glucagon-like peptide-1 provide extended and tunable glucose control," Proc. Natl. Acad. Sci., Feb. 2013, vol. 110, Issue 8, pp. 2792-2797.
Andersen et al., "Extending Half-life by Indirect Targeting of the Neonatal Fc Receptor (FcRn) Using a Minimal Albumin Binding Domain," Journal of Biological Chemistry, Feb. 2011, vol. 286, Issue 7, pp. 5234-5241.
Anselmo et al., "Nanoparticles in the clinic," Bioeng Transl Med, Jun. 2016, 1(1):10-29.
Antos et al., "Lipid Modification of Proteins through Sortase-Catalyzed Transpeptidation," J. Am. Chem. Soc., Dec. 2008, vol. 130, Issue 48, pp. 16338-16343.
Antos et al., "Site-Specific N- and C-Terminal Labeling of a Single Polypeptide Using Sortases of Different Specificity," J. Am. Chem. Soc., Aug. 2009, vol. 131, Issue 31, pp. 10800-10801.
Appleyard et al., "Multiplexed protein quantification with barcoded hydrogel microparticles," Anal Chem, 2011, 83: 193-199.
Arami et al., "In vivo delivery, pharmacokinetics, biodistribution and toxicity of iron oxide nanoparticles," Chem Soc Rev, Dec. 2015, 44(23):8576-8607.
Arias et al., "Superior preclinical efficacy of gemcitabine developed as chitosan nanoparticulate system," Biomacromolecules, Jan. 2011, vol. 12, Issue 1, pp. 97-104.
Armstrong et al., "Antibody against poly(ethylene glycol) adversely affects PEG-asparaginase therapy in acute lymphoblastic leukemia patients," Cancer, Jul. 2007, vol. 110, Issue 1, pp. 103-111.
Armstrong et al., "The Hydrodynamic Radii of Macromolecules and Their Effect on Red Blood Cell Aggregation," Biophys. J., 2004, 87, 4259-4270.
Arner et al., "FGF21 attenuates lipolysis in human adipocytes—a possible link to improved insulin sensitivity," FEBS Lett, May 2008, vol. 582, Issue 12, pp. 1725-1730.
Arnida et al., "Geometry and surface characteristics of gold nanoparticles influence their biodistribution and uptake by macrophages," Eur J Pharm Biopharm, Apr. 2011, vol. 77, Issue 3, pp. 417-423.
Asai et al., "Protein polymer hydrogels by in situ, rapid and reversible self-gelation," Biomaterials, Jul. 2012, vol. 33, Issue 21, pp. 5451-5458.
Astete et al., "Synthesis and characterization of PLGA nanoparticles," Journal of Biomaterials Science, Polymer Edition 2006, 17(3):247-289.
Atun et al., "Expanding global access to radiotherapy," Lancet Oncol, Sep. 2015, vol. 16, Issue 10, pp. 1153-1186.
Averick et al., "ATRP under biologically relevant conditions: grafting from a protein," ACS Macro. Lett., Jan. 2012, vol. 1, Issue 1, pp. 6-10.
Averick et al., "Protein-polymer hybrids: conducting ARGET ATRP from a genetically encoded cleavable ATRP initiator," Eur. Polym. J., Oct. 2013, vol. 49, Issue 10, pp. 2919-2924.
Awai et al., "Studies of the metabolism of I-131-labeled human transferrin," J. Lab. Clin. Med. 61, 1963, 363-396.
Awasthi et al., "Comparative benefits of Nab-paclitaxel over gemcitabine or polysorbate-based docetaxel in experimental pancreatic cancer," Carcinogenesis, Oct. 2013, vol. 34, Issue 10, pp. 2361-2369.
Awasthi et al., "Evaluation of combination treatment benefits of nab-paclitaxel in experimental pancreatic cancer," Journal of Clinical Oncology, 2012, 30, 170.
Axup et al., "Synthesis of site-specific antibody-drug conjugates using unnatural amino acids," Proc Natl Acad Sci USA, Feb. 2012, vol. 109, Issue 40, pp. 16101-16106.
Azhdarinia et al., "Regional radiochemotherapy using in situ hydrogel," Pharm Res., 2005, 22, 776-783.
Babu, "The contribution of intrinsically disordered regions to protein function, cellular complexity, and human disease," Biochem Soc Trans, Oct. 2016, 44(5):1185-1200.
Bache et al., "Investigating the accuracy of microstereotactic-body-radiotherapy utilizing anatomically accurate 3D printed rodent-morphic dosimeters," Medical Physics, Feb. 2015, vol. 42, Issue 2, pp. 846-855.
Badi, "Non-linear PEG-based thermoresponsive polymer systems," Progress in Polymer Science, Mar. 2017, vol. 66, pp. 54-79.
Bae et al., "Targeted drug delivery to tumors: myths, reality and possibility," J Control Release, Elsevier, Aug. 2011, 153(3):198-205.
Baggio et al., "A recombinant human glucagon-like peptide (GLP)-1-albumin protein (Albugon) mimics peptidergic activation of GLP-1 receptor-dependent pathways coupled with satiety, gastrointestinal motility, and glucose homeostasis," Diabetes 53, 2004, 2492-2500.
Baggio et al., "Biology of Incretins: GLP-1 and GIP," Gastroenterology, May 2007, vol. 132, Issue 6, pp. 2131-2157.
Bailey et al., "Genomic analyses identify molecular subtypes of pancreatic cancer," Nature, Mar. 2016, vol. 531, Issue 7592, pp. 47-52.
Bain et al., "Formation of monolayer films by the spontaneous assembly of organic thiols from solution onto gold," Journal of the American Chemical Society, 1989, 111: 321-335.
Balu et al., "An16-resilin: an advanced multi-stimuli-responsive resilin-mimetic protein polymer," Acta Biomater, Nov. 2014, 10:4768-4777.
Bamford et al., "The COSMIC (Catalogue of Somatic Mutations in Cancer) database and website," British Journal of Cancer, 2004, 91, 355-358.
Banani et al., "Biomolecular condensates: organizers of cellular biochemistry," Nat Rev Mol Cell Biol, May 2017, 18(5):285-298.
Banerjee et al., "Nanoparticles in cancer chemotherapy," Prog Mol Biol Transl Sci, Elsevier, Nov. 2011, 104:489-507.
Banga et al., "Parenteral controlled delivery and parmacokinetics of therapeutic peptides and proteins," (CRC Press, Boca Raton, FL, 2005).

(56) References Cited

OTHER PUBLICATIONS

Banjade et al., "Phase transitions of multivalent proteins can promote clustering of membrane receptors," Elife, Oct. 2014, 3:e04123.
Bansal et al., "PEGylation improves pharmacokinetic profile, liver uptake and efficacy of Interferon gamma in liver fibrosis," J. Control. Release, Sep. 2011, vol. 154, Issue 3, pp. 233-240.
Banskota et al., "Genetically encoded stealth nanoparticles of a zwitterionic polypeptide-paclitaxel conjugate have wider therapeutic window than Abraxane in multiple tumor models," Nano Lett, Mar. 2020, 20(4):2396-2409.
Barbuti et al., "Paclitaxel through the ages of anticancer therapy: Exploring its role in chemoresistance and radiation therapy," Cancers, Dec. 2015, vol. 7, Issue 4, pp. 2360-2371.
Barnett et al., "Normal tissue reactions to radiotherapy: towards tailoring treatment dose by genotype," Nat Rev Cancer, Feb. 2009, vol. 9, Issue 2, pp. 134-142.
Barton et al., "Estimating the demand for radiotherapy form the evidence: A review of changes from 2003 to 2012," Radiother Oncol, Jul. 2014, vol. 112, Issue 1, pp. 140-144.
Baskar et al., "Cancer and Radiation Therapy: Current Advances and Future Directions," Int. J. Med. Sci., Feb. 2012, vol. 9, Issue 3, pp. 193-199.
Bates et al., "Block copolymer thermodynamics: theory and experiment," Annu Rev. Phys. Chem., 1990, 41:525-57.
Bedford et al., "WW domain-mediated interactions reveal a spliceosome-associated protein that binds a third class of proline-rich motif: The proline glycine and methionine-rich motif," PNAS, 1998, 95: 10602-10607.
Beenken et al., "The FGF family: biology, pathophysiology and therapy," Nat Rev Drug Discov, Mar. 2009, vol. 8, Issue 3, pp. 235-253.
Begg et al., "Strategies to improve radiotherapy with targeted drugs," Nat Rev Cancer, Apr. 2011, vol. 11, Issue 4, pp. 239-253.
Bellucci et al., "A noncanonical function of sortase enables site-specific conjugation of small molecules to lysine residues in proteins," Angew. Chem. Int. Ed. 54, Jan. 2015, vol. 54, Issue 2, pp. 441-445.
Bellucci et al., "Three-in-One Chromatography-Free Purification, Tag Removal, and Site-Specific Modification of Recombinant Fusion Proteins Using Sortase A and Elastin-like Polypeptides," Angewandte Chemie International Edition, Mar. 2013, vol. 52, Issue 13, pp. 3703-3708.
Bender et al., "Synthesis, Crystallization, and Biological Evaluation of an Orally Active Prodrug of Gemcitabine," J. Med. Chem., Nov. 2009, vol. 52, Issue 22, pp. 6958-6961.
Berisio et al., "Imino Acids and Collagen Triple Helix Stability: Characterization of Collagen-like Polypeptides Containing Hyp-Hyp-Gly Seqeucne Repeats," JACS, 2004, 126: 11402-11403.
Bernacki et al., "Length-dependent aggregation of uninterrupted polyalanine peptides," Biochemistry, Sep. 2011, vol. 50, Issue 43, pp. 9200-9211.
Berndt et al., "Synthetic lipidation of peptides and amino acids: Monolayer structure and properties," J. Am. Chem. Soc., 1995, 117, 9515-9522.
Bessa et al., "Thermoresponsive self-assembled elastin-based nanoparticles for delivery of BMPs," Journal of Controlled Release, Mar. 2010, vol. 142, Issue 3, pp. 312-318.
Best, "Computational and theoretical advances in studies of intrinsically disordered proteins," Curr Opin Struct Biol, Feb. 2017, 42:147-154.
Bhattacharyya et al., "A paclitaxel-loaded recombinant polypeptide nanoparticle outperforms Abraxane in multiple murine cancer models," Nat. Commun., Aug. 2015, Issue 6, Article 7939, 30 pages.
Bhattacharyya et al., "Encapsulating a Hydrophilic Chemotherapeutic into Rod-Like Nanoparticles of a Genetically Encoded Asymmetric Triblock Polypeptide Improves its Efficacy," Advanced functional materials, Mar. 2017, vol. 27, Issue 12, Article 1605421, 9 pages.
Bidwell et al., "Development of elastin-like polypeptide for thermally targeted delivery of doxorubicin," Biochemical Pharmacology, Mar. 2007, vol. 73, Issue 5, pp. 620-631.
Binz et al., "Engineering novel binding proteins from nonimmunoglobulin domains," Nat Biotechnol, 2005, 23(10):1257-68.
Blanco et al., "Principles of nanoparticle design for overcoming biological barriers to drug delivery," Nat Biotechnol, Sep. 2015, 33(9):941-51.
Blasko et al., "Brachytherapy for carcinoma of the prostate: Techniques, patient selection, and clinical outcomes," Seminars in Radiation Oncology, 2002, 12, 81-94.
Blasko et al., "The role of external beam radiotherapy with I-125/Pd-103 brachytherapy for prostate carcinoma," Radiother Oncol, 2000, 57, 273-278.
Blasko et al., "Transperineal percutaneous iodine-125 implantation for prostatic carcinoma using transrectal ultrasound and template guidance," Endocurietherapy/Hyperthermia Oncology, 1987, 3, 131-139.
Bley et al., "Microtubule stabilising agents and ionising radiation: Multiple exploitable mechanisms for combined treatment," Eur J Cancer, Jan. 2013, vol. 49, Issue 1, pp. 245-253.
Bobo et al., "Nanoparticle-based medicines: a review of FDA-approved materials and clinical trials to date." Pharmaceutical research, Oct. 2016, vol. 33, Issue 10, pp. 2373-2387.
Bocci et al., "The pharmacological bases of the antiangiogenic activity of paclitaxel," Angiogenesis, Jul. 2013, vol. 16, Issue 3, pp. 481-492.
Bochicchio et al., "Investigating by CD the molecular mechanism of elasticity of elastomeric proteins," Chirality, Sep. 2008, vol. 20, Issue 9, pp. 985-994.
Boekhorst et al., "Genome-wide detection and analysis of cell wall-bound proteins with LPxTG-like sorting motifs," J. Bacteriol. 187, 2005, 4928-4934.
Boeynaems et al., "Protein Phase Separation: A New Phase in Cell Biology," Trends Cell Biol, Jun. 2018, 28(6):420-435.
Boeynaems et al., "Spontaneous driving forces give rise to protein-RNA condensates with coexisting phases and complex material properties," Proc Natl Acad Sci U S A, 2019, 116:7889-7898.
Boldt, "Use of albumin: an update," Br J. Anaesth., Mar. 2010, vol. 104, Issue 3, pp. 276-284.
Bond, "Exenatide (Byetta) as a novel treatment option for type 2 diabetes mellitus," Proc. (Bayl. Univ. Med. Cent.), Jul. 2006, vol. 19, Issue 3, pp. 281-284.
Bontempo et al., "Streptavidin as a macroinitiator for polymerization: in situ protein-polymer conjugate formation," J. Am. Chem. Soc., 2005, 6508-6509.
Borst et al., "The Therapeutic Antibody LM609 Selectively Inhibits Ligand Binding to Human αVβ3 Integrin via Steric Hindrance," Structure, Nov. 2017, 25(11):1732-1739.e5.
Bowditch et al., "Identification of a novel integrin binding site in fibronectin. Differential utilization by β3 integrins," Journal of Biological Chemistry, 1994, 269(14):10856-10863.
Boyer et al., "Well-Defined Protein-Polymer Conjugates via in Situ RAFT Polymerization," J. Am. Chem. Soc., Jun. 2007, vol. 129, Issue 22, pp. 7145-7154.
Branco et al., "Self-assembling materials for therapeutic delivery," Acta Biomaterialia, Mar. 2009, vol. 5, Issue 3, pp. 817-831.
Brangwynne et al., "Polymer physics of intracellular phase transitions," Nature Physics, Nov. 2015, 11(11):899-904.
Brannon-Peppas et al., "Nanoparticle and targeted systems for cancer therapy," Advanced Drug Delivery Reviews, Elsevier, Sep. 2012, 64(11):206-212.
Broome et al., "Expanding the utility of beta-galactosidase complementation: piece by piece," Mol Pharm, ACS Publications, Feb. 2010, 7(1):60-74.
Broyer et al., "Emerging synthetic approaches for protein-polymer conjugations," Chem. Commun., Feb. 2011, vol. 47, Issue 8, pp. 2212-2226.
Brusa et al., "Antitumor activity and pharmacokinetics of liposomes containing lipophilic gemcitabine prodrugs," Anticancer Res., Jan. 2007, vol. 27, Issue 1A, pp. 195-199.
Burchard, "Light Scattering Techniques," Physical techniques for the study of food biopolymers, 1994, 151-213.

(56) References Cited

OTHER PUBLICATIONS

Burke et al., "Multimodal nanoparticle imaging agents: design and applications," Philos Trans A Math Phys Eng Sci, Nov. 2017, 375:20170261.
Burnouf, "Modern plasma fractionation," Transfus. Med. Rev., Apr. 2007, vol. 21, Issue 2, pp. 101-117.
Buteau et al., "Glucagon-like peptide-1 prevents beta cell glucolipotoxicity," Diabetologia, 2004, 47(5):806-815.
Butler et al., "β-Cell Deficit and Increased β-Cell Apoptosis in Humans With Type 2 Diabetes," Diabetes, 2003, 52(1):102-110.
Cabral et al., "Accumulation of sub-100 nm polymeric micelles in poorly permeable tumours depends on size," Nature Nanotechnology, Oct. 2011, vol. 6, Issue 12, pp. 815-823.
Cabrera et al., "Automated, High-Throughput Assays for Evaluation of Human Pancreatic Islet Function," Cell Transplant, First published Nov. 2007, vol. 16, Issue 10, pp. 1039-1048.
Cabrera et al., "Glutamate Is a Positive Autocrine Signal for Glucagon Release," Cell Metab, Jun. 2008, vol. 7, Issue 6, pp. 545-554.
Cai et al., "Long-acting preparations of exenatide," Drug Des. Devel. Ther., Sep. 2013, vol. 7, pp. 963-970.
Caliceti et al., "Pharmacokinetic and biodistribution properties of poly(ethylene glycol)-protein conjugates," Adv. Drug Deliv. Rev, 2003, 55, 1261-1277.
Callahan et al., "Triple stimulus-responsive polypeptide nanoparticles that enhance intratumoral spatial distribution," Nano Letters, Mar. 2012, vol. 12, Issue 4, pp. 2165-2170.
Camilloni et al., "Determination of secondary structure populations in disordered states of proteins using nuclear magnetic resonance chemical shifts," Biochemistry, Feb. 2012, vol. 51, Issue 11, pp. 2224-2231.
Campbell et al., "Pegylated peptides V. Carboxy-terminal PEGlyted analogs of growth hormone-releasing factor (GRF) display enhanced duration of biological activity in vivo," J. Peptide Res., 1997, 49:527-537.
Cao et al., "Monitoring the effects of anti-angiogenesis on the radiation sensitivity of pancreatic cancer xenografts using dynamic contrast-enhanced computed tomography," Int J Radiation Oncol Biol Phys, Feb. 2014, vol. 88, Issue 2, pp. 412-418.
Cardenes et al., "Locally advanced pancreatic cancer: Current therapeutic approach," The Oncologist, Jun. 2006, vol. 11, Issue 6, pp. 612-623.
Carreiras et al., "Expression and localization of alpha v integrins and their ligand vitronectin in normal ovarian epithelium and in ovarian carcinoma," Gynecol Oncol, 1996, 62(2):260-7.
Carrico et al., "Introducing genetically encoded aldehydes into proteins," Nat Chem Biol, Jun. 2007, vol. 3, Issue 6, pp. 321-322.
Cataldo et al., "Radiation-induced crosslinking of collagen gelatin into a stable hydrogel," Journal of Radioanalytical and Nuclear Chemistry, Sep. 2008, vol. 275, Issue 1, pp. 125-131.
Centers for Disease Control and Prevention, "National Diabetes Statistics Report, 2017," Atlanta, GA: Centers for Disease Control and Prevention, US Department of Health and Human Services; 2017. Reviewed: Feb. 24, 2018.
Ceska et al., "A new and rapid method for the clinical determination of α-amylase activities in human serum and urine. Optimal conditions," Clinica Chimica Acta, 1969, 26, 437-444.
Cha et al., "Microfluidics-assisted fabrication of gelatin-silica core-shell microgels for injectable tissue constructs," Biomacromolecules, 2014, 15: 283-290.
Chakrabartty et al., "Stability of α-Helices," Adv Protein Chem, 1995, 46, 141-176.
Champion et al., "Particle shape: a new design parameter for micro- and nanoscale drug delivery carriers," J Control Release, Elsevier, Aug. 2007, 121(1-2):3-9.
Champion et al., "Role of particle size in phagocytosis of polymeric microspheres," Pharm Res, Srpinger, Mar. 2008, 25(8):1815-21.
Champion et al., "Role of target geometry in phagocytosis," Proc Natl Acad Sci U S A, The National Academy of Sciences of the USA, Mar. 2006, 103(13):4930-4.
Champion et al., "Shape induced inhibition of phagocytosis of polymer particles," Pharm Res, Springer, Jan. 2009, 26(1):244-9.
Chang et al., "Tumor-stroma interaction in orthotopic primary pancreatic cancer xenografts during hedgehog pathway inhibition," Int. J. Cancer, Jul. 2013, vol. 133, Issue 1, pp. 225-235.
Chapin et al., "Rapid microRNA profiling on encoded gel microparticles," Angew Chem Int Ed Engl, 2011, 50: 2289-2293.
Chatterjee et al., "Type 2 diabetes," The Lancet, Jun. 2017, vol. 389, Issue 10085, pp. 2239-2251.
Chaudhury et al., "The major histocompatibility complex-related Fc receptor for IgG (FcRn) binds albumin and prolongs its lifespan," J Exp Med, 2003, 197(3): p. 315-22.
Chen et al., "Anisotropic hydrogels fabricated with directional freezing and radiation-induced polymerization and crosslinking method," Materials Letters, Dec. 2012, vol. 89, pp. 104-107.
Chen et al., "Anti-hypervariable region antibody induced by a defined peptide: An approach for studying the structural correlates of idiotypes," PNAS, 1984, 81:1784-1788.
Chen et al., "Bioinspired Modular Synthesis of Elastin-Mimic Polymers to Probe the Mechanism of Elastin Elasticity," J. Am. Chem. Soc., Mar. 2010, vol. 132, Issue 13, pp. 4577-4579.
Chen et al., "Rheology of Soft Materials," Annual Review of Condensed Matter Physics, May 2010, vol. 1, pp. 301-322.
Chen et al., "Site-specific labeling of cell surface proteins with biophysical probes using biotin ligase," Nat Methods, 2005, 2(2):99-104.
Chen et al., "The use of self-adjuvanting nanofiber vaccines to elicit high-affinity B cell responses to peptide antigens without inflammation," Biomaterials, Nov. 2013, vol. 34, Issue 34, pp. 8776-8785.
Chen, "Small-molecule delivery by nanoparticles for anticancer therapy," Trends Mol Med, Cell Press, Dec. 2010, 16(12):594-602.
Chilkoti et al., "Design of thermally responsive, recombinant polypeptide carriers for targeted drug delivery," Advance Drug Delivery Reviews, 2002, 54:1093-1111.
Chilkoti et al., "Stimulus responsive elastin biopolymers: applications in medicine and biotechnology," Curr Opin Chem Biol, Dec. 2006, vol. 10, Issue 6, pp. 652-657.
Chilkoti et al., "Targeted drug delivery by thermally responsive polymers," Advanced Drug Delivery Reviews, 2002, 54:613-630.
Chin et al., "Addition of p-azido-l-phenylalanine to the genetic code of *Escherichia coli*," Journal of the American Chemical Society, 2002, 124: 9026-9027.
Chithrani et al., "Determining the size and shape dependence of gold nanoparticle uptake into mammalian cells," Nano Lett, Apr. 2006, vol. 6, Issue 4, pp. 662-668.
Chithrani et al., "Elucidating the mechanism of cellular uptake and removal of protein-coated gold nanoparticles of different sizes and shapes," Nano letters, ACS Publications, Jun. 2007, 7(6):1542-1550.
Chitkara et al., "Self-Assembling, Amphiphilic Polymer—Gemcitabine Conjugate Shows Enhanced Antitumor Efficacy Against Human Pancreatic Adenocarcinoma," Bioconjug. Chem., Jun. 2013, vol. 24, Issue 7, pp. 1161-1173.
Cho et al., "Effects of hofmeister anions on the phase transition temperature of elastin-like polypeptides," J. Phys. Chem. B., Nov. 2008, vol. 112, Issue 44, pp. 13765-13771.
Cho et al., "Hydrogen bonding of β-turn structure is stabilized in D(2)O," J Am Chem Soc, Oct. 2009, vol. 131, Issue 42, pp. 15188-15193.
Cho et al., "Therapeutic nanoparticles for drug delivery in cancer," Clin. Cancer Res., Mar. 2008, vol. 14, Issue 5, pp. 1310-1316.
Chockalingam et al., "Design and application of stimulus-responsive peptide systems," Protein Engineering, Design & Selection, Apr. 2007, 20(4):155-161.
Choi et al., "Multiplexed detection of mRNA using porosity-tuned hydrogel microparticles," Anal Chem, 2012, 84: 9370-9378.
Choi et al., "Recent advances in engineering microparticles and their nascent utilization in biomedical delivery and diagnostic applications," Lab Chip, 2017, 17: 591-613.
Choi et al., "Renal Clearance of Nanoparticles," Nature biotechnology, Oct. 2007, vol. 25, Issue 10, pp. 1165-1170.

(56) References Cited

OTHER PUBLICATIONS

Chow et al., "Peptide-based biopolymers in biomedicine and biotechnology," Mater. Sci. Eng. R Reports, Jan. 2008, vol. 62, Issue 4, pp. 125-155.
Chow et al., "Ultra-High Expression of a Thermally Responsive Recombinant Fusion Protein in *E. coli*," Biotechnology Progress, Sep. 2006, vol. 22, Issue 3, pp. 638-646.
Choy et al., "Investigation of taxol as a potential radiation sensitizer," Cancer, 1993, 71, 3774-3778.
Christensen et al., "Fusion order controls expression level and activity of elastin-like polypeptide fusion proteins," Protein Science, Jul. 2009, vol. 18, Issue 7, pp. 1377-1387.
Christensen et al., "Predicting Transition Temperatures of Elastin-Like Polypeptide Fusion Proteins," Biomacromolecules, Mar. 2013, vol. 14, Issue 5, pp. 1514-1519.
Chu et al., "Controllable monodisperse multiple emulsions," Angew Chem Int Ed Engl, 2007, 46:8970-8974.
Cid-Arregui et al., "Perspectives in the treatment of pancreatic adenocarcinoma," World Journal of Gastroenterology, Aug. 2015, vol. 21, Issue 31, pp. 9297-9316.
Ciezki et al., "Brachytherapy or surgery? A composite view," Oncology, Oct. 2009, vol. 23, Issue 11, pp. 960-964.
Cima, "AVMA Guidelines for the Euthanasia of Animal: 2013 Edition," Journal of the American Veterinary Medical Association, Jan. 2013, vol. 242, 102 pages.
Cirulis et al., "Viscoelastic properties and gelation of an elastin-like polypeptide," Journal of Rheology, Sep. 2009, vol. 53, Issue 5, pp. 1215-1228.
Clarke et al., "Tropoelastin massively associates during coacervation to form quantized protein spheres," Biochemistry, Jul. 2006, vol. 45, Issue 33, pp. 9989-9996.
Clavé et al., "Amylase, lipase, pancreatic isoamylase, and phospholipase A in diagnosis of acute pancreatitis," Clinical Chemistry, 1995, 41, 1129-1134.
Coin et al., "Solid-phase peptide synthesis: from standard procedures to the synthesis of difficult sequences," Nat. Protoc., Dec. 2007, vol. 2, Issue 12, 3247-3256.
Colomb et al., "Radiation-Convertible Polymers from Norbornenyl Derivatives. Crosslinking with Ionizing Radiation," Journal of Applied Polymer Science, 1970, 14, 1659-1670.
Conner et al., "Regulated portals of entry into the cell," Nature, 2003, 422(6927):37-44.
Conrad et al., "ELPylated anti-human TNF therapeutic single-domain antibodies for prevention of lethal septic shock," Plant Biotechnology Journal, Jan. 2011, vol. 9, Issue 1, pp. 22-31.
Coskun et al., "Fibroblast Growth Factor 21 Corrects Obesity in Mice," Endocrinology, Dec. 2008, vol. 149, Issue 12, pp. 6018-6027.
Costa et al., "Active Targeting of Cancer Cells by Nanobody Decorated Polypeptide Micelle with Bio-orthogonally Conjugated Drug," Nano letters, Dec. 2018, 19(1):247-254.
Costa et al., "Photo-crosslinkable unnatural amino acids enable facile synthesis of thermoresponsive nano- to microgels of intrinsically disordered polypeptides," Adv Mater, 2018, 30(5): 1704878.
Craik et al., "The future of peptide-based drugs," Chemical biology & drug design 81, Dec. 2013, vol. 81, Issue 1, pp. 136-147.
Cui et al., "Amino acid sequence in constitutionally isomeric tetrapeptide amphiphiles dictates architecture of one-dimensional nanostructures," J. Am. Chem. Soc., Aug. 2014, vol. 136, Issue 35, 12461-12468.
Cui et al., "Self-assembly of peptide amphiphiles: from molecules to nanostructures to biomaterials," Biopolymers, Jan. 2010, vol. 94, Issue 1, pp. 1-18.
Dai et al., "Versatile biomanufacturing through stimulus-responsive cell—material feedback," Nature chemical biology, Sep. 2019, 15(10):1017-1024.
Dalhaimer et al., "Single Molecule Visualization of Stable, Stiffness-Tunable, Flow-Conforming Worm Micelles," Macromolecules, 2003, 36(18):6873-6877.
Dalla Poza et al., "Targeting gemcitabine containing liposomes to CD44 expressing pancreatic adenocarcinoma cells causes an increase in the antitumoral activity," Biochim. Biophys. Acta, May 2013, vol. 1828, Issue 5, pp. 1396-1404.
Darling et al., "Viscoelastic properties of zonal articular chondrocytes measured by atomic force microscopy," Osteoarthritis Cartilage, 2006, 14: 571-579.
Darzynkiewicz et al., "DNA content measurement for DNA ploidy and cell cycle analysis," Current Protocols in Cytometry, 2001, 7.5.1-7.5.24.
Das et al., "Conformations of intrinsically disordered proteins are influenced by linear sequence distributions of oppositely charged residues," Proc Natl Acad Sci U S A, National Academy of Sciences, Aug. 2013, 110(33):13392-13397.
Dasgupta et al., "Isopeptide Ligation Catalyzed by Quintessential Sortase A: Mechanistic Cues From Cyclic and Branched Oligomers of Indolicidin," The Journal of Biological Chemistry, May 2011, vol. 286, No. 27, pp. 23996-24006, Supplemental Information.
Day et al., "A new glucagon and GLP-1 co-agonist eliminates obesity in rodents," Nat Chem Biol, Oct. 2009, 5:749.
De et al., "Temperature-Regulated Activity of Responsive Polymer-Protein Conjugates Prepared by Grafting-from via RAFT Polymerization," J. Am. Chem. Soc. Jul. 2008, 130, 11288-11289.
De Simone et al., "Accurate random coil chemical shifts from an analysis of loop regions in native states of proteins," J Am Chem Soc, Nov. 2009, 131, 16332-16333.
Deer et al., "Phenotype and genotype of pancreatic cancer cell lines," Pancreas, May 2010, 39, 425-435.
Dejana et al., "The role of adherens junctions and VE-cadherin in the control of vascular permeability," J Cell Sci, Jul. 2008, 121, 2115-2122.
Delaglio et al., "NMRPipe: A multidimensional spectral processing system based on UNIX pipes," Journal of Biomolecular NMR 6, 1995, 277-293.
DeLisser et al., "Vascular endothelial platelet endothelial cell adhesion molecule 1(PECAM-1) regulates advanced metastatic progression," PNAS, Oct. 2010, 107, 18616-18621.
Dennis et al., "Albumin binding as a general strategy for improving the pharmacokinetics of proteins," J Biol Chem, 2002, 277(38): p. 35035-43.
Dennis et al., "Co-Translational Myristoylation Alters the Quaternary Structure of HIV-1 Nef in Solution," Proteins: Structure, Function, and Bioinformatics, 2005, 60:658-669.
Depp et al., "Native protein-initiated ATRP: A viable and potentially superior alternative to PEGylation for stabilizing biologics," Acta Biomater. Feb. 2009, 5, 560-569.
Deshayes et al., "Radium 223 dichloride for prostate cancer treatment," Drug Des Devel Ther, Sep. 2017, 11, 2643-2651.
DeYoung et al., "Encapsulation of exenatide in poly-(D,L-lactide-co-glycolide) microspheres produced an investigational long-acting once-weekly formulation for type 2 diabetes," Diabetes Technol Ther, Nov. 2011, 13, 1145-1154.
Diana et al., "Prognostic role and correlation of CA9, CD31, CD68 and CD20 with the desmoplastic stroma in pancreatic ductal adenocarcinoma," Oncotarget, Nov. 2016, 7, 72819-72832.
Diehl et al., "A Good Practice Guide to the Administration of Substances and Removal of Blood Including Routes and Volumes," J Appl Toxicol, 2001, 21, 15-23.
Dignon et al., "Relation between single-molecule properties and phase behavior of intrinsically disordered proteins," Proc Natl Acad Sci U S A, Oct. 2018, 115(40):9929-9934.
Dignon et al., "Sequence determinants of protein phase behavior from a coarse-grained model," PLoS Comput Biol, Jan. 2018, 14(1):e1005941.
Ding et al., "Mechanism for the alpha-helix to beta-hairpin transition," Proteins, 2003, 53, 220-228.
Ding et al., "βKlotho Is Required for Fibroblast Growth Factor 21 Effects on Growth and Metabolism," Cell Metab, Sep. 2012, 16(3):387-393.
Donnelly et al., "DNA Vaccines," Ann. Rev. Immunol., 1997, 15, 617-648.

(56) References Cited

OTHER PUBLICATIONS

Dreher et al., "Evaluation of an elastin-like polypeptide-doxorubicin conjugate for cancer therapy," J. of Controlled Release, 2003, 91:31-43.
Dreher et al., "Temperature triggered self-assembly of polypeptides into multivalent spherical micelles," J. Am. Chem. Soc. Jan. 2008, 130, 687-694.
Dreher et al., "Thermal cycling enhances the accumulation of a temperature-sensitive biopolymer in solid tumors," Cancer Res, May 2007, 67, 4418-4424.
Dreher, M. R. Ph.D. Thesis, Duke University, Durham, NC, Apr. 2006.
Dreis et al., "Preparation, Characterisation and Maintenance of Drug Efficacy of Doxorubicin-Loaded Human Serum Albumin (HSA) Nanoparticles," Int. J. Pharm., Aug. 2007, 341, 207-214.
Drucker "Mechanisms of Action and Therapeutic Application of Glucagon-like Peptide-1," Cell Metab, Apr. 2018, 27(4):740-756.
Drucker et al., "The incretin system: glucagon-like peptide-1 receptor agonists and dipeptidyl peptidase-4 inhibitors in type 2 diabetes," Lancet 368, Nov. 2006, 1696-1705.
Drucker, "Glucagon-like peptides," Diabetes 47, 1998, 159-169.
Drucker, "Incretin action in the pancreas: potential promise, possible perils, and pathological pitfalls," Diabetes, Oct. 2013, 62, 3316-3323.
Du et al., "Endoscope-assisted brachytherapy for pancreatic cancer: From tumor killing to pain relief and drainage," Journal of interventional gastroenterology, Jan. 2011, 1, 23-27.
Du et al., "Tailor-made dual pH-sensitive polymer-doxorubicin nanoparticles for efficient anticancer drug delivery," J. Am. Chem. Soc., Oct. 2011, 133, 17560-17563.
Duan et al., "Fibronectin type III domain based monobody with high activity," Biochemistry, Oct. 2007 46(44):12656-12664.
Duan et al., "Improving the thermostability and catalytic efficiency of Bacillus deramificans pullulanase by site-directed mutagenesis," Appl Environ Microbiol, American Society for Microbiology, Jul. 2013, 79(13):4072-4077.
Dubey et al., "Development and evaluation of folate functionalized albumin nanoparticles for targeted delivery of gemcitabine," Int J Pharm., Aug. 2015, 492(1-2):80-91.
Ducreux et al., "Radiation plus docetaxel and cisplatin in locally advanced pancreatic carcinoma: A non-comparative randomized phase II trial," Digestive and Liver Disease, Oct. 2014, 46, 950-955.
Duke University, "Gemcitabine/Nab-Paclitaxel With HIGRT in Resectable Pancreatic Cancer," Clinical Trial NCT02318095 <https://clinicaltrials.gov/ct2/show/NCT02318095> Webpage accessed Jan. 11, 2017.
Duncan, "The dawning era of polymer therapeutics," Nature Reviews Drug Discovery, 2003, 2, 347-360.
Duncan, R. "Polymer conjugates as anticancer nanomedicines," Nat. Rev. Cancer, Sep. 2006, 6, 688-701.
Duronio et al., "Protein N-myristoylation in *Escherichia coli*: Reconstitution of a eukaryotic protein modification in bacteria," Proc. Natl. Acad. Sci. USA, 1990, vol. 87, pp. 1506-1510.
Dyrberg et al., "Peptide as Atigens," J. Exp. Med., 1986, 164:1344-1349.
Dzuricky et al., "Avidity and Cell Uptake of Integrin Targeting Polypeptide Micelles is Strongly Shape Dependent," Nano letters, Sep. 2019, 19(9):6124-6132.
Dzuricky et al., "The Convergence of Artificial Protein Polymers and Intrinsically Disordered Proteins," Biochemistry, May 2018, 57(17):2405-2414.
Egan et al., "The Insulinotropic Effect of Acute Exendin-4 Administered to Humans: Comparison of Nondiabetic State to Type 2 Diabetes," The Journal of Clinical Endocrinology & Metabolism, 2002, 87, 1282-1290.
Ehlerding et al., "Biodegradable and Renal Clearable Inorganic Nanoparticles," Adv Sci (Weinh), Feb. 2016, 3(2):1500223.
Eisenhaber et al., "Prediction of lipid posttranslational modifications and localization signals from protein sequences: Big-II, NMT and PTS1," Nucleic Acids Res., 2003, 31, 3631-3634.
Eisenhauer et al., "New response evaluation criteria in solid tumours: Revised Recist guideline (version 1.1)," Eur J Cancer, Jan. 2009, 45(2):228-247.
El-Assaad et al., "Saturated Fatty Acids Synergize with Elevated Glucose to Cause Pancreatic β-Cell Death," Endocrinology, 2003, 144(9):4154-4163.
Elbaum-Garfinkle et al., "The disordered P granule protein LAF-1 drives phase separation into droplets with tunable viscosity and dynamics," Proc Natl Acad Sci U S A, Jun. 2015, 112(23):7189-7194.
Ellis, "Macromolecular crowding: obvious but underappreciated," Trends Biochem. Sci., 2001, 26 (10), 597-604.
Elsabahy et al., "Design of polymeric nanoparticles for biomedical delivery applications," Chem Soc Rev, Royal Society of Chemistry, Apr. 2012, 41(7):2545-61.
Elvin et al., "Synthesis and properties of crosslinked recombinant pro-resilin," Nature, 2005, 437(7061):999-1002.
Elzoghby et al., "Implications of Protein- and Peptide-Based Nanoparticles as Potential Vehicles for Anticancer Drugs," Advances in Protein Chemistry and Structural Biology, Academic Press, Elsevier, Mar. 2015, Chapter Six, vol. 98, pp. 169-221.
Engin et al., "Thermoradiotherapy in the management of superficial malignant tumors," Clinical Cancer Research, 1995, 1, 139-145.
Erickson-Miller et al., "Differential toxicity of camptothecin, topotecan and 9-aminocamptothecin to human, canine, and murine myeloid progenitors (CFU-GM) in vitro," Cancer Chemother. Pharmacol., 1997, 39 (5), 467-472.
Etrych et al., "HPMA Copolymer Conjugates of Paclitaxe; and Docetaxel with pH-Controlled Drug Release," Molecular Pharmaceutics, Jun. 2010, 7(4):1015-1026.
Falk et al., "Hyperthermia in oncology," Int J Hyperthermia, 2001, 17, 1-18.
Farazi et al., "Structures of *Saccharomyces cerevisiae* N-myristoyltransferase with bound myristoylCoA and peptide provide insights about substrate recognition and catalysis," Biochemistry, 2001, 40, 6335-6343.
Farmer et al., "Conformational behavior of chemically reactive alanine-rich repetitive protein polymers," Biomacromolecules, 2005, 6, 1531-1539.
Farokhzad et al., "Targeted nanoparticle-aptamer bioconjugates for cancer chemotherapy in vivo," Proc Natl Acad Sci U S A, The National Academy of Sciences of the USA, Apr. 2006, 103(16):6315-20.
Feng et al., "Protein resistant surfaces: comparison of acrylate graft polymers bearing oligo-ethylene oxide and phosphorylcholine side chains," Biointerphases, Mar. 2006, 1 (1), 50.
Fernandez-Colino et al., "Amphiphilic Elastin-Like Block Co-Recombinamers Containing Leucine Zippers: Cooperative Interplay between Both Domains Results in Injectable and Stable Hydrogels," Biomacromolecules, Sep. 2015, 16, 3389-3398.
Finan et al., "A rationally designed monomeric peptide triagonist corrects obesity and diabetes in rodents," Nat Med, Jan. 2015, 21:27-36.
Finan et al., "Unimolecular Dual Incretins Maximize Metabolic Benefits in Rodents, Monkeys, and Humans," Sci Transl Med, Oct. 2013, 5(209):209ra151.
Fluegel et al., "Chain stiffness of elastin-like polypeptides," Biomacromolecules, Oct. 2010, 11, 3216-3218.
Fosgerau et al., "Peptide therapeutics: current status and future directions," Drug Discovery Today, Jan. 2015, 20, 122-128.
Franzmann et al., "Phase separation of a yeast prion protein promotes cellular fitness," Science, Jan. 2018, 359(6371):eaao5654.
Free et al., "A Phase 1, multi-center, randomized, double-blind, placebo controlled study to evaluate the safety/tolerability, pharmacokinetic and hemodynamic response following single ascending subcutaneous doses of PB1046 (Vasomera) in subjects with essential hypertension," Circulation, Mar. 2018, 130:A19112.
Friedman et al., "Directed Evolution to Low Nanomolar Affinity of a Tumor-Targeting Epidermal Growth Factor Receptor-Binding Affibody Molecule," J. Mol. Biol., Mar. 2008, 376, 1388-1402.
Frilling et al., "Recommendations for management of patients with neuroendocrine liver metastases," The lancet oncology, Jan. 2014, 15, e8-21.

(56) References Cited

OTHER PUBLICATIONS

Fu et al., "Nanoparticle Albumin—Bond (NAB) Technology is a Promising Method for Anti-Cancer Drug Delivery," Recent Patents on Anti-Cancer Drug Discovery, Nov. 2009. 4(3):262-272.
Fujiwara et al., "Modulating effect of the PI3-kinase inhibitor LY294002 on cisplatin in human pancreatic cancer cells," Journal of Experimental & Clinical Cancer Research, Nov. 2008, 27, 76.
Furgeson et al., "Structural optimization of a "smart" doxorubicin-polypeptide conjugate for thermally targeted delivery to solid tumors," Journal of Controlled Release, Jan. 2006, 110:362-369.
Furumoto et al., "Effect of coupling of albumin onto surface of PEG liposome on its in vivo disposition," International Journal of Pharmaceutics, Mar. 2007, 329(1-2): p. 110-116.
Gaberc-Porekar et al., "Obstacles and pitfalls in the PEGylation of therapeutic proteins," Curr. Opin. Drug Discov. Devel. 11, Mar. 2008, 242-250.
Gabizon et al., "Prolonged circulation time and enhanced accumulation in malignant exudates of doxorubicin encapsulated in polyethylene-glycol coated liposomes," Cancer Res., Feb. 1994, 54, 987-992.
Gaich et al., "The Effects of LY2405319, an FGF21 Analog, in Obese Human Subjects with Type 2 Diabetes," Cell Metab, Sep. 2013, 18(3):333-340.
Ganson et al., "Control of hyperuricemia in subjects with refractory gout, and induction of antibody against poly(ethylene glycol) (PEG), in a phase I trial of subcutaneous PEGylated urate oxidase," Arthritis Res. Ther. 8, Feb. 2006, R12-R22.
Ganson et al., "Pre-existing anti-polyethylene glycol antibody linked to first-exposure allergic reactions to pegnivacogin, a PEGylated RNA aptamer," J Allergy Clin Immunol, May 2016, 137(5): 1610-1613, e1617.
Gao et al., "In situ growth of a PEG-like polymer from the C terminus of an intein fusion protein improves pharmacokinetics and tumor accumulation" PNAS Early Edition, Jul. 2010, vol. 107, 1-6.
Gao et al., "In situ growth of a PEG-like polymer from the C terminus of an intein fusion protein improves pharmacokinetics and tumor accumulation," Proc. Natl. Acad. Sci., Sep. 2010, 107(38):16432-16437.
Gao et al., "In situ growth of a stoichiometric PEG-like conjugate at a protein's N-terminus with significantly improved pharmacokinetics," Proc. Natl. Acad. Sci., Sep. 2009, 15231-15236.
Gao, "Site-specific and in situ growth of stealth polymer conjugates of proteins with significally improved pharmacology," Journal of Controlled Release, Nov. 2013, 172(1):e116-e117.
Garanger et al., "Structural Evolution of a Stimulus-Responsive Diblock Polypeptide Micelle by Temperature Tunable Compaction of its Core," Macromolecules, Sep. 2015, 48, 6617-6627.
Garay et al., "Antibodies against polyethylene glycol in healthy subjects and in patients treated with PEG-conjugated agents," Expert Opinion. Drug Deliv. 9, Nov. 2012, 1319-1323.
Garcia Quiroz et al., "Syntax of Phase Transition Peptide Polymers with LCST and UCST Behavior," Jan. 1, 2013, Retrieved from the Internet: URL:https://dukespace.lib.duke.edu/dspace/bitstream/handle/10161/7256/GarciaQuirozduke0066D 11972.pdf?sequence=I &isAllowed=y.
Gauthier et al., "Peptide/protein-polymer conjugates: synthetic strategies and design concepts," Chem. Commun., Jul. 2008, 2591-2611.
Ge et al., "Self-Cleavable Stimulus Responsive Tags for Protein Purification without Chromatography" J. Am. Chem. Soc., 2005, 127: 11228-11229.
Genbank Accession NM_001182082.1 (Mar. 2017).
Geng et al., Shape effects of filaments versus spherical particles in flow and drug delivery, Nat Nanotechnol, Nature Research, Apr. 2007, 2(4):249-55.
Ghoorchian et al., "Molecular architecture influences the thermally induced aggregation behavior of elastin-like polypeptides," Biomacromolecules, Oct. 2011, 12, 4022-4029.
Gianni et al., "Nonlinear pharmacokinetics and metabolism of paclitaxel and its pharmacokinetic/pharmacodynamic relationships in humans," J. Clin. Oncol., 1995, 13 (1), 180-190.
Giberti et al., "Radical retropubic prostatectomy versus brachytherapy for low-risk prostatic cancer: a prospective study," World J Urol, Oct. 2009, 27, 607-612.
Gibson et al., "Enzymatic assembly of DNA molecules up to several hundred kilobases," Nat Methods, May 2009, 6, 343-345.
Gilbreth et al., "Structural insights for engineering binding proteins based on non-antibody scaffolds," Curr Opin Struct Biol, Elsevier, Jun. 2012, 22(4):413-20.
Gillies et al., "Dendrimers and dendritic polymers in drug delivery," Drug Discovery Today, 2005, 10(1):35-43.
Gilroy et al., "Fusion of fibroblast growth factor 21 to a thermally responsive biopolymer forms an injectable depot with sustained anti-diabetic action," J Control Release, May 2018, 277:154-164.
Glassman et al., "Toughening of Thermoresponsive Arrested Networks of Elastin-Like Polypeptides to Engineer Cytocompatible Tissue Scaffolds," Biomacromolecules, Feb. 2016, 17, 415-426.
Gluck et al., "Single Vector System for Efficient N-myristoylation of Recombinant Proteins in *E. coli*," Plos One, Apr. 2010, 5(4) e100881.
Göke et al., "Exendin-4 is a high potency agonis and truncated exendin-(9-39)-amide an antagonist at the glucagon-like peptide 1-(7-36)-amide receptor of insulin-secreting b-cells," J. Biol. Chem. 268, 1993, 19650-19655.
Goldsmith et al., "Enzyme engineering: reaching the maximal catalytic efficiency peak," Curr Opin Struct Biol, Dec. 2017, 47:140-150.
Gordon et al., "Protein N-myristoylation," J. Biol. Chem., 1991, 266, 8647-8650.
Gosline et al., "Elastic proteins: biological roles and mechanical properties," Philos Trans R Soc Lond B Biol Sci, 2002, 357, 121-132.
Gottlieb et al., "NMR chemical shifts of common laboratory solvents as trace impurities," J. Org. Chem., 1997, 62, 7512-7515.
Goutelle et al., "The Hill equation: a review of its capabilities in pharmacological modelling. Fundam," Clin. Pharmacol. 22, Dec. 2008, 633-648.
Graff et al., "Theoretical analysis of antibody targeting of tumor spheroids: importance of dosage for penetration, and affinity for retention," Cancer Research, 2003, 63(6):1288-1296.
Gratton et al., "The effect of particle design on cellular internalization pathways," Proc Natl Acad Sci U S A, The National Academy of Sciences of the USA, Aug. 2008, 105(33):11613-8.
Greco et al., "The search for synergy: a critical review from a response surface perspective," Pharmacological Reviews, 1995, 24, 331-385.
Green et al., "Abraxane®, a novel Cremophor®-free, albumin-bound particle form of paclitaxel for the treatment of advanced non-small-cell lung cancer," Annals of Oncology, Aug. 2006, 17, 1263-1268.
Green et al., "Novel dipeptidyl peptidase IV resistant analogues of glucagon-like peptide-1(7-36)amide have preserved biological activities in vitro conferring improved glucose-lowering action in vivo" J. of Mol. Endocrin., 2003, 31(3): 529-540.
Greenfield, "Using circular dichroism spectra to estimate protein secondary structure," Nat. Protoc., Dec. 2006, 1(6):2876-90.
Griffin et al., "Accelerated wound healing by injectable microporous gel scaffolds assembled from annealed building blocks," Nat Mater, 2015, 14: 737-744.
Grimm et al., "Advances in Brachytherapy," Reviews in Urology, 2004, 6, S37-S48.
Grover et al., "Protein-Polymer Conjugates: Synthetic Approaches by Controlled Radical Polymerizations & Interesting Applications", Curr Opin Chem Bioi., Dec. 2010; 14(6): 818-827.
Gu et al., "Enzymatic Synthesis of Nucleobase-Modified Single-Stranded DNA Offers Turnable Resistance to Nuclease Degradation," Biomacromolecules, Jul. 2018, 19, 3525-3535.
Gu et al., "Photocontrolled micellar aggregation of amphiphilic DNA-azobenzene conjugates," Colloids Surfaces B: Biointerfaces, Nov. 2015, 135, 126-132.
Gu et al., "Precise engineering of targeted nanoparticles by using self-assembled biointegrated block copolymers," Proc Natl Acad Sci U S A, The National Academy of Sciences of the USA, Feb. 2008, 105(7):2586-91.

(56) References Cited

OTHER PUBLICATIONS

Güngör et al., "Pancreatic cancer," British Journal of Pharmacology, Jan. 2014, 171, 849-858.
Guo et al., "Nanoparticles escaping RES and endosome: challenges for siRNA delivery for cancer therapy," J. Nanomaterials, Aug. 2011, 2011: 1-12.
Gustafsson, "Nonlinear structured-illumination microscopy: wide-field fluorescence imaging with theoretically unlimited resolution," Proc Natl Acad Sci U S A, 2005, 102, 13081-13086.
Gustafsson, "Surpassing the lateral resolution limit by a factor of two using structured illumination microscopy," Short Communication. Journal of Microscopy, 2000, 198, 82-87.
Guzman et al., "Leiodermatolide, a novel marine natural product, has potent cytotoxic and antimitotic activity against cancer cells, appears to affect microtubule dynamics, and exhibits antitumor activity," Int. J. Cancer, Nov. 2016, 139, 2116-2126.
Ha et al., "Immunoglobulin Fc Heterodimer Platform Technology: From Design to Applications in Therapeutic Antibodies and Proteins," Front Immunol, Oct. 2016, 7(394) (in English).
Haider et al., "Genetically engineered polymers: Status and prospects for controlled release," J. Control. Release, 2004, 95, 1-26.
Halozyme Therapeutics, "PEGPH20 Plus Nab-Paclitaxel Plus Gemcitabine Compared With Nab-Paclitaxel Plus Gemcitabine in Subjects With Stage IV Untreated Pancreatic Cancer (HALO-109-202)," Clinical Trial NCT01839487 <https://clinicaltrials.gov/ct2/show/study/NCT01839487> Accessed May 29, 2018.
Hamada et al., "Novel therapeutic strategies targeting tumor-stromal interactions in pancreatic cancer," Frontiers in Physiology, Nov. 2013, vol. 4, Article 331, 7 pages.
Hamidi et al., "Pharmacokinetic Consequences of Pegylation," Drug Deliv., Dec. 2006, 13, 399-409.
Hamley, "Self-assembly of amphiphilic peptides," Soft Matter, Feb. 2011, 7, 4122.
Hampp et al., "Use of Antidiabetic Drugs in the U.S., 2003-2012," Diabetes Care, May 2014, 37:1367-1374.
Han et al., "Survival of patients with advanced pancreatic cancer after iodine $^{125}$ seeds implantation brachytherapy: A meta-analysis," Medicine, Feb. 2017, 96, e5719.
Harmon et al., "A Model for Hysteresis Observed in Phase Transitions of Thermally Responsive Intrinsically Disordered Protein Polymers," Biophysical Journal, Feb. 2017, 112(3):207a.
Harries et al., "Nanoparticle Albumin-Bound Paclitaxel for Metastatic Breast Cancer," J. Clin. Oncol., 2005, 23(31):7768-7771.
Harris et al., "Pegylation," Clinical Pharmacokinetics, 2001, 40(7):539-551.
Hart et al., "Attenuation of FGF signalling in mouse β-cells leads to diabetes," Nature, 2000, 408:864.
Hartgerink et al., "Self-assembly and mineralization of peptide-amphiphile nanofibers," Science, 2001, 294, 1684-8.
Hassouneh et al., "Elastin-like Polypeptide Diblock Copolymers Self-Assemble into Weak Micelles," Macromolecules, Jun. 2015, 48, 4183-4195.
Hassouneh et al., "Elastin-Like Polypeptides as a Purification Tag for Recombinant Proteins," Curr Protoc Protein Sci., Aug. 2010, Chapter 6. Unit 6.11. 10.1002/0471140864.ps0611s61.
Hassouneh et al., "Fusions of elastin-like polypeptides to pharmaceutical proteins," Methods Enzymol., Jan. 2012, 502, 215-37.
Hassouneh et al., "Unexpected Multivalent Display of Proteins by Temperature Triggered Self-assembly of Elastin-like Polypeptide Block Copolymers," Biomacromolecules, Apr. 2012, vol. 13, Issue 4, pp. 1598-1605.
Hathout et al., "Analysis of seed loss and pulmonary seed migration in patients treated with virtual needle guidance and robotic seed delivery," American journal of clinical oncology, Oct. 2011, 34, 449-453.
He et al., "Comparative genomics of elastin: Sequence analysis of a highly repetitive protein," Matrix Biology, Sep. 2007, 26:524-540.
He et al., "Improving protein resistance of α-Al2O3 membranes by modification with POEGMA brushes," Applied Surface Science, Nov. 2011, 258(3):1038-1044.
Heagerty et al., Biometrics, "Time-dependent ROC curves for censored survival data and a diagnostic marker," Jun. 2000, 56(2):337-44.
Heal et al., "N-Myristoyl transferase-mediated protein labelling in vivo," Org. Biomol. Chem., Aug. 2008, 6(13):2308-2315.
Heal et al., "Site-specific N-terminal labelling of proteins in vitro and in vivo using N-myristoyl transferase and bioorthogonal ligation chemistry," Chem. Commun., Jan. 2008, 3, 480-482.
Heredia et al., "In Situ Preparation of Protein-"Smart" Polymer Conjugates with Retention of Bioactivity," J. Am. Chem. Soc. Jan. 2006, 127, 16955-16960.
Herrero-Vanrell et al., "Self-assembled particles of an elastin-like polymer as vehicles for controlled drug release," J Control Release, 2005, 102, 113-122.
Hershfield et al., "Induced and pre-existing anti-polyethylene glycol antibody in a trial of every 3-week dosing of pegloticase for refractory gout, including in organ transplant recipients," Arthritis Res. Ther. 16, Mar. 2014, R63.
Hidalgo, "Pancreatic Cancer," N Engl J Med, Apr. 2010, 362, 1605-1617.
Hingorani et al., "Phase lb Study of PEGylated Recombinant Human Hyaluronidase and Gemcitabine in Patients with Advanced Pancreatic Cancer," Clinical Cancer Research, Jun. 2016, 22, 2848-2854.
Ho et al., "Chemoenzymatic Labeling of Proteins for Imaging in Bacterial Cells," J. Am. Chem. Soc., Nov. 2016, 138(46):15098-15101.
Ho et al., "Internal radiation therapy for patients with primary or metastatic hepatic cancer: a review," Cancer, 1998, 83, 1894-1907.
Hober et al., "Protein A chromatography for antibody purification," Journal of Chromatography B 848, Mar. 2007, pp. 40-47.
Hochkoeppler, "Expanding the landscape of recombinant protein production in *Escherichia coli*," Biotechnol. Lett., Dec. 2013, 35, 1971-1981.
Hofmann et al., "A kinetic study on the enzymatic hydrolysis of fluoresceindiacetate and fluorescein-di-β-D-galactopyranoside," Analytical biochemistry, 1983, 131(1):180-186.
Holehouse et al., "CIDER: Classification of Intrinsically Disordered Ensemble Regions," Biophysical Journal, Feb. 2015, vol. 108, Issue 2, Supplement 1, p. 228a.
Holehouse et al., "Functional Implications of Intracellular Phase Transitions," Biochemistry, May 2018, 57(17):2415-2423.
Holm et al., "Transperineal $^{125}$iodine seed implantation in prostatic cancer guided by transrectal ultrasonography," The Journal of urology, 2002, 167, 985-988.
Hopp et al., "The effects of affinity and valency of an albumin-binding domain (ABD) on the half-life of a single-chain diabody-ABD fusion protein," Protein Engineering Design and Selection, Sep. 2010, 23(11): p. 827-834.
Hortobágyi, "Anthracyclines in the Treatment of Cancer," Drugs, 1997, vol. 54, No. 4, pp. 1-7.
Howell et al., "The MIRD Perspective 1999," J Nucl Med, 1999, 40, 3S-10S.
Hruby et al., "New bioerodable thermoresponsive polymers for possible radiotherapeutic applications," Journal of Controlled Release, May 2007, 119, 25-33.
Hruby et al., "Thermoresponsive polymeric radionuclide delivery system—an injectable brachytherapy," Eur J Pharm Sci., Feb. 2011, 42, 484-488.
Hrycushko et al., "Direct intratumoral infusion of liposome encapsulated rhenium radionuclides for cancer therapy: effects of non-uniform intratumoral dose distribution," Med Phys, Mar. 2011, 38, 1339-1347.
Hu et al., "Design of tumor-homing and pH-responsive polypeptide-doxorubicin nanoparticles with enhanced anticancer efficacy and reduced side effects," Chemical Communications, Jun. 2015, 51, 11405-11408.
Hu et al., "Nanografting De Novo Proteins onto Gold Surfaces," Langmuir, 2005, vol. 21:9103-9109.
Huang et al., "Photodynamic Therapy Synergizes with Irinotecan to Overcome Compensatory Mechanisms and Improve Treatment Outcomes in Pancreatic Cancer," Cancer Research, Mar. 2016, 76, 1066-1077.

(56) References Cited

OTHER PUBLICATIONS

Huber et al., "Designer amphiphilic proteins as building blocks for the intracellular formation of organelle-like compartments," Nat Mater, Jan. 2015, 14(1):125-132.
Huotari et al., "Endosome maturation," EMBO J, Aug. 2011, 30 (17), 3481-3500.
Hutter et al., "Calibration of atomic-force microscope tips," Review of Scientific Instruments, 1993, 64: 1868-1873.
Hwang et al., "Caprolactonic poloxamer analog: PEG-PCL-PEG," Biomacromolecules, 2005, 6, 885-890.
Hwang et al., "Differentially degradable janus particles for controlled release applications," Macromol Rapid Commun, 2012, 33: 1178-1183.
Hwang et al., "Gene therapy for primary and metastatic pancreatic cancer with intraperitoneal retroviral vector bearing the wild-type p53 gene," Surgery, 1998, 124, 143-151.
Ibrahim et al., "Phase I and pharmacokinetic study of ABI-007, a Cremophor-free, protein-stabilized, nanoparticle formulation of paclitaxel," Clin. Cancer Res., 2002, 8 (5), 1038-1044.
Ilangovan et al., "Structure of sortase, the transpeptidase that anchors proteins to the cell wall of *Staphylococcus aureus*," Proc. Natl. Acad. Sci. 98, 2001, 6056-6061.
Inostroza-Brito et al., "Co-assembly, spatiotemporal control and morphogenesis of a hybrid protein-peptide system," Nat. Chem., Nov. 2015, 7, 1-8.
Ishida et al., "Accelerated blood clearance (ABC) phenomenon upon repeated injection of PEGylated liposomes," International Journal of Pharmaceutics, May 2008, 354(1-2):56-62.
Ito et al., "Impaired negative feedback suppression of bile acid synthesis in mice lacking βKlotho," J Clin Invest, 2005, 115(8):2202-2208.
Ito et al., "In vivo antitumor effect of the mTOR inhibitor CCI-779 and gemcitabine in xenograft models of human pancreatic cancer," International Journal of Cancer, May 2006, 118, 2337-2343.
Jacob et al., "Human phagocytes employ the myeloperoxidase-hydrogen peroxide system to synthesize dityrosine, trityrosine, pulcherosine, and isodityrosine by a tyrosyl radical-dependent pathway," J. Biol. Chem., 1996, 271, 19950-19956.
Jain, "Barriers to Drug-Delivery in Solid Tumors," Sci Am, 1994, 271, 58-65.
Jakubowski et al., "Activators regenerated by electron transfer for atom-transfer radical polymerization of (meth)acrylates and related block copolymers," Angew. Chem. Int. Ed., Jun. 2006, 4482-4486.
Janes et al., "Chitosan nanoparticles as delivery systems for doxorubicin," J. Control Release, 2001, 73, 255-267.
Jang et al., "Engineering Globular Protein Vesicles through Tunable Self-Assembly of Recombinant Fusion Proteins," Small, 2017, 13(36): 1700399.
Jenkins et al., In vivo monitoring of tumor relapse and metastasis using bioluminescent PC-3M-luc-C6 cells in murine models of human prostate cancer. Clinical & Experimental Metastasis, 2003, 20, 745-756.
Ji et al., "RGD-conjugated albumin nanoparticles as a novel delivery vehicle in pancreatic cancer therapy," Cancer Biology & Therapy, Feb. 2012, 13, 206-215.
Jia et al., "Preparation, physicochemical characterization and cytotoxicity in vitro of gemcitabine-loaded PEG-PDLLA nanovesicles," World J. Gastroenterol., Feb. 2010, 16(8):1008-1013.
Jiang et al., "Nanoparticle-mediated cellular response is size-dependent," Nat Nanotechnol, Nature Research, Mar. 2008, 3(3):145-50.
Jiang et al., "The internal structure of self-assembled peptide amphiphiles nanofibers," Soft Matter, Feb. 2007, 3, 454.
Jin et al., "Protein-resistant polyurethane prepared by surface-initiated atom transfer radical graft polymerization (ATRgP) of water-soluble polymers: effects of main chain and side chain lengths of grafts," Colloids and surfaces. B, Biointerfaces, Apr. 2009, 70 (1), 53-9.
Johansson et al., "Structure, Specificity, and Mode of Interaction for Bacterial Albumin-binding Modules," J. Biol. Chem. 2002, 277 (10), 8114-8120.
Johansson et al., "The GA module, a mobile albumin-binding bacterial domain, adopts a three-helix-bundle structure," FEBS Lett, 1995, 374(2): 257-261.
Johnson et al., "Fibroblast Growth Factor 21 Reduces the Severity of Cerulein-Induced Pancreatitis in Mice," Gastroenterology, Nov. 2009, 137(5):1795-1804.
Jokerst et al., "Nanoparticle PEGylation for imaging and therapy," Nanomedicine (Lond), Future Medicine, Jun. 2011, 6(4):715-28.
Jonsson et al., "Engineering of a femtomolar affinity binding protein to human serum albumin," Protein Engineering Design and Selection, Aug. 2008, 21(8): 515-527.
Junutula et al., "Site-specific conjugation of a cytotoxic drug to an antibody improves the therapeutic index," Nat Biotechnol, Aug. 2008, 26(8):925-932.
Jurney et al., "Unique size and shape-dependent uptake behaviors of non-spherical nanoparticles by endothelial cells due to a shearing flow," J Control Release, Jan. 2017, 245:170-176.
Kaighn et al., "Establishment and characterization of a human prostatic carcinoma cell line (PC-3)," Investigative urology, 1979, 17, 16-23.
Kaitin et al., "Pharmaceutical innovation in the 21st century: new drug approvals in the first decade, 2000-2009," Clin Pharmacol Ther, Feb. 2011, 89, 183-188.
Kamaly et al., "Targeted polymeric therapeutic nanoparticles: design, development and clinical translation," Chem Soc Rev, Royal Society of Chemistry, Apr. 2012, 41(7):2971-3010.
Kamisawa et al., "Pancreatic cancer," Lancet, Jul. 2016, 388, 73-85.
Kanoski et al., "The role of nausea in food intake and body weight suppression by peripheral GLP-1 receptor agonists, exendin-4 and liraglutide," Neuropharmacology 62, Apr. 2012, 1916-1927.
Kanyama et al., "Usefulness of Repeated Direct Intratumoral Gene Transfer Using Hemagglutinating Virus of Japan-Liposome Method for Cytosine Deaminase Suicide Gene Therapy," Cancer Research, 2001, 61, 14-18.
Karagoz et al., "Polymerization-Induced Self-Assembly (PISA)—control over the morphology of nanoparticles for drug delivery applications," Polym. Chem., Jan. 2014, 5(2):350-355.
Karamanolis et al., "Increased expression of VEGF and CD31 in postradiation rectal tissue: implications for radiation proctitis," Mediators Inflamm, May 2013, 515048.
Karperien, A. FracLac for Image J, version 2.5 <http://rsb.info.nih.gov/ij/plugins/fraclac/FLHelp/Introduction.htm> 1999-2012.
Kaspar et al., "Future directions for peptide therapeutics development," Drug Discovery Today, Sep. 2013, 18, 807-817.
Katakura, "Nuclear Data Sheets for A = 125," Nuclear Data Sheets, Mar. 2011, 112, 495-705.
Kataoka et al., "Block copolymer micelles for drug delivery: Design, characterization and biological significance," Advanced Drug Delivery Reviews, 2001, 47:113-131.
Kato et al., "Acidic extracellular microenvironment and cancer," Cancer Cell Int, Sep. 2013, 13, 89, 8 pages.
Katti et al., "Amino acid repeat patterns in protein sequences: Their diversity and structural-functional implications," Protein Science, 2000, 9: 1203-1209.
Keefe et al., "Poly(zwitterionic)protein conjugates offer increased stability without sacrificing binding affinity or bioactivity," Nat Chem, Jan. 2012, 4(1):59-63.
Keller et al., "Empirical Statistical Model to Estimate the Accuracy of Peptide Identifications Made by MS/MS and Database Search," Anal. Chem. 2002, 74, 5383-5392.
Kelly et al., "How to study proteins by circular dichroism," Biochim. Byophys. Acta—Proteins Proteomics, 2005, 1751(2):119-39.
Kelly et al., "Shape-specific, monodisperse nano-molding of protein particles," J Am Chem Soc, ACS Publications, Apr. 2008, 130(16):5438-9.
Kesharwani et al., "Dendrimer as nanocarrier for drug delivery," Progress in Polymer Science, Feb. 2014, 39(2):268-307.
Keten et al., "Nanoconfinement controls stiffness, strength and mechanical toughness of β-sheet crystals in silk," Nat Mater, Mar. 2010, 9, 359-367.

(56) References Cited

OTHER PUBLICATIONS

Khademhosseini et al., "Micromolding of photocrosslinkable hyaluronic acid for cell encapsulation and entrapment," J Biomed Mater Res A, 2006, 79: 522-532.
Khandare et al., "Polymer-drug conjugates: Progress in polymeric drugs," Prog. Polym. Sci., 2005, vol. 31, pp. 359-397.
Khanna et al., "The dog as a cancer model," Nat. Biotechnol., Sep. 2006, 24, 1065-1066.
Kharitonenkov et al., "FGF-21 as a novel metabolic regulator," J Clin Invest, 2005, 115(6):1627-1635.
Kharitonenkov et al., "FGF21 Revolutions: Recent Advances Illuminating FGF21 Biology and Medicinal Properties," Trends Endocrinol Metab, Nov. 2015, 26(11):608-617.
Kharitonenkov et al., "Fibroblast growth factor 21 night watch: advances and uncertainties in the field," J Intern Med, Nov. 2016, 281(3):233-246.
Kharitonenkov et al., "Inventing new medicines: The FGF21 story," Mol Metab, Jun. 2014, 3(3):221-229.
Khazov et al., "Nuclear Data Sheets for A = 131," Nuclear Data Sheets, 2006, 107, 2715-2930.
Khoo et al., "Activation of mitogen-activating protein kinase by glucose is not required for insulin secretion," Proc Natl Acad Sci USA, 1997, 94(11):5599-5604.
Khoo et al., "Regulation of Insulin Gene Transcription by ERK1 and ERK2 in Pancreatic β Cells," J Biol Chem, 2003, 278(35):32969-32977.
Kim et al., "Effects of Once-Weekly Dosing of a Long-Acting Release Formulation of Exenatide on Glucose Control and Body Weight in Subjects With Type 2 Diabetes," Diabetes Care, Jun. 2007, 30, 1487-93.
Kim et al., "Generation of core-shell microcapsules with three-dimensional focusing device for efficient formation of cell spheroid," Lab Chip, 2011, 11: 246-252.
Kim et al., "Recombinant elastin-mimetic biomaterials: Emerging applications in medicine," Adv Drug Deliv Rev, Dec. 2010, 62, 1468-1478.
Kim et al., "Site-Specific PEGylated Exendin-4 Modified with a High Molecular Weight Trimeric PEG Reduces Steric Hindrance and Increases Type 2 Antidiabetic Therapeutic Effects," Bioconjugate Chem., Nov. 2012, 23, 2214-2220.
Kim et al., "Ultrasensitive Carbon nanotube-based biosensors using antibody-binding fragments," Analytical Biochemistry, Jul. 2008, 381, 193-198.
Knop et al., "Poly(ethylene glycol) in Drug Delivery: Pros and Cons as Well as Potential Alternatives," Angewandte Chemie International Edition, Aug. 2010, 49(36):6288-6308.
Knudsen, "Glucagon-like Peptide-1: The Basis of a New Class of Treatment for Type 2 Diabetes" J. Med. Chem, 2004, 47: 4128-4134.
Kobashigawa et al., "Attachment of an NMR-Invisible Solubility Enhancement Tag Using A Sortase-Mediated Protein Ligation Method," J Biomol NMR. Mar. 2009, vol. 43, No. 3; pp. 145-150.
Kobayashi et al., "Summary of recombinant human serum albumin development," Biologicals, Mar. 2006, 34(1): 55-59.
Koehler et al., "Albumin affinity tags increase peptide half-life in vivo," Bioorganic & Medicinal Chemistry Letters, 2002, 12(20): 2883-2886.
Kontos et al., "Drug development: longer-lived proteins," Chemical Society Reviews, Feb. 2012, 41(7):2686-2695.
Koong et al., "Phase II study to assess the efficacy of conventionally fractionated radiotherapy followed by a stereotactic radiosurgery boost in patients with locally advanced pancreatic cancer," Int J Radiation Oncol Biol Phys, 2005, 63, 320-323.
Kothare et al., "Pharmacokinetics, pharmacodynamics, tolerability, and safety of exenatide in Japanese patients with type 2 diabetes mellitus," J. Clin. Pharmacol. 48, Jan. 2009, 1389-1399.
Kowalczyk et al., "Elastin-like Polypeptides as a Promising Family of Genetically-Engineered Protein Based Polymers," World Journal of Microbiology and Biotechnology, Springer, Apr. 2014, 30(8):2141-2152.
Kramer et al., "Quantitative Side-Chain Modifications of Methionine-Containing Elastin-Like Polypeptides as a Versatile Tool to Tune Their Properties," ACS Macro Lett., Nov. 2015, 4(11):1283-1286.
Kraulis et al., "The serum albumin-binding domain of streptococcal protein G is a three-helical bundle: a heteronuclear NMR study," FEBS letters, 1996, 378(2): p. 190-194.
Krause et al., "Structure and function of claudins," Biochmica et Biophysica Acta, Mar. 2008, 1778, 631-645.
Krempien et al., "Neoadjuvant chemoradiation in patients with pancreatic adenocarcinoma," HPB (Oxford), Feb. 2006, 8(1):22-28.
Kruger et al., "Analysis of the Substrate Specificity of the *Staphylococcus aureus* Sortase Transpeptidase SrtA†," Biochemistry, 2004, 43, 1541-1551.
Kulkarni et al., "Bioorthogonal Chemoenzymatic Functionalization of Calmodulin for Bioconjugation Applications," Bioconjug. Chem., Oct. 2015, 26(10):2153-2160.
Kulkarni et al., "Design of lipid nanoparticles for in vitro and in vivo delivery of plasmid DNA," Nanomedicine, May 2017, 13(4):1377-1387.
Kulkarni et al., "Selective functionalization of the protein N terminus with N-myristoyl transferase for bioconjugation in cell lysate," ChemBioChem, Oct. 2013, 14, 1958-1962.
Kumar et al., "N-Terminal Region of the Catalytic Domain of Human N-Myristoyltransferase 1 Acts as an Inhibitory Module," PLoS One, May 2015, 10(5):e0127661.
Kupelian et al., "Radical prostatectomy, external beam radiotherapy <72 Gy, external beam radiotherapy > or =72 Gy, permanent seed implantation, or combined seeds/external beam radiotherapy for stage T1-T2 prostate cancer," International journal of radiation oncology, biology, physics, 2004, 58, 25-33.
Kurosu et al., "Tissue-specific Expression of βKlotho and Fibroblast Growth Factor (FGF) Receptor Isoforms Determines Metabolic Activity of FGF19 and FGF21," J Biol Chem, Sep. 2007, 282(37):26687-26695.
Kyte et al., "A Simple Method for Displaying the Hydropathic Character of a Protein," J. Mol. Biol., 1982, 157:105-132.
Labelle et al., "Vascular endothelial cadherin promotes breast cancer progression via transforming growth factor β signaling," Cancer Res, Mar. 2008, 68, 1388-1397.
Lacroix et al., "Elucidating the folding problem of alpha-helices: local motifs, long-range electrostatics, ionic-strength dependence and prediction of NMR parameters," J Mol Biol, 1998, 284, 173-191.
Langer et al., "Designing materials for biology and medicine," Nature, 2004, 428, 487-92.
Laybutt et al., "Endoplasmic reticulum stress contributes to beta cell apoptosis in type 2 diabetes," Diabetologia, Apr. 2007, 50(4):752-763.
Le Droumaguet et al., "Recent advances in the design of bioconjugates from controlled/living radical polymerization," Polym. Chem. Jan. 2010, 1, 563-598.
Le Meins et al., "Hybrid polymer/lipid vesicles: State of the art and future perspectives," Mater. Today, Oct. 2013, 16, 397-402.
Leader et al., "Protein therapeutics: a summary and pharmacological classification," Nat. Rev. Drug Discov. 7, Jan. 2008, 21-39.
Lee et al., "Atomistic molecular dynamics simulations of peptide amphiphile self-assembly into cylindrical nanofibers," J. Am. Chem. Soc., Feb. 2011, 133, 3677-3683.
Lee et al., "Immunohistochemical analysis of claudin expression in pancreatic cystic tumors," Oncology Reports, Apr. 2011, 25(4): 971-978.
Lee et al., "In vivo bioluminescent imaging of irradiated orthotopic pancreatic cancer xenografts in nonobese diabetic-severe combined immunodeficient mice: a novel method for targeting and assaying efficacy of ionizing radiation," Transl. Oncol., Jun. 2010, 3, 153-159.
Lee et al., "Mechanical properties of cross-linked syntheti elastomeric polypentapeptides," Macromolecules, 2001, 34, 5968-5974.
Lee et al., "Nanoparticle-Delivered Chemotherapy: Old Drugs in New Packages." Oncology (Williston Park, NY) 31.3 (Mar. 2017): 198-208.
Lee et al., "Phase transition and elasticity of protein-based hydrogels," J. Biomater. Sci. Polymer Edn, 2001, 12, 229-242.

(56) References Cited

OTHER PUBLICATIONS

Lee et al., "Polymersomes for drug delivery: design, formation and characterization," J Control Release, Elsevier, Jul. 2012, 161(2):473-83.
Lee et al., "Structures of β-klotho reveal a 'zip code'-like mechanism for endocrine FGF signaling," Nature, Jan. 2018, 553:501-505.
Lee et al., "Theranostic nanoparticles with controlled release of gemcitabine for targeted therapy and MRI of pancreatic cancer," ACS Nano, Mar. 2013, 7(3):2078-2089.
Leibowitz et al., "Glucose-Regulated Proinsulin Gene Expression Is Required for Adequate Insulin Production during Chronic Glucose Exposure," Endocrinology, 2002, 143(9):3214-3220.
Lele et al., "Synthesis of uniform protein-polymer conjugates," Biomacromolecules 6, 2005, 3380-3387.
Lennen et al., "Membrane Stresses Induced by Overproduction of Free Fatty Acids in *Escherichia coli*," Appl Environ Microb., Nov. 2011, 77(22):8114-28.
Leung et al., "Bio-Click Chemistry: Enzymatic Functionalization of PEGylated Capsules for Targeting Applications**," Angew. Chem. Int. Ed. Jul. 2012, 51, 7132-7136.
LeVine et al., "Thioflavine T interaction with synthetic Alzheimer's disease beta-amyloid peptides: detection of amyloid aggregation in solution," Protein Sci., 1993, 2, 404-10.
Levy et al., "Novel Exenatide Analogs with Peptidic Albumin Binding Domains: Potent Anti-Diabetic Agents with Extended Duration of Action," PLoS ONE, Feb. 2014, 9(2): e87704, 9 pages.
Lewis et al., "Use of digitized video microscopy with a fluorogenic enzyme substrate to demonstrate cell-and compartment-specific gene expression in *Salmonella enteritidis* and Bacillus subtilis," Molecular microbiology, 1994, 13:655-662.
Li et al., "Elastin is an essential determinant of arterial morphogenesis," Nature, 1998, 393, 276-280.
Li et al., "FGF21 Is Not a Major Mediator for Bone Homeostasis or Metabolic Actions of PPARα and PPARγ Agonists," J Bone Miner Res, Apr. 2017, 32(4):834-845.
Li et al., "Molecular description of the LCST behavior of an elastin-like polypeptide," Biomacromolecules, Aug. 2014, 15, 3522-3530.
Li et al., "Nanoparticles Evading the Reticuloendothelial System: Role of the Supported Bilayer," Biochim. Biophys. Acta, Oct. 2009, 1788 (10), 2259-2266.
Li et al., "Pancreatic cancer," Lancet, 2004, 363, 1049-1057.
Li et al., "Phase transitions in the assembly of multivalent signalling proteins," Nature, Nature Research, Mar. 2012, 483(7389):336-340.
Li et al., "Prediction of solvent-induced morphological changes of polyelectrolyte diblock copolymer micelles," Soft Matter, Nov. 2015, 11(42): 8236-45.
Li et al., "Protein adsorption on oligo(ethylene glycol)-terminated alkanethiolate self-assembled monolayers: The molecular basis for nonfouling behavior," The journal of physical chemistry. B, 2005, 109 (7), 2934-41.
Li et al., "Temperature-Triggered Phase Separation of a Hydrophilic Resilin-Like Polypeptide," Macramol. Rapid Commun., Jan. 2015, 36(1):90-95.
Li et al., "Tunable Assembly of Protein-Microdomains in Living Vertebrate Embryos," Advanced Biosystems, Oct. 2018, 2(10):1800112.
Liao et al., "Removal of N-terminal methionine from recombinant proteins by engineered *E. coli* methionine aminopeptidase," Prot. Sci. 13, 2004, 1802-1810.
Liechty et al., "Polymers for Drug Delivery Systems," Annual review of chemical and biomolecular engineering, Aug. 2010, 1:149-173.
Lillie et al., "The viscoelastic basis for the tensile strength of elastin," Int J Biol Macromol, 2002, 30, 119-127.
Lim et al., "Improved Non-Chromatographic Purification of a Recombinant Protein by Cationic Elastin-like Polypeptides" Biomacromolecules, May 2007, 8(5): 1417-1424.
Lim et al., "In situ cross-linking of elastin-like polypeptide block copolymers for tissue repair," Biomacromolecules, Feb. 2008, 9, 222-230.
Lim et al., "In vivo post-translational modifications of recombinant mussel adhesive protein in insect cells," Biotechnol. Prog., Sep.-Oct. 2011, 27(5):1390-1396.
Lin et al., "Adiponectin Mediates the Metabolic Effects of FGF21 on Glucose Homeostasis and Insulin Sensitivity in Mice," Cell Metab, May 2013, 17(5):779-789.
Lin et al., "Formation and Maturation of Phase-Separated Liquid Droplets by RNA-Binding Proteins," Mol Cell, Oct. 2015, 60(2):208-219.
Lin et al., "Functional expression of a biologically active fragment of soluble gp130 as an ELP-fusion protein in transgenic plants: purification via inverse transition cycling," Biochem J, Sep. 2006, 398(3):577-583.
Lin et al., "Intrinsically disordered sequences enable modulation of protein phase separation through distributed tyrosine motifs," J Biol Chem, Nov. 2017, 292(46): 19110-19120.
Lin et al., "Phase Separation and Single-Chain Compactness of Charged Disordered Proteins are Strongly Correlated," Biophys J, May 2017, 112(10):2043-2046.
Lin et al., "Sequence-Specific Polyampholyte Phase Separation in Membraneless Organelles," Phys Rev Lett, Oct. 2016, 117(17):178101.
Lin et al., "Statistical properties of the traditional algorithm-based designs for phase I cancer clinical trials," Biostatistics, 2001, 2(2):203-215.
Lin et al., "Utility of immunohistochemistry in the pancreatobiliary tract," Arch Pathol Lab Med, Jan. 2015, 139, 24-38.
Linder et al., "Lipid Modifications of G Protein Subunits," J. Biol. Chem., 1991, 266(7):4654-4659.
Ling et al., "Protein thioester synthesis enabled by sortase," J. Am Chem Soc, Jul. 2012, 134(26):10749-10752.
Liong et al., "Multifunctional inorganic nanoparticles for imaging, targeting, and drug delivery," ACS Nano, ACS Publications, May 2008, 2(5):889-96.
Litiere et al., "Recist—learning from the past to build the future," Nat Rev Clin Oncol, Mar. 2017, 14, 187-192.
Liu et al., "Brachytherapy using injectable seeds that are self-assembled from genetically encoded polypeptides in situ," Cancer Res, Nov. 2012, 72, 5956-5965.
Liu et al., "Hydrophobic modifications of cationic polymers for gene delivery," Prog. In Polym. Sci., Sep. 2010, 35, 1144-1162.
Liu et al., "In Situ Formation of Protein-Polymer Conjugates through Reversible Addition Fragmentation Chain Transfer Polymerization**," Angew. Chem. Int. Ed. Apr. 2007, 46, 3099-3103.
Liu et al., "Injectable intratumoral depot of thermally responsive polypeptide-radionuclide conjugates delays tumor progression in a mouse model," J. Control Release, May 2010, 144(1):2-9.
Liu et al., "Integrin $\alpha_v\beta_3$—Targeted Cancer Therapy," Drug Dev Res, Wiley, Sep. 2008, 69(6):329-339.
Liu et al., "Tracking the in vivo fate of recombinant polypeptides by isotopic labeling," Journal of Controlled Release, Sep. 2006, 114, 184-192.
Liu et al., "Tumor accumulation, degradation and pharmacokinetics of elastin-like polypeptides in nude mice," Journal of Controlled Release, Nov. 2006, 116, 170-178.
Liu, L. et al., "Monodisperse core-shell chitosan microcapsules for pH-responsive burst release of hydrophobic drugs," Soft Matter, 2011, 7: 4821-4827.
Livingstone, "Theoretical property predictions. Curr Top Med Chem Field Full Journal Title: Current topics in medicinal chemistry," Curr. Top. Med. Chem. 2003, 3, 1171-1192.
Loh et al., "Utilising inorganic nanocarriers for gene delivery," Biomater Sci, Jan. 2016, 4(1):70-86.
LoPresti et al., "Polymersomes: nature inspired nanometer sized compartments," Journal of Materials Chemistry, RSC Publishing, Jun. 2009, 19(22):3576-3590.
Lovshin et al., "Incretin-based therapies for type 2 diabetes mellitus," Nat. Rev. Endocrinol. 5, Jun. 2009, 262-269.
Ludden, "Nonlinear pharmacokinetics: clinical Implications," Clin. Pharmacokinet., 1991, 20 (6), 429-446.

(56) References Cited

OTHER PUBLICATIONS

Luginbuhl et al., "One-week glucose control via zero-order release kinetics from an injectable depot of glucagon-like peptide-1 fused to a thermosensitive biopolymer," Nat. Biomed. Eng. 1, Jun. 2017, Article No. 0078.
Luginbuhl et al., "Recombinant Synthesis of Hybrid Lipid-Peptide Polymer Fusions that Self-Assemble and Encapsulate Hydrophobic Drugs," Angew Chem Int Ed Engl., Nov. 2017, 56(45):13979-13984.
Lukyanov et al., "Micelles From Lipid Derivatives of Water-Soluble Polymers as Delivery Systems for Poorly Soluble Drugs," Adv. Drug Deliver. Rev., 2004, 56(9):1273-1289.
Lukyanov et al., "Tumor-targeted liposomes: doxorubicin-loaded long-circulating liposomes modified with anti-cancer antibody," J Control Release, 2004, 100(1):135-44.
Lund et al., "Phase II study of gemcitabine (2',2'-difluorodeoxycytidine) in previously treated ovarian cancer patients," J. Natl. Cancer. Inst. 1994, 86(20):1530-1533.
Luo et al., "Noncovalent Modulation of the Inverse Temperature Transition and Self-Assembly of Elastin-b-Collagen-like Peptide Bioconjugates," J Am Chem Soc, Dec. 2015, 137, 15362-15365.
Lutz et al., "About the Phase Transitions in Aqueous Solutions of Thermoresponsive Copolymers and Hydrogels Based on 2-(2-methoxyethoxy)ethyl Methacrylate and Oligo(ethylene glycol) Methacrylate," Macromolecules, Mar. 2007, 40, 2503-2508.
Lutz et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules, Jan. 2006, 39, 893-896.
Lyons et al., "Comparisons of Recombinant Resilin-like Proteins: Repetitive Domains are Sufficient to Confer Resilin-like Properties," Biomacromolecules, ACS Publications, Oct. 2009, 10(11):3009-3014.
Lyons et al., "Design and facile production of recombinant resilin-like polypeptides: Gene construction and a rapid protein purification method," Protein Engineering Design & Selection, Oxford university Press, Jan. 2007, 20(1):25-32.
Ma et al., "Core-shell hydrogel microcapsules for improved islets encapsulation," Adv Healthc Mater, 2013, 2: 667-672.
Ma et al., "Non-fouling" oligo(ethylene glycol)-functionalized polymer brushes synthesized by surface-initiated atom transfer radical polymerization, Advanced Materials 2004, 16 (4), 338.
Ma et al., "Protein-resistant polymer coatings on silicon oxide by surface-initiated atom transfer radical polymerization," Langmuir: the ACS journal of surfaces and colloids, Mar. 2006, 22 (8), 3751-6.
Ma et al., "Surface-Initiated Atom Transfer Radical Polymerization of Oligo(ethylene glycol) Methyl Methacrylate from a Mixed Self-Assembled Monolayer on Gold," Advanced Functional Materials, Mar. 2006, 16 (5), 640-648.
MacEwan et al., "Applications of elastin-like polypeptides in drug delivery," Journal of Controlled Release, Sep. 2014, 190: p. 314-330.
MacEwan et al., "Controlled apoptosis by a thermally toggled nanoscale amplifier of cellular uptake," Nano Letters, Apr. 2014, 14, 2058-2064.
MacEwan et al., "Digital switching of local arginine density in a genetically encoded self-assembled polypeptide nanoparticle controls cellular uptake," Nano Lett., Jun. 2012, 12, 3322-3328.
MacEwan et al., "Elastin-like polypeptides: Biomedical applications of tunable biopolymers," Biopolymers, Jan. 2010, 94, 60-77.
MacEwan et al., "Non-chromatographic Purification of Recombinant Elastin-like Polypeptides and their Fusions with Peptides and Proteins from *Escherichia coli*," Jun. 2014, 88, p. e51583.
MacEwan et al., "Phase Behavior and Self-Assembly of Perfectly Sequence-Defined and Monodisperse Multiblock Copolypeptides," Biomacromolecules, Jan. 2017, 18(2):599-609.
Mack et al., "Antiobesity action of peripheral exenatide (exendin-4) in rodents: effects on food intake, body weight, metabolic status and side-effect measures," Int. J. Obes. 30, Sep. 2006, 1332-1340.
MacKay et al., "Self-assembling chimeric polypeptide-doxorubicin conjugate nanoparticles the abolish tumors after single injection," Nat Mater, Dec. 2009, 8(12):993-999.
Maeda et al., "Tumor vascular permeability and the EPR effect in macromolecular therapeutics: a review," J. Control. Release, Mar. 2000, 65(1-2)271-284.
Maeda et al., "Tumoritropic and lymphotropic principles of macromolecular drugs," Critical reviews in therapeutic drug carrier systems, 1989, 6(3):193-210.
Maeda, "The enhanced permeability and retention (EPR) effect in tumor vasculature: the key role of tumor-selective macromolecular drug targeting," Advances in Enzyme Regulation, 2001, 41(1):189-207.
Magnusson et al., "In Situ Growth of Side-Chain PEG Polymers from Functionalized Human Growth Hormone-A New Technique for Preparation of Enhanced Protein-Polymer Conjugates," Bioconjugate Chem. 21, Mar. 2010, 671-678.
Magnusson et al., "Ion-Sensitive "Isothermal" Responsive Polymers Prepared in Water," Journal of the American Chemical Society, Aug. 2008, 130, 10852-10853.
Maitra et al., "Pancreatic Cancer," Annu Rev Pathol Mech Dis, Feb. 2008, 3, 157-188.
Malam et al., "Liposomes and nanoparticles: nanosized vehicles for drug delivery in cancer," Trends Pharmacol Sci, Cell Press, Nov. 2009, 30(11):592-9.
Malik et al., "Recent advances in protein and peptide drug delivery systems," Curr. Drug Deliv. 2, Apr. 2007, 141-151.
Manders et al., "Dynamics of three-dimensional replication patterns during the S-phase, analysed by double labelling of DNA and confocal microscopy," Journal of cell science, 1992, 103(Pt 3):857-862.
Mann et al., "Proteomic analysis of post-translational modifications," Nat. Biotechnol., 2003, 21, 255-61.
Manzoor et al., "Overcoming limitations in nanoparticle drug delivery: triggered, intravascular release to improve drug penetration into tumors," Cancer Res, Nov. 2012, 72, 5566-5575.
Mao et al., "DNA repair by nonhomologous end joining and homologous recombination during cell cycle in human cells," Cell cycle, Sep. 2008, 7, 2902-2906.
Mao et al., "Net charge per residue modulates conformational ensembles of intrinsically disordered proteins," Proc Natl Acad Sci U S A, 2010, 107(18):8183-8188.
Mao et al., "Sortase-mediated protein ligation: a new method for protein engineering," J. Am. Chem. Soc., 2004, 126(9):2670-2671.
Maraffini et al., "Sortases and the art of anchoring proteins to the envelopes of Gram-positive bacteria," Microbiol Mol Biol Rev, Mar. 2006, 70(1):192-221.
Mariam et al., "Albumin corona on nanoparticles—a strategic approach in drug delivery," Drug Deliv., Oct. 2016, 23 (8), 2668-2676.
Marr et al., "Effect of Temperature on the Composition of Fatty Acids in *Escherichia Coli*," J Bacteriol., 1962, 84(6):1260-7.
Marten et al., "A randomized multicentre phase II trial comparing adjuvant therapy in patients with interferon alpha-2b and 5-FU alone or in combination with either external radiation treatment and cisplatin (CapRI) or radiation alone regarding event-free survival—CapRI-2," BMC Cancer, Feb. 2009, 9, 1-8.
Maskarinec et al., "Protein engineering approaches to biomaterials design," Curr. Opin. Biotechnol., 2005, 16, 422-426.
Masood, "Polymeric nanoparticles for targeted drug delivery system for cancer therapy," Mater Sci Eng C Mater Biol Appl, Mar. 2016, 60:569-578.
Massey et al., "Self-Assembly of a Novel Organometallic-Inorganic Block Copolymer in Solution and the Solid State: Nonintrusive Observation of Novel Wormlike Poly(ferrocenyldimethylsilane)-b-Poly(dimethylsiloxane) Micelles," J. Am. Chem. Soc. 1998, 120(37):9533-9540.
Mastria et al., "Doxorubicin-conjugated polypeptide nanoparticles inhibit metastasis in two murine models of carcinoma," J Control Release, Jun. 2015, 208:52-8.
Mastria et al., "Nanoparticle formulation improves doxorubicin efficacy by enhancing host antitumor immunity," J Control Release, Jan. 2018, 269:364-373.

(56) References Cited

OTHER PUBLICATIONS

Matsumura et al., "A new concept for macromolecular therapeutics in cancer chemotherapy: mechanism of tumoritropic accumulation of proteins and the antitumor agent smancs," Cancer Res. 1986, 46, 6387-6392.
Matsumura, "Cancer stromal targeting (CAST) therapy," Advanced Drug Delivery Reviews, Jun. 2012, 64, 710-719.
Matsunaga et al., "Molding cell beads for rapid construction of macroscopic 3D tissue architecture," Adv Mater, 2011, 23: H90-94.
Matthews et al., "Pharmacodynamics, Pharmacokinetics, Safety, and Tolerability of Albiglutide, a Long-Acting Glucagon-Like Peptide-1 Mimetic, in Patients with Type 2 Diabetes," J Clin Endocrinol Metab, Dec. 2008, 93(12):4810-4817.
Matyjaszewski et al., "Atom transfer radical polymerization," Chem. Rev. 101, Sep. 2001, 2921-2990.
Matyjaszewski et al., "Macromolecular engineering by atom transfer radical polymerization," J. Am. Chem. Soc. 136, 2014, 6513-6533.
Maurer-Stroh et al., "N-terminal N-myristoylation of proteins: prediction of substrate proteins from amino acid sequence" J Mol Biol., 2002, 317(4):541-557.
Maurer-Stroh et al., "N-terminal N-myristoylation of proteins: Refinement of the sequence motif and its taxon-specific differences," J Mol Biol., 2002, 317(4):523-540.
Mayo et al., "Cell Adhesion Promoting Peptide GVKGDKGNPGWPGAP from the Collagen Type IV Triple Helix: Cis/Trans Proline-Induced Multiple 1H NMR Conformations and Evidence for a KG/PG Multiple Turn Repeat Motif in the All-Trans proline State," Biochemistry, 1991, 30: 8251-8267.
McConkey et al., "Molecular Characterization of Pancreatic Cancer Cell Lines," Pancreatic Cancer, Jan. 2010, 457-469.
McDaniel et al., "A unified model for de novo design of elastin-like polypeptides with tunable inverse transition temperatures," Biomacromolecules, Aug. 2013, 14(8):2866-2872.
McDaniel et al., "Actively targeting solid tumours with thermoresponsive drug delivery systems that respond to mild hyperthermia," Int J Hyperthermia, Aug. 2013, 29, 501-510.
McDaniel et al., "Doxorubicin-conjugated chimeric polypeptide nanoparticles that respond to mild hyperthermia," Control. Release, May 2012, 159 (3), 362-367.
McDaniel et al., "Drug delivery to solid tumors by elastin-like polypeptides," Adc. Drug Deliver. Rev., Dec. 2010, 62(15):1456-1467.
McDaniel et al., "Noncanonical Self-Assembly of Highly Asymmetric Genetically Encoded Polypeptide Amphiphiles into Cylindrical Micelles," Nano Lett., Sep. 2014, 14(11):6590-6598.
McDaniel et al., "Rational design of "heat seeking" drug loaded polypeptide nanoparticles that thermally target solid tumors," Nano Letters, Apr. 2014, 14, 2890-2895.
McDaniel et al., "Recursive Directional Ligation by Plasmid Reconstruction Allows Rapid and Seamless Cloning of Oligomeric Genes," Biomacromolecules, Feb. 2010, 11(4):944-952.
McDaniel et al., "Self-assembly of thermally responsive nanoparticles of a genetically encoded peptide polymer by drug conjugation," Chem. Int. Ed. Feb. 2013, 52, 1683-1687.
McDaniel, "Assembly of Highly Asymmetric Genetically-Encoded Amphiphiles for Thermally Targeted Delivery of Therapeutics," Dissertation, 2013, 295 pages, Published Mar. 1, 2014.
McHale et al., "Synthesis and in vitro evaluation of enzymatically cross-linked elastin-like polypeptide gels for cartilaginous tissue repair," Tissue Eng., 2005, 11, 1768-1779.
McIlhinney et al., "Characterization of a polyhistidine-tagged form of human myristoyl-CoA: protein N-myristoyltransferase produced in *Escherichia coli*," European Journal of Biochemistry, 1994, 222(1):137-146.
McKenzie et al., "Multivalent Binding of a Ligand-Coated Particle: Role of Shape, Size, and Ligand Heterogeneity," Biophys J, Apr. 2018, 114(8):1830-1846.
Meier et al., "Determination of Optimal Sample Size for Quantification of β-Cell Area, Amyloid Area and β-Cell Apoptosis in Isolated Islets," J Histochem Cytochem, Aug. 2015, 63(8):663-673.
Mejuch et al., "Synthesis of lipidated proteins," Bioconjug. Chem. 27, Jul. 2016, 1771-1783.
Meng et al., "Stimuli-responsive polymersomes for programmed drug delivery," Biomacromolecules, ACS Publications, Feb. 2009, 10(2):197-209.
Merkel et al., "Using mechanobiological mimicry of red blood cells to extend circulation times of hydrogel microparticles," Proc Natl Acad Sci U S A, The National Academy of Sciences of the USA, Jan. 2011, 108(2):586-91.
Mero et al., "Transglutaminase-mediated PEGylation of proteins: direct identification of the sites protein medification by mass spectrometry using a novel monodisperse PEG," Bioconjug Chem, Feb. 2009, 20(2):384-389.
Merriam Webster Dictionary, "Plurality," <https://www.merriam-webster.com/dictionary/plurality> webpage accessed Jun. 25, 2020.
Merrick et al., "Seed fixity in the prostate/periprostatic region following brachytherapy," International journal of radiation oncology, biology, physics, 2000, 46, 215-220.
Meyer et al., "Drug targeting using thermally responsive polymers and local hyperthermia," Journal of Controlled Release, 2001, 74, 213-224.
Meyer et al., "Genetically Encoded Synthesis of Protein-Based Polymers with Precisely Specified Molecular Weight and Sequence by Recursive Directional Ligation: Examples from the Elastin-like Polypeptide System," Biomacromolecules, 2002, 3:357-367.
Meyer et al., "Purification of recombinant proteins by fusion with thermally-responsive polypeptide," Nat. Biotechnol., 1999, 17(11):1112-1115.
Meyer et al., "Quantification of the effects of chain length and concentration on the thermal behavior of elastin-like polypeptides," Biomacromolecules, 2004, 5(3):846-51.
Meyer et al., "Targeting a Genetically Engineered Elastin-Like Polypeptide to Solid Tumors by Local Hyperthermia," Cancer Res., 2001, 61(4):1548-1554.
Miao et al., "Sequence and domain arrangements influence mechanical properties of elastin-like polymeric elastomers," Biopolymers, Jun. 2013, 99, 392-407.
Miao et al., "Structural determinants of cross-linking and hydrophobic domains for self-assembly of elastin-like polypeptides," Biochemistry, 2005, 44, 14367-14375.
Michl et al., "Current concepts and novel targets in advanced pancreatic cancer," Gut, Jan. 2013, 62, 317-326.
Micsonai et al. "Accurate secondary structure prediction and fold recognition for circular dichroism spectroscopy," Proc Natl Acad Sci U S A, Jun. 2015, 112, E3095-3103.
Milenic et al., "Antibody-targeted radiation cancer therapy," Nature Reviews Drug Discovery, 2004, 3, 488-498.
Miller et al., "Solubilized, Spaced Polyalanines: A Context-Free System for Determining Amino Acid α-Helix Propensities," Journal of the American Chemical Society, 2002, 124, 945-962.
Mitragotri et al., "Physical approaches to biomaterial design," J. Nat Mater, Nature Publishing Group, Jan. 2009, 8(1):15-23.
Miyata et al., "Polymeric micelles for nano-scale drug delivery," Reaction & Functional Polymers, Mar. 2011, 71, 227-234.
Mjelle et al., "Cell cycle regulation of human DNA repair and chromatin remodeling genes," DNA Repair, Jun. 2015, 30, 53-67.
Modery et al., "Heteromultivalent liposomal nanoconstructs for enhanced targeting and shear-stable binding to active platelets for site-selective vascular drug delivery," Biomaterials, Elsevier, Dec. 2011, 32(35):9504-9514.
Molliex et al., "Phase separation by low complexity domains promotes stress granule assembly and drives pathological fibrillization," Cell, Sep. 2015, 163(1):123-133.
Moosmann et al., "Alpha complementation of LacZ in mammalian cells," Nucleic Acids Res, 1996, 24(6):1171-1172.
Morgan et al., "The combination of epidermal growth factor receptor inhibitors with gemcitabine and radiation in pancreatic cancer," Clin Cancer Res, Aug. 2008, 14, 5142-5149.
Mosbach et al., "Formation of proinsulin by immobilized Bacillus subtilis," Nature, 1983, 302, 543-545.

(56) References Cited

OTHER PUBLICATIONS

Mozhdehi et al., "Genetically Encoded Cholesterol-Modified Polypeptides," Journal of the American Chemical Society, Jan. 2019, 141(2):945-951.
Mozhdehi et al., "Genetically encoded lipid—polypeptide hybrid biomaterials that exhibit temperature-triggered hierarchical self-assembly," Nature chemistry, May 2018, 10(5):496-505.
Mu et al., "FGF21 Analogs of Sustained Action Enabled by Orthogonal Biosynthesis Demonstrate Enhanced Antidiabetic Pharmacology in Rodents," Diabetes, Feb. 2012, 61(2):505-512.
Muiznieks et al., "Modulated growth, stability and interactions of liquid-like coacervate assemblies of elastin," Matrix Biology 36, Jun. 2014, pp. 39-50.
Muiznieks et al., "Proline periodicity modulates the self-assembly properties of elastin-like polypeptides," J Biol Chem, The American Society for Biochemistry and Molecular Biology, Inc, Dec. 2010, 285(51):39779-39789.
Muiznieks et al., "Structural changes and facilitated association of tropoelastin," Archives of Biochemistry and Biophysics, 2003, 410, 317-323.
Muñoz et al., "Elucidating the folding problem of helical peptides using empirical parameters," Nature Structural Biology, 1994, 1, 399-409.
Muñoz et al., "Elucidating the Folding Problem of Helical Peptides using Empirical Parameters. II†. Helix Macrodipole Effects and Rational Modification of the Helical Content of Natural Peptides," Journal of Molecular Biology, 1995, 245, 275-296.
Muñoz et al., "Elucidating the folding problem of helical peptides using empirical parameters. III. Temperature and pH dependence," J Mol Biol, 1995, 245, 297-308.
Muralidharan et al., "Protein Ligation: an Enabling Technology for the Biophysical Analysis of Proteins," Nature Methods, Jun. 2006, vol. 3, No. 6, pp. 429-438.
Muro, "Challenges in design and characterization of ligand-targeted drug delivery systems," J Control Release, Elsevier, Dec. 2012, 164(2):125-37.
Murphy et al., "A dosimetric model of duodenal toxicity after stereotactic body radiotherapy for pancreatic cancer," Int J Radiation Oncology Biol Phys, Dec. 2010, 78, 1420-1426.
Na et al., "Thermoresponsive pore structure of biopolymer microspheres for a smart drug carrier," Langmuir, Jun. 2010, 26, 11165-11169.
Nagarsekar et al., "Genetically Engineered Polymers for Drug Delivery," Journal of Drug Targeting, 1999, 7(1):11-32.
Nahire et al., "Multifunctional Polymersomes for Cytosolic Delivery of Gemcitabine and Doxorubicin to Cancer Cells," Biomaterials, Aug. 2014, 35(24):6482-6497.
Nairn et al., "A Synthetic Resilin Is Largely Unstructured," Biophysical Journal, Oct. 2008, vol. 95 3358-3365.
Nakaoka et al., "Prolongation of the serum half-life period of superoxide dismutase by poly(ethylene glycol) modification," Journal of Controlled Release, 1997, 46(3):253-261.
Nanoprecision Medical, "Pipeline, Type II Diabetes," <http://www.nanoprecisionmedical.com/pipeline/diabetes> webpage available as early as Aug. 2018.
Napier et al., "Nanoparticle drug delivery platform," Journal of Macromolecular Science, Part C: Polymer Reviews, Taylor & Francis Group, LLC, Aug. 2007, 47(3):321-327.
National Institute of Mental Health, "Methods and Welfare Considerations in Behavioral Research with Animals: Report of a National Institutes of Health Workshop," NIH Publication No. 02-54083, Washington, DC: U.S. Government Printing Office. (Mar. 2002).
Nauck "Glucagon-like Peptide 1 (GLP-1) in the Treatment of Diabetes," Horm Metab Res, 2004, 36(11/12):852-858 (in English).
Nayeem et al., "Engineering enzymes for improved catalytic efficiency: a computational study of site mutagenesis in epothilone-B hydroxylase," Protein Eng Des Sel, Oxford Academy, Apr. 2009, 22(4):257-266.
Neidigh et al., "Exendin-4 and glucagon-like-peptide-q: NMR structural comparisons in the solution and micelle-associated states," Biochemistry 40, 2001, 13188-13200.
Nettles et al., "Applications of elastin-like polypeptides in tissue engineering," Adv Drug Deliv Rev, Dec. 2010, 62, 1479-1485.
Nettles et al., "In situ crosslinking elastin-like polypeptide gels for application to articular cartilage repair in a goat osteochondral defect model," Tissue Eng Part A, Jul. 2008, 14, 1133-1140.
Newcomb et al., "Advances in cryogenic transmission electron microscopy for the characterization of dynamic self-assembling nanostructures," Current Opinion in Colloid and Interface Science, Dec. 2012, 17, 350-359.
Newton et al., "Commissioning a small-field biological irradiator using point, 2D, and 3D dosimetry techniques," Medical Physics, Dec. 2011, 38, 6754-6762.
Ni et al., "Engineering of inorganic nanoparticles as magnetic resonance imaging contrast agents," Chem Soc Rev, Nov. 2017, 46(23):7438-7468.
Nichols et al., "Claudin 4 protein expression in primary and metastatic pancreatic cancer," Am J Clin Pathol, 2004, 121, 226-230.
Nicolas et al., "Fluorescently tagged polymer bioconjugates from protein derived macroinitiators," Chem. Commun. Jan. 2007, 45, 4697-4699.
Nie, "Understanding and overcoming major barriers in cancer nanomedicine," Nanomedicine (Lond) Jun. 2010, 5 (4), 523-528.
Nielsen, "Incretin mimetics and DPP-IV inhibitors for the treatment of type 2 diabetes," Drug Discov. Today 10, 2005, 703-710.
Nies et al., "Fibroblast Growth Factor Signaling in Metabolic Regulation," Front Endocrinol, Jan. 2016, 6(193) (in English).
Nilvebrant et al., "The albumin-binding domain as a scaffold for protein engineering," Computational and Structural Biotechnology Journal, Mar. 2013, 6: e201303009, 8 pages.
Niu et al., "The role of adhesion molecules, αvβ3, αvβ5 and their ligands in the tumor cell and endothelial cell adhesion," Eur J Cancer Prev, Wolters Kluwer, Dec. 2007, 16(6):517-27.
Nott et al., "Phase transition of a disordered nuage protein generates environmentally responsive membraneless organelles," Mol Cell, Mar. 2015, 57(5):936-947.
Nucci et al., "The therapeutic value of poly(ethylene glycol)-modified proteins," Adv. Drug Deliv. Rev., 1991, 6(2):133-151.
Nuhn et al., "Secondary structure formation and LCST behavior of short elastin-like peptides," Biomacromolecules, Sep. 2008, 9, 2755-2763.
O'Day et al., "Therapeutic Protein-polymer Conjugates: Advancing beyond PEGylation," J. Am. Chem. Soc., Sep. 2014, vol. 136, pp. 14323-14332.
Ogawara et al., "Pre-coating with serum albumin reduces receptor-mediated hepatic disposition of polystyrene nanosphere: implications for rational design of nanoparticles," Journal of Controlled Release, 2004, 100(3): 451-455.
Oh et al., "The development of microgels/nanogels for drug delivery applications," Progress in Polymer Science, 2008, 33(4): 448-477.
Olafsen et al., "Covalent disulfide-linked anti-CEA diabody allows site-specific conjugation and radiolabeling for tumor targeting applications," Protein Engineering, Design & Selection, 2004, 17(1):21-27.
Ortega et al., "Hydrodynamic properties of rodlike and dislike particles in dilute solution," The Journal of Chemical Physics, 2003, 119(18):9914-9919.
Ortony et al., "Internal dynamics of a supramolecular nanofibre," Nat. Mater., Aug. 2014, 13, 1-5.
Ozer et al., "Site-Specific and Stoichiometric Stealth Polymer Conjugates of Therapeutic Peptides and Proteins," Bioconjug Chem, Mar. 2017, 28(3):713-723.
Pace et al., "How to measure and predict the molar absorption coefficient of a protein" Protein Science 1995, 4: 2411-2423.
Pagani et al., "International guidelines for management of metastatic breast cancer: can metastatic breast cancer be cured?," Journal of the National Cancer Institute, Apr. 2010, 102, 456-463.

(56) References Cited

OTHER PUBLICATIONS

Pak et al., "Sequence Determinants of Intracellular Phase Separation by Complex Coacervation of a Disordered Protein," Mol Cell, Jul. 2016, 63(1):72-85.
Palmerston Mendes et al., "Dendrimers as Nanocarriers for Nucleic Acid and Drug Delivery in Cancer Therapy," Molecules, Aug. 2017, 22(9):1401.
Palta et al., "Interim Acute Toxicity Analysis and Surgical Outcomes of Neoadjuvant Gemcitabine/nab-Paclitaxel and Hypofractionated Image Guided Intensity Modulated Radiation Therapy in Resectable and Borderline Resectable Pancreatic Cancer (ANCHOR) Study," International Journal of Radiation Oncology • Biology • Physics, Oct. 2016, 96, S204-S205.
Palva et al., "Secretion of interferon by Bacillus subtilis," Gene, 1983, 22, 229-235.
Panda et al., "Stop-flow lithography to generate cell-laden microgel particles," Lab Chip, 2008, 8: 1056-1061.
Pang et al., "A Modular Method for the High-Yield Synthesis of Site-Specific Protein-Polymer Therapeutics," Angew Chem Int Ed Engl, Jul. 2016, 55, 10296-10300.
Paolino et al., "Folate-targeted supramolecular vesicular aggregates as a new frontier for effective anticancer treatment in in vivo model," Eur. J. Pharm. Biopharm., Jun. 2012, 82(1):94-102.
Paolino et al., "Gemcitabine-loaded PEGylated unilamellar liposomes vs GEMZAR: biodistribution, pharmacokinetic features and in vivo antitumor activity," J. Control. Release Jun. 2010, 144(2):144-150.
Paoloni et al., "Translation of new cancer treatments from pet dogs to humans," Nat. Rev. Cancer Feb. 2008, 8 (2), 147-156.
Papa et al., "PEGylated Liposomal Gemcitabine: Insights Into a Potential Breast Cancer Therapeutic," Cell Oncol. (Dordr), Oct. 2013, 36(6):449-457.
Paramonov et al., "Self-assembly of peptide-amphiphile nanofibers: The roles of hydrogen bonding and amphiphilic packing," J. Am. Chem. Soc., May 2006, 128, 7291-7298.
Pardridge, "The blood-brain barrier: bottleneck in brain drug development," NeuroRx, 2005, 2(1):3-14.
Park et al., "Exendin-4 and exercise improve hepatic glucose homeostasis by promoting insulin signaling in diabetic rats," Metabolism, Janury 2010, 59, 123-133.
Park et al., "Formulation optimization and in vivo proof-of-concept study of thermosensitive liposomes balanced by phospholipid, elastin-like polypeptide, and cholesterol," PLoS One, Jul. 2014, 9: e103116, 13 pages.
Park et al., "Protein stitchery: Design of a protein for selective binding to a specific DNA sequence," PNAS, 1992, vol. 89:9094-9096.
Parker et al., "Antibody mimics based on human fibronectin type three domain engineered for thermostability and high-affinity binding to vascular endothelial growth factor receptor two," Protein Eng Des Sel, 2005, 18(9):435-44.
Parkes et al. "Discovery and development of exenatide: the first antidiabetic agent to leverage the multiple benefits of the incretin hormone, GLP-1," Expert Opinion. Drug Deliv., Feb. 2013, 8(2):219-244.
Parveen et al., "Nanomedicine," Clinical Pharmacokinetics, Oct. 2006, 45(10):965-988.
Pastuszka et al., "A tunable and reversible platform for the intracellular formation of genetically engineered protein microdomains," Biomacromolecules, ACS Publications, Oct. 2012, 13(11):3439-3444.
Patil et al., "Cellular delivery of doxorubicin via pH-controlled hydrazone linkage using multifunctional nano vehicle based on poly(beta-l-malic acid)," Int J Mol Sci, Sep. 2012, 13, 11681-11693.
Paulsen et al., "Optofluidic fabrication for 3D-shaped particles," Nat Commun, 2015, 6: 6976.
Peeler et al., "Genetically encoded initiator for polymer growth from proteins," J. Am. Chem. Soc. 132, Oct. 2010, 13575-13577.
Peng et al., "Length-dependent prediction of protein intrinsic disorder," BMC Bioinformatics, Springer Nature, Apr. 2006, 7:208.
Peters, "Serum albumin," Adv. Protein Chem. 37, 1985, 161-245.
Petitdemange et al., "Tuning Thermoresponsive Properties of Cationic Elastin-like Polypeptides by Varying Counterions and Side-Chains," Bioconjug. Chem., May 2017, 28(5):1403-1412.
Petros et al., "Strategies in the design of nanoparticles for therapeutic applications," Nat Rev Drug Discov, Nature Research, Aug. 2010, 9(8):615-27.
Phan et al., "Temperature-responsive self-assembly of charged and uncharged hydroxyethylcellulose-graft-poly(N-isopropylacrylamide) copolymer in aqueous solution," Colloid Polym. Sci., Apr. 2011, 289 (9), 993-1003.
Pinkas et al., "Tunable, post-translational hydroxylation of collagen domains in *Escherichia coli*," ACS Chem. Biol., Apr. 2011, 6(4):320-324.
Pliarchopoulou et al., "Pancreatic cancer: Current and future treatment strategies," Cancer Treatment Reviews, Aug. 2009, 35, 431-436.
Poitout et al., "Glucolipotoxicity: Fuel Excess and β-Cell Dysfunction," Endocr Rev, May 2008, 29(3):351-366.
Pometun et al., "Quantitative observation of backbone disorder in native elastin," J Biol Chem, 2004, 279, 7982-7987.
Popp et al., "Site-specific labeling via sortase-mediated transpeptidation," Curr. Protoc. Protein Sci. 56, Apr. 2009, 15.13.1-15.13.9.
Popp et al., "Sortase-Catalyzed Transformations That Improve the Properties of Cytokines," PNAS, Feb. 2011, vol. 108, No. 8, pp. 3169-3174.
Potters et al., "12-year outcomes following permanent prostate brachytherapy in patients with clinically localized prostate cancer," The Journal of urology, 2005, 173, 1562-1566.
Potters et al., "Monotherapy for stage T1-T2 prostate cancer: radical prostatectomy, external beam radiotherapy, or permanent seed implantation," Radiotherapy and oncology: journal of the European Society for Therapeutic Radiology and Oncology, 2004, 71, 29-33.
Potters et al., "Potency after permanent prostate brachytherapy for localized prostate cancer," International journal of radiation oncology, biology, physics, 2001, 50(5): 1235-1242.
Potthoff et al., "Endocrine fibroblast growth factors 15/19 and 21: from feast to famine," Genes Dev, Feb. 2012, 26(4):312-324.
Prestwich et al., "Beta dose point kernels for radionuclides of potential use in radioimmunotherapy," J Nucl Med, 1989, 30, 1036-1046.
Privratsky et al., "PECAM-1: regulator of endothelial junctional integrity," Cell Tissue Res, Mar. 2014, 355, 607-619.
Prostate Seed Center, "Brachytherapy seed pre-plan rendering," <http://www.prostateseedcenter.com/dynamics-of-brachytherapy> webpage available as early as Aug. 30, 2012.
Provenzano et al., "Enzymatic targeting of the stroma ablates physical barriers to treatment of pancreatic ductal adenocarcinoma," Cancer cell, Mar. 2012, 21, 418-429.
Provenzano et al., "Hyaluronan, fluid pressure, and stromal resistance in pancreas cancer," Br J Cancer, Jan. 2013, 108, 1-8.
Pulaski et al., "Mouse 4T1 breast tumor model," Curr. Protoc. Immunol., 2001, Chapter 20, Unit 20.2.
Qamar et al., "FUS Phase Separation Is Modulated by a Molecular Chaperone and Methylation of Arginine Cation-pi Interactions," Cell, Apr. 2018, 173(3):720-734.e15.
Qi et al., "A brush-polymer conjugate of exendin-4 reduces blood glucose for up to five days and eliminates poly(ethylene glycol) antigenicity," Nat Biomed Eng, Nov. 2016, 1:0002.
Qi et al., Dataset for a brush-polymer conjugate of exendin-4 reduces blood glucose for up to five days and eliminates poly(ethylene glycol) antigenicity. Figshare, Nov. 2016, <http://dx.doi.org/10.6084/m9.figshare.3976761>.
Qi et al., "Growing polymers from peptides and proteins: a biomedical perspective," Polym. Chem., Jan. 2014, 5(2):266-276.
Qi et al., "Protein-polymer conjugation—moving beyond PEGylation," Curr. Opin. Chem. Biol. 28, Oct. 2015, 181-193.
Qi et al., "Sortase-catalyzed initiator attachment enables high yield growth of a stealth polymer from the C terminus of a protein," Macromol. Rapid Commun., Aug. 2013, 34(15):1256-1260.
Qiu et al., "Development of Orthotopic Pancreatic Tumor Mouse Models," Methods Mol Biol, Jan. 2013, 980: 215-223.
Qiu et al., "Polymer Architecture and Drug Delivery," Pharmaceutical Research, Feb. 2006, 23(1):1-30.

(56) References Cited

OTHER PUBLICATIONS

Quarmby et al., "Irradiation induces upregulation of CD31 in human endothelial cells," Arterioscler Thromb Vasc Biol, 1999, 19, 588-597.
Quarmby et al., "Radiation-induced normal tissue injury: role of adhesion molecules in leukocyte-endothelial cell interactions," Int J Cancer, 1999, 82, 385-395.
Quiroz et al., "Intrinsically disordered proteins access a range of hysteretic phase separation behaviors," Scientific advances, Oct. 2019, 5(10):eaax5177.
Quiroz et al., "Sequence heuristics to encode phase behaviour in intrinsically disordered protein polymers," Nat. Mater., Nov. 2015, 14(11):1164-1171.
Rabotyagova et al., "Protein-based block copolymers," Biomacromolecules, Feb. 2011, 12(2): 269-289.
Radivojac et al., "Intrinsic Disorder and Functional Proteomics," Biophysical Journal, Mar. 2007, vol. 92, Issue 5, pp. 1439-1456.
Ragupathi et al., "Abstract A73: Antitumor activity of MVT-5873, a monoclonal antibody targeting sialyl Lewisa, alone and in combination with gemcitabine/nab-paclitaxel in a BxPC3 human pancreatic cancer xenograft model," Cancer Research, Dec. 2016, 76.
Rankine et al., "Investigating end-to-end accuracy of image guided radiation treatment delivery using a micro-irradiator," Physics in Medicine and Biology, Nov. 2013, 58(21):7791-7801.
Rao et al., "Synthetic nanoparticles camouflaged with biometric erythrocyte membranes for reduced reticuloendothelial system uptake," Nanotechnology, Jan. 2016, 27 (8), 85106, 9 pages.
Rapaka et al., "Coacervation of Sequential Polypeptide Models of Tropoelastin," Int J Peptide Protein Res, 1978, 11: 97-108.
Ratner et al., "Radiation-grafted hydrogels for biomaterial applications as studied by the ESCA technique," Journal of Applied Polymer Science, 1978, 22, 643-664.
Ratner, "A pore way to heal and regenerate: 21st century thinking on biocompatibility," Regen Biomater, Feb. 2016, 3(2):107-110.
Rauscher et al. "Proline and Glycine Control Protein Self-Organization into Elastomeric or Amyloid Fibrils," Structure, Nov. 2006, 14(11):1667-1676.
Ravikumar et al., "Mimicking adhesive functionalities of blood platelets using ligand-decorated liposomes," Bioconjugate chemistry, ACS Publications, May 2012, 23(6):1266-1275.
Ray et al., "Aptamer-mediated delivery of chemotherapy to pancreatic cancer cells." Nucleic acid therapeutics, Oct. 2012, 22(5): 295-305.
Regier et al., American Heart Association 2014 Scientific Sessions, May 2015, vol. 7, pp. 299-303.
Reguera et al., "Thermal Behavior and Kinetic Analysis of the Chain Unfolding and Refolding and of the Concomitant Nonpolar Solvation and Desolvation of Two Elastin-like Polymers," Macromolecules, 2003, 36, 8470-8476.
Ren et al., "Mesenchymal stem cell-mediated immunosuppression occurs via concerted action of chemokines and nitric oxide," Cell Stem Cell, Feb. 2008, 2(2): p. 141-150.
Resh, "Covalent Lipid Modifications of Proteins," Curr Biol., May 2013, 23(10): R431-R435.
Ribeiro et al., "Influence of the amino-acid sequence on the inverse temperature transition of elastin-like polypeptides," Biophysical Journal, Jul. 2009, 97(1):312-320.
Richards et al., "Engineered fibronectin type III domain with a RGDWE sequence binds with enhanced affinity and specificity to human avB3 integrin," J Mol Biol, 2003, 326(5):1475-1488.
Richards et al., "Man's best friend: what can pet dogs teach us about non-Hodgkin lymphoma?" Inmunol Rev., Jan. 2015, 263 (1): 173-191.
Riddles et al., "Ellman's reagent: 5,5'-dithiobis(2-nitrobenzoic acid)—a reexamination," Anal Biochem. 1979, 94(1):75-81.
Riedel et al., "Engineered glucagon-like peptide-1-producing hepatocytes lower plasma glucose levels in mice," Am J Physiol Endocrinol Metab, Apr. 2009, 296(4):E936-E944.
Rincon et al., "Biocompatibility of elastin-like polymer poly(VPAVG) microparticles: in vitro and in vivo studies," Journal of Biomedical Materials Research, 2005, 78A, 343-351.
Rios-Doria et al., "Doxil synergizes with cancer immunotherapies to enhance antitumor responses in syngeneic mouse models," Neoplasia, Aug. 2015, 17(8):661-670.
Ritcher et al., "Antibodies against polyethylene glycol produced in animals by immunization with monomethoxy polyethylene glycol modified proteins," Int. Arch. Allergy Appl. Immunol. 70, 1983, 124-131.
Ritcher et al., "Polyethylene glycol reactive antibodies in man: titer distribution in allergic patients treated with monomethoxy polyethylene glycol modified allergens or placebo, and in healthy blood donors," Int. Arch. Allergy Appl. Immunol. 74, 1984, 36-39.
Rivory et al., "Effects of lipophilicity and protein binding on the hepatocellular uptake and hepatic disposition of two anthracyclines, doxorubicin and iododoxorubicin," Cancer Chemother Pharmacol, 1996, 38(5):439-445.
Roberts et al., "Elastin-like polypeptides as models of intrinsically disordered proteins," FEBS Lett., Sep. 2015, 589, 2477-2486.
Roberts et al., "Injectable tissue integrating networks from recombinant polypeptides with tunable order," Nature Materials, 2018, 17(12): 1154-1163.
Robinet et al. "Elastin-derived peptides enhance angiogenesis by promoting endothelial cell migration and tubulogenesis through upregulation of MT1-MMP," J. Cell Science, 2005, 118:343-356.
Rodriguez-Cabello et al., "Elastin-like polypeptides in drug delivery," Adv Drug Deliv Rev, 2016, 97: 85-100.
Rodriguez-Diaz et al., "Alpha cells secrete acetylcholine as a non-neuronal paracrine signal priming beta cell function in humans," Nat Med, Jun. 2011, 17:888-892.
Rolland et al., "Direct fabrication and harvesting of monodisperse, shape-specific nanobiomaterials," J Am Chem Soc, 2005, 127(28):10096-100.
Römer et al., "The elaborate structure of spider silk: structure and function of a natural high performance fiber," Prion, Nov. 2008, 2(4):154-161.
Roopenian et al., "FcRn: the neonatal Fc receptor comes of age," Nat. Rev. Immunol., Sep. 2007, vol. 7, No. 9, 715-725.
Rosenberg et al., "Present and future innovations in radiation oncology," Surg Oncol Clin N Am, Jul. 2013, 22(3):599-618.
Rosenholm et al., "Towards multifunctional, targeted drug delivery systems using mesoporous silica nanoparticles—opportunities & challenges," Nanoscale, Royal Society of Chemistry, Oct. 2010, 2(10):1870-83.
Rösler et al., "Advanced drug delivery devices via self-assembly of amphiphilic block copolymers," Advanced Drug Delivery Reviews, 2001, 53:95-108.
Rozak et al., "G148-GA3: a streptococcal virulence module with atypical thermodynamics of folding optimally binds human serum albumin at physiological temperatures," Biochim Biophys Acta, 2005, 1753(2): p. 226-33.
Ruiz van Haperen et al., "Regulation of phosphorylation of deoxycytidine and 2',2'-difluorodeoxycytidine (gemcitabine); effects of cytidine 5'-triphosphate and uridine 5'-triphosphate in relation to chemosensitivity for 2',2'-difluorodeoxycytidine," Biochem. Pharmacol. 1996, 51(7):911-908.
Russo et al., "The role of neoadjuvant therapy in pancreatic cancer: a review," Future Oncol, Mar. 2016, 12(5):669-685.
Ryerson et al., "Annual report to the nation on the status of cancer, 1975-2012, featuring the Increasing incidence of liver cancer," Cancer, May 2016, 122(9): 1312-1337.
Ryu et al., "Elastin-like polypeptide for improved drug delivery for anticancer therapy: preclinical studies and future applications," Expert Opinion on Drug Delivery, Informa Healthcare, Oct. 2014, 12(4):653-667.
Saba et al., "A Comparative Oncology Study of Iniparib Defines Its Pharmacokinetic Profile and Biological Activity in a Naturally-Occurring Canine Cancer Model," PLoS One, Feb. 2016, 11(2): 1-11.
Safran et al., "Gemcitabine, paclitaxel, and radiation for locally advanced pancreatic cancer: A phase I trial," Int J Radiation Oncology Biol Phys, 2002, 54, 137-141.

(56) References Cited

OTHER PUBLICATIONS

Sagle et al., "Investigating the hydrogen-bonding model of urea denaturation," J Am Chem Soc, Jun. 2009, 131(26): 9304-9310.
Saifer et al., "Selectivity of binding of PEGs and PEG-like oligomers to anti-PEG antibodies induced by methoxyPEG-proteins," Molecular Immunology, Feb. 2014, 57(2):236-246.
Sandler et al., "Gemcitabine: Single-Agent and Combination Therapy in Non-Small Cell Lung Cancer," Oncologist 1999, 4(3)241-251.
Sanna et al., "Targeted therapy using nanotechnology: focus on cancer," Int J Nanomedicine, Jan. 2014, 9:467-83.
Schaal et al., "Biopolymer ß-brachytherapy delivered with concomitant paclitaxel outperforms traditional x-ray radiation to include complete regression in multiple pancreatic tumor xenograft models through synergistic modulation of the tumor microenvironment," Poster #5831, 2018.
Schaal et al., "Injectable polypeptide micelles that form radiation crosslinked hydrogels in situ for intratumoral radiotherapy," Journal of Controlled Release, Apr. 2016, 228, 58-66.
Schellenberg et al., "Gemcitabine chemotherapy and single-fraction stereotactic body radiotherapy for locally advanced pancreatic cancer," Int J Radiation Oncol Biol Phys, Nov. 2008, 72(3): 678-686.
Schellenberg et al., "Single-fraction stereotactic body radiation therapy and sequential gemcitabine for the treatment of locally advanced pancreatic cancer," Int J Radiation Oncology Biol Phys, Sep. 2011, 81(1): 181-188.
Schellenberger et al., "A recombinant polypeptide extends the in vivo half-life of peptides and proteins in a tunable manner," Nat. Biotechnol., Dec. 2009, 27(12):1186-1188.
Schlaff et al., "Bringing the heavy: carbon ion therapy in the radiobiological clinical context," Radiation Oncology, Mar. 2014, 9, Article 88, 1-18.
Schneider et al., "NIH Image to ImageJ: 25 years of image analysis," Nature Methods, Jul. 2012, 9(7): 671-675.
Schnell et al., "Expression of integrin αvβ3 in gliomas correlates with tumor grade and is not restricted to tumor vasculature," Brain Pathol, International Society of Neuropathology, Aug. 2008, 18(3):378-86.
Schwendeman et al., "Injectable controlled release depots for large molecules," J Control Release, Sep. 2014, 190, 240-253.
Senin et al., "N-Myristoylation of recoverin enhances its efficiency as an inhibitor of rhodopsin kinase," Febs. Lett., 1995, 376, 87-90.
Senior et al., "Val-Gly-Val-Ala-Pro-Gly, a Repeating Peptide in Elastin, Is Chemotactic for Fibroblasts and Monocytes," The Journal of Cell Biology, 1984, 99: 870-874.
Serrano et al., "An infrared spectroscopic study of the conformational transition of elastin-like polypeptides," Biophys. J., Oct. 2007, 93(7):2429-2435.
Shadwick, "Mechanical design in arteries," J Exp Biol, 1999, 202, 3305-3313.
Shang et al., "pH-Dependent Protein Conformational Changes in Albumin:Gold Nanoparticle Bioconjugates: A Spectroscopic Study," Langmuir, Feb. 2007, 23 (5), 2714-2721.
Shao et al., "Super-resolution 3D microscopy of live whole cells using structured illumination," Nat Methods, Oct. 2011, 8(12): 1044-1046.
Sharma et al., "Dendrimer nanoarchitectures for cancer diagnosis and anticancer drug delivery," Drug Discov Today, Feb. 2017, 22(2):314-326.
Sharma et al., "PLGA-based nanoparticles: A new paradigm in biomedical applications," TrAC Trends in Analytical Chemistry, Jun. 2016, 80:30-40.
Sharma et al., "Polymer particle shape independently influences binding and internalization by macrophages," Journal of Controlled Release, Elsevier, Nov. 2010, 147(3):408-412.
Shen et al., "Conjugation site modulates the in vivo stability and thearpeutic activity of antibody-drug conjugates," Nat Biotechnol, Jan. 2012, 30(2):184-189.
Sheparovych et al., "Stimuli-Responsive Properties of Peptide-Based Copolymers Studied via Directional Growth of Self-Assembled Patterns on Solid Substrate," Biomacromolecules, Jul. 2009, 10:1955-1961.
Sherman et al., "Next-Generation PEGylation Enables Reduced Immunoreactivity of PEG-Protein Conjugates," Drug and Development & Delivery, Jun. 2012, vol. 12, No. 5, 36-42.
Sherman et al., "Role of the Methoxy Group in Immune Responses to mPEG-Protein Conjugates," Bioconjugate Chemistry, Mar. 2012, 23(3): 485-499.
Shi et al., "Cell adhesion on a POEGMA-modified topographical surface," Langmuir: the ACS journal of surfaces and colloids, Dec. 2012, 28 (49), 17011-8.
Shi et al., "Triggered sorting and co-assembly of genetically engineered protein microdomains in the cytoplasm," Adv Mater, Wiley, Jan. 2014, 26(3):449-454.
Shimoboji et al., "Temperature-Induced Switching of Enzyme Activity with Smart Polymer-Enzyme Conjugates," Bioconjugate Chem. 2003, 14, 517-525.
Shin et al., "Liquid phase condensation in cell physiology and disease," Science, Sep. 2017, 357(6357):eaaf4382.
Shusharina et al., "Micelles of Diblock Copolymers with Charged and Neutral Blocks: Scaling and Mean-Field Lattice Approaches," Macromolecules, 2000, 33(10): 3892-3901.
Sickmeier et al., "DisProt: the Database of Disordered Proteins," Nucleic Acids Res, Oxford Academy, Jan. 2007, 35:D786-793.
Siegel et al., "Absorbed fractions for electrons and beta particles in spheres of various sizes," J Nucl Med, 1994, 35, 152-156.
Siegwart et al., "ATRP in the Design of Functional Materials for Biomedical Applications," Prog Polymer Science, Jan. 2012, vol. 37, No. 1, pp. 18-37.
Silberstein et al., "The SNM Practice Guideline for Therapy of Thyroid Disease with $^{131}I$, 3.0," J Nucl Med, Jul. 2012, 53, 1-19.
Silva et al., "Selective differentiation of neural progenitor cells by high-epitope density nanofibers," Science, 2004, 303, 1352-5.
Simakova et al., "Aqueous ARGET ATRP," Macromolecules, Aug. 2012, 45(16):6371-6379.
Simnick et al., "In vivo tumor targeting by a NGR-decorated micelle of a recombinant diblock copolypeptide," J Control Release, Oct. 2011, 155(2): 144-151.
Simnick et al., "Morphing low-affinity ligands into high-avidity nanoparticles by thermally triggered self-assembly of a genetically encoded polymer," ACS Nano, Apr. 2010, 4(4):2217-2227.
Simon et al., "Engineered Ribonucleoprotein Granules Inhibit Translation in Protocells," Molecular cell, Jul. 2019, 75(1):66-75.
Simon et al., "Programming molecular self-assembly of intrinsically disordered proteins containing sequences of low complexity," Nat Chem, Jun. 2017, 9(6):509-515.
Singhal et al., "Fibroblast Growth Factor 21 (FGF21) Protects against High Fat Diet Induced Inflammation and Islet Hyperplasia in Pancreas," PLoS One, Feb. 2016, 11(2):e0148252.
Sisson et al., "Radiation safety in the treatment of patients with thyroid diseases by radioiodine 131I: practice recommendations of the American Thyroid Association," Thyroid, Apr. 2011, 21(4):335-346.
Skerra, "Alternative non-antibody scaffolds for molecular recognition," Curr Opin Biotechnol, Elsevier, Aug. 2007, 18(4):295-304.
Smith et al., "The Role of Beta Cell Glucagon-like Peptide-1 Signaling in Glucose Regulation and Response to Diabetes Drugs," Cell Metab, Jun. 2014, 19(6):1050-1057.
Smits et al., "Elastin-Like Polypeptide Based Nanoparticled: Design Rationale Toward Nanomedicine," Macromolecular Bioscience, Macromolecular Journals, Jan. 2015, 15(1):36-51.
Sonawane et al., "Hydrazo linkages in pH responsive drug delivery systems," European Journal Pharmaceutical Sciences, Mar. 2017, 99, 45-65.
Song et al., "Budding-like division of all-aqueous emulsion droplets modulated by networks of protein nanofibrils," Nat Commun, 2018, 9: 2110.
Sorkin et al., "Signal transduction and endocytosis: close encounters of many kinds," Nat Rev Mol Cell Biol, 2002, 3(8):600-614.

(56) References Cited

OTHER PUBLICATIONS

Sousa et al., "Production of a polar fish antimicrobial peptide in *Escherichia coli* using an ELP-intein tag," J Biotechnol, Sep. 2016, 234:83-89.
Srinivas et al., "Aptamer-functionalized microgel particles for protein detection," Anal Chem, 2011, 83: 9138-9145.
Sriraman et al., "Barriers to drug delivery in solid tumors," Tissue Barriers, Jul. 2014, 2(3): 2-10.
Stanislaus et al., "A Novel Fc-FGF21 With Improved Resistance to Proteolysis, Increased Affinity Toward β-Klotho, and Enhanced Efficacy in Mice and Cynomolgus Monkeys," Endocrinology, May 2017, 158(5):1314-1327.
Stefl et al., "RNA sequence-and shape-dependent recognition by proteins in the ribonucleoprotein particle" EMBO reports (2005) 6(1):33-38.
Steichen et al., "A Review of Current Nanoparticle and Targeting Moieties for the Delivery of Cancer Therapeutics," Eur J Pharm Sci, Elsevier, Feb. 2013, 48(3):416-27.
Stock et al., "Penile erectile function after permanent raioactive seed implantation for treatment of prostate cancer," The Journal of urology, 2001, 165, 436-439.
Stork et al., "A novel tri-functional antibody fusion protein with improved pharmacokinetic properties generated by fusing a bispecific single-chain diabody with an albumin-binding domain from streptococcal protein G," Protein Engineering Design and Selection, Nov. 2007, 20(11): p. 569-576.
Strohmaier et al., "Comparison of $^{60}$Co and $^{192}$Ir sources in HDR brachytherapy," J Contemp Brachyther, Dec. 2011, 3(4): 199-208.
Strulson et al., "RNA catalysis through compartmentalization," Nat Chem, Nature Publishing Group, Nov. 2012, 4(11):941-946.
Stutz et al., "Seed loss through the urinary tract after prostate brachytherapy: examining the role of cystoscopy and urine straining post implant," Medical physics, 2003, 30, 2695-2698.
Sugyo et al., "Evaluation of efficacy of radioimmunotherapy with 90Y-labeled fully human anti-transferring receptor monoclonal antibody in pancreatic cancer mouse models," PLoS One, Apr. 2015, 10, 1-17.
Suk et al., "PEGylation as a Strategy for Improving Nanoparticle-Based Drug and Gene Delivery," Adv Drug Deliv Rev, Apr. 2016, 99(Pt A):28-51.
Sumerlin, "Proteins as Initiators of Controlled Radical Polymerization: Grafting-from via ATRP and RAFT," ACS Macro Lett. Jan. 2012, 1(1): 141-145.
Sun et al., "Autofluorescence Imaging of Living Pancreatic Islets Reveals Fibroblast Growth Factor-21 (FGF21)-Induced Metabolism," Biophys J, Dec. 2012, 103(11):2379-2388.
Sun et al., "Contributions of the extracellular and cytoplasmic domains of platelet-endothelial cell adhesion molecule-1 (PECAM-1/CD31) in regulating cell-cell localization," J. Cell Sci., 2000, 113, 1459-1469.
Sun et al., "Efficacy and safety of the hypoxia-activated prodrug TH-302 in combination with gemcitabine and nab-paclitaxel in human tumor xenograft models of pancreatic cancer," Cancer Biology & Therapy, Feb. 2015, 16(3): 438-449.
Sun et al., "EUS-guided interstitial brachytherapy of the pancreas: a feasibility study," Gastrointestinal Endoscopy, 2005, 62, 775-779.
Sun et al., "On the Thermally Reversible Dynamic Hydration Behavior of Oligo(ethylene glycol) Methacrylate-Based Polymers in Water," Macromolecules, Jan. 2013, 46(1): 236-246.
Sunamura et al., "Gene Therapy for Pancreatic Cancer Targeting the Genomic Alterations of Tumor Suppressor Genes using Replication-selective Oncolytic Adenovirus," Human Cell, 2002, 15, 138-150.
Surwit et al., Diet-induced type II diabetes in C57BL/6J mice, Diabetes 37, 1988, 1163-1167.
Sussman et al., "Porous implants modulate healing and induce shifts in local macrophage polarization in the foreign body reaction," Ann Biomed Eng, Jul. 2014, 42(7): 1508-1516.
Swee et al., "Sortase-mediated modification of αDEC205 affords optimization of antigen presentation and immunization against a set of viral epitopes," Proc Natl Acad Sci USA, Jan. 2013, 110(4):1428-1433.
Swers et al., Multivalent Scaffold Proteins as Superagonists of Trail Receptor 2-Induced Apoptosis, Mol Cancer Ther, Jul. 2013, 12(7): 1235-1244.
Swider et al., "Customizing Poly(lactic-Co-Glycolic Acid) Particles for Biomedical Applications," Acta Biomater, Jun. 2018, 73:38-51.
Takalkar et al., "Radium-223 dichloride bone-targeted alpha particle therapy for hormone-refractory breast cancer metastatic to bone," Exp Hematol Oncol, Sep. 2014, 8, Article No. 23.
Talelli et al., "Core-Crosslinked Polymeric Micelles: Principles, Preparation, Biomedical Applications and Clinical Translation," Nano Today, Feb. 2015, 10(1):93-117.
Tallarida, "Quantitative methods for assessing drug synergism," Genes & Cancer, Nov. 2011, 2(11): 1003-1008.
Talukdar et al., "A Long-Acting FGF21 Molecule, PF-05231023, Decreases Body Weight and Improves Lipid Profile in Non-human Primates and Type 2 Diabetic Subjects," Cell Metab, Mar. 2016, 23(3):427-440.
Tamburro et al., "Dissection of human tropoelastin: exon-by-exon chemical synthesis and related conformational studies," Biochemistry, 2003, 42, 13347-13362.
Tamburro et al., "Localizing alpha-helices in human tropoelastin: assembly of the elastin "puzzle"," Biochemistry, Aug. 2006, 45(31): 9518-9530.
Tan et al., "Characterization of a new primary human pancreatic tumor line," Cancer investigation, 1986, 4, 15-23.
Tang et al., "Combinatorial codon scrambling enables scalable gene synthesis and amplification of repetitive proteins," Nature Mater., Apr. 2016, 15(4): 419-424.
Tang et al., "Enzymatic Polymerization of High Molecular Weight DNA Amphiphiles That Self-Assemble into Star-Like Micelles," Advanced Materials, Feb. 2014, 26(19): 3050-3054.
Tang et al., "High-Molecular-Weight Polynucleotides by Transferase-Catalyzed Living Chain-Growth Polycondensation," Angew. Chem., Jun. 2017, 56(24): 6778-6782.
Tang et al., "Identification of PECAM-1 in solid tumor cells and its potential involvement in tumor cell adhesion to endothelium," J. Biol. Chem., 1993, 268, 22883-22894.
Tantakitti et al., "Energy landscapes and functions of supramolecular systems," Nat. Mater., Apr. 2016, 15(4): 469-476.
Tedja et al., "Effect of TiO2 nanoparticle surface functionalization on protein adsorption, cellular uptake and cytotoxicity: the attachment of PEG comb polymers using catalytic chain transfer and thiol-ene chemistry," Polymer Chemistry, Oct. 2012, 3 (10), 2743-2751.
Teicher, "In vivo/ex vivo and in situ assays used in cancer research: a brief review," Toxicol. Pathol., Jan. 2009, 37 (1), 114-122.
Thakor et al., "Clinically Approved Nanoparticle Imaging Agents," J Nucl Med, Oct. 2016, 57(12):1833-1837.
Theillet et al., "The alphabet of intrinsic disorder: I. Act like a Pro: On the abundance and roles of proline residues in intrinsically disordered proteins," Intrinsically Disord Proteins, Taylor & Francis, Apr. 2013, 1(1):e24360.
Therasse et al., "New guidelines to evaluate the response to treatment in solid tumors," J Natl Cancer Inst, 2000, 92, 205-216.
Thorens et al., "Cloning and functional expression of the human islet GLP-1 receptor: demonstration that Exendin-4 Is an agonist and Exendin-(9-39) an antagonist of the receptor," Diabetes 42, 1993, 1678-1682.
Tomiyama et al., "Relevant use of Klotho in FGF19 subfamily signaling system in vivo," Proc Natl Acad Sci USA, Jan. 2010, 107(4):1666-71.
Tompa et al., "Fuzzy complexes: polymorphism and structural disorder in protein-protein interactions," Trends Biochem Sci, Jan. 2008, 33(1): 2-8.
Tong et al., "Protein Modification with Amphiphilic Block Copoly(2-oxazoline)s as a New Platform for Enhanced Cellular Delivery," Mol. Pharm., Aug. 2010, vol. 7, No. 4, pp. 984-992.
Ton-That et al., "Assembly of pili on the surface of Corynebacterium diptheriae," 2003, 50(4):1429-1438.

(56) References Cited

OTHER PUBLICATIONS

Ton-That et al., "Purification and characterization of sortase, the transpeptide that cleaves surface proteins of *Staphylococcus aureus* and the LPXTG motif," Proc Natl Acad Sci USA, 1999, 96(22):12424-12429.
Torchilin, "Recent advances with liposomes as pharmaceutical carriers," Nature Rev. Drug Discov. 2005, 4(2):145-160.
Towler et al., "Purification and Characterization of Yeast Myristoyl-Coa—Protein N-Myristoyltransferase," P Natl Acad Sci USA, 1987, 84(9):2708-12.
Trabbic-Carlson et al., "Effect of protein fusion on the transition temperature of an environmentally responsive elastin-like polypeptide: a role for surface hydrophobicity?," Protein Engineering Design and Selection, 2004, 17(1): 57-66.
Trabbic-Carlson et al., "Expression and purification of recombinant proteins from *Escherichia coli*: Comparison of an elastin-like polypeptide fusion with an oligohistidine fusion" Protein Science, 2004, 13: 3274-3284.
Trakul et al., "Stereotactic body radiotherapy in the treatment of pancreatic cancer," Semin Radiat Oncol, Apr. 2014, 24(2): 140-147.
Trieu et al., "P0157 Preclinical evaluation of NBN-paclitaxel in pancreatic cancer xenograft models," Eur J Cancer, May 2014, 50(4): e53.
Triola et al., "Chemical biology of lipidated proteins," ACS Chemical Biology, Jan. 2012, 7(1): 87-99.
Troyanskaya et al., "Nonparametric methods for identifying differentially expressed genes in microarray data," Bioinformatics, 2002, 18(11):1454-61.
Truong et al., "Polymeric filomicelles and nanoworms: two decades of synthesis and application," Polymer Chemistry, Jun. 2016, 7(26):4295-4312.
Truong et al., "The Importance of Nanoparticle Shape in Cancer Drug Delivery," Expert Opin Drug Deliv, Jan. 2015, 12(1):129-42.
Truong, et al., "The effect of hydration on molecular chain mobility and the viscoelastic behavior of resilin-mimetic protein-based hydrogels," Biomaterials, Elsevier, Nov. 2011, 32(33):8462-73.
Tsarevsky et al., "Deactivation efficiency and degree of control over polymerization in ATRP in protic solvents," Macromolecules 37, 2004, 9768-9778.
Tschöp et al., "Unimolecular Polypharmacy for Treatment of Diabetes and Obesity," Cell Metab, Jul. 2016, 24(1):51-62.
Tsuda et al., "Monodisperse cell-encapsulating peptide microgel beads for 3D cell culture," Langmuir, 2010, 26: 2645-2649.
Tsume et al., "The development of orally administrable gemcitabine prodrugs with D-enantiomer amino acids: Enhanced membrane permeability and enzymatic stability," Eur. J. Pharm. Biopharm., Apr. 2014, 86(3):514-523.
Tu et al., "Stages in tropoelastin coalescence during synthetic elastin hydrogel formation," Micron, Apr. 2010, 41(3): 268-272.
Turunen et al., "Paclitaxel Succinate Analogs: Anionic Introduction as a Strategy to Impart Blood Brain Barrier Permeability," Bioorg Med Chem Lett, Nov. 2008, 18(22):5971-5974.
Tward et al., "Survival of men with clinically localized prostate cancer treated with prostatectomy, brachytherapy, or no definitive treatment: impact of age at diagnosis," Cancer, Oct. 2006, 107(10): 2392-2400.
Uchida et al., "Potential of adenovirus-mediated REIC/Dkk-3 gene therapy for use in the treatment of pancreatic cancer," Journal of Gastroenterology and Hepatology, Apr. 2014, 29(5):973-983.
Urry et al., "Calculation of distorted circular dichroism curves for poly-L-glutamic acid suspensions," Arch Biochem Biophys, 1970, 137, 214-221.
Urry et al., "Coacervation of solubilized elastin effects a notable conformational change," Nature, 1969, 222, 795-796.
Urry et al., "Differential scatter of left and right circularly polarized light by optically active particulate systems," Proc Natl Acad Sci U S A, 1970, 65, 845-852.
Urry et al., "Distortions in circular dichroism patterns of particulate (or membranous) systems," Arch Biochem Biophys, 1968, 128, 802-807.
Urry et al., "Elastic protein-based polymers in soft tissue augmentation and generation," J. Biomater. Sci. Polym. Ed., 1998, 9, 1015-1048.
Urry et al., "Hydrophobicity Scale for Proteins Based on InverseTemperature Transitions," Biopolymers, 1992, 32:1243-1250.
Urry et al., "Physical chemistry of biological free energy transduction as demonstrated by elastic protein-based polymers," J. of Phys. Chem. B., 1997, 101, 11007-11028.
Urry et al., "Temperature dependence of length of elastin and its polypentapeptide," Biochem Biophys Res Commun, 1986, 141, 749-755.
Urry et al., "Temperature of polypeptide inverse temperature transition depends on mean residue hydrophobicity," J. Am. Chem. Soc., 1991, 113(11):4346-4348.
Urry, "Free energy transduction in polypeptides and proteins based on inverse temperature transitions," Prog Biophys Mol Biol, Jan. 1992, 57(1):23-57.
Urry, "Protein elasticity based on conformations of sequential polypeptides: The biological elastic fiber," J Protein Chemistry, 1984, 3, 403-436.
Utada et al., "Monodisperse double emulsions generated from a microcapillary device," Science, 2005, 308: 537-541.
Uversky et al., "Intrinsically disordered proteins as crucial constituents of cellular aqueous two phase systems and coacervates," FEBS Lett, Jan. 2015, 589(1):15-22.
Uversky et al., "Understanding protein non-folding," Biochim Biophys Acta, Elsevier, Jun. 2010, 1804(6):1231-1264.
Uversky, "Protein intrinsic disorder-based liquid-liquid phase transitions in biological systems: Complex coacervates and membraneless organelles," Adv Colloid Interface Sci, 2017, 239: 97-114.
Valkenburg et al., "Targeting the tumour stroma to improve cancer therapy," Nature Reviews Clinical Oncology, Jun. 2018, 15, 366-381.
van der Lee et al., "Classification of intrinsically disordered regions and proteins," Chem Rev, Jul. 2014, 114(13): 6589-6631.
Van Roey et al., "Short linear motifs: ubiquitous and functionally diverse protein interaction modules directing cell regulation," Chem Rev, Jul. 2014, 114(13): 6733-6778.
Van Roy, "Beyond E-cadherin: roles of other cadherin superfamily members in cancer," Nat Rev Cancer, Feb. 2014, 14(2): 121-134.
Vasey et al., "Phase I clinical and Pharmacokinetic study of PK1 (N-(2- Hydroxypropyl)methacrylamide Copolymer Doxorubicin): First member of a New Class of Chemotherapeutic Agents-Drugs-Polymer Conjugates" Clinical Cancer Research, 1999, 5:83-94.
Vazquez-Lombardi et al., "Challenges and Opportunities for Non-Antibody Scaffold Drugs," Drug Discov Today, Oct. 2015, 20(10):1271-83.
Vega et al., "Targeting Doxorubicin to Epidermal Growth Factor Receptors by Site-Specific Conjugation of C225 to Poly(L-Glutamic Acid) through a Polyethylene Glycol Spacer," Pharmaceutical Research, 2003, 20(5):826-832.
Venkataraman et al., "The Effects of Polymeric Nanostructure Shape on Drug Delivery," Adv Drug Deliv Rev, Elsevier, Nov. 2011, 63(14-15):1228-46.
Verma et al., "Effect of surface properties on nanoparticle-cell interactions," Small, Wiley, Jan. 2010, 6(1):12-21.
Veronese et al., "PEGylation, successful approach to drug delivery," Drug Discovery Today, 2005, 10(21):1451-1458.
Veronese, "Peptide and protein PEGylation: a review of problems and solutions," Biomaterials 22, 2001, 405-417.
Vicini et al., "An interinstitutional and interspecialty comparison of treatment outcome data for patients with prostate carcinoma based on predefined prognostic categories and minimum follow-up," Cancer, 2002, 95, 2126-2135.
Viegas et al., "Polyoxazoline: Chemistry, properties and applications," Bioconjugate Chem., May 2011, 22(5): 976-986.
Vlieghe et al., "Synthetic therapeutic peptides: science and market," Drug Discovery Today, Jan. 2010, 15(1-2): 40-56.
Voelker et al., "Alteration of the specificity and regulation of fatty acid synthesis of *Escherichia coli* by expression of a plant medium-chain acyl-acyl carrier protein thioesterase," J Bacteriol., 1994, 176(23):7320-7.

(56) References Cited

OTHER PUBLICATIONS

Volkova et al., "Anthracycline Cardiotoxicity: Prevalence, Pathogenesis and Treatment," Curr. Cardiol. Rev., Nov. 2011, vol. 7, No. 4, pp. 214-220.
Volodkin et al., "One-Step Formulation of Protein Microparticles with Tailored Properties: Hard Templating at Soft Conditions," Advanced Functional Materials, 2012, 22: 1914-1922.
von Roemeling et al., "Breaking Down the Barriers to Precision Cancer Nanomedicine," Trends Biotechnol, Feb. 2017, 35(2):159-171.
Vonarbourg et al., "Evaluation of pegylated lipid nanocapsules versus complement system activation and macrophage uptake," J Biomed Mater Res A, Wiley, Sep. 2006, 78(3):620-8.
Vrhovski et al., "Biochemistry of tropoelastin," Eur J Biochem, 1998, 258, 1-18.
Vrhovski et al., "Coacervation Characteristics of Recombinant Human Tropoelastin," European Journal of Biochemistry, 1997, 250(1):92-98.
Vrignaud et al., "Strategies for the nanoencapsulation of hydrophilic molecules in polymer-based nanoparticles," Biomaterials, Nov. 2011, 32(33):8593-8604.
Walczak, "Death Receptor—Ligand Systems in Cancer, Cell Death, and Inflammation," Cold Spring Harb. Perspect. Biol., May 2013, 5(5): a008698.
Wali et al., "Measuring Death of Pancreatic Beta Cells in Response to Stress and Cytotoxic T Cells," Methods in Molecular Biology, Mar. 2015, 1292:165-176.
Walsh et al., "Post-translational modifications in the context of therapeutic proteins," Nat. Biotechnol., Oct. 2006, 24(10): 1241-1252.
Walsh et al., "Posttranslationale Proteinmodifikation: die Chemie der Proteomdiversifizierung," Angew Chem, 2005, 117, 7508-7539.
Walsh et al., "Protein posttranslational modifications: The chemistry of proteome diversifications," Angew. Chem. Int. Ed., 2005, 44, 7342-7372.
Wang et al., "A Molecular Grammar Governing the Driving Forces for Phase Separation of Prion-like RNA Binding Proteins," Cell, Jul. 2018, 174(3):688-699.e616.
Wang et al., "Enhanced Tumor Delivery of Gemcitabine via PEG-DSPE/TPGS Mixed Micelles," Mol. Pharm., Apr. 2014, 11(4): 1140-1150.
Wang et al., "Extending Half Life of H-Ferritin Nanoparticle by Fusing Albumin Binding Domain for Doxorubicin Encapsulation," Biomacromolecules, Mar. 2018, 19(3):773-781.
Wang et al., "Functional polymeric microparticles engineered from controllable microfluidic emulsions," Acc Chem Res, 2014, 47: 373-384.
Wang et al., "More effective nanomedicines through particle design," Small, Wiley, Jul. 2011, 7(14):1919-31.
Wang et al., "Nanoparticle delivery of cancer drugs," Annu Rev Med, Annual Reviews, Feb. 2012, 63:185-98.
Wang et al., "Quantitative Mapping of the Spatial Distribution of Nanoparticles in Endo-Lysosomes by Local pH," Nano Lett., Feb. 2017, 17(2): 1226-1232.
Wang et al., "Size and dynamics of caveolae studied using nanoparticles in living endothelial cells," ACS nano, Dec. 2009, 3(12): p. 4110-4116.
Wang et al., "Stimuli-responsive Dendrimers in Drug Delivery," Biomater Sci, Mar. 2016, 4(3):375-90.
Wang et al., "The Weak Link: Optimization of the Ligand-Nanoparticle Interface to Enhance Cancer Cell Targeting by Polymer Micelles," Nano Lett Oct. 2017, 17(10):5995-6005.
Waterman et al., "Edema associated with I-125 or Pd-103 prostate brachytherapy and its impact on post-implant dosimetry: an analysis based on serial CT acquisition," International journal of radiation oncology, biology, physics, 1998, 41, 1069-1077.
Wechsel et al., "Renal Cell Carcinoma: Immunohistological Investigation of Expression of the Integrin αvβ3," Anticancer research, 1999, 19(2C):1529-1532.
Wei et al., "Anticancer drug nanomicelles formed by self-assembling amphiphilic dendrimer to combat cancer drug resistance," Proceedings of the National Academy of Sciences of the United States of America, Mar. 2015, 112(10): 2978-2983.
Wei et al., "Fibroblast growth factor 21 promotes bone loss by potentiating the effects of peroxisome proliferator-activated receptor γ," Proc Natl Acad Sci USA, Feb. 2012, 109(8):3143-3148.
Weis et al., "αV Integrins in Angiogenesis and Cancer," Cold Spring Harb Perspect Med, Cold Spring Harbor Laboratory Press, Sep. 2011, 1(1):a006478.
Weitzhandler et al., "Micellar Self-Assembly of Recombinant Resilin-/Elastin-Like Block Copolypeptides," Biomacromolecules, Aug. 2017, 18(8):2419-2426.
Wendt et al., "DNA-mediated Folding and Assembly of MyoD-E47 Heterodimers," Journal of Biol. Chem., 1998, 273(10):5735-5743.
Wente et al., "Fibroblast Growth Factor-21 Improves Pancreatic β-Cell Function and Survival by Activation of Extracellular Signal—Regulated Kinase 1/2 and Akt Signaling Pathways," Diabetes, Sep. 2006, 55(9):2470-2478.
Werle et al., "Strategies to improve plasma half life time of peptide and protein drugs," Amino Acids 30, Jun. 2006, 30(4):351-367.
Wienkers et al., "Predicting in vivo drug interactions from in vitro drug discovery data," Nat. Rev. Drug. Discov. 2005, 4(10):825-833.
Wilkins et al., "Hydrodynamic Radii of Native and Denatured Proteins Measured by Pulse Field Gradient NMR Techniques," Biochemistry, 1999, 38(50):16424-16431.
Williams et al., "Targeted radionuclide therapy," Medical Physics, Jul. 2008, 35(7): 3062-3068.
Williamson et al., "Efficient N-terminal labeling of proteins by use of sortase," Angew Chem Int ed Engl, Sep. 2012, 51(37):9377-9380.
Wimley et al., "Experimentally determined hydrophobicity scale for proteins at membrane interfaces," Nature Structural & Molecular Biology, 1996, 3(10):842-848.
Winzell et al., "The high-fat diet-fed mouse: a model for studying mechanisms and treatment of impaired glucose tolerance and type 2 diabetes," Diabetes 53, 2004, S215-S219.
Wold, "In vivo chemical modification of proteins," Annu. Rev. Med., 1981, 50, 783-814.
Wood et al., "Experiences Using Chloramine-T and 1,3,4,6-Tetrachloro-3-Alpha,6-Alpha-Diphenylglycoluril (lodogen) for Radioiodination of Materials for Radioimmunoassay," J Clin Chem Clin Bio, 1981, 19, 1051-1056.
Wright et al., "Intrinsically disordered proteins in cellular signalling and regulation," Nat Rev Mol Cell Biol, Jan. 2015, 16(1):18-29.
Wright et al., "Self-assembly of block copolymers derived from elastin-mimetic polypeptide sequences," Advanced Drug Delivery Reviews, 2002, 54, 1057-1073.
Wright et al., "Thermoplastic elastomer hydrogels via self-assembly of an elastin-mimetic triblock polypeptide," Advanced Functional Materials, 2002, 12, 149-154.
Wu et al., "Site-specific chemical modification of recombinant proteins produced in mammalian cells by using the genetically encoded aldehyde tag," Proc Natl Acad Sci USA, Mar. 2009, 106(9):3000-3005.
Wu et al., "Sortase A-Catalyzed Transpeptidation of Glycosylphosphatidylinositol Derivatives for Chemoenzymatic Synthesis of GPI-Anchored Proteins," J. Am. Chem. Soc., Feb. 2010, 132(5): 1567-1571.
Wust et al., "Hyperthermia in combined treatment of cancer," The Lancet Oncology, 2002, 3, 487-497.
Xavier et al., "HPLC Method for the Dosage of Paclitaxel in Copaiba Oil: Development, Validation, Application to the Determination of the Solubility and Partition Coefficients," Chromatographia, Apr. 2016, 79(7-8): 405-412.
Xia et al., "Tunable self-assembly of genetically engineered silk—elastin-like protein polymers," Biomacromolecules, Nov. 2011, 12(11): 3844-3850.
Xie et al., "The Effect of Shape on Cellular Uptake of Gold Nanoparticles in the Forms of Stars, Rods, and Triangles," Sci Rep, Jun. 2017, 7(1):3827.

(56) References Cited

OTHER PUBLICATIONS

Xiong et al., "Engineering of amphiphilic block copolymers for polymeric micellar drug and gene delivery," J Control Release, Elsevier, Oct. 2011, 155(2):248-61.
Xu et al., "A quality by design (QbD) case study on liposomes containing hydrophilic API: II. Screening of critical variables, and establishment of design space at laboratory scale," Int. J. Pharm., Feb. 2012, 423(2):543-553.
Xu et al., "Downregulation of GLP-1 and GIP Receptor Expression by Hyperglycemia," Diabetes, Jun. 2007, 56(6):1551-58.
Xu et al., "Exendin-4 stimulates both beta-cell replication and neogenesis, resulting in increased beta-cell mass and improved glucose tolerance in diabetic rats," Diabetes 48, 1999, 2270-2276.
Xu et al., "Fibroblast Growth Factor 21 Reverses Hepatic Steatosis, Increases Energy Expenditure, and Improves Insulin Sensitivity in Diet-Induced Obese Mice," Diabetes, Jan. 2009, 58(1):250-259.
Xu et al., "Genetically engineered block copolymers: influence of the length and structure of the coiled-coil blocks on hydrogel self-assembly," Pharm Res, Mar. 2008, 25, 674-682.
Xu et al., "Inorganic nanoparticles as carriers for efficient cellular delivery," Chemical Engineering Science, Elsevier, Feb. 2006, 61(3):1027-1040.
Xu et al., "Role of pancreatic stellate cells in pancreatic cancer metastasis," Am J of Pathology, Nov. 2010, 177(5): 2585-2596.
Xu et al., "Self-assembly behavior of peptide amphiphiles (PAs) with different length of hydrophobic alkyl tails," Colloids Surfaces B Biointerfaces, Nov. 2010, 81(1): 329-335.
Yamamoto et al., "ATRP Synthesis of Thermally Responsive Molecular Brushes from Oligo(ethylene oxide) Methacrylates," Macromolecules, Dec. 2007, 40(26): 9348-9353.
Yang et al., "Long Term Exendin-4 Treatment Reduces Food Intake and Body Weight and Alters Expression of Brain Homeostatic and Reward Markers," Endocrinology, Sep. 2014, 155(9): 3473-3483.
Yang et al., "Poly(carboxybetaine) nanomaterials enable long circulation and prevent polymer-specific antibody production," Nano Today, Feb. 2014, 9(1):10-16.
Yates et al., "Contemporary management of patients with high-risk non-muscle-invasive bladder cancer who fail intravesical BCG therapy," World journal of urology, May 2011, 29(4): 415-422.
Yeh et al., "Micromolding of shape-controlled, harvestable cell-laden hydrogels," Biomaterials, 2006, 27: 5391-5398.
Yeo et al., "Coacervation of tropoelastin," Adv Colloid Interface Sci, Sep. 2011, 167(1-2):94-103.
Yokoe et al., "Albumin-conjugated PEG liposome enhances tumor distribution of liposomal doxorubicin in rats," International Journal of Pharmaceutics, May 2008, 353(1-2): 28-34.
Yoo et al., "A systemic Small RNA Signaling System in Plants" The Plant Cell (2004) vol. 16, pp. 1979-2000.
Yoo et al., "Biodegradable Nanoparticles Containing Doxorubicin-Plga Conjugate for Sustained Release," Pharm. Res., 1999, 16(7):1114-1118.
Youn et al., "Evaluation of therapeutic potentials of site-specific PEGylated glucagon-like peptide-1 isomers as a type 2 anti-diabetic treatment: Insulinotropic activity, glucose-stabilizing capability, and proteolytic stability" Biochem. Pharmacol, 2007, 73: 84-93.
Youn et al., "High-yield production of biologically active mono-PEGylated salmon calcitonin by site-specific PEGylation," J. Control. Release, Feb. 2007, 117(3):371-379.
Yousefpour et al., "Co-opting biology to deliver drugs," Biotechnol Bioeng, Sep. 2014, 111(9): p. 1699-1716.
Yousefpour et al., "Genetically Encoding Albumin Binding into Chemotherapeutic-loaded Polypeptide Nanoparticles Enhances Their Antitumor Efficacy," Nano Lett., Dec. 2018, 18(12): 7784-7793.
Yu et al., "Effectiveness and security of CT-guided percutaneous implantation of (125)l seeds in pancreatic carcinoma," The British journal of radiology, Jul. 2014, 87(1039): 20130642, 7 pages.
Yusta et al., "GLP-1 receptor activation improves β cell function and survival following induction of endoplasmic reticulum stress," Cell Metab, Nov. 2006, 4(5):391-406.
Zhang et al., "A self-assembly pathway to aligned monodomain gels," Nat. Mater., Jul. 2010, 9(7): 594-601.
Zhang et al., "In Depth Analysis on the Unusual Multistep Aggregation Process of Oligo(ethylene glycol) Methacrylate-Based Polymers in Water," Macromolecules, Jul. 2014, 47(14): 4728-4737.
Zhang et al., "Nanoparticles in medicine: therapeutic applications and developments," Clin. Pharmacol. Ther., May 2008, 83(5):761-769.
Zhang et al., "Novel agents for pancreatic ductal adenocarcinoma: emerging therapeutics and future directions," Jounral of Hematology & Oncology, Jan. 2018, 11:14, 17 pages.
Zhang et al., "Sensitive and Quantitative Detection of Anti-Poly(ethylene glycol) (PEG) Antibodies by Methoxy-PEG-Coated Surface Plasmon Resonance Sensors," Anal Chem, Aug. 2017, 89(16): 8217-8222.
Zhang et al., "Shape Effects of Nanoparticles Conjugated with Cell-Penetrating Peptides (HIV Tat PTD) on CHO Cell Uptake," Bioconjugate Chem, Sep. 2008, 19(9):1880-1887.
Zhao et al., "A new Bliss Independence model to analyze drug combination data," J Biomol Screen, Jun. 2014, 19(5): 817-821.
Zhao et al., "Cellular uptake, intracellular trafficking, and cytotoxicity of nanomaterials," Small, Wiley, May 2011, 7(10):1322-37.
Zhao et al., "Fluorescence probe techniques used to study micelle formation in water-soluble block copolymers," Langmuir 1990, 6(2):514-516.
Zhao et al., "Tumor αvβ3 Integrin Is a Therapeutic Target for Breast Cancer Bone Metastases," Cancer Res, AACR Publications, Jun. 2007, 67(12):5821-30.
Zimm, "Apparatus and Methods for Measurement and Interpretation of the Angular Variation of Light Scattering; Preliminary Results on Polystyrene Solutions," J. Chem. Phys. 1948, 16, 1099-1116.
Zini et al., "Contemporary management of adrenocortical carcinoma," European urology, Nov. 2011, 60(5): 1055-1065.
Zong et al., "Crystal structures of *Staphylococcus aureus* sortase A and its substrate complex," J. Biol. Chem. 279, 2004, 31383-31389.
Zununi Vahed et al., "Targeted cancer drug delivery with aptamer-functionalized polymeric nanoparticles," Journal of drug targeting, Mar. 2019, 27(3):292-299.
International Search Report and Written Opinion for Application No. PCT/US2008/084159 dated Feb. 27, 2009 (8 pages).
International Search Report and Written Opinion for Application No. PCT/US2016/024202 dated Aug. 26, 2016 (9 pages).
International Search Report and Written Opinion for Application No. PCT/US2016/045655 dated Dec. 2, 2016 (13 pages).
International Search Report and Written Opinion for Application No. PCT/US2016/068141 dated Jul. 19, 2017 (12 pages).
International Search Report and Written Opinion for Application No. PCT/US2016/068142 dated Jul. 19, 2017 (12 pages).
International Search Report and Written Opinion for Application No. PCT/US2018/032785 dated Sep. 25, 2018 (16 pages).
International Search Report and Written Opinion for Application No. PCT/US2017/035530 dated Aug. 23, 2017 (13 pages).
International Search Report and Written Opinion for Application No. PCT/US2017/052887 dated Jan. 26, 2018 (20 pages).
International Search Report and Written Opinion for Application No. PCT/US2017/051661 dated Jan. 2, 2018 (12 pages).
International Search Report and Written Opinion for Application No. PCT/US2018/013611 dated May 30, 2018 (18 pages).
International Search Report and Written Opinion for Application No. PCT/US2018/040409 dated Nov. 5, 2018 (16 pages).
International Search Report and Written Opinion for Application No. PCT/US2019/015176 dated Jun. 3, 2019 (12 pages).
International Search Report and Written Opinion for Application No. PCT/US2019/023583 dated Jul. 5, 2019 (10 pages).
International Search Report and Written Opinion for Application No. PCT/US2019/030022 dated Jul. 25, 2019 (8 pages).
International Search Report and Written Opinion for Application No. PCT/US2019/044911 dated Dec. 10, 2019 (11 pages).
International Search Report and Written Opinion for Application No. PCT/US2019/050077 dated Jan. 27, 2020 (19 pages).
International Search Report and Written Opinion for Application No. PCT/US2019/061144 dated May 21, 2020 (15 pages).

(56) References Cited

OTHER PUBLICATIONS

United States Patent Office Action for U.S. Appl. No. 13/904,836 dated Mar. 27, 2014 (10 pages).
United States Patent Office Notice of Allowance for U.S. Appl. No. 13/904,836 dated Jul. 30, 2014 (6 pages).
United States Patent Office Action for U.S. Appl. No. 13/942,037 dated Jan. 15, 2016 (19 pages).
United States Patent Office Action for U.S. Appl. No. 13/942,037 dated Jun. 4, 2015 (33 pages).
United States Patent Office Action for U.S. Appl. No. 13/942,037 dated Nov. 28, 2016 (22 pages).
United States Patent Office Action for U.S. Appl. No. 13/942,037 dated Feb. 9, 2018 (29 pages).
United States Patent Office Notice of Allowance for U.S. Appl. No. 13/245,459 dated Feb. 27, 2013 (13 pages).
United States Patent Office Action for U.S. Appl. No. 14/572,391 dated Oct. 26, 2016 (11 pages).
United States Patent Office Notice of Allowance for U.S. Appl. No. 14/572,391 dated Jun. 16, 2017 (10 pages).
United States Patent Office Action for U.S. Appl. No. 15/387,536 dated Sep. 27, 2018 (11 pages).
United States Patent Office Action for U.S. Appl. No. 15/387,540 dated Sep. 27, 2018 (12 pages).
United States Patent Office Action for U.S. Appl. No. 15/561,799 dated Dec. 27, 2018 (8 pages).
United States Patent Office Notice of Allowance for U.S. Appl. No. 15/387,536 dated Mar. 13, 2019 (13 pages).
United States Patent Office Notice of Allowance for U.S. Appl. No. 15/561,799 dated Apr. 2, 2019 (6 pages).
United States Patent Office Notice of Allowance for U.S. Appl. No. 15/387,540 dated Apr. 17, 2019 (9 pages).
United States Patent Office Action for U.S. Appl. No. 16/058,924 dated Nov. 26, 2019 (23 pages).
United States Patent Office Action for U.S. Appl. No. 16/064,424 dated Apr. 22, 2020 (18 pages).
United States Patent Office Action for U.S. Appl. No. 16/064,425 dated Apr. 22, 2020 (18 pages).
United States Patent Office Action for U.S. Appl. No. 16/058,924 dated Jul. 6, 2020 (51 pages).
United States Patent Office Action for U.S. Appl. No. 15/749,797 dated May 11, 2020 (14 pages).
United States Patent Office Action for U.S. Appl. No. 15/749,797 dated Oct. 20, 2020 (16 pages).
United States Patent Office Action for U.S. Appl. No. 16/335,734 dated Nov. 20, 2020 (15 pages).
United States Patent Office Action for U.S. Appl. No. 16/525,374 dated Dec. 7, 2020 (9 pages).
United States Patent Office Action for U.S. Appl. No. 16/305,696 dated Jan. 28, 2021 (15 pages).
United States Patent Office Notice of Allowance for U.S. Appl. No. 16/332,865 dated Apr. 2, 2021 (10 pages).
United States Patent Office Action for U.S. Appl. No. 16/477,229 dated Apr. 12, 2021 (14 pages).
Ren et al., "Stimulus-Responsive Polymer Prodrugs," Progress in Chemistry, 2013, 25(5): 10 pages.
United States Patent Office Action for U.S. Appl. No. 16/614,282 dated Apr. 27, 2022 (15 pages).
United States Patent Office Notice of Allowance for U.S. Appl. No. 16/305,696 dated May 23, 2022 (10 pages).
United States Patent Office Notice of Allowance for U.S. Appl. No. 16/305,696 dated Jun. 10, 2022 (4 pages).
United States Patent Office Notice of Allowance for U.S. Appl. No. 15/749,797 dated Jun. 2, 2022 (6 pages).
United States Patent Office Action for U.S. Appl. No. 16/477,229 dated Jun. 13, 2022 (11 pages).
U.S. Appl. No. 13/245,459, filed Sep. 26, 2011, U.S. Pat. No. 8,470,967, Jun. 25, 2013.
U.S. Appl. No. 13/904,836, filed May 29, 2013, U.S. Pat. No. 8,912,310, Dec. 16, 2014.
U.S. Appl. No. 14/572,391, filed Dec. 16, 2014, U.S. Pat. No. 9,771,396, Jun. 25, 2013.
U.S. Appl. No. 15/679,751, filed Aug. 17, 2017, 2018/0037609, Feb. 8, 2018.
U.S. Appl. No. 62/138,847, filed Mar. 26, 2015.
PCT/US2016/024202, Mar. 25, 2016, WO2016/154530, Sep. 26, 2016.
U.S. Appl. No. 15/561,799, filed Sep. 26, 2017, U.S. Pat. No. 10,385,115, Aug. 20, 2019.
U.S. Appl. No. 16/525,374, filed Jul. 29, 2019, 2019/0345228, Nov. 14, 2019.
U.S. Appl. No. 62/399,123, filed Sep. 23, 2016.
PCT/US2017/052887, Sep. 22, 2017, WO2018/057847, Mar. 29, 2018.
U.S. Appl. No. 16/335,734, filed Mar. 22, 2019, 2020/0017557, Jan. 16, 2020.
U.S. Appl. No. 13/942,037, filed Jul. 15, 2015, 2014/0024600, Jan. 23, 2014.
U.S. Appl. No. 16/058,924, filed Aug. 8, 2018, 2019/0023743, Jan. 24, 2019.
U.S. Appl. No. 62/270,401, filed Dec. 21, 2015.
U.S. Appl. No. 62/310,534, filed Mar. 18, 2016.
U.S. Appl. No. 62/329,800, filed Apr. 29, 2016.
U.S. Appl. No. 62/407,403, filed Oct. 12, 2016.
PCT/US2016/068141, Dec. 21, 2016, WO2017/112825, Jun. 29, 2017.
PCT/US2016/068142, Dec. 21, 2016, WO2017/112826, Jun. 29, 2017.
U.S. Appl. No. 15/387,536, filed Dec. 21, 2016, U.S. Pat. No. 10,364,451, Jul. 30, 2019.
U.S. Appl. No. 15/387,540, filed Dec. 21, 2016, U.S. Pat. No. 10,392,611, Aug. 27, 2019.
U.S. Appl. No. 16/064,424, filed Jun. 20, 2018, 2019/0015520, Jan. 17, 2019.
U.S. Appl. No. 16/064,425, filed Sep. 12, 2016, 2018/0369399, Dec. 27, 2018.
U.S. Appl. No. 62/506,593, filed May 15, 2017.
U.S. Appl. No. 62/534,442, filed Jul. 19, 2017.
U.S. Appl. No. 62/544,720, filed Aug. 11, 2017.
U.S. Appl. No. 62/545,313, filed Aug. 14, 2017.
PCT/US20168/032785, May 15, 2018, WO2018/213320, Nov. 22, 2018.
U.S. Appl. No. 16/614,282, filed Nov. 15, 2019.
U.S. Appl. No. 62/200,726, filed Aug. 4, 2015.
PCT/US2016/045655, Aug. 4, 2016, WO2017/024182, Feb. 9, 2017.
U.S. Appl. No. 15/749,797, filed Feb. 2, 2018, 2018/0228908, Aug. 16, 2018.
U.S. Appl. No. 62/394,662, filed Sep. 14, 2016.
PCT/US2017/051661, Sep. 14, 2017, WO2018/053201, Mar. 22, 2018.
U.S. Appl. No. 16/332,865, filed Mar. 13, 2019, 2020/0164082, May 28, 2020.
U.S. Appl. No. 62/445,504, filed Jan. 12, 2017.
U.S. Appl. No. 62/479,977, filed Mar. 31, 2017.
PCT/US2018/013611, Jan. 12, 2018, WO2018/132732, Jul. 19, 2018.
U.S. Appl. No. 16/477,229, filed Jul. 11, 2019, 2019/0328662, Oct. 31, 2019.
U.S. Appl. No. 62/527,836, filed Jun. 30, 2017.
U.S. Appl. No. 62/534,019, filed Jul. 18, 2017.
PCT/US2018/040409, Jun. 29, 2018, WO2019/006374, Jan. 3, 2019.
U.S. Appl. No. 16/625,899, filed Dec. 23, 2019, 2020/0148724, May 14, 2020.
U.S. Appl. No. 62/343,926, filed Jun. 1, 2016.
U.S. Appl. No. 62/414,877, filed Oct. 31, 2016.
PCT/US2017/035530, Jun. 1, 2017, WO2017/210476, Dec. 7, 2018.
U.S. Appl. No. 16/305,696, filed Nov. 29, 2018, 2020/0378916, Dec. 3, 2020.
U.S. Appl. No. 62/767,736, filed Nov. 15, 2018.
PCT/US2019/061144, Nov. 13, 2019, WO2020/102324, May 22, 2020.

(56) References Cited

OTHER PUBLICATIONS

U.S. Appl. No. 17/294,368, filed May 14, 2021.
U.S. Appl. No. 62/622,249, filed Jan. 26, 2018.
PCT/US2019/015176, Jan. 25, 2019, WO2019/147954, Aug. 1, 2019.
U.S. Appl. No. 16/964,832, filed Jul. 24, 2020.
U.S. Appl. No. 62/647,199, filed Mar. 23, 2018.
PCT/US2019/023583, Mar. 22, 2019, WO2019/183476, Sep. 26, 2019.
U.S. Appl. No. 62/664,512, filed Apr. 30, 2018.
PCT/US2019/030022, Apr. 30, 2019, WO2019/213150, Nov. 7, 2019.
U.S. Appl. No. 17/051,202, filed Oct. 28, 2020.
U.S. Appl. No. 62/700,939, filed Jul. 20, 2018.
U.S. Appl. No. 62/873,306, filed Jul. 12, 2019.
U.S. Appl. No. 16/927,982, filed Jul. 13, 2020, 2021/0009999, Jan. 14, 2021.
U.S. Appl. No. 62/713,752, filed Aug. 2, 2018.
PCT/US2019/044911, Aug. 2, 2019, WO2020/028806, Feb. 6, 2020.
U.S. Appl. No. 17/265,165, filed Feb. 1, 2021.
U.S. Appl. No. 62/985,174, filed Mar. 4, 2020.
U.S. Appl. No. 62/985,179, filed Mar. 4, 2020.
U.S. Appl. No. 62/898,353, filed Sep. 12, 2019.
U.S. Appl. No. 17/015,315, filed Sep. 9, 2020, 2021/0046188, Feb. 18, 2021.
U.S. Appl. No. 62/975,479, filed Feb. 12, 2020.
PCT/US2021/017809, Feb. 12, 2021.
Alghoul et al., "The effect of hyaluronan hydrogel on fat graft survival," Aesthet Surg J, 2012, 32: 622-633.
American Society of Plastic Surgeons, "2017 Plastic Surgery Statistics Report," Oct. 2018, 25 pages.
Balaji, "Subdermal fat grafting for Parry-Romberg syndrome," Ann Maxillofac Surg, 2014, 4: 55-59.
Banyard et al., "Preparation, Characterization, and Clinical Implications of Human Decellularized Adipose Tissue Extracellular Matrix (hDAM): A Comprehensive Review," Aesthet Surg J, 2016, 36: 349-357.
Bennett et al., "Association of Fat Grafting With Patient-Reported Outcomes in Postmastectomy Breast Reconstruction," JAMA Surg, 2017, 152: 944-950.
Brzezienski et al., "Autologous Fat Grafting to the Breast Using Revolve System to Reduce Clinical Costs," Ann Plast Surg, 2016, 77: 286-289.
Chang et al., "Thermoprecipitation of Glutathione S-Transferase by Glutathione-Poly(N-isopropylacrylamide) Prepared by RAFT Polymerization," Macromolecular Rapid Communications, Oct. 2010, 31: 1691-1695.
De Leon-Rodriguez et al., "Multifunctional thermoresponsive designer peptide hydrogels," Acta Biomaterialia, 2017, 47: 40-49.
Eom et al., "The number of operations required for completing breast reconstruction," Plast Reconstr Surg Glob Open, 2012, 2: e242.
Frandsen et al., "Recombinant protein-based polymers for advanced drug delivery," Chem Soc Rev, 2012, 41: 2696-2706.
Gabriel et al., "Fat grafting and breast reconstruction: tips for ensuring predictability," Gland Surg, 2015, 4: 232-243.
Gylbert, "Applanation tonometry for the evaluation of breast compressibility," Scand J Plast Reconstr Surg Hand Surg, 1989, 23: 223-229.
Hess et al., "Graphene Transistors for Multifunctional Polymer Brushes for Biosensing Applications," Applied Materials & Interfaces, 2014, 6: 9705-9710.
Hsu et al., "Fat grafting's past, present, and future: why adipose tissue is emerging as a critical link to the advancement of regenerative medicine," Aesthet Surg J, 2015, 32: 892-899.
Hwang et al., "Synthesis and Characterization of Polystyrene Brushes for Organic Thin Film Transistors," Journal of Nanoscience and Nanotechnology, 2012, 12: 4137-4141.
Kronowitz et al., "Delayed-Immediate Breast Reconstruction," Plastic and Reconstructive Surgery, 2004, 113: 1617- 1628.
Minteer et al., "Fat Grafting for Pedal Fat Pad Atrophy in a 2-Year, Prospective, Randomized, Crossover, Single-Center Clinical Trial," Plast Reconstr Surg, 2018, 142: 862e-871e.
Pan et al., "A Pig Model for the Histological Analysis of Adipocytes after Co—injections of Autologous Fat with Fillers," International Journal of Surgery & Surgical Techniques, 2016, 2: 7 pages.
Park et al., "Polymer Brush as a Facile Dielectric Surface Treatment for High-Performance, Stable, Soluble Acene-Based Transistors," Chemistry of Materials, 2010, 22: 5377-5382.
Rasmussen et al., "A Novel Porcine Model for Future Studies of Cell-enriched Fat Grafting," Plast Reconstr Surg Glob Open, 2018, 6: e1735.
Roca et al., "Autologous Fat Grafting for Treatment of Breast Implant Capsular Contracture: A Study in Pigs," Aesthet Surg J, 2014, 34: 769-775.
Sandberg et al., "The Structure of the Elastic Fiber: An Overview," The Journal of Investigative Dermatology, 1982, 79(S1): 128s-132s.
Simonacci et al., "Procedure, applications, and outcomes of autologous fat grafting," Ann Med Surg (Lond), 2017, 20: 49-60.
Strong et al., "The Current State of Fat Grafting: A Review of Harvesting, Processing, and Injection Techniques," Plast Reconstr Surg, 2015, 136: 897-912.
Tamburro et al., "Fractal aspects of elastin supramolecular organization," J Biomol Struct Dyn, 1995, 12: 1161-1172.
Toshima et al., "Three-dimensional architecture of elastin and collagen fiber networks in the human and rat lung," Arch Histol Cytol, 2004, 67: 31-40.
UniProtKB—P15214 (GST_PROMI) acessed online at <https://www.uniprot.org/uniprot/P152146/> on Jun. 8, 2021, 7 pages.
Wang et al., "Pigs Can Be Used as a Large Animal Model for Autologous Fat Grafting," Ophthalmic Plast Reconstr Surg, 2016, 32: 73-74.
Wu et al., "An injectable adipose matrix for soft-tissue reconstruction," Plast Reconstr Surg, 2012, 129: 1247-1257.
United States Patent Office Action for U.S. Appl. No. 15/749,797 dated May 12, 2021 (19 pages).
United States Patent Office Notice of Allowance for U.S. Appl. No. 16/332,865 dated May 17, 2021 (5 pages).
United States Patent Office Notice of Allowance for U.S. Appl. No. 16/335,734 dated Jun. 16, 2021 (9 pages).
United States Patent Office Action for U.S. Appl. No. 16/305,696 dated Jun. 22, 2021 (20 pages).
Chen et al., "Polyethylene Glycol Immunogenicity: Theoretical, Clinical, and Practical Aspects of Anti-Polyethylene Glycol Antibodies," ACS Nano, 2021, 15(9): 14022-14048.
United States Patent Office Action for U.S. Appl. No. 17/294,368 dated Sep. 12, 2024 (11 pages).
Antonicelli et al., "Elastin-elastases and inflamm-aging," Curr Top Dev Biol, 2007, 79: 99-155.
Carvalho et al., "Modern Trends for Peripheral Nerve Repair and Regeneration: Beyond the Hollow Nerve Guidance Conduit," Front Bioeng Biotechnol, 2019, 7: 337.
Gu et al., "Construction of tissue engineered nerve grafts and their application in peripheral nerve regeneration," Prog Neurobiol, 2011, 93: 204-230.
Heggestad et al., "Rapid test to assess the escape of SARS-CoV-2 variants of concern," Science Advances, 2021, 7 (49): 1-12.
Mohammad et al., "Development and validation of a rapid and easy-to-perform point-of-care lateral flow immunoassay (LFIA) for the detection of SARS-CoV-2 spike protein," Frontiers in Immunology, 2023, 14: 1-15.
Parker et al., "Nerve guidance conduit development for primary treatment of peripheral nerve transection injuries: A commercial perspective," Acta Biomater, 2021, 135: 64-86.
Roberts et al., "Complex microparticle architectures from stimuli-responsive intrinsically disordered proteins," Nat Commun, 2020, 11: 1342.
Rosso et al., "Implications of Schwann Cells Biomechanics and Mechanosensitivity for Peripheral Nervous System Physiology and Pathophysiology," Front Mol Neurosci, 2017, 10: 345.

(56) References Cited

OTHER PUBLICATIONS

Rosso et al., "Schwann cells and neurite outgrowth from embryonic dorsal root ganglions are highly mechanosensitive," Nanomedicine, 2017, 13: 493-501.
Saffari et al., "Surgical Angiogenesis of Decellularized Nerve Allografts Improves Early Functional Recovery in a Rat Sciatic Nerve Defect Model," Plast Reconstr Surg, 2021, 148: 561-570.
Saffari et al., "The role of vascularization in nerve regeneration of nerve graft," Neural Regen Res, 2020, 15: 1573-1579.
Shakhbazau et al., "Aligned collagen-GAG matrix as a 3D substrate for Schwann cell migration and dendrimer-based gene delivery," J Mater Sci Mater Med, 2014, 25: 1979-1989.
Taskindoust et al., "Recombinant Elastin Biomatrix Improves Autologous Fat Grafting for Soft Tissue Reconstruction," Plastic and Reconstructive Surgery Global Open, 2022, 10(10S): 74-75.
Weber, "Improving Cloning Procedures and Particle Architectures of Elastin-like Polypeptide-based Drug Delivery Vehicles," Master Thesis, Duke University, Nov. 13, 2019, 92 pages.
International Search Report and Written Opinion for Application No. PCT/US2023/082105 dated Apr. 10, 2024 (8 pages).
United States Patent Office Action for U.S. Appl. No. 16/964,832 dated Jun. 21, 2024 (6 pages).
United States Patent Office Action for U.S. Appl. No. 18/303,530 dated Jun. 21, 2024 (14 pages).
Singh et al., "Polymeric microneedles for controlled transdermal drug delivery," Journal of Controlled Release, 2019, 315: 97-113.
Vancoillie et al., "Thermoresponsive poly(oligo ethylene glycol acrylates)," Progress in Polymer Science, 2014, 39(6):1074-1095.
Zhang et al., "A triple thermoresponsive schizophrenic diblock copolymer," Polymer Chemistry, 2013, 4(16):4322-4325.
International Search Report and Written Opinion for Application No. PCT/US2024/050476 dated Nov. 25, 2024 (18 pages).
United States Patent Office Notice of Allowance for U.S. Appl. No. 17/051,202 dated Nov. 15, 2024 (7 pages).
United States Patent Office Notice of Allowance for U.S. Appl. No. 16/964,832 dated Jan. 6, 2025 (14 pages).
Adamus et al., "The revival of CpG oligonucleotide-based cancer immunotherapies," Contemp Oncol (Pozn), 2018, 22: 56-60.
Bailey-Downs et al., "Development and characterization of a preclinical model of breast cancer lung micrometastatic to macrometastatic progression," PLoS One, 2014, 9(5): e98624.
Bieniasz-Krzywiec et al., "Isolation and separation of murine tumor-associated macrophages (TAMs) subpopulations from orthotopic 4T1 breast tumors," STAR Protoc, 2021, 2(2): 100481.
Bird, "CpG-rich islands and the function of DNA methylation," Nature, 1986, 321(6067): 209-213.
Bode et al., "CpG DNA as a vaccine adjuvant," Expert Rev Vaccines, 2011, 10: 499-511.
Bonaventura et al., "Cold Tumors: A Therapeutic Challenge for Immunotherapy," Front Immunol, 2019, 10: 168.
Borden et al., "Cancer Neoantigens: Challenges and Future Directions for Prediction, Prioritization, and Validation," Frontiers in Oncology, 2022, 12: 836821.
Brincker, "Direct intratumoral chemotherapy," Critical Reviews in Oncology/Hematology, 1993, 15: 91-98.
Chen et al., "Hypoxic microenvironment in cancer: molecular mechanisms and therapeutic interventions," Signal Transduct Target Ther, 2023, 8: 70.
D'Alterio et al., "Paradoxical effects of chemotherapy on tumor relapse and metastasis promotion," Seminars in Cancer Biology, 2020, 60: 351-361.
De Gassart et al., "MHC class II stabilization at the surface of human dendritic cells is the result of maturation-dependent March I down-regulation," Proceedings of the National Academy of Sciences, 2008, 105(9): 3491-3496.
de Jong et al., "The immunostimulatory activity of unmethylated and methylated CpG oligodeoxynucleotide is dependent on their ability to colocalize with TLR9 in late endosomes," The Journal of Immunology, 2010, 184(11): 6092-6102.
Deng et al., "Doxorubicin and CpG loaded liposomal spherical nucleic acid for enhanced Cancer treatment," Journal of Nanobiotechnology, 2022, 20: 140.
Dillekås et al., "Are 90% of deaths from cancer caused by metastases?" Cancer Med, 2019, 8(12): 5574-5576.
Dongye et al., "Toll-like receptor 9 agonists and combination therapies: strategies to modulate the tumour immune microenvironment for systemic anti-tumour immunity," British Journal of Cancer, 2022, 127: 1584-1594.
duPre et al., "Murine mammary carcinoma 4T1 induces a leukemoid reaction with splenomegaly: association with tumor-derived growth factors," Experimental and Molecular Pathology, 2007, 82: 12-24.
Erkamp et al., "Spatially non-uniform condensates emerge from dynamically arrested phase separation," Nature Communications, 2023, 14: 684.
Hosseinpour et al., "Improving tumor treatment through intratumoral injection of drug-loaded magnetic nanoparticles and low-intensity ultrasound," Scientific Reports, 2024, 14: 1452.
Hu et al., "Harnessing innate immune pathways for therapeutic advancement in cancer," Signal Transduction and Targeted Therapy, 2024, 9: 68.
Jakob et al., "Activation of Cutaneous Dendritic Cells by CpG-Containing Oligodeoxynucleotides: A Role for Dendritic Cells in the Augmentation of Th1 Responses by Immunostimulatory DNA," The Journal of Immunology, 1998, 161: 3042-3049.
Jenkins et al., "Genetically Encoded Elastin-Like Polypeptides for Drug Delivery," Advanced Healthcare Materials, 2021, 10(13): 2100209.
Kashkooli et al., "Controlled anti-cancer drug release through advanced nano-drug delivery systems: Static and dynamic targeting strategies," Journal of Controlled Release, 2020, 327: 316-349.
Kayraklioglu et al., "CpG Oligonucleotides as Vaccine Adjuvants," Methods Mol Biol, 2021, 2197: 51-85.
Kelly et al., "Intratumoral delivery of brachytherapy and immunotherapy by a thermally triggered polypeptide depot," J Control Release, 2022, 343: 267-276.
Kim et al., "Eradication of metastatic mouse cancers resistant to immune checkpoint blockade by suppression of myeloid-derived cells," Proceedings of the National Academy of Sciences, 2014, 111(32): 11774-11779.
Krishnamachari et al., "Innovative strategies for co-delivering antigens and CpG oligonucleotides," Adv Drug Deliv Rev, 2009, 61(3): 205-217.
Landmann et al., "Maturation of dendritic cells is accompanied by rapid transcriptional silencing of class II transactivator (CIITA) expression," J Exp Med, 2001, 194(4): 379-391.
Le et al., "Adjuvant effects of combination monophosphoryl lipid A and poly I:C on antigen-specific immune responses and protective efficacy of influenza vaccines," Scientific Reports, 2023, 13: 12231.
Lelekakis et al., "A novel orthotopic model of breast cancer metastasis to bone," Clin Exp Metastasis, 1999, 17(2): 163-170.
Liu et al., "Clinical cancer immunotherapy: Current progress and prospects," Front Immunol, 2022, 13: 961805.
Liu et al., "Injectable intratumoral depot of thermally responsive polypeptide-radionuclide conjugates delays tumor progression in a mouse model," Journal of Controlled Release, 2010, 144: 2-9.
Liu et al., "Membrane Anchored Immunostimulatory Oligonucleotides for in Vivo Cell Modification and Localized Immunotherapy," Angewandte Chemie International Edition, 2011, 50(31): 7052-7055.
Maeda ate al., "Analyses of repeated failures in cancer therapy for solid tumors: poor tumor-selective drug delivery, low therapeutic efficacy and unsustainable costs," Clinical and Translational Medicine, 2018, 7: 11.
Mani et al., "Causes of death among people living with metastatic cancer," Nature Communications, 2024, 15: 1519.
Marciscano et al., "The role of dendritic cells in cancer and anti-tumor immunity," Semin Immunol, 2021, 52: 101481.
Martins et al., "Vaccine adjuvant uses of poly-IC and derivatives," Expert Rev Vaccines, 2015, 14(3): 447-459.
Maurer et al., "CpG-DNA aided cross-presentation of soluble antigens by dendritic cells," Eur J Immunol, 2002, 32(8): 2356-2364.

(56) References Cited

OTHER PUBLICATIONS

McCoy et al., "Activation of RAW264.7 Macrophages by Bacterial DNA and Lipopolysaccharide Increases Cell Surface DNA Binding and Internalization," Journal of Biological Chemistry, 2004, 279(17): 17217-17223.
Milligan et al., "A Nanoparticle's Journey to the Tumor: Strategies to Overcome First-Pass Metabolism and Their Limitations," Cancers, 2022, 14(7): 1741.
Milligan et al., "Genetically encoded elastin-like polypeptide nanoparticles for drug delivery," Current Opinion in Biotechnology, 2022, 74: 146-153.
Moseman et al., "Human plasmacytoid dendritic cells activated by CpG oligodeoxynucleotides induce the generation of CD4+CD25+ regulatory T cells," J Immunol, 2004, 173(7): 4433-4442.
Nastiuk et al., "Opportunities and challenges in combination gene cancer therapy," Adv Drug Deliv Rev, 2016, 98: 35-40.
Ouyang et al., "Overcoming cold tumors: a combination strategy of immune checkpoint inhibitors," Front Immunol, 2024, 15: 1344272.
Roberts et al., "Differences in macrophage activation by bacterial DNA and CpG-containing oligonucleotides," The Journal of Immunology, 2005, 175(6): 3569-3576.
Schaal et al., "Brachytherapy via a depot of biopolymer-bound 131I synergizes with nanoparticle paclitaxel in therapy-resistant pancreatic tumours," Nat Biomed Eng, 2022, 6: 1148-1166.
Senapati et al., "Controlled drug delivery vehicles for cancer treatment and their performance," Signal Transduction and Targeted Therapy, 2018, 3: 7.
Shih et al., "Ultrasound-triggered release reveals optimal timing of CpG-ODN delivery from a cryogel cancer vaccine," Biomaterials, 2021, 279: 121240.
Singh-Jasuja et al., "The mouse dendritic cell marker CD11c is down-regulated upon cell activation through toll-like receptor triggering. Immunobiology," Immunobiology, 2013, 218: 28-39.
Sun et al., "Intra-tumor heterogeneity of cancer cells and its implications for cancer treatment," Acta Pharmacologica Sinica, 2015, 36(10): 1219-1227.
Tsujimura et al., "Toll-like receptor 9 signaling activates NF-kappaB through IFN regulatory factor-8/IFN consensus sequence binding protein in dendritic cells," J Immunol, 2004, 172(11): 6820-6827.
Turley et al., "Immunological hallmarks of stromal cells in the tumour microenvironment," Nature Reviews Immunology, 2015, 15(11): 669-682.
Utaisincharoen et al., "CpG ODN activates NO and iNOS production in mouse macrophage cell line (RAW 264.7)," Clin Exp Immunol, 2002, 128(3): 467-473.
van den Boorn et al., "Chapter 1—Nucleic Acid Adjuvants: Toward an Educated Vaccine," Advances in Immunology, 2012, 114: 1-32.
Wilson et al., "Dendritic cells constitutively present self antigens in their immature state in vivo and regulate antigen presentation by controlling the rates of MHC class II synthesis and endocytosis," Blood, 2004, 103(6): 2187-2195.
Xie et al., "Neoantigens: promising targets for cancer therapy," Signal Transduction and Targeted Therapy, 2023, 8(1): 9.
Yang et al., "Advanced biomaterials for cancer immunotherapy," Acta Pharmacologica Sinica, 2020, 41(7): 911-927.
Yang et al., "Sustained release of tumor cell lysate and CpG from an injectable, cytotoxic hydrogel for melanoma immunotherapy," Nanoscale Advances, 2023, 5: 2071-2084.
Aslan et al. "Targeted Therapies for Pancreatic Cancer and Hurdles Ahead," Anticancer Research, 2018, 38: 6591-6606.
Bowen, "Particle Size Distribution Measurement from Millimeters to Nanometers and from Rods to Platelets," Journal of Dispersion Science and Technology, 2002, 631-662.
United States Patent Office Notice of Allowance for U.S. Appl. No. 18/303,530 dated May 7, 2025 (8 pages).
United States Patent Office Action for U.S. Appl. No. 17/294,368 dated Jul. 7, 2025 (18 pages).
Piasecki et al., "Purified Viable Fat Suspended in Matrigel Improves Volume Longevity," Aesthetic Surg. J., 2008, 28: 24-32.
United States Patent Office Action for U.S. Appl. No. 18/042,032 dated Oct. 1, 2025 (14 pages).
United States Patent Office Action for U.S. Appl. No. 17/908,427 dated Oct. 15, 2025 (16 pages).
United States Patent Office Notice of Allowance for U.S. Appl. No. 18/303,530 dated Oct. 28, 2025 (8 pages).
Bae et al., "Intelligent biosynthetic nanobiomaterials for hyperthermic combination chemotherapy and thermal drug targeting of HSP90 inhibitor geldanamycin," Journal of Controlled Release, 2007, 122: 16-23.
WIPO English Translation of CN112946261A (Year 2021).
Punta et al., "The Rough Guide to In Silica Function Prediction, or How To Use Sequence and Structure Information To Predict Protein Function," PLOS Comput Biol, 2008, 4(10): e1000160.
Whisstock et al., "Prediction of protein function from protein sequence and structure," Quarterly Reviews in Biophysics, 2007, 36(3): 307-340.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol., 1990, 111: 2129-2138.
Song et al., "A Single Amino Acid Change (Asp 533Ala53) Converts Survivin from Anti-apoptotic to Pro-apoptotic," Molecular Biology of the Cell, 2004, 15: 1287-1296.
Defeo-Jones et al., "Substitution of Lysine for Arginine at Position 42 of Human Transforming Growth Factor-a Eliminates Biological Activity without Changing Internal Disulfide Bonds," Molecular and Cellular Biology, Sep. 1989, p. 4083-4086.
Bork, "Powers and Pitfalls in Sequence Analysis: The 70% Hurdle," Genome Research, 2000, 10: 398-400.
International Search Report and Written Opinion for Application No. PCT/US2025/019969 dated Oct. 3, 2025 (14 pages).
United States Patent Office Action for U.S. Appl. No. 17/798,868 dated Nov. 19, 2025 (28 pages).
United States Patent Office Action for U.S. Appl. No. 17/957,373 dated Nov. 5, 2025 (19 pages).
United States Patent Office Action for U.S. Appl. No. 17/908,415 dated Nov. 25, 2025 (19 pages).
Ni et al., "Chemical Modifications of Nucleic Acid Aptamers for Therapeutic Purposes," Int. J. Mol. Sci, 2017, 18: 1683.
International Search Report and Written Opinion for Application No. PCT/US2025/049197 dated Feb. 3, 2026 (12 pages).
United States Patent Office Notice of Allowance for U.S. Appl. No. 18/303,530 dated Feb. 12, 2025 (5 pages).

* cited by examiner

1: ABDH-CP-DOX
2: ABDN-CP-DOX
3: CP-DOX
4: MSA
5: ABDH-CP-DOX + MSA
6: ABDN-CP-DOX + MSA
7: CP-DOX + MSA
8: HSA
9: ABDH-CP-DOX + HSA
10: ABDN-CP-DOX + MSA
11: CP-DOX + HSA

| $EC_{50}$ (nM) | $IC_{50}$ (nM) |
|---|---|
| 14.3 | 22.4 |
| 7.3 | 10.9 |
| 9.5 | 9.8 |

SEQUENCE LISTING

```
<160> NUMBER OF SEQ ID NOS: 8

<210> SEQ ID NO 1
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(5)
<223> OTHER INFORMATION: Repeat unit:  repeating one or more times
<220> FEATURE:
<221> NAME/KEY: MISC_FEATURE
<222> LOCATION: (4)..(4)
```

<223> OTHER INFORMATION: Xaa is any amino acid except proline

<400> SEQUENCE: 1

Val Pro Gly Xaa Gly
1 5

<210> SEQ ID NO 2
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is an amino acid or a combination of amino acids
<220> FEATURE:
<221> NAME/KEY: REPEAT
<222> LOCATION: (1)..(5)
<223> OTHER INFORMATION: Repeat unit: may repeat 40 to 400 times

<400> SEQUENCE: 2

Xaa Gly Val Pro Gly
1 5

<210> SEQ ID NO 3
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is A, or V or A or G, which appears in a ratio of V:A:G=1:7:8 in the repeating segment
<220> FEATURE:
<221> NAME/KEY: REPEAT
<222> LOCATION: (1)..(5)
<223> OTHER INFORMATION: Repeat unit: repeating 160 times

<400> SEQUENCE: 3

Xaa Gly Val Pro Gly
1 5

<210> SEQ ID NO 4
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(3)
<223> OTHER INFORMATION: Repeat unit: repeating two or more times

<400> SEQUENCE: 4

Cys Gly Gly
1

<210> SEQ ID NO 5
<211> LENGTH: 24
<212> TYPE: PRT
<213> ORGANISM: Artificial Sequence
<220> FEATURE:
<223> OTHER INFORMATION: Synthetic

<400> SEQUENCE: 5

Cys Gly Gly Cys Gly Gly Cys Gly Gly Cys Gly Gly Cys Gly Gly Cys

-continued

```
1               5                   10                  15

Gly Gly Cys Gly Gly Cys Gly Gly
            20


<210> SEQ ID NO 6
<211> LENGTH: 46
<212> TYPE: PRT
<213> ORGANISM: Artificial Sequence
<220> FEATURE:
<223> OTHER INFORMATION: Synthetic

<400> SEQUENCE: 6

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Asn Ala Lys Thr Val Glu
            20                  25                  30

Gly Val Lys Ala Leu Ile Asp Glu Ile Leu Ala Ala Leu Pro
        35                  40                  45


<210> SEQ ID NO 7
<211> LENGTH: 46
<212> TYPE: PRT
<213> ORGANISM: Artificial Sequence
<220> FEATURE:
<223> OTHER INFORMATION: Synthetic

<400> SEQUENCE: 7

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val Glu Ala Leu Lys Leu His Ile Leu Ala Ala Leu Pro
        35                  40                  45


<210> SEQ ID NO 8
<211> LENGTH: 4
<212> TYPE: PRT
<213> ORGANISM: Artificial Sequence
<220> FEATURE:
<223> OTHER INFORMATION: Synthetic

<400> SEQUENCE: 8

Lys Glu Lys Glu
1
```

NANOPARTICULATE DRUG DELIVERY SYSTEMS

CROSS-REFERENCE TO RELATED APPLICATIONS

This patent application is the U.S. national stage entry, under 35 U.S.C. § 371, of International Application Number PCT/US2019/055077, filed Sep. 6, 2019, which claims priority to U.S. Provisional Application No. 62/728,582, filed Sep. 7, 2018, the entire contents of each of which are hereby incorporated by reference.

STATEMENT REGARDING FEDERALLY-SPONSORED RESEARCH OR DEVELOPMENT

This invention was made with government support under grant number R01EB000188 and R01EB007205 awarded by the National Institutes of Health and DCI/NCSU Consortium for Canine Comparative Oncology grant (2016) The government has certain rights in the invention.

SEQUENCE LISTING

The sequence listing is filed with the application in electronic format only and is incorporated by reference herein. The sequence listing text file "028193-9286-WO01_As_Filed_Sequence_Listing.txt" was created on Sep. 6, 2019, and is 2,971 bytes in size.

TECHNICAL FIELD

The present disclosure relates to novel nanoparticulate drug delivery systems.

BACKGROUND OF THE INVENTION

Self-nature of cancer cells and therefore off-target toxicity is the main challenge undermining the efficacy of chemotherapeutic agents. Because of their size, nano-sized carriers in the past decades have provided the opportunity to improve the selectivity of the anti-cancer agents by taking advantage of physiological and anatomical differences between the tumor cells and normal cells. This physical selectivity occurs through a phenomenon known as the enhanced permeation and retention (EPR) effect, caused by the leaky angiogenic vessels and poor lymphatic drainage in tumor tissues. In addition, many anticancer small molecules drugs suffer from poor bioavailability resulting from low water solubility and short plasma half-life. Nanocarriers are sized above the renal filtration cutoff of 5-6 nm and avoid the renal clearance and increase the half-life of their cargo drugs.

Nanocarriers can solubilize hydrophobic drugs via chemical conjugation or physical entrapment of drugs in their hydrophobic cores. Recently, self-assembling micelles have become popular pharmaceutical nanocarriers for the delivery of poorly water-soluble anticancer drugs on account of their relatively high drug loading and uncomplicated preparation conditions. However, self-assembling micelles are unstable after injection into the human body due to dilution in the blood stream. Furthermore, micelles can be recognized and taken up by the macrophages of the reticuloendothelial system (mainly the liver and the spleen), which leads to their removal from the systematic circulation. Therefore, there remains a need for new nanoparticulate drug delivery systems that can overcome these disadvantages yet provide efficacy for delivery of poorly water-soluble anti-cancer agents.

BRIEF SUMMARY OF THE INVENTION

In one aspect, disclosed are compositions comprising an assembly of self-assembling conjugates, each self-assembling conjugate comprising a polypeptide having a transition temperature ($T_t$) above 50° C. when the polypeptide is not attached to the conjugate; an albumin binding domain (ABD) attached to a first end of the polypeptide; and at least one molecule attached to a second end of the polypeptide through a cysteine group, wherein the molecule has an octanol-water distribution coefficient (log D) of greater than or equal to 1.5 at a pH of 7.4 when the molecule is not attached to the conjugate, wherein the conjugate has a $T_t$ above 40° C. at a concentration of 100 μM.

In another aspect, disclosed are compositions comprising an assembly of self-assembling conjugates, each self-assembling conjugate comprising a polypeptide having a transition temperature ($T_t$) above 50° C. when the polypeptide is not attached to the conjugate; an albumin binding domain (ABD) attached to a first end of the polypeptide, wherein the ABD attached to the polypeptide lowers the $T_t$ of the polypeptide no more than 5° C. relative to the polypeptide's $T_t$ when the polypeptide is not attached to the ABD or the conjugate; and at least one molecule attached to a second end of the polypeptide through a cysteine group, wherein the molecule has an octanol-water distribution coefficient (log D) of greater than or equal to 1.5 at a pH of 7.4 when the molecule is not attached to the conjugate.

In another aspect, the disclosure provides a method of killing multiple cancer cells comprising contacting multiple cancer cells with the compositions described herein.

In another aspect, the disclosure provides a method of treating a disease or disorder in a subject comprising administering to the subject the compositions described herein. In another aspect, the disclosure provides a method of treating a disease or disorder in a subject comprising administering to the subject the compositions described herein wherein the disease or disorder is cancer.

In another aspect, the disclosure provides a method of localizing a molecule to a tissue or organ in a subject, the method comprising administering to the subject the compositions described herein, wherein following administration of the composition the molecule is localized in the liver at less than 30% of the injected dose/gram of tissue or organ (ID/g).

In another aspect, the disclosure provides a method of localizing a molecule to a tissue or organ in a subject, the method comprising administering to the subject the compositions described herein, wherein following administration of the composition the molecule is localized in the spleen at less than 10% of the injected dose/gram of tissue or organ (ID/g).

In another aspect, the disclosure provides a method of localizing a molecule to a tissue or organ in a subject, the method comprising administering to the subject the compositions described herein, wherein following administration of the composition the amount of the molecule localized in a tissue or organ is decreased when compared to the same molecule in a self-assembling conjugate without an albumin binding domain and wherein the tissue or organ is the kidney, liver, spleen or any combination thereof.

In another aspect, the disclosure provides a method of localizing a molecule to a tumor in a subject, the method comprising administering to the subject the compositions described herein, wherein following administration of the composition the amount of the molecule localized to the tumor is increased when compared to the same molecule in a self-assembling conjugate without an albumin binding domain.

BRIEF DESCRIPTIONS OF THE DRAWINGS

FIG. 1 shows a schematic overview of inverse transition cycling which may be used to purify elastin-like polypeptide (ELP) proteins.

FIG. 2A, FIG. 2B and FIG. 2C show the characterization of albumin binding domain (ABD)-ELP monomers. FIG. 2A shows the sodium dodecyl sulfate-polyacrylamide gel electrophoresis (SDS-PAGE) analysis of purified albumin binding domain N and H (ABDN/H-) ELP polypeptides. Successful purification of (ABDN/H-)ELPs by inverse transition cycling is confirmed by SDS-PAGE. Main band corresponds to the molecular weight of ELP (63.6 kDa), ABDN-ELP (68.5 kDa), and ABDH-ELP (68.6 kDa) and a second faint band indicates the presence of the corresponding polypeptide dimers. FIG. 2B shows the Native-PAGE analysis of interaction of human serum albumin (HSA) and mouse serum albumin (MSA) with (ABDN/H-) ELP. For lanes 5-7 and lanes 9-11, polypeptide carriers were mixed at a molar ratio of 1:1 with MSA and HSA, respectively. FIG. 2C shows the pharmacokinetics of ELP, ABDN-ELP and ABDH-ELP carriers. Polypeptides were labeled with Alexa488 and were administered via tail vein to Balb/C mice (n=6-7) and plasma concentrations were measured at intervals over 72 h. The data was fitted to a two-compartment model from which pharmacokinetic parameters were estimated as shown in Table 1.

FIG. 3A, FIG. 3B and FIG. 3C show the calorimetric titrations of HSA with (ABDN/H-) ELP. The experiments were performed in phosphate buffered saline (pH 7.4) at 37° C. The solid line indicates the best-fit binding isotherm. FIG. 3A shows the titration of HSA into ELP with a binding stoichiometry N=0.75±0.16 and dissociation constant $K_D$=69.03±15.51 μM. FIG. 3B shows the titration of HSA into ABDN-ELP with a binding stoichiometry N=1.04±0.00 and dissociation constant $K_D$=48.4±3.82 nM. FIG. 3C shows the titration of HSA into ABDH-ELP with a binding stoichiometry N=1.07±0.00 and dissociation constant $K_D$=4.19±1.07 nM.

FIG. 4A, FIG. 4B and FIG. 4C show calorimetric titrations of MSA with (ABDN/H-) ELP. The experiments were performed in phosphate buffered saline (pH 7.4) at 37° C. The solid line indicates the best-fit binding isotherm. FIG. 4A shows the titration of MSA into ELP with a binding stoichiometry N=0.1525±0.17 and dissociation constant $K_D$=71.4±12.24 μM. FIG. 4B shows the titration of MSA into ABDN-ELP with a binding stoichiometry N=1.12±0.00 and dissociation constant $K_D$=66.36±10.65 nM. FIG. 4C shows the titration of MSA into ABDH-ELP with a binding stoichiometry N=1.04±0.00 and dissociation constant $K_D$=5.19±1.85 nM.

FIG. 5 shows a schematic of intravenous administration of assemblies of self-assembling conjugates.

FIG. 6A, FIG. 6B, FIG. 6C and FIG. 6D show the in vitro characterization of ABD-chimeric polypeptide (CP-CP and ELP are used interchangeably herein)-Doxorubicin (DOX) micelles. FIG. 6A shows the native-PAGE analysis of the interactions of HSA and MSA with (ABDN/H-) ELP. For lanes 5-7 and lanes 9-11, polypeptide carriers were mixed at a molar ratio of 1:1 with MSA and HSA, respectively. FIG. 6B shows the cytotoxicity of ABDN-CP-DOX vs. CP-DOX and free DOX in C26 cells after 72 h incubation. IC50 was measured as 0.09 μM for free DOX, 0.30 μM for CP-DOX, and 0.31 μM for ABDN-CP-DOX. Error bars represent standard error of the mean (n=3). FIG. 6C shows the cryo-TEM micrographs of CP-DOX (left) and ABDN-CP-DOX micelles (right). FIG. 6D shows the in vitro drug release profile from CP-DOX and ABDN-CP-DOX micelles. The micelles released the loaded DOX under acidic conditions at pH 5.0 corresponding to intracellular space, but remained stable at pH 7.4 corresponding to vascular and extracellular space.

FIG. 7A, FIG. 7B and FIG. 7C show the calorimetric titrations of MSA with (ABDN/H-)CP-DOX micelles. The experiments were performed in phosphate buffered saline (pH 7.4) at 37° C. The solid line indicates the best-fit binding isotherm. FIG. 7A shows the titration of MSA into CP-DOX with a binding stoichiometry N=0.0386±0.09 and dissociation constant $K_D$=91.91±68.36 μM. FIG. 7B shows the titration of MSA into ABDN-CP-DOX with a binding stoichiometry N=1.01±0.00 and dissociation constant $K_D$=317.56±53.55 nM. FIG. 7C shows the titration of MSA into ABDH-CP-DOX with a binding stoichiometry N=0.99±0.01 and dissociation constant $K_D$=66.09±20.20 nM.

FIG. 8A, FIG. 8B, FIG. 8C and FIG. 8D show the thermal phase transition behavior of (ABDN/H-)ELP and (ABDN/H-)CP-DOX. The Transition temperature ($T_t$) of empty carriers and DOX-conjugated micelles was determined by monitoring the turbidity as a function of temperature in PBS, FBS, and MS. FIG. 8A shows that ELP and CP-DOX exhibited a lower $T_t$ in FBS and MS than that in PBS. In addition, CP-DOX exhibited a lower and less-concentration-dependent $T_t$ than the empty carrier ELP. ABDN-CP-DOX (FIG. 8B) and ABDH-CP-DOX (FIG. 8C) also exhibited a lower and less-concentration-dependent $T_t$ than their corresponding empty carriers. For ABDN-ELP and ABDH-ELP, the difference in $T_t$ in FBS and PBS was not as significant as that for ELP. ABDN-CP-DOX and ABDH-CP-DOX exhibited a higher $T_t$ in FBS than in PBS. None of the ABDN- and ABDH-fused carriers and micelles transitioned in MS. FIG. 8D shows a summary of transition temperatures of CP, ABD-CP and DOX conjugates in PBS.

FIG. 9A and FIG. 9B show dynamic light scattering graphs for CP-ABDN-DOX (FIG. 9A) and KEKE-CP-ABDN-DOX (FIG. 9B).

FIG. 10A, FIG. 10B, FIG. 10C, FIG. 10D and FIG. 10E show the in vivo characterization of ABD-CP-DOX micelles. FIG. 10A shows the pharmacokinetics of ABDN-CP-DOX micelles vs CP-DOX micelles. CP-DOX and ABDN-CP-DOX micelles were administered via tail vein to Balb/C mice (n=5-6) at 10 and 20 mg/kg body weight (BW) DOX equivalent and plasma DOX concentration was measured at intervals over 72 h. The data was fitted to a two-compartment model from which pharmacokinetic parameters were estimated as shown in Table 3. FIG. 10B and FIG. 10C show the biodistribution of ABDN-CP-DOX micelles vs CP-DOX micelles. C26 tumor cells were implanted subcutaneously and allowed to grow to approximately 75-100 $mm^3$. Mice were treated with free DOX, CP-DOX, and ABDN-CP-DOX all at 10 and 20 mg DOX Equiv. kg-1BW. The DOX concentration was measured in tumor and normal tissues at 2 h (FIG. 10C) and 24 h (FIG. 10B) post-administration. FIG. 10D and FIG. 10E show the anti-tumor activity of ABDN-CP-DOX micelles. C26 tumor cells were implanted subcutaneously and allowed to grow to approximately 75-100 $mm^3$. Mice were treated on day 0 with free DOX (10 mgkg-1 BW), CP-DOX (20 mg DOX Equiv. kg-1BW), and ABDN-CP-DOX (20 mg DOX Equiv. kg-1BW). FIG. 10D shows the tumor volume up to day 60 (mean±SEM; n=6-10). FIG. 10E shows the cumulative survival of mice up to day 60 (n=6-10).

FIG. 11 shows a line graph of the pharmacokinetics of ABDN-CP-DOX micelles in dogs. Free DOX, CP-DOX micelles and ABDN-CP-DOX micelles were administered via the cephalic vein at 27 DOX Equiv.$m^{-2}$ body surface area for dogs weighing greater than 10 kg and 0.9 mg DOX Equiv.$kg^{-1}$ of body weight for dogs weighing less than 10 kg, and plasma DOX concentration was measured at intervals over 72 h. The data was fit to a two-compartment model from which pharmacokinetic parameters were estimated.

FIG. 12A, FIG. 12B, FIG. 12C, FIG. 12D, FIG. 12E, FIG. 12F and FIG. 12G show the biodistribution of ABDN-CP-DOX micelles vs CP-DOX micelles at 2 h post administration. C26 tumor cells were implanted subcutaneously and allowed to grow to approximately 75-100 $mm^3$. Mice were treated with free DOX at 10 $mgkg^{-1}$BW, and with CP-DOX, and ABDN-CP-DOX at 10 and 20 mg DOX Equiv. $kg^{-1}$BW. The DOX concentration was measured in tumor (FIG. 12A), liver (FIG. 12B), spleen (FIG. 12C), heart (FIG. 12D), lung (FIG. 12E), kidney (FIG. 12F), and muscle (FIG. 12G) at 2 h post-administration. Error bars represent standard error of the mean (n=4-7). *P<0.05, P<0.01, *P<0.001.

FIG. 13A, FIG. 13B, FIG. 13C, FIG. 13D, FIG. 13E, FIG. 13F and FIG. 13G show the biodistribution of ABDN-CP-DOX micelles vs CP-DOX micelles at 24 h post administration. C26 tumor cells were implanted subcutaneously and allowed to grow to approximately 75-100 $mm^3$. Mice were treated with free DOX at 10 $mgkg^{-1}$BW, and with CP-DOX, and ABDN-CP-DOX at 10 and 20 mg DOX Equiv. $kg^{-1}$BW. The DOX concentration was measured in tumor (FIG. 13A), liver (FIG. 13B), spleen (FIG. 13C), heart (FIG. 13D), lung (FIG. 13E), kidney (FIG. 13F), and muscle (FIG. 13G) at 2 h post-administration. Error bars represent standard error of the mean (n=6-8). *P<0.05, P<0.01, *P<0.001.

FIG. 14A, FIG. 14B, FIG. 14C and FIG. 14D show the anti-tumor activity of ABDN-CP-DOX micelles. C26 tumor cells were implanted subcutaneously and allowed to grow to approximately 75-100 $mm^3$. Mice were treated on day 0 with CP-DOX and ABDN-CP-DOX. Tumor volume up to day 60 (mean±SEM; n=6-10) following treatment at the dose of 10 mg and 40 mg (FIG. 14C) DOX Equiv. kg-1BW. Cumulative survival of mice up to day 60 (n=6-10) following treatment at the dose of 10 mg (FIG. 14B) and 40 mg (FIG. 14D) DOX Equiv. kg-1BW.

FIG. 15A, FIG. 15B and FIG. 15C show the dose escalation in healthy mice. Increasing concentrations of free DOX (A), CP-DOX (B), and ABDN-CP-DOX (C) were administered intravenously in healthy Balb/C mice on day 0. Concentrations include 5, 10, 15, and 20 mg Dox Equiv kg-1 BW for free DOX and 20, 40, 50, and 60 mg DOX equiv/kg BW for CP-DOX, and ABDN-CP-DOX. Non-DOX-conjugated ELP and ABDN-ELP carriers were administered at protein concentration equivalent to the protein concentration in 60 mg DOX equiv/kg BW CP-DOX and ABDN-CP-DOX treatments. Error bars represent standard error of the mean (n=5).

DETAILED DESCRIPTION OF THE INVENTION

Figure 1:
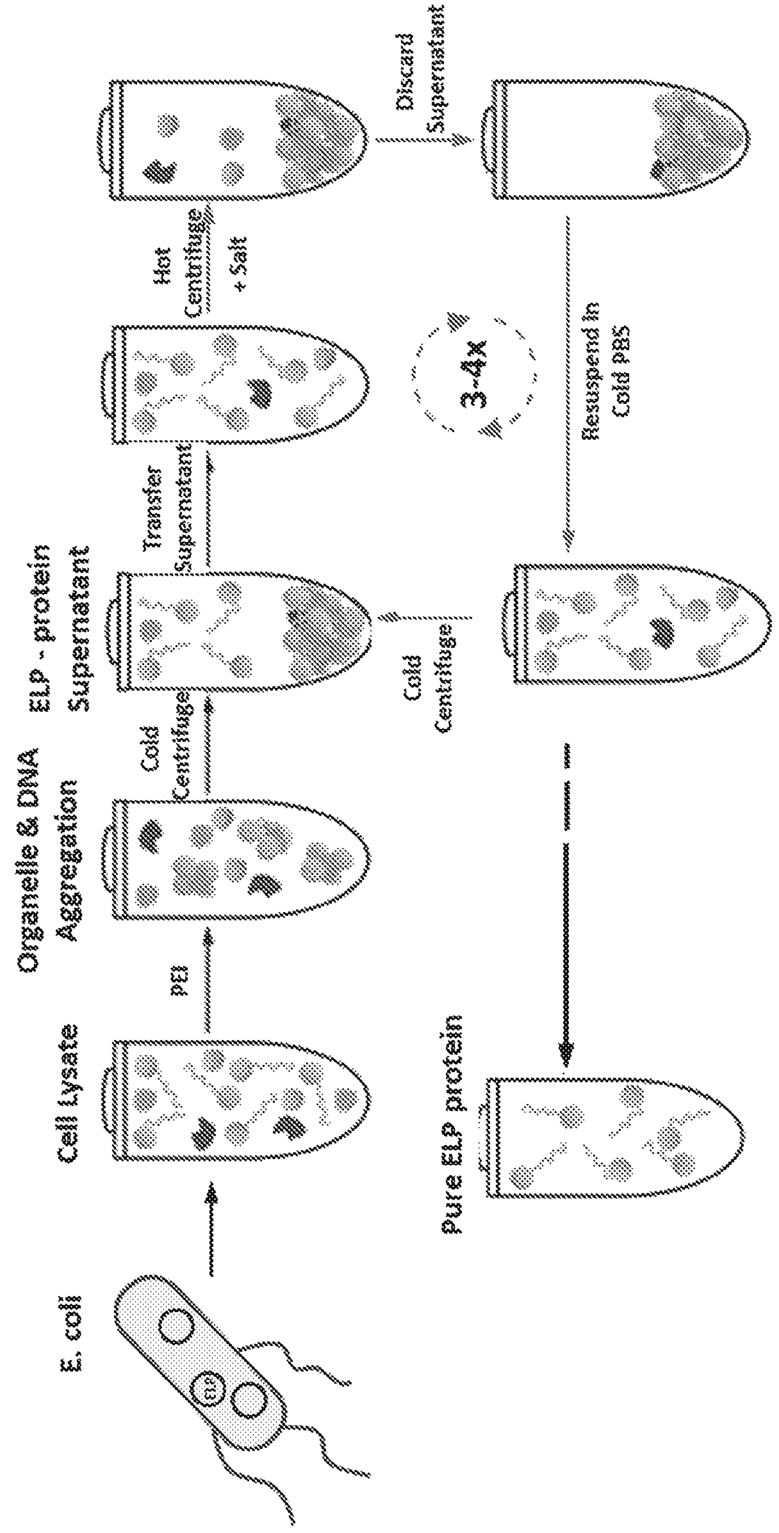

Disclosed herein are compositions for nanoparticulate delivery systems. The compositions comprise an assembly of self-assembling conjugates which provide improved pharmacokinetics and biodistribution of a molecule. The self-assembling conjugates can increase localization of a molecule to a tumor and can decrease molecule accumulation in the organs and tissues of the reticuloendothelial system and, therefore, can provide enhanced antitumor activity of a chemotherapeutic.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, the terms "administering," "providing" and "introducing" are used interchangeably herein and refer to the placement of the compositions of the disclosure into a subject by a method or route which results in at least partial localization of the composition to a desired site. The compositions can be administered by any appropriate route which results in delivery to a desired location in the subject.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

As used herein, the term "chemotherapeutic" or "anticancer drug" includes any drug used in cancer treatment. Chemotherapeutics include, but are not limited to, cyclophosphamide, methotrexate, 5-fluorouracil, doxorubicin, cyclophosphamide, docetaxel, doxorubicin, daunorubicin, bleomycin, vinblastine, dacarbazine, cisplatin, paclitaxel and docetaxel.

The terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration, the type or extent of supplemental therapy used, ongoing disease process and type of treatment desired (e.g., aggressive vs. conventional treatment).

As used herein, the term "hydrodynamic radius" or "$R_h$" refers to the measurement from dynamic light scattering for the radius of an equivalent hard sphere diffusing at the same rate as the molecule under observation. As such, the radius reflects the apparent size of the solvated, tumbling molecule. Alternatively, the radius of gyration ($R_g$), is the mass weighted average distance from the core of the molecule to each mass element in the molecule.

The term "imaging agent," as used herein, refers to a molecule or compound that can be detected directly or after applying a stimulus. Imaging agents may include luminescent labels which emit radiation on exposure to an external source of radiation or other stimulus, radioactive labels, NMR-active labels, or heavy atoms.

As used herein, the term "micelle" refers to an organized auto-assembly of molecules formed in a liquid where the hydrophilic regions are in contact with the surrounding solvent and the hydrophobic regions are sequestered in the center or core of the micelle. In some embodiments, the micelle may be a nanoparticle.

As used herein, the term "nanoparticle" refers to a particle with at least one dimension less than about 100 nm. Nanoparticles include, but are not limited to, nanopowders, nanoclusters, nanocrystals, and micelles.

As used herein, the term "octanol-water distribution coefficient" refers to a measure of the degree of hydrophilicity or hydrophobicity of a chemical substance, for example a drug. The measurement is the ratio of the sum of the concentrations of all forms of the compound (ionized plus un-ionized) in each of two immiscible phases, one hydrophobic and one hydrophilic phase, at equilibrium. The measurement is pH dependent, and the aqueous phase is usually buffered to a specific value. The larger the octanol-water distribution coefficient; the more hydrophobic the chemical substance becomes. The smaller the octanol-water distribution coefficient, the more hydrophilic.

A "peptide" or "polypeptide" is a linked sequence of two or more amino acids linked by peptide bonds. The polypeptide can be natural, synthetic, or a modification or combination of natural and synthetic. Domains are portions of a polypeptide or protein that form a compact unit and are typically 15 to 350 amino acids long.

A "subject" or "patient" may be human or non-human and may include, for example, animal strains or species used as "model systems" for research purposes, such as a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments of the methods and compositions provided herein, the mammal is a human.

As used herein, the term "thiol" refers to a carbon-bonded sulfhydryl (—SH) group.

As used herein, the term "transition temperature" or "$T_t$" refers to the temperature at which the conjugate (or polypeptide) changes from one state to another, for example, soluble to insoluble. For example, below the $T_t$, the conjugate may be highly soluble. Upon heating above the transition temperature, for example, the conjugate may aggregate, forming a separate phase.

As used herein, "treat," "treating" and the like mean a slowing, stopping or reversing of progression of a disease or disorder when provided a composition described herein to an appropriate subject. The terms can also mean a reversing of the progression of such a disease or disorder to a point of eliminating or greatly reducing the cell proliferation. As such, "treating" means an application or administration of the compositions described herein to a subject, where the subject has a disease or a symptom of a disease, where the purpose is to cure, heal, alleviate, relieve, alter, remedy, ameliorate, improve or affect the disease or symptoms of the disease.

2. SELF-ASSEMBLING CONJUGATES

Provided herein are compositions comprising an assembly of self-assembling conjugates. The disclosed assembly of self-assembling conjugates can encapsulate drugs, while also being able to bind albumin. The ability of the self-assembling conjugate (and assembly thereof) to bind albumin can improve pharmacokinetic properties of the drug, which can ultimately be useful for drug delivery applications.

The ability of the assembly to encapsulate drugs and bind albumin can be attributed to the different components of the self-assembling conjugate (also referred to as "conjugate" herein). For example, each self-assembling conjugate independently comprises a polypeptide having a transition temperature ($T_t$) above 50° C. when the polypeptide is not attached to the conjugate (e.g., when the polypeptide is an individual molecule relative to part of the conjugate); an albumin binding domain (ABD) attached to a first end of the polypeptide; and at least one molecule attached to a second end of the polypeptide through a cysteine group, wherein the molecule has an octanol-water distribution coefficient (log D) of greater than or equal to 1.5 at a pH of 7.4 when the molecule is not attached to the conjugate, wherein the conjugate has a $T_t$ above 40° C. at a concentration of 100 μM.

In some embodiments, the assembly of self-assembling conjugates comprises a polypeptide having a $T_t$ above 50° C. when the polypeptide is not attached to the conjugate; a ABD attached to a first end of the polypeptide, wherein the ABD attached to the polypeptide lowers the $T_t$ of the polypeptide no more than 5° C. relative to the polypeptide's $T_t$ when the polypeptide is not attached to the ABD or the conjugate; and at least one molecule attached to a second end of the polypeptide through a cysteine group, wherein the molecule has an octanol-water distribution coefficient (log D) of greater than or equal to 1.5 at a pH of 7.4 when the molecule is not attached to the conjugate.

The assembly of self-assembling conjugates can comprise a plurality of conjugates. For example, the assembly of self-assembling conjugates may include about 10 to about 200 self-assembling conjugates per assembly, such as about 10 to about 100 self-assembling conjugates per assembly, about 50 to about 200 self-assembling conjugates per assembly, about 10 to about 75 self-assembling conjugates per assembly, about 15 to about 60 self-assembling conjugates per assembly, or about 20 to about 60 self-assembling conjugates per assembly.

a) Polypeptide

The self-assembling conjugate may include a polypeptide. The polypeptide can have a $T_t$, which makes it thermally responsive. In some embodiments, the polypeptide comprises one or more thermally responsive polypeptides. The unconjugated polypeptide (e.g., the polypeptide as an individual molecule not conjugated to the ABD domain or molecule) may have phase transition behavior, wherein the unconjugated polypeptide changes phase at its $T_t$. Phase transition may refer to the aggregation of the polypeptide, which may occur sharply and in some instances reversibly at or above the $T_t$. The $T_t$ of the polypeptide can be adjusted by varying the amino acid sequence of the polypeptide, by varying the length of the polypeptide, or a combination thereof. The $T_t$ of the unconjugated polypeptide may be above 50° C., such as above 55° C., above 60° C., or above 65° C. In some embodiments, the $T_t$ of the unconjugated polypeptide may be below 80° C., below 75° C., or below 70° C. In addition, the $T_t$ of the unconjugated polypeptide may instill phase transition behavior to the self-assembling conjugate. Accordingly, the $T_t$ of the unconjugated polypeptide may affect the $T_t$ of the conjugate.

Thermally responsive polypeptides may include, for example, elastin-like polypeptides (ELP). In some embodiments, the polypeptide is an ELP. "ELP" refers to a polypeptide comprising the pentapeptide repeat sequence $(VPGXG)_n$ (SEQ ID NO:1), wherein X is any amino acid except proline and n is an integer greater than or equal to 1. In some embodiments, the polypeptide comprises an amino acid sequence of $(X^1GVPG)_x$ (SEQ ID NO:2), wherein $X^1$ is an amino acid or a combination of amino acids and x is an integer from 40 to 400. In some embodiments, x is an integer from 40 to 300, from 40 to 200, from 40 to 100, from 100 to 200, from 100 to 300, from 100 to 400, from 200 to 300, from 200 to 400, or from 300 to 400. In some embodiments, $X^1$ is A, V, G, or a combination thereof. In some embodiments, the polypeptide comprises an amino acid sequence of $(X^1GVPG)_m$ (SEQ ID NO:3), wherein $X^1$ is A or V:A:G at a ratio of 1:7:8 and m is 160. In some embodiments, the polypeptide is an amino acid sequence of $(X^1GVPG)_m$ (SEQ ID NO:3), wherein $X^1$ is A or V:A:G at a ratio of 1:7:8 and m is 160.

In some embodiments, the polypeptide comprises a short cysteine containing sequence that can be used for fluorophore labeling, dug conjugation, or a combination thereof. In some embodiments, the short cysteine containing sequence is on the C-terminus of the polypeptide. In some embodiments, the short cysteine containing sequence is on the N-terminus of the polypeptide. In some embodiments, the polypeptide comprises an amino acid sequence of $(CGG)_z$ (SEQ ID NO:4), wherein z is an integer greater than 1. In some embodiments, z is an integer from 1 to 40, from 1 to 30, from 1 to 20, or from 1 to 10. In some embodiments, z is an integer from 5 to 10. In some embodiments, the polypeptide comprises an amino acid sequence of $(CGG)_8$ (SEQ ID NO:5) at its C-terminus.

b) Albumin Binding Domain

The self-assembling conjugate may include an albumin binding domain (ABD). The albumin binding domain can bind albumin in vivo or in vitro. The ABD may be attached to the C-terminus or the N-terminus of the polypeptide. In some embodiments, the ABD is attached to the N-terminus of the polypeptide. In some embodiments, the ABD comprises a 46 amino acid polypeptide (SEQ ID NO:6) derived from bacterial protein G (also referred to as "ABDN"). In some embodiments, the ABD may be SEQ ID NO:6. The albumin binding domain may be from any animal species, including but not limited to, human and rodent.

In some embodiments, the ABD may comprise an engineered variant of ABDN (SEQ ID NO:7) (also referred to as "ABDH"). In some embodiments, the ABD may be SEQ ID NO:7. In some embodiments, the ABD may be an engineered variant of ABDN that exhibits a different binding affinity for albumin compared to ABDN. For example, ABDH exhibits higher affinity for albumin compared to ABDN.

As described above, the unconjugated polypeptide can have phase transition behavior. Attachment of the ABD to the end of the polypeptide may affect the phase transition behavior of the polypeptide. In some embodiments, the ABD attached to the polypeptide lowers the $T_t$ of the polypeptide no more than 5° C. relative to the polypeptide's $T_t$ when the polypeptide is not attached to the ABD or the conjugate, such as no more than 4.5° C. relative to the polypeptide's $T_t$ when the polypeptide is not attached to the ABD or the conjugate, no more than 4° C. relative to the polypeptide's $T_t$ when the polypeptide is not attached to the ABD or the conjugate, no more than 3.5° C. relative to the polypeptide's $T_t$ when the polypeptide is not attached to the ABD or the conjugate, or no more than 3° C. relative to the polypeptide's $T_t$ when the polypeptide is not attached to the ABD or the conjugate. In some embodiments, the ABD attached to the polypeptide lowers the $T_t$ of the polypeptide no more than 5° C. relative to the polypeptide's $T_t$ when the polypeptide is not attached to the ABD or the conjugate. The $T_t$ of the polypeptide (and conjugate) can be adjusted by varying the amino acid sequence of the ABD, by varying the length of the ABD, or a combination thereof.

c) Molecule

The self-assembling conjugate may include a molecule. The molecule may be located in the core of the assembly of self-assembling conjugates. The molecule may be characterized by its octanol-water distribution coefficient (log D), where a larger value indicates greater hydrophobicity. For example, the molecule may have a log(D) of greater than or equal to 1.5 at a pH of 7.4, greater than or equal to 2 at a pH of 7.4, greater than or equal to 3 at a pH of 7.4, greater than or equal to 4 at a pH of 7.4, or greater than or equal to 5 at a pH of 7.4. In some embodiments, the molecule has a log D of about 1.5 to about 5 at a pH of 7.4.

The molecule may be a drug molecule, such as a chemotherapeutic. Such chemotherapeutic agents are well known in the art and may include, for example, doxorubicin, paclitaxel, gemcitabine, docetaxel, taxol, SN-38, irinotecan and letrozole. In some embodiments, the chemotherapeutic is doxorubicin or paclitaxel.

The molecule may be an imaging agent. Imaging agents include luminescent labels which emit radiation on exposure to an external source of radiation or other stimulus, e.g. fluorescent materials or fluorophores, chemiluminescent materials, electroluminescent materials, phosphorescent materials, quantum dots and thermoluminescent materials. Examples of fluorophores include fluoresceins, xanthenes, cyanines, naphthalenes, coumarins, oxadiazoles, pyrenes, oxazines, acridines, arylmethines, Alexa Fluors and tetrapyrroles.

Other imaging agents include radioactive labels, including positron emitting nuclei such as $^{18}F$, $^{64}Cu$ or $^{124}I$ which can be detected by imaging techniques such as positron emission topography (PET). Other radioactive labels such as $^{14}C$, $^{3}H$, or iodine isotopes such as $^{123}I$ and $^{131}I$, which can be detected using autoradiographic analysis or scintillation detection for example, can also be used. Imaging agents may include those which can be detected by magnetic resonance techniques, for example magnetic resonance imaging (MRI) or nuclear magnetic resonance (NMR) detectors, the agents typically comprising one or more NMR-active nuclei that are not generally found in concentrated form elsewhere in the organism or biological sample, for example, $^{13}C$, $^{2}H$ (deuterium) or $^{19}F$. Further imaging agents include those which are effective contrast agents for X-ray photographic techniques or computed tomography (CT) imaging techniques generally comprising atoms with large nuclei, for example atoms with atomic number of 35 or more, preferably 40 or more and even more preferably 50 or more, for example iodine or barium.

The self-assembling conjugate may include varying amounts of the molecule. In some embodiments, the self-assembling conjugate may include at least one molecule. In some embodiments, the self-assembling conjugate may include about 1 to about 15 molecules. In some embodiments, the self-assembling conjugate may include about 2 to about 12 molecules, about 3 to about 10 molecules, or about 5 to about 8 molecules.

In some embodiments, the molecule is attached to the polypeptide through a thiol group. The thiol group may react with many chemical groups known in the art including, but not limited to, haloacetyls, maleimides, hydrazides, aziridines and acryloyls. The attachment of the molecule to the polypeptide may be through a hydrazide linkage. In some embodiments, the molecule is attached to the polypeptide through a pH dependent linker.

d) Phase Transition

As mentioned above, the self-assembling conjugate can have phase transition behavior. The self-assembling conjugate can have a $T_t$ that is the same or different than that of the polypeptide. As described above with respect to the polypeptide, the conjugate may also have phase transition behavior wherein the conjugate changes phase at its $T_t$. Phase transition may refer to the aggregation of the conjugate(s), which may occur sharply and in some instances reversibly at or above the $T_t$. The $T_t$ of the conjugate may be dependent on the $T_t$ of the unconjugated polypeptide. In addition, the $T_t$ of the conjugate may be affected by the ABD and/or the molecule. Accordingly, the conjugate can have a varying $T_t$ depending on the components/domains that it comprises. For example, the conjugate can have a $T_t$ above 40° C., above 45° C., above 50° C., or above 60° C. In some embodiments, the conjugate can have a $T_t$ below 80° C., below 75° C., below 70° C., or below 65° C.

The conjugate may undergo phase transition at varying concentrations. For example, the conjugate may phase transition at a concentration of about 5 μM to about 1 M, such as about 10 μM to about 500 μM, about 15 μM to about 250 μM, about 20 μM to about 150 μM, or about 25 μM to about 100 μM. In some embodiments, the conjugate phase transitions at a concentration that is suitable for administration to a subject. In some embodiments, the conjugate can have a $T_t$ above 40° C. at a concentration of 100 μM, a $T_t$ above 45° C. at a concentration of 100 μM, a $T_t$ above 50° C. at a concentration of 100 μM, or a $T_t$ above 60° C. at a concentration of 100 μM.

Phase transition behavior may also enable purification of the conjugate using inverse transition cycling, thereby eliminating the need for chromatography. "Inverse transition cycling" refers to a protein purification method for polypeptides having phase transition behavior, and the method may involve the use of the conjugate's reversible phase transition behavior to cycle the solution through soluble and insoluble phases, thereby removing contaminants and eliminating the need for chromatography.

e) Nanoparticles

The assembly of self-assembling conjugates may self-assemble into a variety of shapes and sizes. In some embodiments, the assembly of self-assembling conjugates may be a nanoparticle. The nanoparticle may be rod-shaped or spherical, or the composition may include combinations of differently shaped nanoparticles. In some embodiments, the molecule is located in the core of the nanoparticle. In some embodiments, the ABD is located on the periphery of the nanoparticle. In some embodiments, the nanoparticle is a micelle.

The nanoparticle may have a varying average hydrodynamic radius. In some embodiments, the nanoparticle can have an average hydrodynamic radius of about 10 nm to about 100 nm, such as about 25 nm to about 75 nm, or about 40 nm to about 60 nm. In some embodiments, the nanoparticle may have an average hydrodynamic radius of greater than 10 nm, greater than 20 nm, greater than 30 nm, greater than 40 nm, or greater than 50 nm. In some embodiments, the nanoparticle may have an average hydrodynamic radius of less than 100 nm, less than 90 nm, less than 80 nm, less than 70 nm, less than 60 nm, or less than 50 nm.

The nanoparticle may also be described by its average radius of gyration. For example, the nanoparticle may have an average radius of gyration of about 10 nm to about 100 nm, such as about 25 nm to about 75 nm or about 40 nm to about 60 nm. In some embodiments, the nanoparticle may have an average radius of gyration of greater than 10 nm, greater than 20 nm, greater than 30 nm, greater than 40 nm, or greater than 50 nm. In some embodiments, the nanoparticle may have an average radius of gyration of less than 100 nm, less than 90 nm, less than 80 nm, less than 70 nm, less than 60 nm, or less than 50 nm.

3. METHODS OF USE a) Method of Killing Cancer Cells

The present disclosure also provides a method of killing multiple cancer cells. The method may include contacting multiple cancer cells with the composition as detailed herein to the subject. The cancer cells may be in an in vitro environment or an in vivo environment. In some embodiments, the cancer cells are in a subject. Many different types of cancer cells may be killed by chemotherapeutics. The compositions as detailed herein may be used to deliver chemotherapeutics to any cancer cell type.

b) Method of Treating a Disease or Disorder

The present disclosure also provides methods of treating a disease or disorder. The methods comprise administering an effective amount of the composition as detailed herein to the subject.

In some embodiments, the disease or disorder is cancer. Many different cancer types and subtypes may be treated by chemotherapeutics. The compositions as detailed herein may be used to deliver chemotherapeutics to any cancer type or subtype. In some embodiments, the cancer may be a carcinoma, sarcoma, lymphoma, leukemia, melanoma, mesothelioma, multiple myeloma, or seminoma. In certain embodiments, the cancer is leukemia. The cancer may be a cancer of the bladder, blood, bone, brain, breast, cervix, colon/rectum, endometrium, head and neck, kidney, liver, lung, muscle tissue, ovary, pancreas, prostate, skin, spleen, stomach, testicle, thyroid, or uterus.

The disease or disorder may be a cancer comprising solid tumors. Examples of cancers that comprise solid tumors include, but are not limited to, pancreatic, bladder, non-small cell lung cancer (NSCLC), breast, and ovarian cancers.

c) Method of Localizing a Molecule

The present disclosure also provides methods of localizing a molecule to a tissue or organ in a subject. In some embodiments, the methods comprise administering to the subject the composition as described herein, wherein following administration of the composition the molecule is localized in the liver at less than 30% of the injected dose/gram of tissue or organ (ID/g). In some embodiments, following administration of the composition the molecule is localized in the liver at about 1% to about 30% of the injected dose/gram of tissue or organ (ID/g).

In some embodiments, the methods comprise administering to the subject the composition as described herein, wherein following administration of the composition the molecule is localized in the spleen at less than 10% of the injected dose/gram of tissue or organ (ID/g). In some embodiments, following administration of the composition the molecule is localized in the spleen at about 1% to about 10% of the injected dose/gram of tissue or organ (ID/g).

In some embodiments, the methods comprise administering to the subject the composition as described herein, wherein following administration of the composition the amount of the molecule localized in a tissue or organ is decreased when compared to the same molecule in a self-assembling conjugate without an albumin binding domain and wherein the tissue or organ is the kidney, liver, spleen or any combination thereof. The amount of the molecule localized in a tissue or organ may be decreased at least two-fold when compared to the same molecule in a self-assembling conjugate without an albumin binding domain and wherein the tissue or organ is the kidney, liver, spleen or any combination thereof. In some embodiments, the amount of the molecule localized in a tissue or organ may be decreased about two-fold to about ten-fold when compared to the same molecule in a self-assembling conjugate without an albumin binding domain and wherein the tissue or organ is the kidney, liver, spleen or any combination thereof.

The present disclosure also provides methods of localizing a molecule to a tumor in a subject. In some embodiments, the methods comprise administering to the subject the composition as described herein, wherein following administration of the composition the amount of the molecule localized to the tumor is increased when compared to the same molecule in a self-assembling conjugate without an albumin binding domain. The amount of the molecule localized to the tumor may be increased at least two-fold when compared to the same molecule in a self-assembling conjugate without an albumin binding domain. In some embodiments, the amount of the molecule localized to the tumor may be increased about two-fold to about 20-fold when compared to the same molecule in a self-assembling conjugate without an albumin binding domain.

4. ADMINISTRATION

The disclosed compositions may be incorporated into pharmaceutical compositions suitable for administration to a subject (such as a patient, which may be a human or non-human) well known to those skilled in the pharmaceutical art. The pharmaceutical composition may be prepared for administration to a subject. Such pharmaceutical compositions can be administered in dosages and by techniques well known to those skilled in the medical arts taking into consideration such factors as the age, sex, weight, and condition of the particular subject, and the route of administration.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols, such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator. The route by which the composition is administered and the form of the composition will dictate the type of carrier to be used.

The composition can be administered prophylactically or therapeutically. In prophylactic administration, the composition can be administered in an amount sufficient to induce a response. In therapeutic applications, the composition can be administered to a subject in need thereof in an amount sufficient to elicit a therapeutic effect. An amount adequate to accomplish this is defined as "therapeutically effective dose." Amounts effective for this use will depend on, e.g., the particular composition of the conjugate regimen administered, the manner of administration, the stage and severity of the disease, the general state of health of the patient, and the judgment of the prescribing physician.

The compositions can be administered by methods well known in the art as described in Donnelly et al. (*Ann. Rev. Immunol.* 1997, 15, 617-648); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), which are all incorporated by reference herein in their entirety. One skilled in the art would know that the choice of a pharmaceutically acceptable carrier, including a physiologically acceptable compound, depends, for example, on the route of administration.

The compositions can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, the conjugate is administered intravenously, intraarterially, or intraperitoneally to the subject.

The composition may conveniently be presented in a single dose or as divided doses administered at appropriate intervals, for example, as two, three, four or more sub-doses per day. The sub-dose itself may be further divided, e.g., into a number of discrete loosely spaced administrations.

As will be readily apparent to one skilled in the art, the useful in vivo dosage to be administered and the particular mode of administration will vary depending upon the age, weight, the severity of the affliction, and subjects treated, the particular compounds employed, and the specific use for which these compounds are employed. The determination of effective dosage levels, that is the dosage levels necessary to achieve the desired result, can be accomplished by one skilled in the art using routine methods, for example, human clinical trials, in vivo studies and in vitro studies.

Dosage amount and interval may be adjusted individually to provide plasma levels of the molecule which are sufficient to maintain the modulating effects, or minimal effective concentration (MEC). The MEC will vary for each molecule but can be estimated from in vivo and/or in vitro data. Dosages necessary to achieve the MEC will depend on individual characteristics and route of administration. However, assays well known to those in the art can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the symptoms to be treated and the route of administration. Further, the dose, and perhaps dose frequency, will also vary according to the age, body weight, and response of the individual patient. A program comparable to that discussed above may be used in veterinary medicine.

A therapeutically effective amount of the composition disclosed herein may be administered alone or in combination with a therapeutically effective amount of at least one additional therapeutic agents. In some embodiments, effective combination therapy is achieved with a single composition or pharmacological formulation that includes both agents, or with two distinct compositions or formulations, administered at the same time, wherein one composition includes a compound of this invention, and the other includes the second agent(s). Alternatively, in other embodiments, the therapy precedes or follows the other agent treatment by intervals ranging from minutes to months.

A wide range of second therapies may be used in conjunction with the compositions of the present disclosure. The second therapy may be a combination of a second therapeutic agent or may be a second therapy not connected to administration of another agent. Such second therapies include, but are not limited to, surgery, immunotherapy, radiotherapy, or a second chemotherapeutic agent.

5. EXAMPLES

It will be readily apparent to those skilled in the art that other suitable modifications and adaptations of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

Example 1: Materials and Methods (ABDN/H-)ELP biosynthesis and purification. (ABDN/H-) ELPs were expressed from the cloned gene in *E. coli* cells as described previously. The amino acid sequence of ABDN is LAEAKVLANRELDKYGVSDYYKNLINNAKTVEGVKALIDEILAALP (SEQ ID NO:6). The amino acid sequence of ABDH is LAEAKVLANRELDKYGVSDFYKRLINKAKTVEGVEALKLHILAALP (SEQ ID NO:7). The genes encoding the (ABDN/

H-) ELPs were assembled by recursive directional ligation (Pre-RDL) in a modified pET plasmid in NEB 5-alpha cells (Invitrogen Corporation, Carlsbad, CA), and were extracted using the QIAprep™ spin miniprep kit (Qiagen; Germantown, MD) (Novagen, Madison, WI). Genes encoding ABDs and the multi-cysteine drug conjugation tail were appended respectively to the N-terminus and C-terminus of the (ABDN/H-) ELPs gene by Pre-RDL. 5'-phosphorylated oligonucleotides encoding ABDs and cysteine rich tail were purchased from Integrated DNA technologies (Coralville, IA) and were annealed and ligated into the vector containing the CP (also referred to as ELP herein) gene using T4 DNA ligase (Invitrogen; Carlsbad, CA) for 1 hr at room temperature, transformed into chemically competent NEB 5-alpha cells. Transformants were selected on TB-agar plates containing 100 μg mL-lkanamycin and positives were confirmed by bidirectional DNA sequencing. Plasmids were transformed into expression host BLR(DE3)TM cells (Novagen, Madison, WI). To express (ABDN/H-) ELPs, transformed cells were used to start 50 ml Terrific Broth (TB) seed cultures containing kanamycin (100 μg/ml) at 250 rpm and 37° C. These cultures were used to inoculate 1 liter of TB medium, and the culture was grown under the same conditions. At mid-log phase cells were induced with 1 mM IPTG and incubated at 37° C. overnight with shaking. Cells were harvested after 10-12 hours, re-suspended in 2.5 mL PBS per liter culture, and disrupted by ultrasonication (Misonix; Farmingdale, NY). Polyethyleneimine (20% v/v, 2 mL per liter culture) was added to remove nucleic acids nucleoproteins. (ABDN/H-)ELPs were purified from the clarified supernatant using two cycles of inverse transition cycling, as shown in FIG. 1. In the first inverse transition cycle, (ABDN/H-)ELP solutions were incubated for 10 min at 50° C., followed by 10 min on ice, and were centrifuged at 4° C. (13,000 rpm, 10 min). The (ABDN/H-) ELP supernatant was supplemented with sodium chloride to a final concentration of ~2.5 M and were heated to 37° C. to initiate the inverse phase transition; (ABDN/H-)ELP coacervates were collected by centrifugation (14,000 rpm, 10 min, 30-35° C.) and were resuspended in tris(2-carboxyethyl)phosphine hydrochloride (TCEP; Pierce Biotechnology, Rockford, IL) (TCEP, 30 mM, pH adjusted to 7.0). Second cycle was performed same as the first one except that 0.5 M final concentration of sodium chloride was used for triggering the phase transition of ELP. After inverse transition cycling purification, (ABDN/H-)ELP purity was determined by SDS-PAGE electrophoresis. The purified CPs were then dialyzed against water and lyophilized.

DOX Drug conjugation and determination. DOX (Carbosynth, Berkshire, UK) was covalently conjugated to cysteine residues of $(Cys-Gly-Gly)_8$ (SEQ ID NO:5) segment of the CP via the pH sensitive linker 3,3'-N-[ε-Maleimidocaproic acid] hydrazide (EMCH, Pierce Biotechnology, Rockford, IL). The conjugation reaction included two steps. In the first step, DOX was conjugated by its carbonyl group to EMCH. In the second step, activated DOX was coupled to the cysteine thiols of (ABDN/H-)ELPs via a hydrazine bond. To perform the first step, 220 mg of DOX was reacted with 114 mg of EMCH 100 mL anhydrous methanol with 100 μL of tri-fluoroacetic acid for 16 hrs in dark and at room temperature. In the second step, the reaction solution was concentrated to 20 mL using rotary evaporation and was added dropwise to (ABDN/H-)ELP suspended in 10 mL reaction buffer (0.1 M Na PO4, 1 mM EDTA, pH 7.0) and 3 mM TCEP. The reactants were stirred for 20 hrs in the dark and at room temperature. Unreacted DOX was removed by Amicon ultra-15 centrifugal filter units (MWCO 10 kDa, Millipore) and with 30% acetonitrile and 70% PBS as the eluent. Following removal of unreacted DOX, acetonitrile was removed by Amicon filtration against PBS. To calculate the conjugation efficiency, a small fraction of the CP-DOX was Amicon filtered against water, and lyophilized. The lyophilized CP-DOX was weighed and dissolved in PBS. The concentration of CP and DOX was calculated by gravimetry and spectrophotometry at 488 nm, using an extinction coefficient of 11500 $M^{-1}$ $cm^{-1}$, respectively. The conjugation number was defined as the concentration of DOX divided by the concentration of CP.

Synthesis of paclitaxel-levulinic acid (PTX-LEV) and conjugation of paclitaxel with CP. As shown in Scheme 1, PTX-LEV was synthesized as described previously (Bhattacharyya et al. Nat Commun. 2015; 6: 7939, which is incorporated by reference herein in its entirety).

Scheme 1

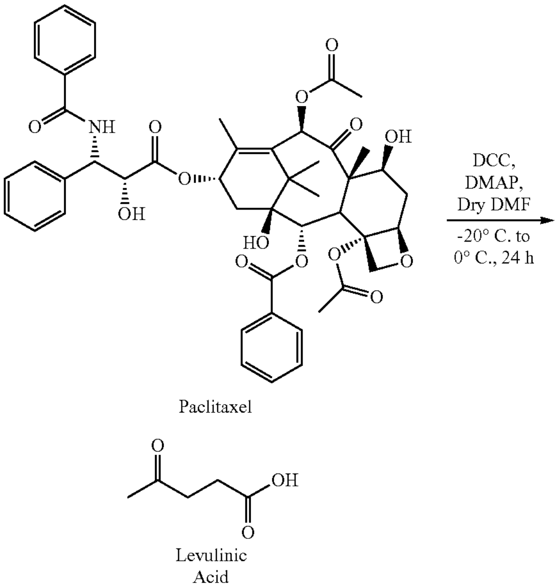

Paclitaxel

Levulinic Acid

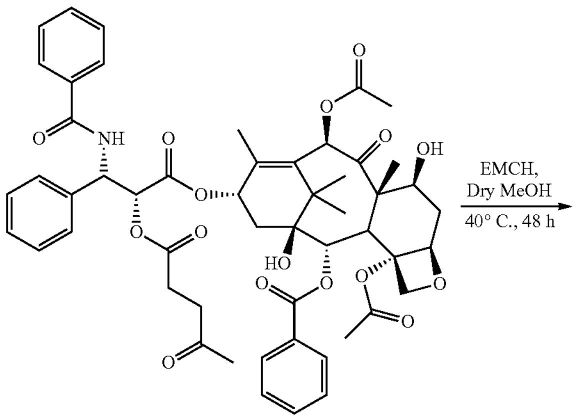

-continued

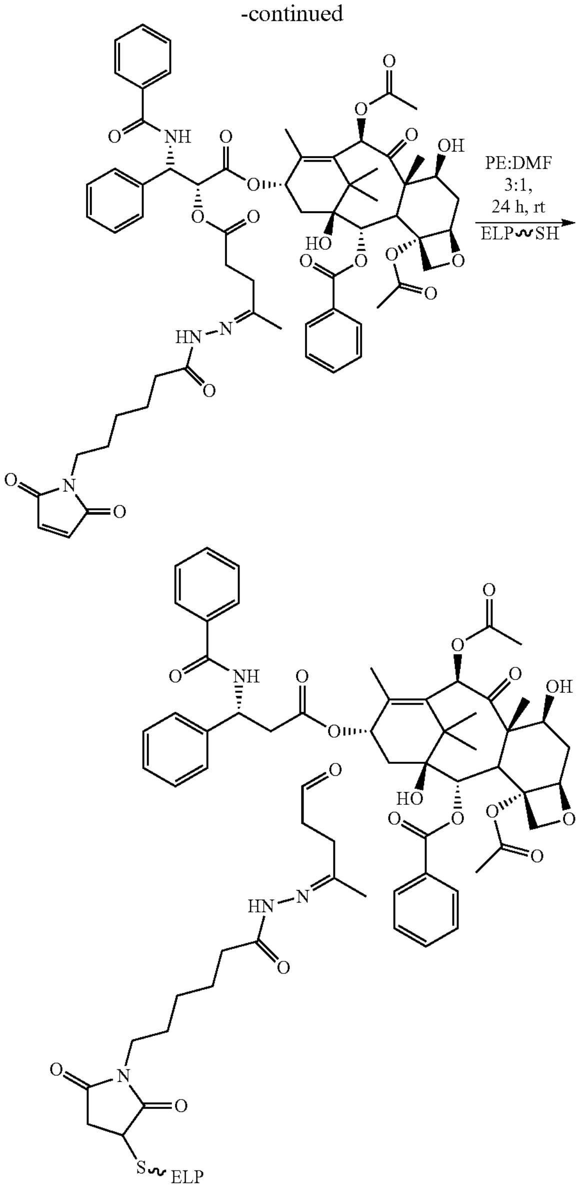

Briefly, levulinic acid (0.08 g, 0.7 mmol) and N,N'-Dicyclohexylcarbodiimide (DCC) (0.145 g, 0.7 mmol) was dissolved in dry Dimethylformamide (DMF) and mixed to each other, stirred for 30 mins at −20° C. PTX (0.5 g, 0.58 mmol) and 4-Dimethylaminopyridine (DMAP) (0.5 g, 0.58 mmol) were dissolved in dry DMF and were added to the above mixture. The reaction mixture was left stirred for 24 h at 4° C. The reaction mixture was filtered and the DMF was evaporated to dryness. The compound was purified with column chromatography with silica gel and 1.5% methanol (MeOH) in chloroform as eluent. Retention Factor ($R_f$): 0.48 in EtOAc/Hexane=2:1. PTX-LEV (0.05 g, 0.05 mmol) and N-ε-Maleimidocaproic acid hydrazide (EMCH) (0.018 g, 0.07 mmol) was dissolved in dry MeOH and left stirring in the dark for 36 h at 45° C. After that, the MeOH was evaporated to dryness and the compound was purified with silica gel column chromatography with 2-2.5% MeOH in chloroform as eluent. PTX-LEV-EMCH was immediately used for next step. $R_f$: 0.6 in 10% MeOH in $CHCl_3$. ESI-MS: 1159 [M+H]. $^1H$ NMR (400 MHz, DMSO-d6): δ 10.24 (s, 1H, 12'), 9.28 (d, 1H, —HNBz), 7.97/7.7/7.67 (5H, aromatic: O-Bz), 7.82/7.48 (5H, aromatic: N-Bz), 7.44/7.17 (5H, aromatic: Ph3'-), 6.99 (s, 2H, 12'), 6.27 (s, 3H, 10-OCOCH3), 5.97 (m, 1H, 13), 5.4 (d, 1H, 2), 5.25 (dd, 1H, 3'), 4.91 (m, 1H, 5), 4.61 (d, 2H, 2'), 4.09 (m, 1H, 7), 3.99 (dd, 2H, 4-$CCH_2O$), 3.57 (m, 1H, 3), 3.37 (m, 2H, 5'), 3.33 (s, 3H, 10-OCOCH3), 3.17 (t, 2H, 4'), 3.16 (t, 3H, 11'), 2.6 (m, 2H, 6), 2.35 (m, 2H, 7'), 2.25 (s, 3H, 6'), 2.1 (s, 3H, 4-OCOCH3), 1.82 (s, 3H, 8-$CH_3$), 1.75 (d, 2H, 14), 1.48 (s, 3H, 12-$CH_3$), 1.49 (m, 2H, 8'), 1.23 (m, 2H, 10'), 0.992/1.01 (s, 3H, 15-$2CH_{3,5}$), 0.84 (m, 2H, 9'). NMR: (125 MHz, DMSO-d6): δ 207.8, 202.35, 190.22, 174.52, 171.78, 171.05, 169.59, 166.279, 165.19, 155.51, 139.41, 134.43, 131.51, 129.92, 129.55, 128.64, 128.25, 127.56, 127.42, 127.23, 83.55, 80.18, 76.61, 75.20, 74.69, 70.67, 70.36, 65.31, 57.35, 54.47, 46.02, 42.87, 36.48, 34.40, 33.49, 32.97, 31.97, 29.75, 27.79, 26.30, 25.84, 24.65, 22.38, 21.36, 20.64, 16.76, 13.92, 9.72. HRMS (ESI): m/z calcd for $C_{62}H_{71}N_4O_{18}$ ($[M+H]^+$): 1159.476341, found: 1159.47380.

Prior to conjugation with activated PTX, purified CP was suspended in reaction buffer (0.1 M NaPO4, 1 mM ethylenediaminetetraacetic acid (EDTA), pH 7.0) and reduced with 1 mL of Tris(2-carboxyethyl)phosphine hydrochloride (TCEP) at neutral pH (100 mM, pH 7.0) at ~5× excess to thiol. Excess TCEP was removed from the solution by initiating the phase transition with sodium chloride (2.5 M) and centrifugation at 4,000 rpm at 25° C. for 10 minutes. The CP pellet obtained by centrifugation was re-suspended in ~2 mL of reaction buffer. Purified PTX-LEV-EMCH was re-suspended in ~2 mL of DMF and slowly transferred to the stirring CP solution. 1 mL of pH neutral TCEP (100 mM) was added and the reactants were stirred for 16 hrs at 20° C. in the dark. After reaction, the unreacted PTX-LEV-EMCH precipitate was separated by centrifugation at 13,000 rpm at 10° C. for 10 minutes. The supernatant was further purified by diluting it in 20% acetonitrile in PBS and centrifuging the solution in an Amicon Ultra-15 Centrifugal Filter Units (MWCO: 10 kDa, Millipore) at 2,500 rpm at 10° C. The CP-PTX solution was washed twice with $NH_4HCO_3$ solution (pH 7.4) and then freeze dried.

pH dependent drug release. To study pH dependent drug release from CP-DOX micelles, the fraction of unbound drug was determined as a function of time at physiological pH 7.4 and acidic pH 5.0. CP-DOX micelles in PBS (400 uM DOX equivalent) were diluted 1:1 v/v into either pH 5.0 (0.1 M Na acetate) or pH 7.4 (0.1 M $NaH_2PO_4$). Samples were incubated at 37° C. for 0.0, 0.25, 25, 0.5, 1, 2, 4, 6, or 24 hr and were neutralized by addition of pH 7.4 (0.1 M $NaH_2PO_4$). 25 uL of sample at each time point was injected into LC10 HPLC (Shimadzu Scientific Instruments; Columbia, MD) with Shodex OHPak SB-804 column (New York, NY) and acetonitrile: PBS (7:3) as the mobile phase at an isocratic flow rate of 0.5 mL $min^{-1}$. Eluting peaks were detected with a UV-Visible detector set at 490 nm. Free DOX at various known concentrations were injected as standard. HPLC data was quantified by integrating the area under the peak corresponding to the free drug. The concentrations of unbound DOX in samples were calculated using the regression coefficients obtained from the linear regression analysis of the calibration curve ($r^2=0.998$, $F_{1,11}=4,932$, $p=6\times10^{-16}$). The cumulative percent released drug (F %, released) at each time point was defined as the concentration of unbound DOX at that time point divided by total DOX concentration times 100. For pH 5.0 samples, data points were fit by nonlinear regression to a first order release model: F %, released=a[1−exp(−ln(2) t/$t_{1/2}$)] (1) where t is the time (hrs) after incubation, $t_{1/2}$ is the half-life (hrs) of release, and a (%) is the maximum extent of drug release. DOX release at pH 7.4 was negligible and no correlation with time was observed.

Thermal Turbidimetry. Thermal profiles of CPs and CP conjugates were determined by measuring the transition temperature ($T_t$) over a range of concentrations (5, 10, 25, 50, and 100 uM) in PBS, FBS, and MS using a Cary UV-visible spectrophotometer equipped with temperature controller (Agilent Technologies, CA, USA). $T_t$ values were determined by measuring the turbidity at wavelength 350 nm for CP monomers and 650 nm for CP-DOX conjugates by raising the temperature at 1° C./min. The transition temperature was defined as the maximum first derivative of the optical density.

Light Scattering. Dynamic and static light scattering measurements were performed using an ALV/CGS-3 goniometer system (Germany). CP monomers and conjugates were prepared in PBS at 25 μM and filtered through 0.22 μm Millex-GV filters into a 10 mm disposable borosilicate glass tube (Fischer). To study the effect of albumin binding on micellar self-assembly, mouse albumin was added to the samples at 1:1 albumin-CP molar ratio in PBS. Measurements were obtained at 25° C. and 37° C. for angles between 30-150° at 5° increments with each angle consisting of 3 runs and 10 s each at each run. Hydrodynamic radius ($R_h$) was determined by dynamic light scattering. The radius of gyration ($R_g$) and the average molecular weight of the particle (MW) were calculated from the slope and intercept of a partial Zimm plot, respectively, using ALV/Dynamic and Static FIT and PLOT software and according. The micelle aggregation number $N_{agg}$, or the number of polypeptide chains per nanoparticle, was calculated by dividing the micelle molecular weight by the molecular weight of the polypeptide monomer.

Interaction with albumin. Interaction of CP monomers and micelles with human and mouse albumin was analyzed by isothermal titration calorimetry (ITC). ITC was conducted using a VP-ITC instrument ((MicroCal LLC, Northampton, MA, USA). Aliquots of 5 uL of 500 uM albumin in PBS were titrated via a 250 μl syringe into CP or CP-DOX at 50 μM concentration, stirring at 300 rpm at 37° C. For background correction, PBS (in the cell) was titrated with albumin (in the syringe) at the same concentrations and conditions. Background was subtracted from the final curves and the binding and thermodynamic parameters—binding constant ($K_D$), number of binding sites (n), and enthalpy (ΔH)—were computed by non-linear fitting to an independent-binding site model using Origin Lab software (USA) for the VP-ITC calorimeter.

For PTX conjugates, ITC was conducted using a Nano ITC system (TA Instruments, Utah, USA). Aliquots of 10 uL of 500 uM albumin in PBS were titrated via a 250 μl syringe into CP-PTX at 50 uM concentration, stirring at 300 rpm at 37° C. For background correction, PBS (in the cell) was titrated with albumin (in the syringe) at the same concentrations and conditions. Background was subtracted from the final curves and the binding and thermodynamic parameters binding constant ($K_D$), number of binding sites (n), and enthalpy (ΔH)—were computed by non-linear fitting to an independent-binding site model using TA Instruments NanoAnalyze software.

SDS- and Native-PAGE characterization. SDS-PAGE was used to analyze the purity and apparent molecular weight of purified ABD-ELP monomers and their interaction with albumin, respectively. Native-PAGE analysis was used to visualize the interaction of CP monomers and micelles with albumin. ABD-ELP monomers were loaded at around 20 ug (10 uL loading volume) on 4-20% Mini-PROTEAN® TGX Stain-Free™ Gel (BioRad, Hercules, CA). Electrophoresis was performed in Tris-glycine buffer (25 mM Tris, 192 mM glycine, 0.1% SDS, pH 8.3) containing 0.1% SDS at 180 V for 30 min. For Native-PAGE, ABD-ELP monomers and micelles were mixed at equal molarity with albumin and were loaded (20 ug per protein) on the gel. Native electrophoresis was run under the same conditions and with the same stacking gel and running buffer as SDS-PAGE, except that no SDS was used. The gels were silver-stained for the protein portion.

Size and morphology of CP conjugated micelles. The radius and the aggregation number of the self-assembled micelles were determined, in the presence and absence of albumin, by dynamic and static light scattering at 37° C. using an ALV/CGS-3 goniometer system (Germany). Freeze fracture electron microscopy was performed to visualize the micelles and estimate their radius and morphology.

Cell culture and tumor inoculation. The C26 murine colon adenocarcinoma cell line was used to evaluate the potency of DOX both in vitro and in vivo. Cells were grown at 37° C. with 5% carbon dioxide in T-75 flasks in a humidified incubator. Culture medium included RPMI-1640 (R8758; Sigma, St. Louis, MO), supplemented with 10% fetal bovine serum (F0392; Sigma, St. Louis, MO), 4.5 g L-1 D-glucose (G8769; Sigma), 10 mM HEPES (15630-080; Invitrogen; Carlsbad, CA), penicillin, streptomycin and 1 mM sodium pyruvate (11360-070, Invitrogen). Cells were passaged every 2-3 days by enzymatic detachment with 0.05% trypsin+0.5 mM EDTA (25300-054; Invitrogen). After 5 min at 37° C. trypsin was removed from detached cells by centrifugation at 400 g for 4 min, and cells were resuspended in 10 mL media. 500 uL of cells were transferred to a new T-75 flask containing 15 mL medium. For in vivo implantation, detached cells were washed twice in Minimum Essential Medium (MEM, 51200-038; Invitrogen; Carlsbad, CA). Tumor inoculation was performed by injecting $4\times10^5$ cells in 30 μl of medium into the right flank. Tumors were allowed to grow for 8-10 days to a size of around 75 $mm^3$. All animals were treated in accordance with National Institute of Health Guide for Supplemental methods and data the Care and Use of Laboratory Animals under protocols approved by the Duke University Institutional Animal Care and Use Committee.

In vitro Cytotoxicity. In vitro cytotoxicity of the ABDN-CP-DOX versus that of naked CP-DOX and free DOX was determined using the calorimetric MTS assay. C26 murine colon adenocarcinoma cells were seeded (5000 cells/well) in a 96-well plate. After 24 h, cells were treated in triplicate with 3-fold serial dilutions of drugs beginning with 100 uM. After 72 h incubation, 20 μL of CellTiter 96 AQueous™ (Promega; Madison, WI) 3-(4,5-dimethlthiazol-2-yl)-5-(3-carboxymethoxphenyl)-2-(4-sulfophenyl)-2H-tetrazolium (MTS) reagent was added to each well followed by 3 h incubation at 37° C. The absorbance at 490 nm was determined using a Victor3™ microplate reader (Perkin Elmer; Waltham, MA). For each plate, blank wells (with no cells) were defined as 0% viability and wells treated with PBS were defined as 100% viability. The background absorbance at 490 nm was corrected by subtracting the average absorbance of the blank wells from each well. The percent viability was defined as the absorbance of each well normalized to the absorbance of wells treated with PBS. Inhibitory concentration (IC 50) values were calculated using a four-parameter logistic fit in the Prism program (GraphPad Software, San Diego, CA, USA).

In vitro cytotoxicity of the ABDN-CP-PTX versus that of naked CP-PTX and free PTX was determined using the calorimetric MTS assay. MDA-MB-231 human breast cancer cells were seeded (3000 cells/well) in a 96-well plate. After 24 h, cells were treated in triplicate with 3-fold serial dilutions of drugs beginning with 100 uM. After 72 h incubation, 20 μL of CellTiter 96 AQueous™ (Promega; Madison, WI) 3-(4,5-dimethlthiazol-2-yl)-5-(3-carboxymethoxphenyl)-2-(4-sulfophenyl)-2H-tetrazolium (MTS) reagent was added to each well followed by 3 h incubation at 37° C. The absorbance at 490 nm was determined using a Victor3 TM microplate reader (Perkin Elmer; Waltham, MA). For each plate, blank wells (with no cells) were defined as 0% viability and wells treated with PBS were defined as 100% viability. The background absorbance at 490 nm was corrected by subtracting the average absorbance of the blank wells from each well. The percent viability was defined as the absorbance of the each well normalized to the absorbance of wells treated with PBS. Inhibitory concentration (IC 50) values were calculated using a four-parameter logistic fit in the Prism program (GraphPad Software, San Diego, CA, USA). The MTS assay was repeated twice to ensure validity of results.

Pharmacokinetics of ABD-ELP monomers and ABD-CP-DOX micelles. For pharmacokinetics analysis, ABD-ELP and ELP-monomers were traced in vivo by fluorescent labeling. A single cysteine was added to the C-terminus of polypeptides and was reacted with Alexa 488-maleimide (Life Technologies, Carlsbad, CA, USA). 50 uL Alexa 488-maleimide at 27.75 uM in DMSO was added to the polypeptide solution in the reaction (250 uM) and was allowed to stir for 3 hr at room temperature in the dark. Unbound Alexa488 was then removed by Amicon ultra-15 centrifugal filter units (MWCO 10 kDa, Millipore) and in PBS. Alexa488 concentration and conjugation efficiency was then determined.

Alexa488 labeled polypeptides were injected intravenously into Balb/C mice and 10 uL blood samples were collected at 40 s (15 uL from the tail vein at 40 s), 15 and 30 min, 2, 4, 8, 24, 48, and 72 hrs after injection, diluted into 100 uL heparinized PBS (1,000 U mL-1), and centrifuged (5,000 g, 5 min, 4° C.) to remove cells and debris. 125 uL of the supernatant was loaded onto a black 96-well plate (BD Biosciences) in duplicate. Free Alexa488-maleimide solutions at various known concentrations were prepared in heparinized PBS and were loaded onto the plate as standards. Alexa488 fluorescence was measured on a Wallac Victor3 TM microplate reader (Perkin Elmer; Waltham, MA). The relationship between background-corrected fluorescence and concentration of DOX standards successfully fit into a linear regression.

Pharmacokinetics profile of CP-DOX micelles was explored by intravenous injection into female Balb/C mice (10 and 20 mg DOX Equiv kg-1 BW) via the tail vein. 10 uL blood sample was collected from the tail vein at 40 s, 15 and 30 min, 2, 4, 8, 24, 48, and 72 hrs after injection, diluted into 100 uL heparinized PBS (1,000 U mL-1), and centrifuged (5,000 g, 5 min, 4° C.) to remove cells and debris. To release DOX from the micelles, 10 uL of plasma was incubated in 490 μL of acidified isopropanol (75 mM HCl, 10% water, 90% isopropanol) overnight at 4° C. in the dark. The isopropanol extract was then centrifuged (14,000 RPM, 10 min, 4° C.) and 125 uL of the supernatant was loaded onto a black 96-well plate (BD Biosciences) in duplicate. Free DOX solutions at various known concentrations were prepared in acidified isopropanol and were loaded onto the plate as standards. DOX fluorescence was measured on a Wallac Victor3 TM microplate reader (Perkin Elmer; Waltham, MA) using excitation at 485 nm and emission at 590 nm. The relationship between background-corrected fluorescence and concentration of DOX standards successfully fit into a linear regression.

Canine pharmacokinetics and toxicities. Healthy beagles and hounds, purchased from a commercial vendor (Covance Inc, Princeton, NJ) were used to investigate the pharmacokinetics of ABDN-CP-DOX micelles. All procedures and protocols involving care, handling, and dosing for this study were reviewed and approved by the Institutional Animal Care and Use Committee (IACUC) at North Carolina State University College of Veterinary Medicine, which is an AAALAC-accredited facility. The animals' health status were monitored daily by the animal technicians and veterinary staff, paying particular attention for signs of gastrointestinal toxicities including vomiting, diarrhea, lethargy, and inappetence. If noted, supportive care was provided. ABDN-CP-DOX, CP-DOX and DOX were infused via cephalic vein at a 10% reduced dose of the maximally tolerated dose (MTD) of native DOX in dogs, i.e. 27 DOX Equiv. $m^{-2}$ body surface area (BSA) for dogs weighing greater than 15 kg and 0.9 mg DOX Equiv. $kg^{-1}$ of body weight (BW) for dogs weighing less than 15 kg. Due to the limited animal availability and the high cost of the canine experiments, pharmacokinetics were studied with 3 dogs for CP-DOX and free DOX, and with 2 dogs for ABDN-CP-DOX. 2 mL blood samples were drawn from jugular vein at 40 s, 15 and 30 min, 2, 4, 8, 24, 48, and 72 h after injection, diluted into 400 μL heparinized PBS (1000 $UmL^{-1}$). Sample processing and analysis were performed as with murine pharmacokinetics studies. Blood samples (2 ml) were also drawn 7 days after the injections for hematology and serum biochemistry analysis, since temporary bone marrow dyscrasias typically occur 7 days after the injection of most chemotherapeutic drugs.

Biodistribution. The biodistribution profile of CP-DOX micelles was explored by intravenous injection into female Balb/C mice (5 and 10 mg DOX Equiv kg-1 BW) via the tail vein. At 2 and 24 h after injection, tissues (tumor, muscle, heart, lung, liver, spleen and kidney) were removed, weighed and suspended in 1.0 mL acidified isopropanol (75 mM HCl, 10% water, 90% isopropanol). Tissues were then homogenized using 2 mm diameter zirconia beads and a MiniBeadbeater-1TM (Biospec; Bartlesville, OK) for 2 min at 5,000 beats per minute and were incubated overnight at 4° C. in the dark. The isopropanol extracts were then vortexed, and centrifuged (14,000 RPM, 10 min, 4° C.) and 125 uL of the supernatant was loaded onto a black 96-well plate (BD Biosciences) in duplicate. Free DOX solutions at various known concentrations were prepared in acidified isopropanol and were loaded onto the plate as standards. To correct for background tissue fluorescence, tissues were removed from three untreated control mice and were processed similarly. For each tissue, a background (counts per mg tissue) curve was created using 2-fold dilutions of the processed tissues in acidified isopropanol. DOX fluorescence was measured on a Victor3 TM microplate reader (Perkin Elmer; Waltham, MA) using excitation at 485 nm and emission at 590 nm. The background fluorescence was subtracted from each well and DOX concentration in each well was calculated using the DOX fluorescence standard curve.

Maximum tolerated dose. A dose escalation experiment was performed to determine the maximum tolerated dose (MTh) and toxicity profile of CP-DOX micelles. CP-DOX micelles were administered via tail vein into female Balb/C mice (7 weeks old) at increasing dose levels. Body weight was monitored as a measure of toxicity for up to 10 days. To rule out the possibility of CP toxicity, free CP was injected at the dose equal to the ELP dose at the highest CP-DOX dose level i.e. 60 mg/kg BW. MTh was defined as the dose above which body weight loss exceeded 15% of the initial body weight within 10 days.

Tumor regression and survival. CP-DOX micelles were injected intravenously at 10, 20, and 40 mg/kg BW DOX equivalent into the female Balb/C mice (6-8 weeks old) bearing dorsal C26 tumors 8-10 days after tumor implantation when a tumor size of around 75 $mm^3$ was reached. Tumor size and body weight were monitored over a span of two months. Tumor volume was calculated as follows: Volume [$mm^3$]=length×width 2×π/6. Mice with a tumor volume greater 1000 $mm^3$ or body weight loss greater than 15% were euthanized.

Example 2: Development of an Albumin Binding Chimeric Polypeptide

Figure 2A:
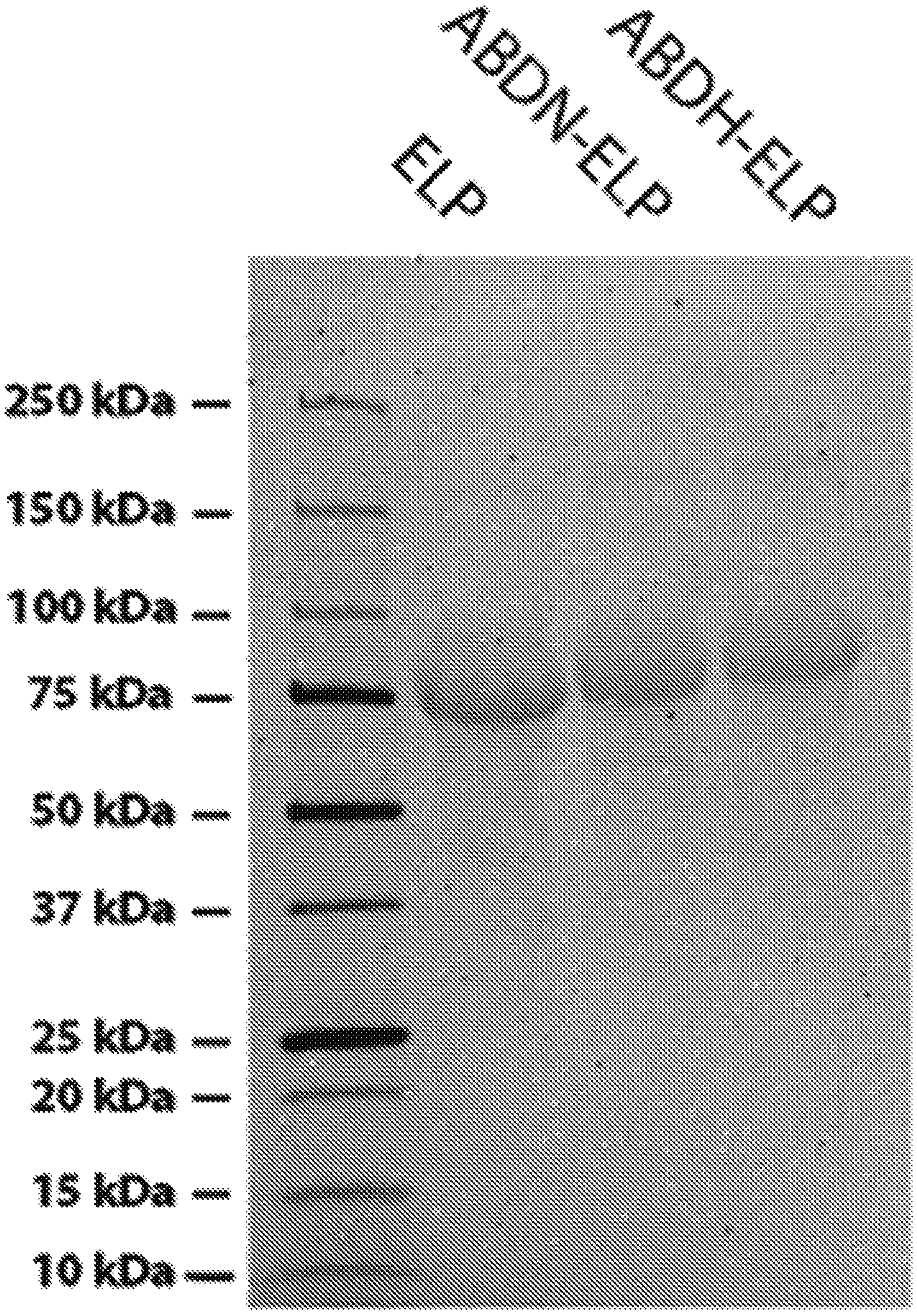
Figure 2B:
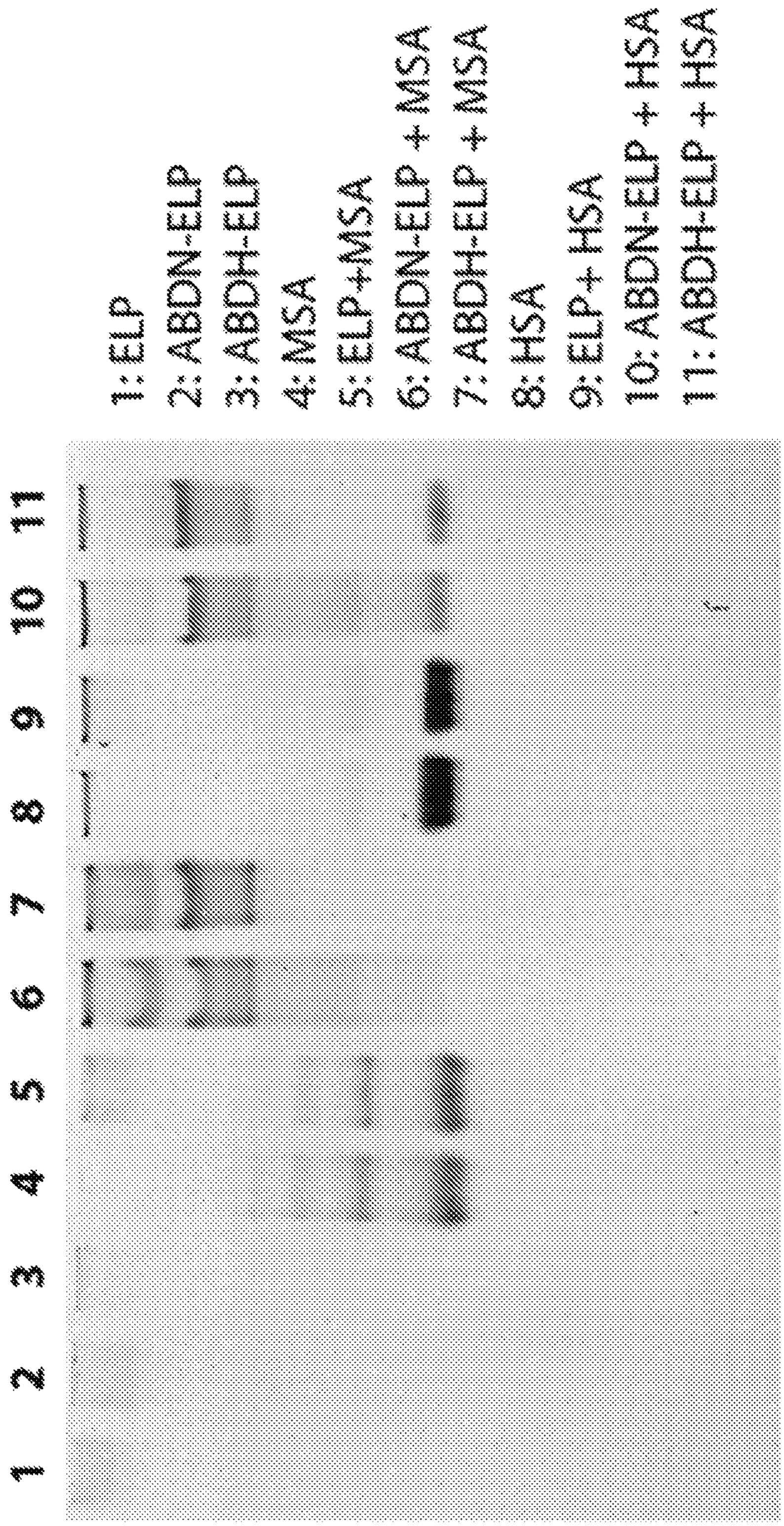
Figure 3A:
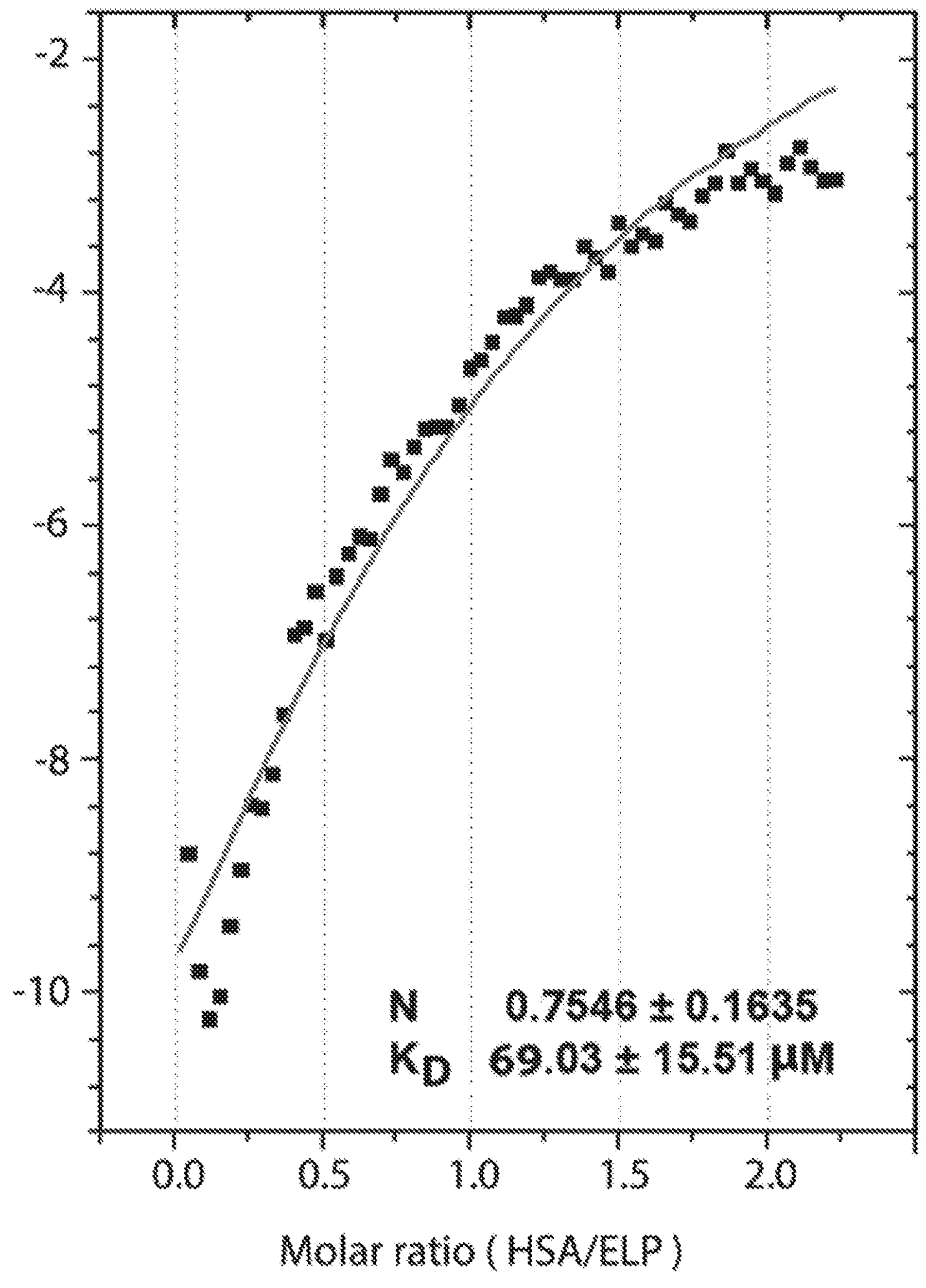
Figure 3B:
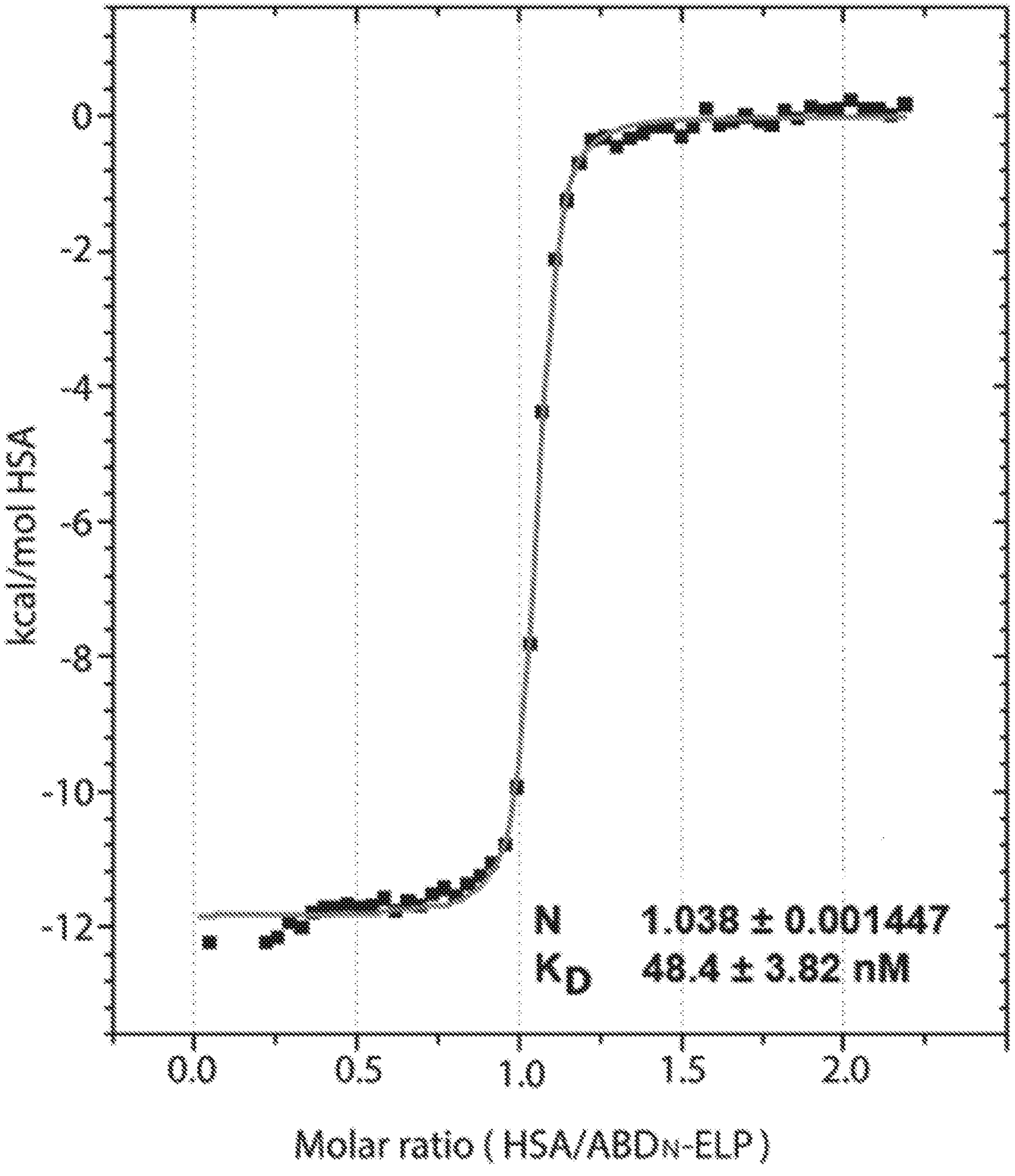
Figure 3C:
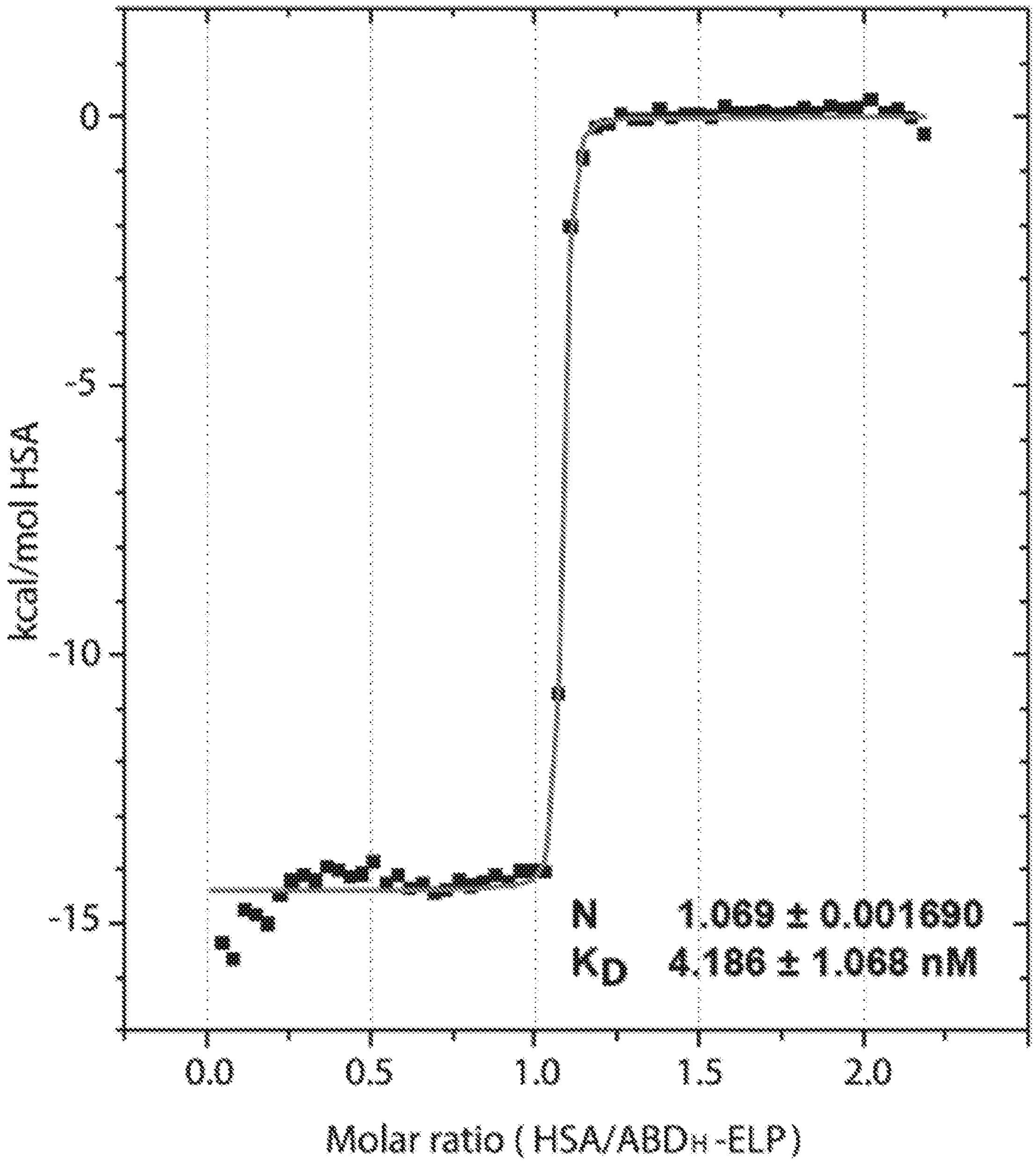
Figure 4A:
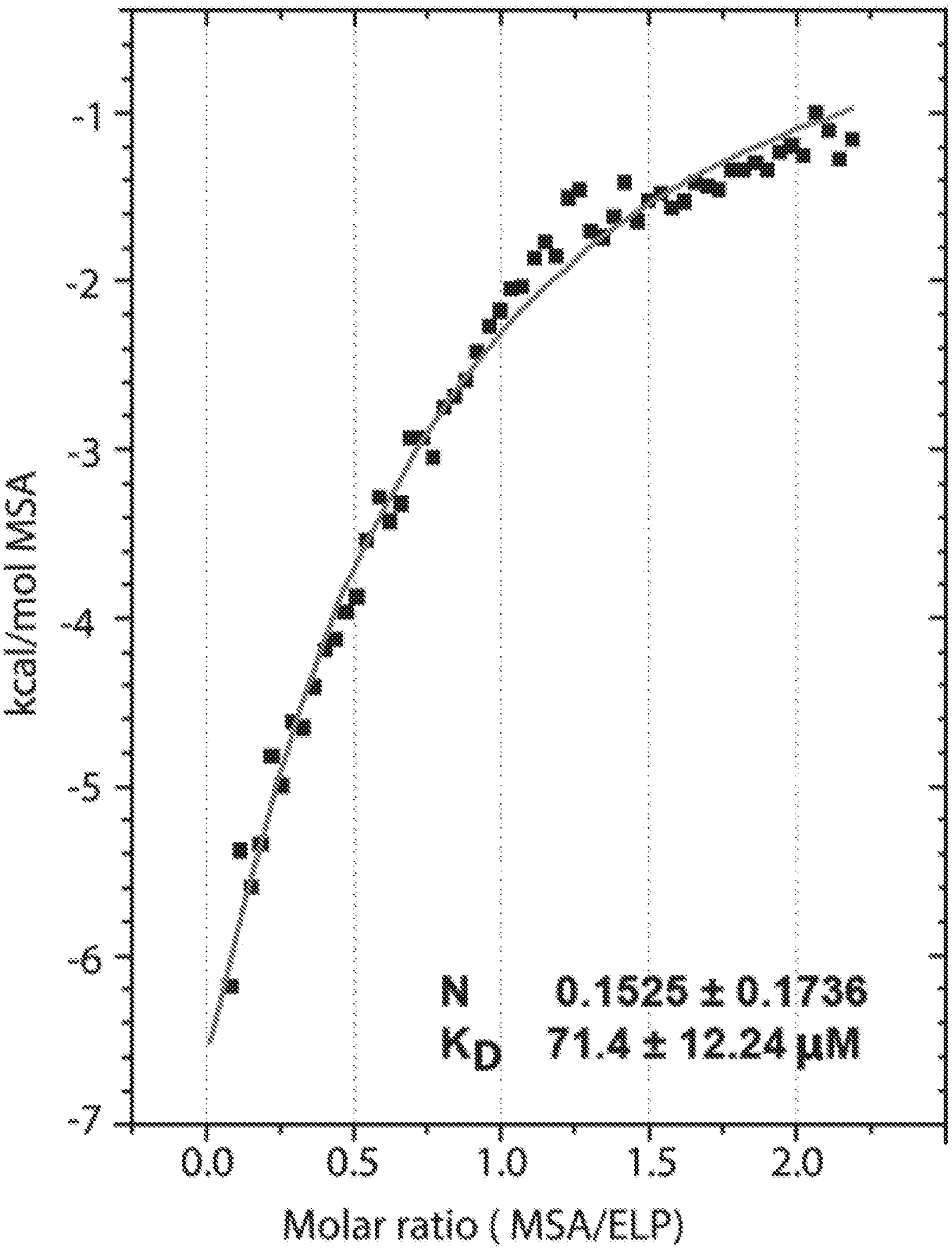
Figure 4B:
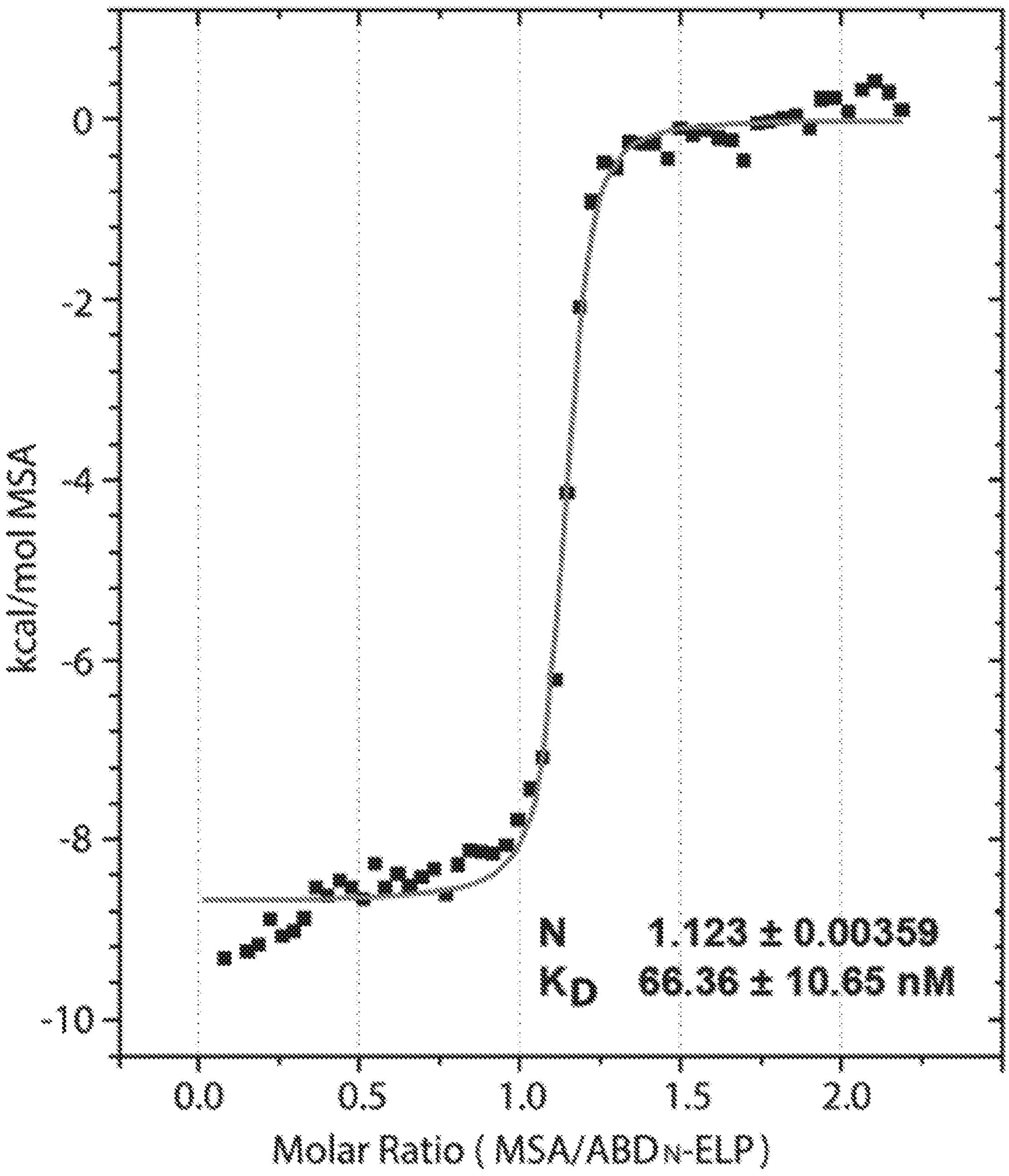
Figure 4C:
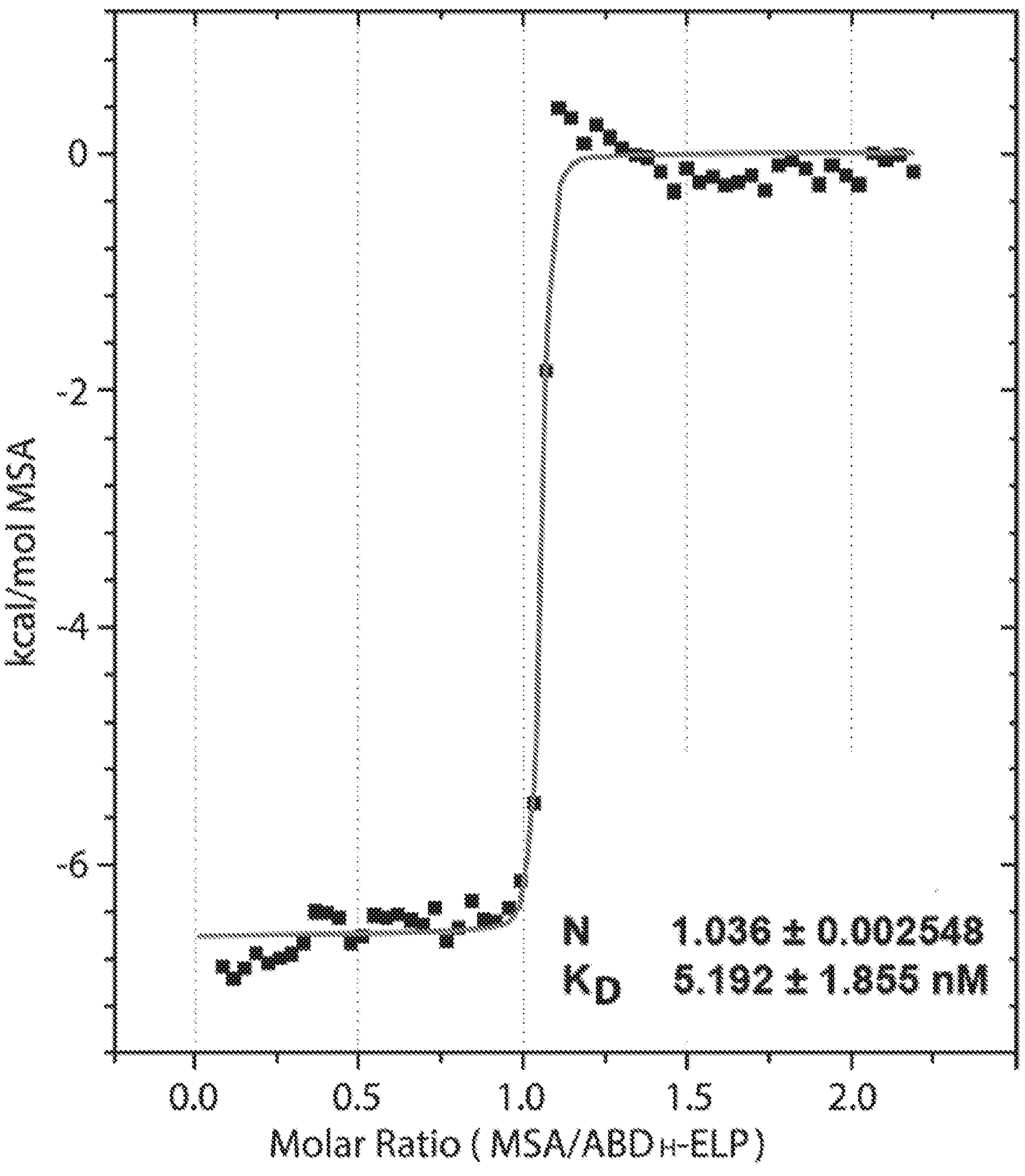
Figure 5:
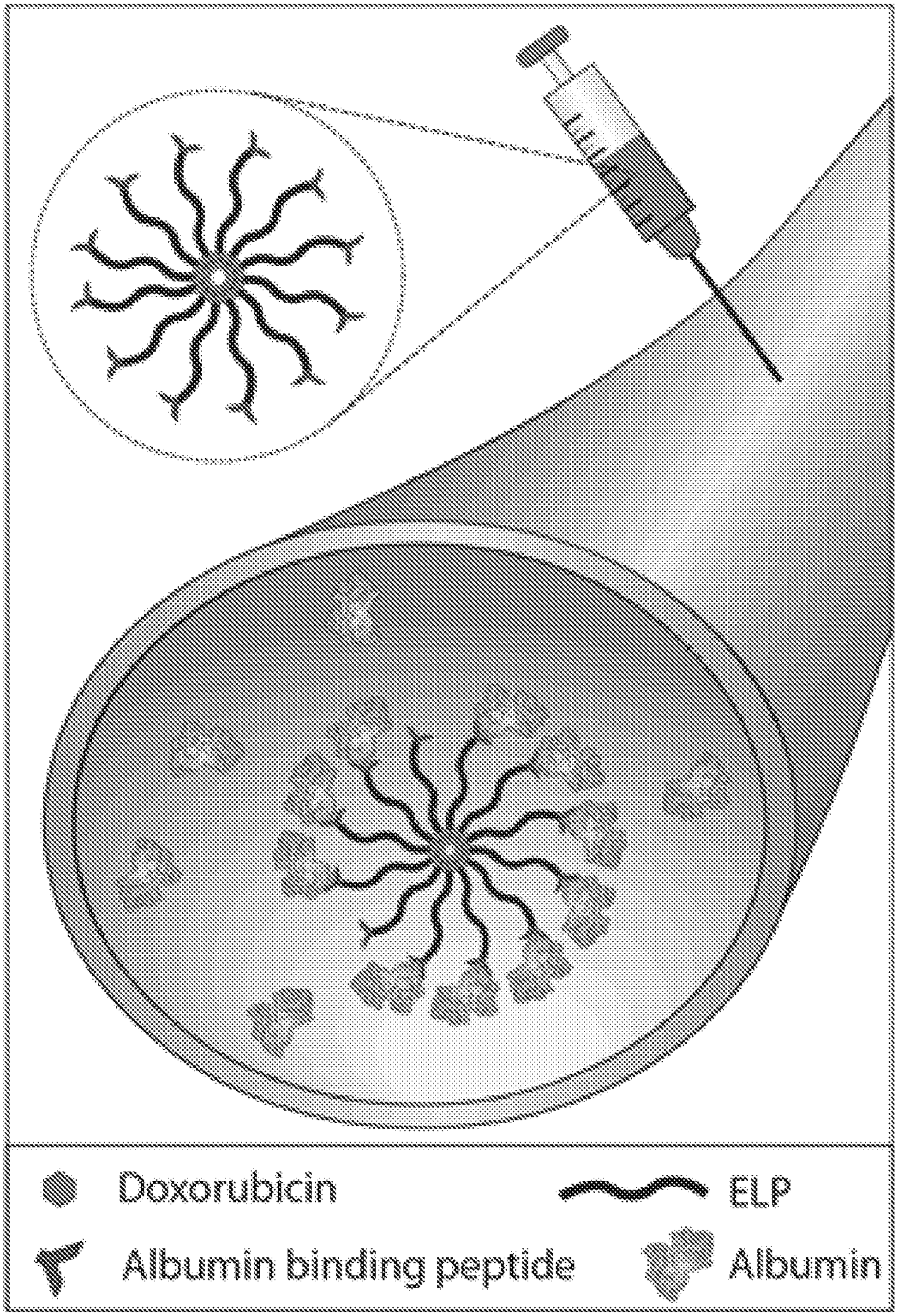

Albumin binding domain fused chimeric polypeptides called ABD-ELPs were designed and included three segments: 1) an ELP scaffold; 2) an albumin binding domain fused to the N-terminus; 3) a short cysteine containing sequence fused to C-terminus for fluorophore labeling and dug conjugation. Naked ELPs (i.e. ELPs) with no ABD at their N-terminus were used as controls. To ensure self-assembly into micelles upon later drug conjugation, a highly hydrophilic ELP was engineered that contained 160 repeats of the Val-Pro-Gly-X-Gly with X=Ala. (ABDN/H-)ELPs were purified from *E. coli* by inverse transition cycling (FIG. 1 and FIG. 2A) with high yield (100-200 $mgL^{-1}$). The binding affinity of ABDN-ELP and ABDH-ELP for human and mouse albumin was analyzed quantitatively by ITC (FIG. 3A-FIG. 3C and FIG. 4A-FIG. 4C, respectively) and qualitatively by native-PAGE (FIG. 2B). The binding data also showed that both ABDN-ELP and ABDH-ELP bind to mouse albumin with 1:1 stoichiometry and nanomolar affinity ($K_D$=66.36±10.65 nM for ABDN-ELP (FIG. 4B) and $K_D$=5.192±1.855 nM for ABDH-ELP (FIG. 4C)), whereas ELP controls displayed no specific affinity (FIG. 4A). The binding data showed that both ABDN-ELP and ABDH-ELP bind to human albumin with 1:1 stoichiometry and nanomolar affinity ($K_D$=48.4±3.82 nM for ABDN-ELP (FIG. 3B) and $K_D$=4.186±1.068 nM for ABDH-ELP (FIG. 3C)), whereas ELP controls displayed no specific affinity.

Figure 2C:
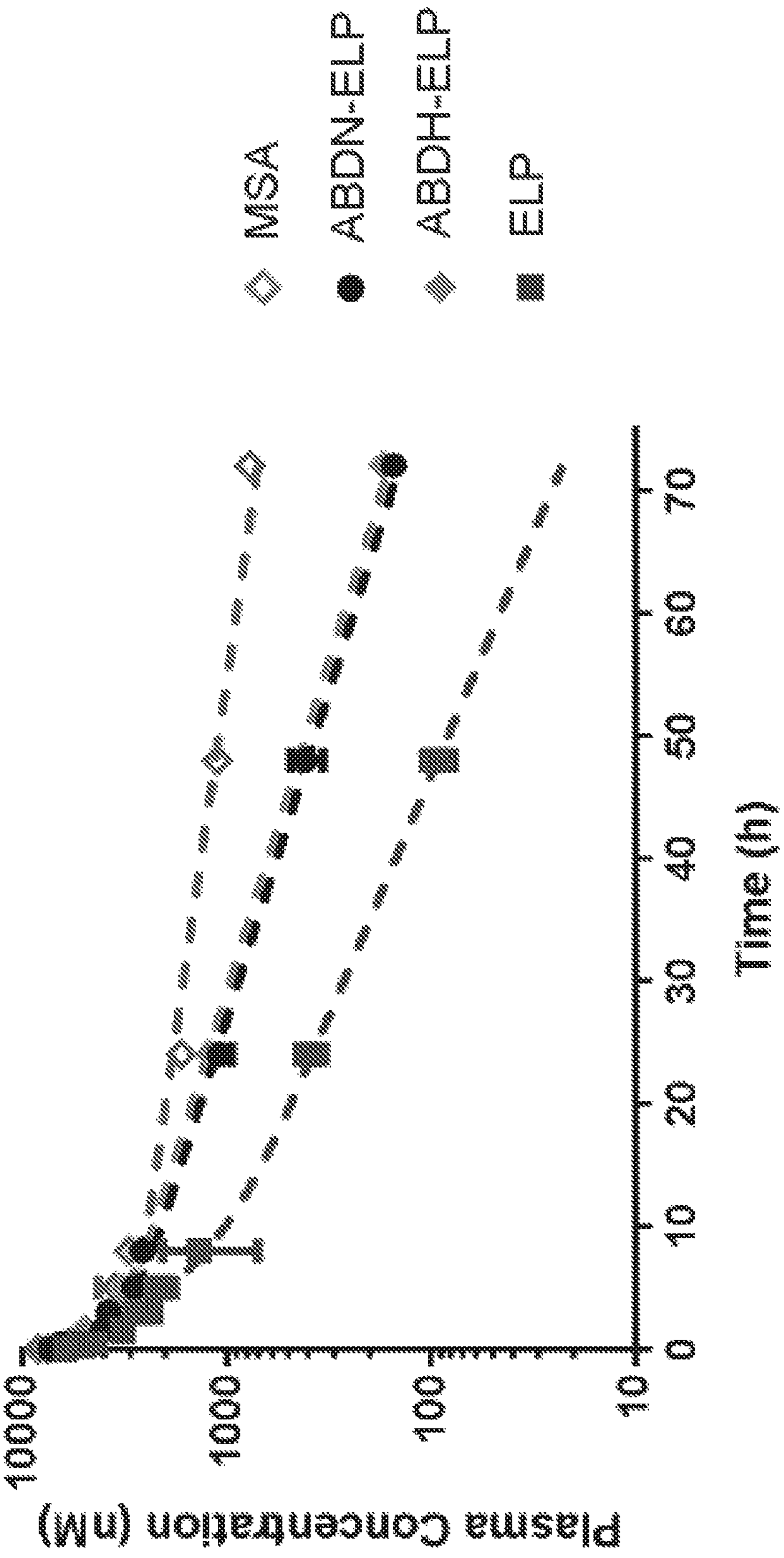

An in vivo pharmacokinetics study was performed by labeling (ABDN/H-)ELPs with Alexa488 and examining the concentration-time profile (FIG. 2C) following intravenous administration. Data were fitted to a two-compartment model and showed that fusion to ABDs increases the half-life of ELPs from 11.2±0.6 h to 16.8±0.5 h for ABDN-ELP and 16.9±0.3 h for ABDH-ELP (Table 1). Despite higher binding affinity of ABDH-CP for albumin than ABDN-CP, no significance difference was observed between the half-life of ABDH-CP and ABDN-CP in vivo. Both ABDH-CP and ABDN-CP increased the half-life of CP from 11 h to 17 h (FIG. 2C, Table 1).

Furthermore, bioavailability was measured by calculating the area under the curve (AUC) and was determined to increase from 38.8±0.8 μM. h for ELP to 80.2±1.9 μM. h for ABDN-ELP and 88.3±1.3 μM. h for ABDH-ELP (Table 1). Mouse serum albumin was also labeled with Alexa488 and was administered as a positive control. The half-life of MSA was found to be 34.6±1.9 h which is in good agreement with the expected half-life for endogenous MSA (approximately 35 h).

TABLE 1

Pharmacokinetic parameters of ELP, ABDN-ELP, ABDH-ELP, and MSA. Values are shown as mean (SD).

| Parameter | Symbol [unit] | ABDN-CP | ABDH-CP | CP | MSA |
|---|---|---|---|---|---|
| Elimination half-life | α $t_{1/2}$ [h] | 16.8 ± 0.5 | 16.9 ± 0.3 | 11.2 ± 0.6 | 34.6 ± 1.9 |
| Area under the curve | AUC [μM•h] | 80.2 ± 1.9 | 88.3 ± 1.3 | 38.8 ± 0.8 | 157.3 ± 4.3 |
| Distribution half-life | β $t_{1/2}$ [min] | 74.7 ± 17.7 | 93.2 ± 12.7 | 127.3 ± 12.7 | 72.7 ± 10.2 |
| Apparent distribution volume | $V_D$ [mL $g^{-1}$] | 0.27 ± 0.01 | 0.25 ± 0.00 | 0.33 ± 0.01 | 2.78 ± 0.11 |
| Plasma clearance | CL [mL $h^{-1}$ $g^{-1}$] | 0.012 ± 0.000 | 0.011 ± 0.000 | 0.026 ± 0.001 | 0.058 ± 0.002 |
| Elimination rate constant | $k_e$ [$h^{-1}$] | 0.08 ± 0.00 | 0.07 ± 0.00 | 0.14 ± 0.01 | 0.05 ± 0.00 |
| Tissue to plasma rate constant | $k_{tp}$ [$h^{-1}$] | 0.31 ± 0.07 | 0.25 ± 0.04 | 0.14 ± 0.02 | 0.24 ± 0.04 |
| Plasma to tissue rate constant | $k_{pt}$ [$h^{-1}$] | 0.21 ± 0.06 | 0.16 ± 0.03 | 0.11 ± 0.02 | 0.30 ± 0.05 |

Figure 6A:
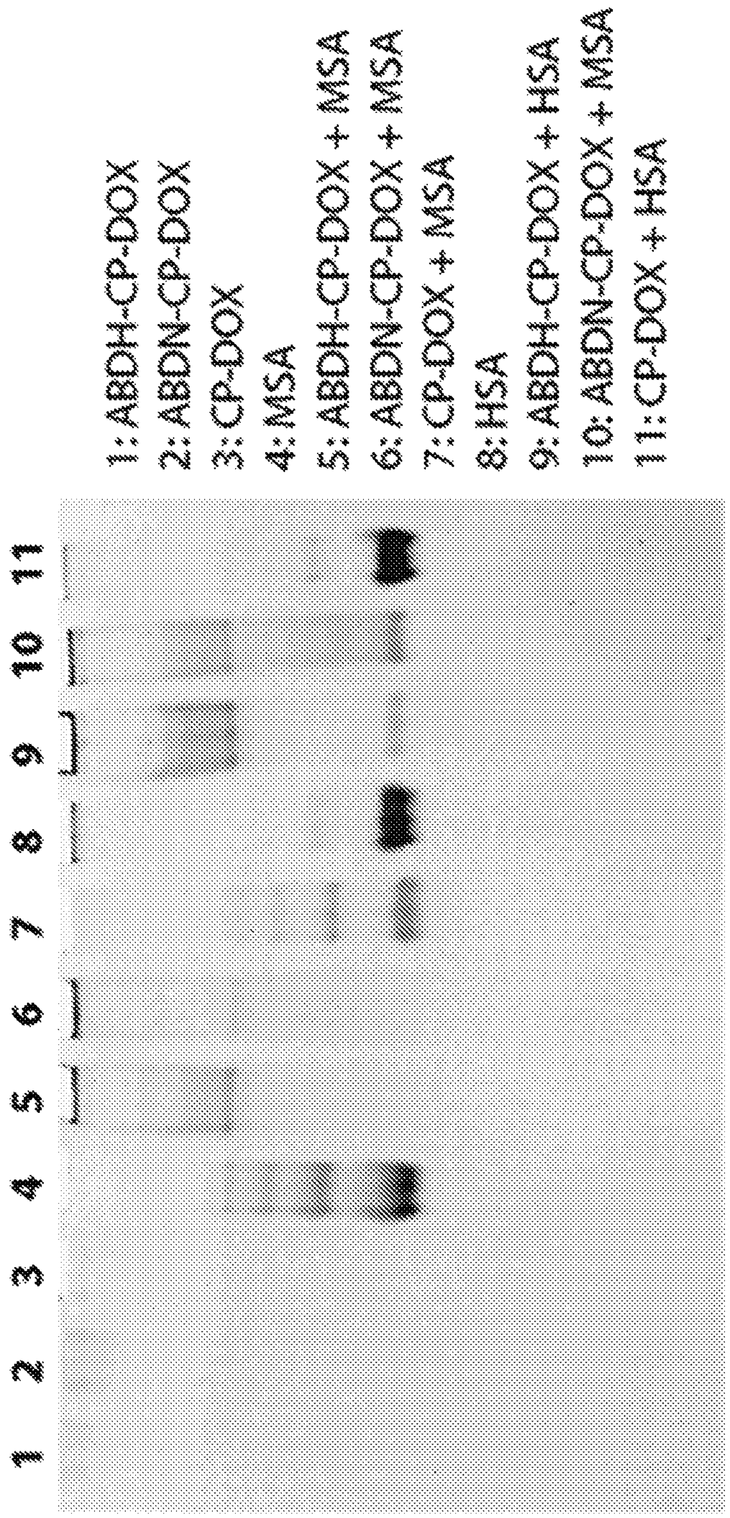
Figure 6B:
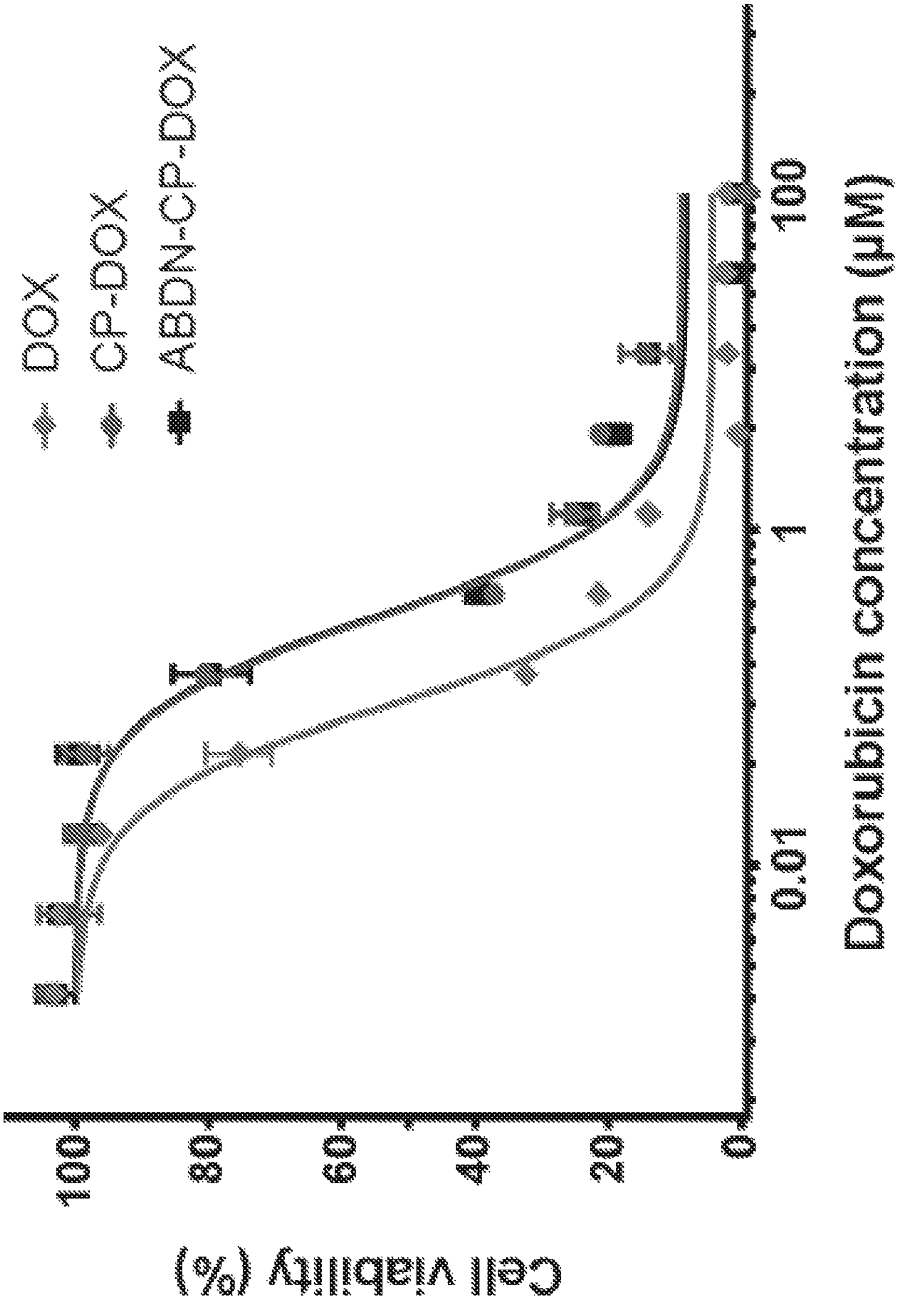
Figure 6C:
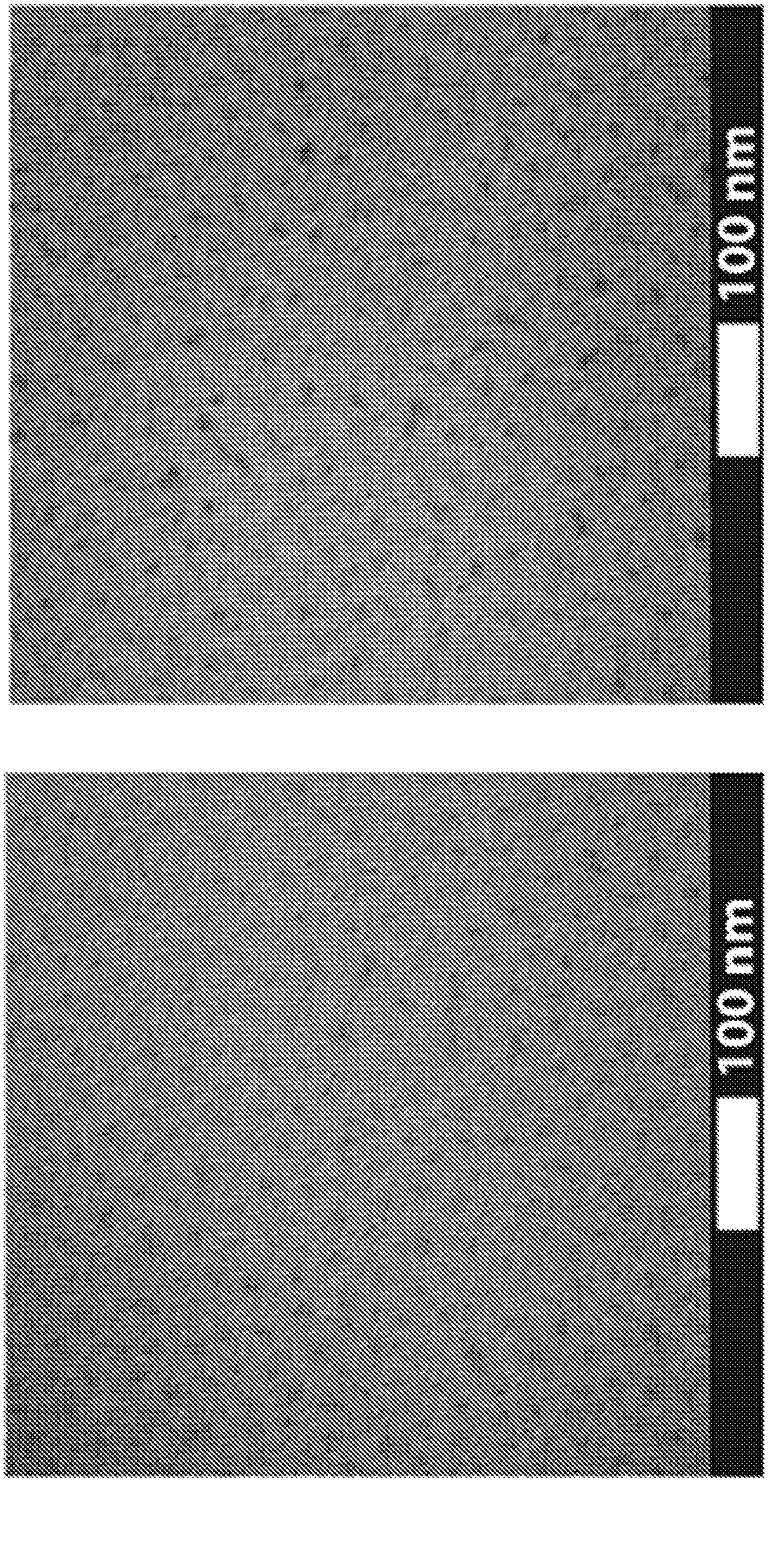
Figure 6D:
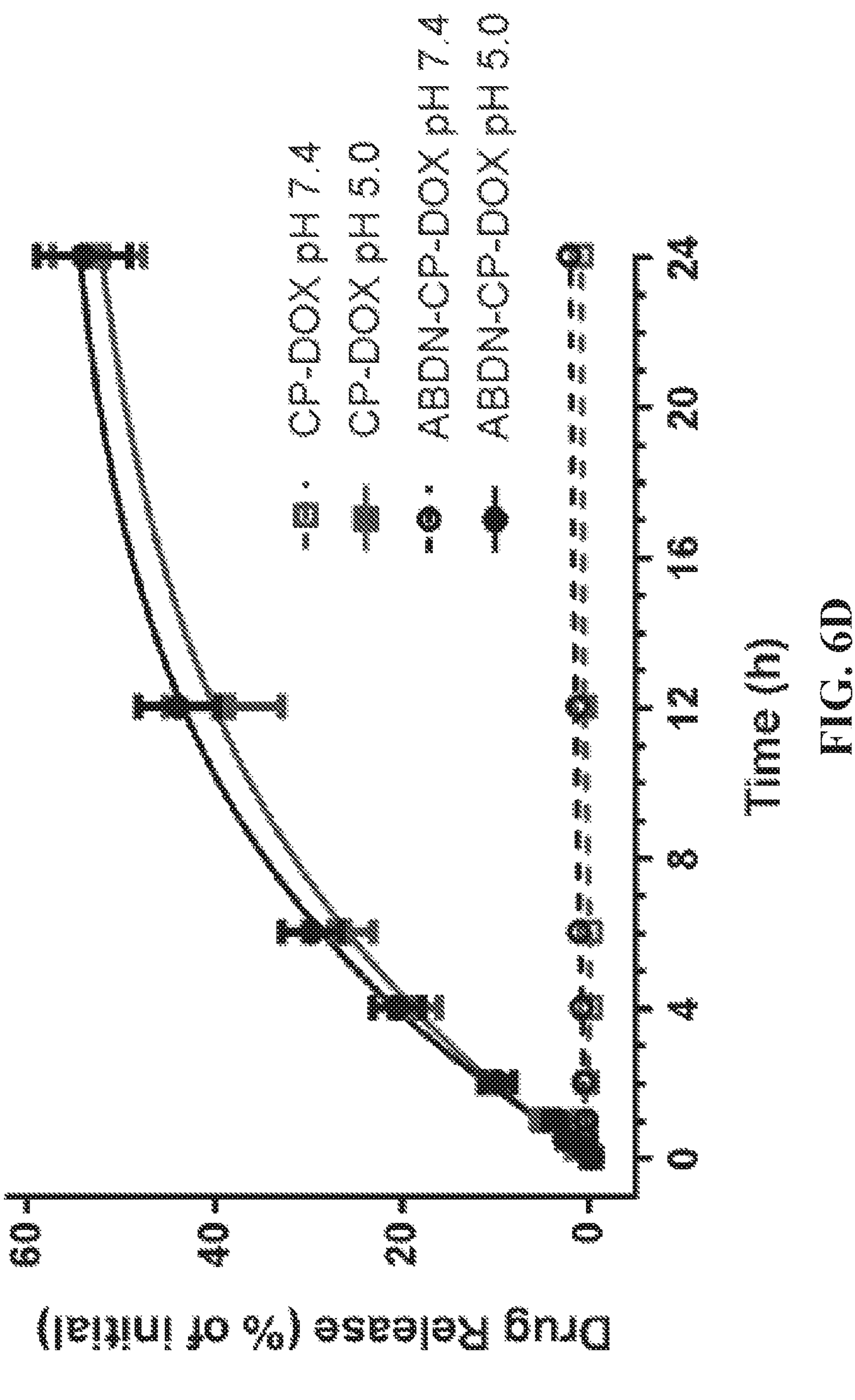
Figure 7A:
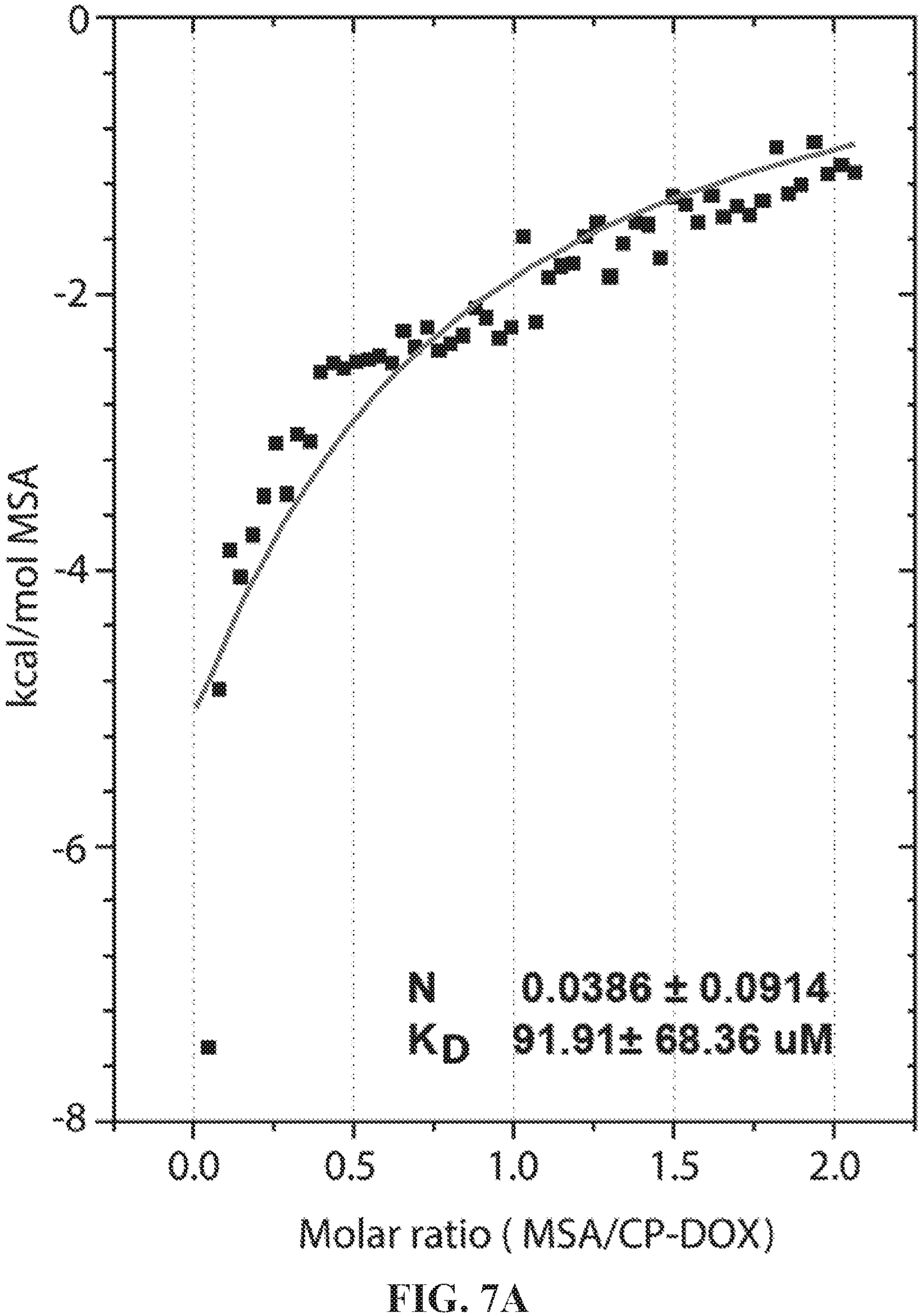
Figure 7B:
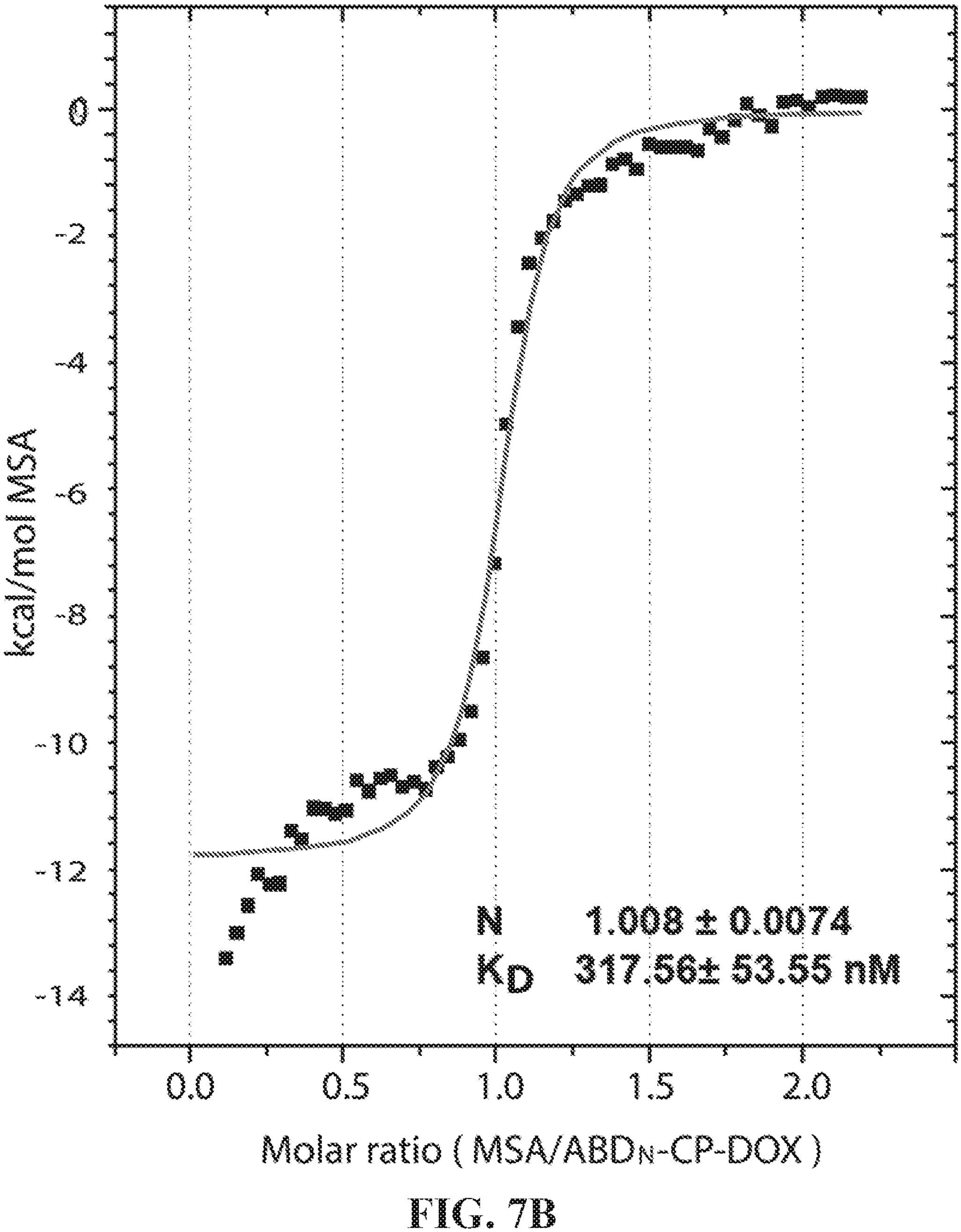
Figure 7C:
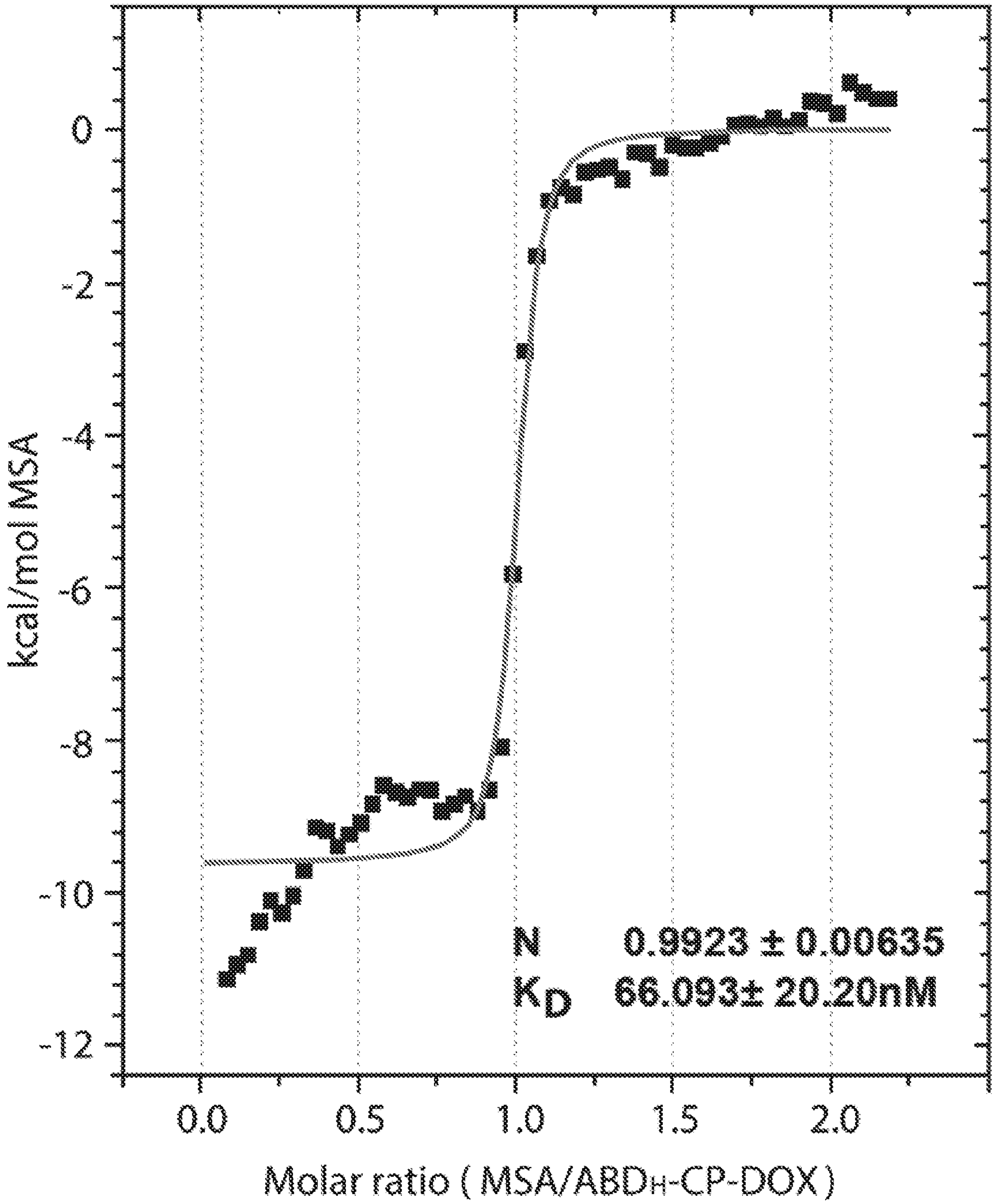

Example 3: Development of Albumin Binding Self-Assembling Micelles with Doxorubicin DOX was conjugated to cysteines included in the short cysteine containing sequence, e.g., $(Gly\text{-}Gly\text{-}Cys)_8$ (SEQ ID NO:5) appended at the C-terminus of the (ABDN/H-)ELPs via a pH-labile hydrazone bond (FIG. 6C). Drug conjugation imparts amphiphilicity and drives self-assembly of the conjugates. The conjugation efficiency was 5.1±0.5 and 4.6±0.6 and 4.7±0.3 doxorubicin molecules per polypeptide for CP-DOX, ABDN-CP-DOX and ABDH-CP-DOX, respectively. As with the (ABD-)ELP monomers, binding affinity of the (ABD-)CP-DOX micelles to mouse albumin was analyzed qualitatively and quantitatively by ITC (FIG. 7A-FIG. 7C) and native-PAGE (FIG. 6A). It was observed that DOX conjugated (ABDN/H-)ELPs still displayed 1:1 stoichiometry and strong sub-μM affinity for albumin ($K_D$=317.56±53.55 for ABDN-CP-DOX (FIG. 7B) and $K_D$=66.093±20.20 nM for ABDH-CP-DOX (FIG. 7C))

though their affinity was lower than their non DOX-conjugated counterparts (FIG. 7A).

Example 4: Binding to Albumin Increases the Transition Temperature

Figure 8A:
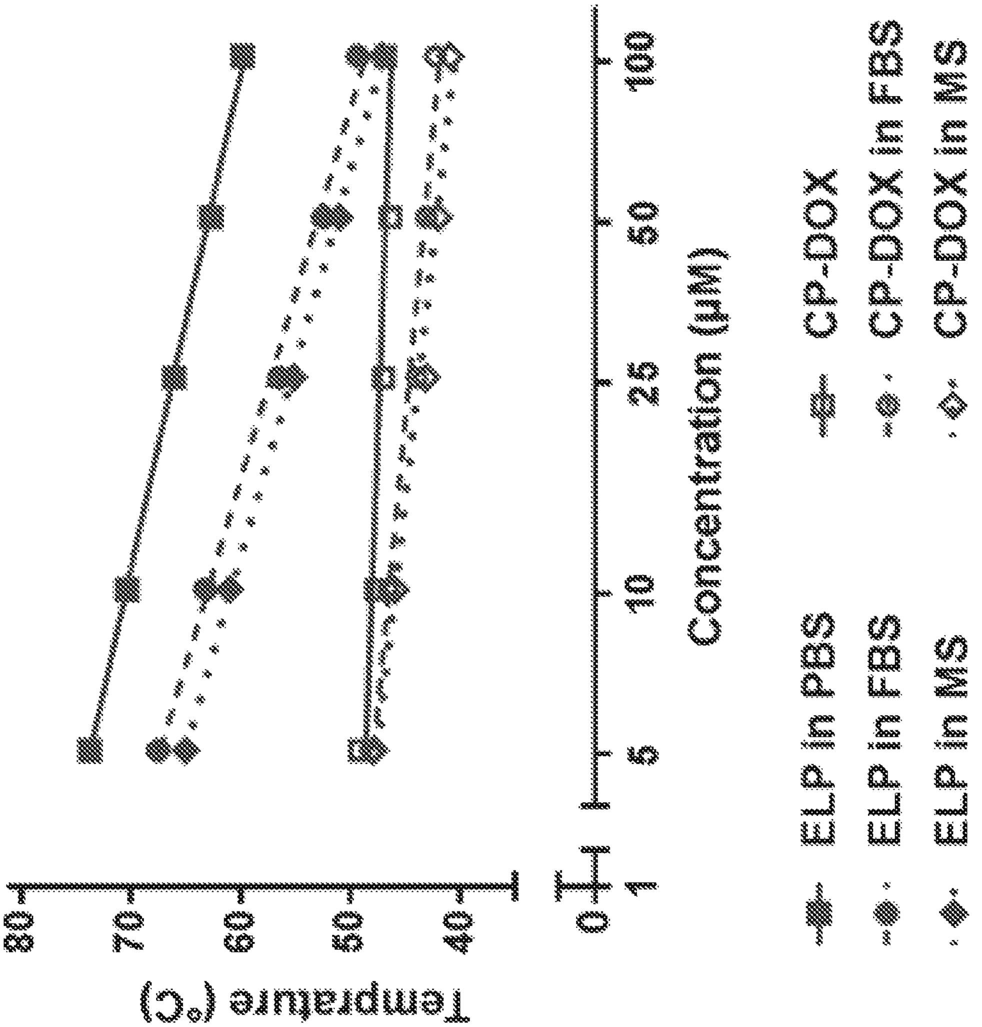
Figure 8B:
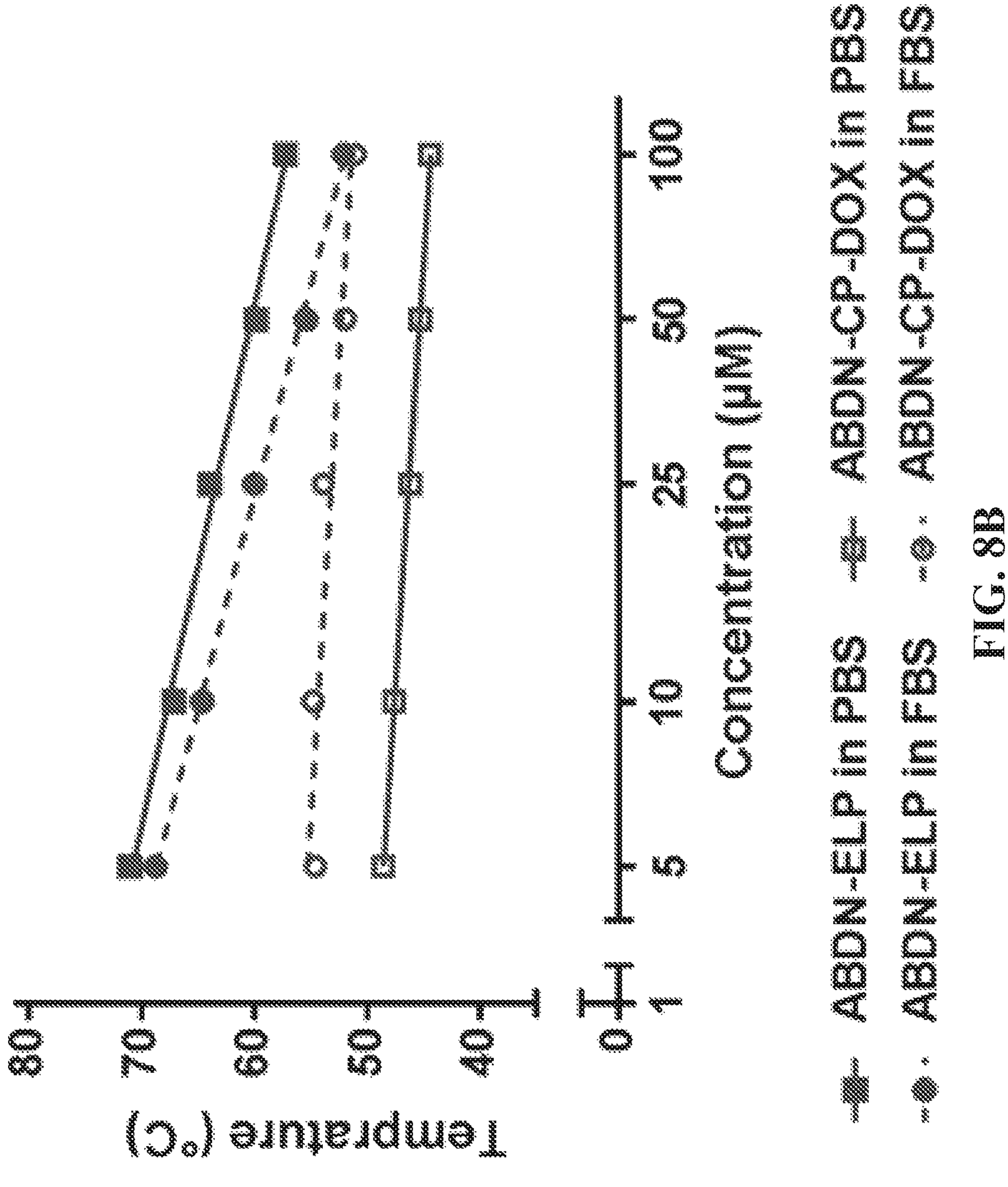
Figure 8C:
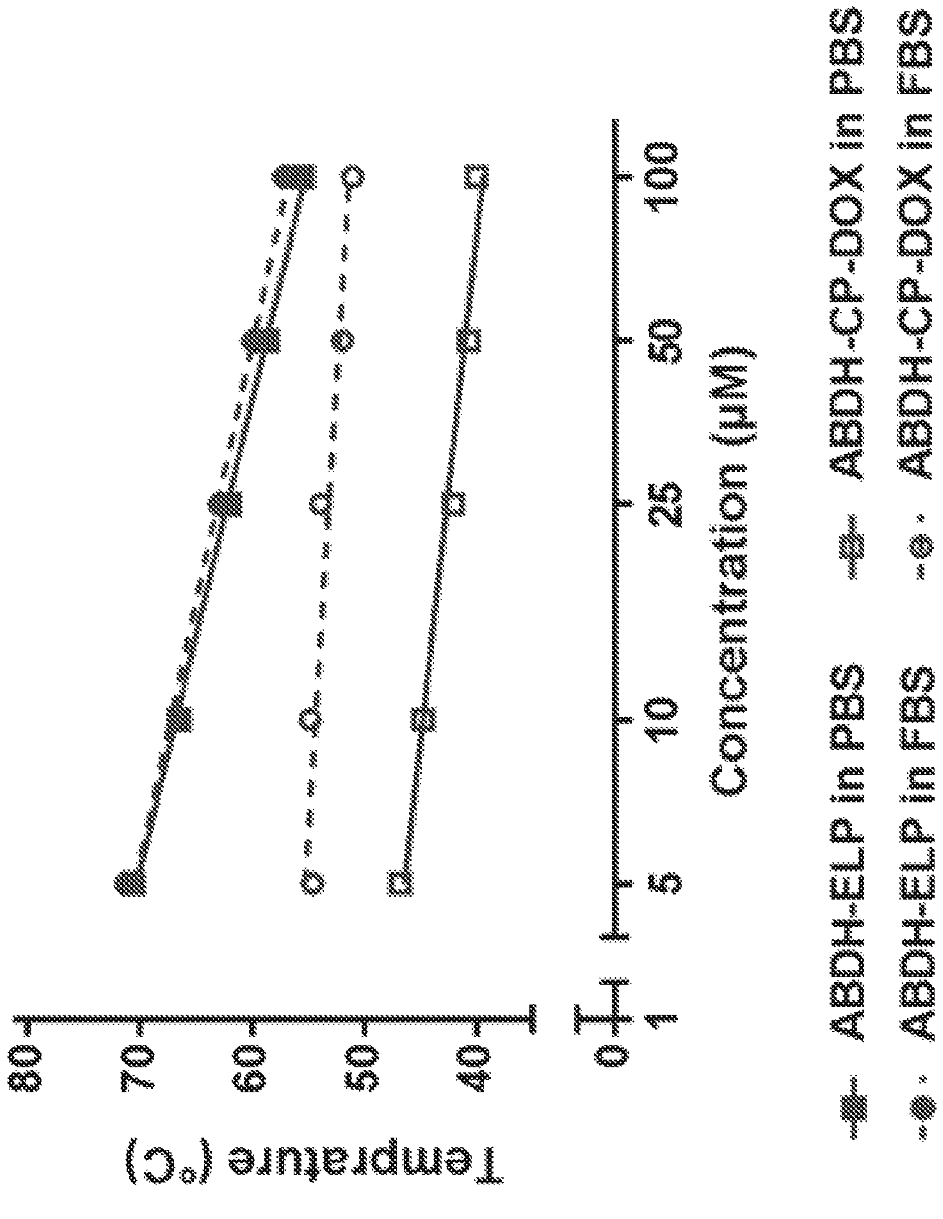
Figure 8D:
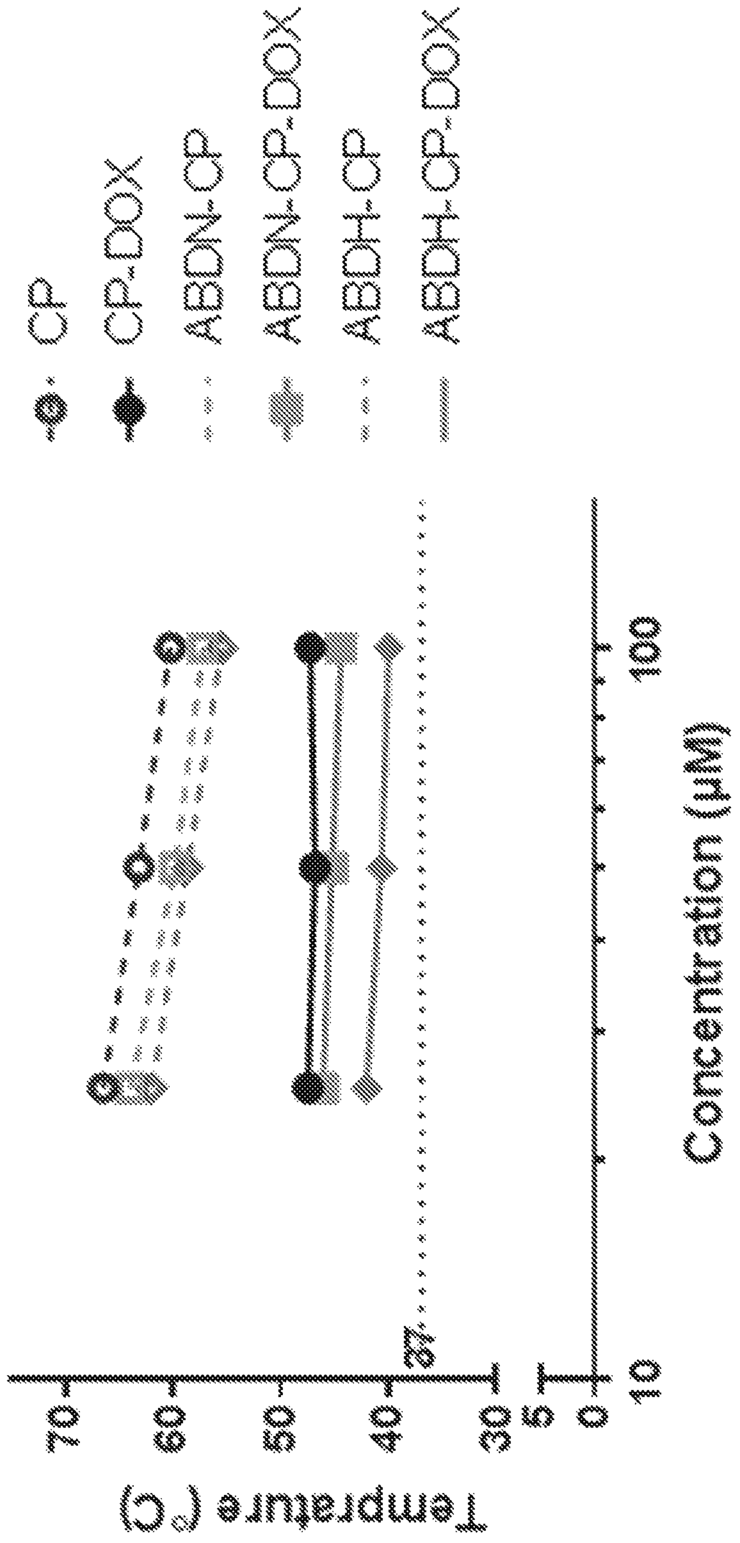

The effects of ABD fusion and albumin binding on the thermal behavior of (ABDN/H-)ELP monomers and (ABDN/H-)CP-DOX micelles were examined by studying the turbidity profile of these constructs in PBS, fetal bovine serum, mouse serum and human serum as a function of temperature (FIG. 8A-FIG. 8D). Fusion of ABDN/H decreased the transition temperature of ELP from 60° C. at 100 μM concentration in PBS to 57° C. and 55° C. under the same conditions for ABDN-ELP and ABDH-ELP, respectively. This decrease in transition temperature is attributed to the hydrophobic nature of ABDs. The decrease in the transition temperature is more pronounced after drug (DOX) conjugation where ABDN-CP-DOX and ABDH-CP-DOX transition at 44° C. and 40° C. compared with 47° C. for CP-DOX (FIG. 8D). Moreover, phase transition of (ABDN/H-)CP-DOX micelles occurred at a lower temperature and a less concentration dependent manner than their non-drug conjugated counterparts. The lower transition temperature and weaker concentration dependence of micelle structures with respect to monomer may be due to close proximity of the (ABD/H-)CPs in the corona of the micelles, which maximizes the local concentration of (ABD/H-)ELPs. Furthermore, ABDN/H-ELP monomers as well as ABDN/H-CP-DOX micelles showed a higher transition temperature in FBS than PBS and showed no transition in MS and HS up to 70° C. whereas naked ELP monomers and CP-DOX micelles transitioned at a lower temperature in FBS, MS, and HS than in PBS as described previously.

Therefore, among various ABDs, only ABDs that do not lower the transition temperature of the CP-drug conjugate to 40° C. or lower will be useful for preparing albumin binding nanoparticulate systems.

Example 5: Binding to Albumin does not Break the Micelles

Self-assembly of CP-DOX conjugates into micelles was confirmed by light scattering and freeze-fracture transmission electron microscopy. (ABDN/H-)CP-DOX micelles showed a narrow size distribution with a hydrodynamic radius ($R_h$) of 36.29 nm, 59.0 nm, and 51.28 nm at 22° C. for CP-DOX, ABDN-CP-DOX, and ABDH-CP-DOX micelles, respectively, and 22.33 nm and 45.63 nm at 37° C. for CP-DOX, and ABDN-CP-DOX micelles, respectively, as measured by dynamic light scattering (DLS) (Table 2). Neither ABDN-CP-DOX nor ABDH-CP-DOX conjugates aggregate at room temperature (25° C.), however, at body temperature (37° C.), ABDH-CP-DOX conjugates show aggregates, but ABDN-CP-DOX conjugates remain aggregate-free. This was thought to be due to the initiation of thermal phase transition of ABDH-CP-DOX micelles around 37° C. due to the lower transition temperature of the ABDH-CP-DOX micelles (FIG. 8). Therefore, considering lower stability of ABDH-CP-DOX micelles at body temperature together with similar pharmacokinetics of ABDN-CP-DOX and ABDH-CP-DOX micelles, ABDN-CP-DOX micelles were preferred.

Static light scattering (SLS) provided the micelle radius of gyration (Rg) and aggregation number ($N_{agg}$) (Table 2). At 37° C., $R_g$ and $N_{agg}$ were found to be, respectively 18.74 nm and 16.69 for CP-DOX conjugates, and 34.97 nm and 42.04 for ABDN-CP-DOX conjugate. $R_g$ and $N_{agg}$ could not be determined for ABDH-CP-DOX conjugate at 37° C. due to presence of aggregates. In addition, the shape factor ($p=R_g/R_h$) of the micelles was calculated as 0.839, and 0.766 for CP-DOX and ABDH-CP-DOX micelles, respectively, both of which indicated a spherical morphology. In addition, CP-DOX and ABDN-CP-DOX micelles were fast-frozen from 37° C. and were observed with freeze-fracture transmission electron microscopy (FF-TEM) (FIG. 6C). The observed images corroborated the mean size and morphology obtained by DLS. Light scattering analysis in the presence of equimolar concentration of mouse albumin showed that binding to albumin did not break the micelle structure. Binding to albumin resulted in increasing the $N_{agg}$ and decreasing the $R_h$ of ABDN/H-CP-DOX micelles. In case of ABDH-CP-DOX micelles, no aggregates were detected in the presence of mouse albumin at 37° C.; this is consistent with the thermal profile data where binding to albumin prevented the phase transition and aggregation of ABDN/H-CP-DOX micelles.

TABLE 2

Light scattering data for (ABDN/H-) CP-DOX micelles in the presence and absence of albumin.

| Sample | Temperature (° C.) | $N_{agg}$ | $R_g$ (nm) | $R_h$ (nm) | $\rho = R_g/R_h$ |
|---|---|---|---|---|---|
| CP-DOX | 22 | 10.92 | 28.05 | 36.29 | 0.773 |
| | 37 | 16.69 | 18.74 | 22.33 | 0.839 |
| CP-DOX : MSA | 22 | NM[a] | NM[a] | 36.22 | NM[a] |
| (1:1) | 37 | NM | NM[a] | 30.24 | NM[a] |
| ABDN-CP-DOX | 22 | 34.97 | 36.95 | 59.00 | 0.62 |
| | 37 | 42.04 | 34.97 | 45.63 | 0.766 |
| ABDN-CP-DOX : MSA | 22 | 58.63 | 38.44 | 50.21 | 0.766* |
| (1:1) | 37 | 57.89 | 29.52 | 38.23 | 0.777 |
| ABDH-CP-DOX | 22 | 17.06 | 34.55 | 51.28 | 0.694 |
| | 37 | Agg[b] | — | — | — |
| ABDH-CP-DOX : MSA | 22 | 31.15 | 37.50 | 47.17 | 0.794 |
| (1:1) | 37 | 36.14 | 36.75 | 46.919 | 0.783 |

[a]Non-measurable
[b]Aggregated

Figure 9A:
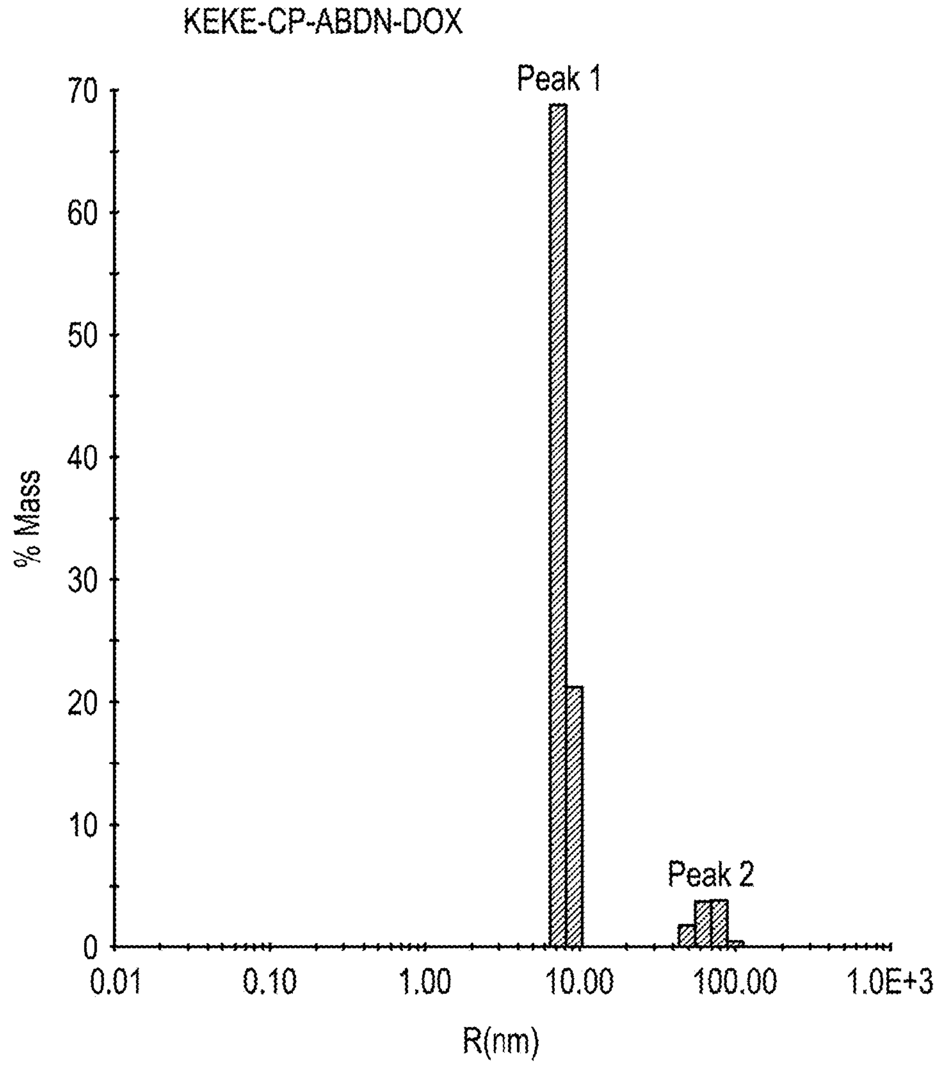
Figure 9B:
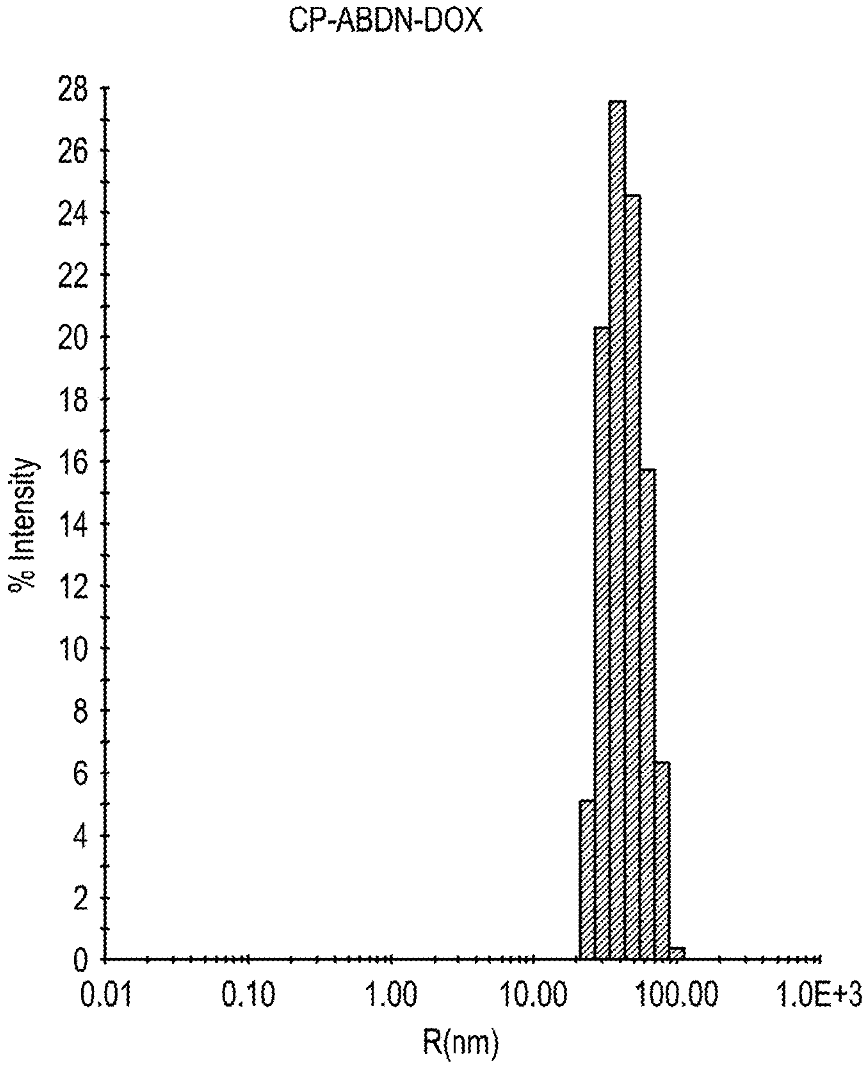

The sequence and arrangement of ABDN-CP is important for nanoparticle formation. ABDN-CP-DOX and CP-ABDN-DOX form nanoparticles, but when a small zwitterionic KEKE (SEQ ID NO: 8) sequence was added to the N-terminus, KEKE-CP-ABDN-DOX did not form nanoparticles (Table 3, FIG. 9A and FIG. 9B).

TABLE 3

Light scattering data for ABDN-CP-DOX, CP-ABDN-DOX, and KEKE-CP-ABDN-DOX

| Conjugate | $R_h$ | Mass | Polydispersity |
|---|---|---|---|
| ABDN-CP-DOX | See Table 2 | | |
| CP-ABDN-DOX | 45.8 nm | 100% | 32.2% |
| KEKE-CP-ABDN-DOX | 7.8 nm | 90.2% | 10.7% |
| | 68.9 nm | 9.8% | 19.4% |

Figure 10A:
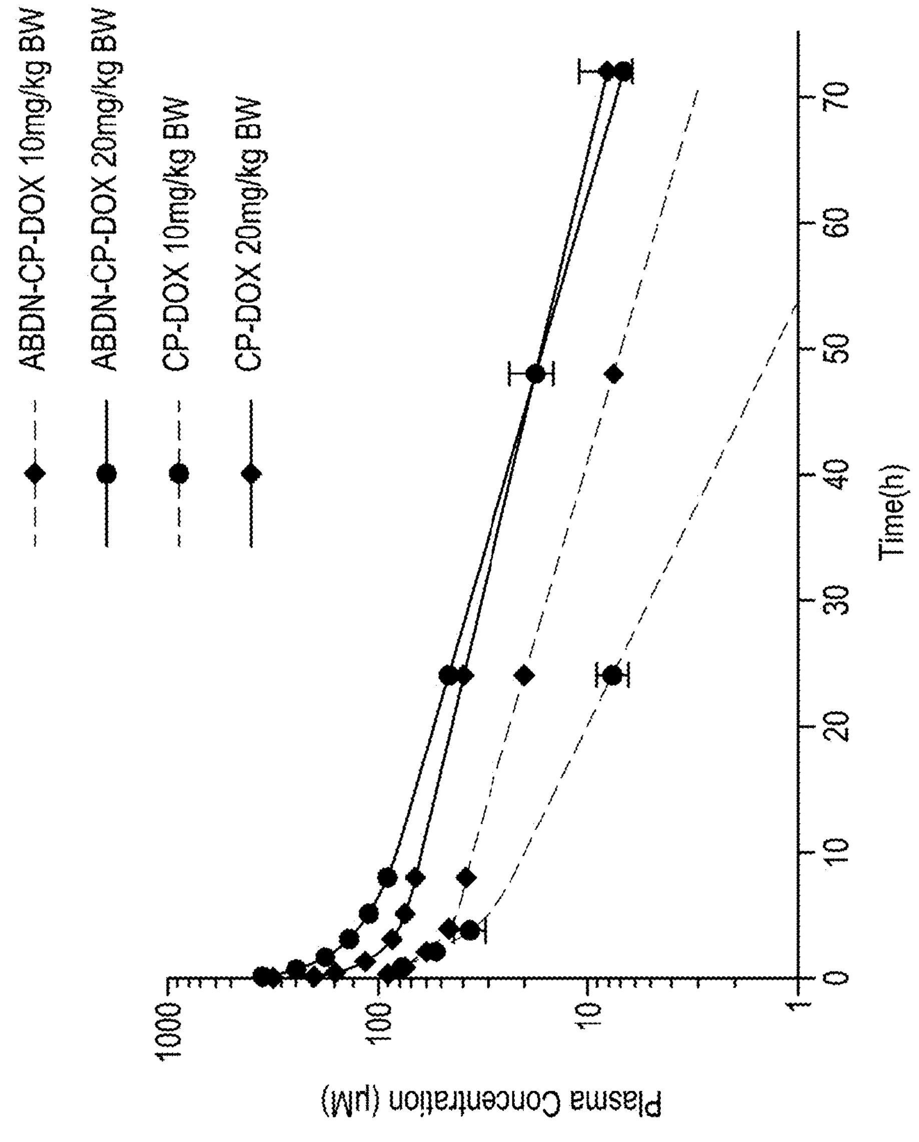

Example 6: Albumin Binding Prolongs the Circulation Time of Monomers but not Micelles Pharmacokinetics studies of (ABDN-)CP-DOX micelles were performed at a DOX equivalent dose of 10 and 20 mg/kg BW. DOX concentration versus time profiles of (ABDN/H-CP-DOX micelles were determined using intrinsic DOX fluorescence and were fitted to a two-compartment model (FIG. 10A). At the dose of 10 mg/kg BW DOX equivalent, no significant difference was observed between ABDN-CP-DOX and CP-DOX micelles as to their half-life (17.5±0.8 h for ABDN-CP-DOX and 20.1±0.6 h for CP-DOX) and bioavailability i.e. AUC (3328.5±100.3 μM. h for ABDN-CP-DOX and 2994±59.0 μM. h for CP-DOX), whereas at the dose of 10 mg/kg BW DOX equivalent, ABDN-CP-DOX micelles displayed a half-life of 18.3±0.6 h and AUC of 1400.4±34.2 μM. h while the half-life and AUC of CP-DOX micelles were measured as 9.7±0.6 h and 724.82±33.1 μM. h, respectively (Table 4). These data are suggestive of linear pharmacokinetics for ABDN-CP-DOX and non-linear pharmacokinetics for CP-DOX.

TABLE 4

Pharmacokinetic parameters of CP-DOX, ABDN-CP-DOX, and ABDN-DOX. Values are shown as mean (SD).

| | | CP-DOX 10 mg/kg | ABDN-CP-DOX 10 mg/kg | CP-DOX 20 mg/kg | ABDN-CP-DOX 20 mg/kg |
|---|---|---|---|---|---|
| Elimination half-life | α $t_{1/2}$ [h] | 9.7 ± 0.6 | 18.3 ± 0.6 | 20.1 ± 0.9 | 17.5 ± 0.8 |
| Area under the curve | AUC [μM•h] | 724.8 ± 33.1 | 1400.4 ± 34.2 | 2994.5 ± 50.0 | 3328.5 ± 100.3 |
| Distribution half-life | β $t_{1/2}$ [min] | 13.8 ± 2.4 | 12.4 ± 1.4 | 42.1 ± 5.5 | 71.7 ± 17.5 |
| Apparent distribution volume | $V_D$ [mL $g^{-1}$] | 0.20 ± 0.01 | 0.34 ± 0.01 | 0.39 ± 0.01 | 0.25 ± 0.11 |
| Plasma clearance | CL [mL $h^{-1}$ $g^{-1}$] | 0.023 ± 0.001 | 0.013 ± 0.000 | 0.013 ± 0.000 | 0.011 ± 0.000 |
| Elimination rate constant | $k_g$ [$h^{-1}$] | 0.38 ± 0.04 | 0.10 ± 0.01 | 0.09 ± 0.00 | 0.08 ± 0.00 |
| Tissue to plasma rate constant | $k_{tp}$ [$h^{-1}$] | 0.84 ± 0.12 | 1.22 ± 0.13 | 0.35 ± 0.04 | 0.29 ± 0.07 |
| Plasma to tissue rate constant | $k_{pt}$ [$h^{-1}$] | 1.90 ± 0.40 | 2.08 ± 0.27 | 0.58 ± 0.08 | 0.25 ± 0.07 |

Figure 11:
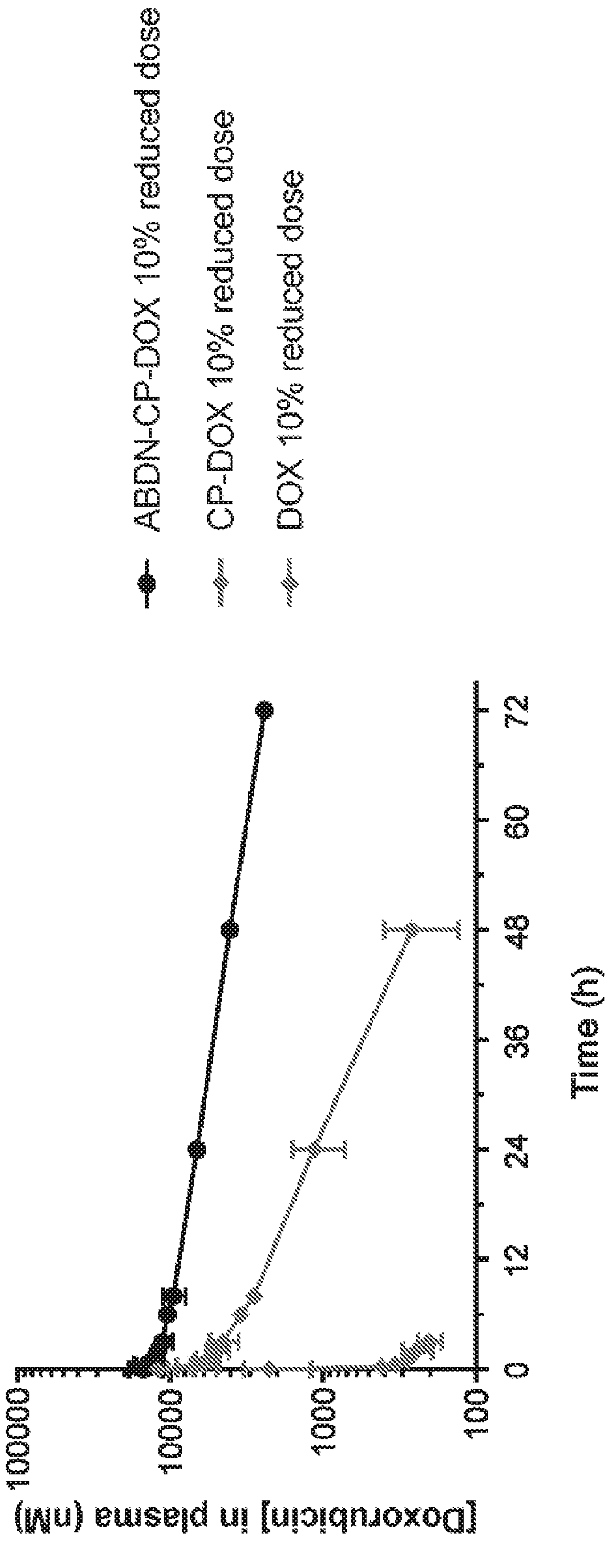

The effect of albumin binding on pharmacokinetics was further investigated in dogs, as they are large, long-lived animals that share stronger similarities in their anatomy and physiology with humans than mice and are therefore a better model to understand the advantages and limitations of new cancer therapeutics and delivery modalities. All three formulations were injected at a dose that was reduced by 10% relative to the clinical therapeutic dose of DOX. Observing the relatively small animal-to-animal variation and given the high cost of these experiments and limited animal availability, the pharmacokinetic study was closed with three dogs for CP-DOX and free DOX, and two dogs for ABDN-CP-DOX. As with the pharmacokinetics study in mice, DOX concentration in blood as a function of time following i.v. injection of free DOX, CP-DOX and ABDN-CP-DOX was measured by quantifying the intrinsic fluorescence of DOX, and the data were fitted to a two-compartment model (FIG. 11). Free DOX formulation had an elimination half-life ($t_{1/2}$) of 2.9±0.8 h and an area under the curve (AUC) of 1769.1±498.0 μM. h. In contrast CP-DOX micelles exhibited a three-fold longer fin of 9.8±1.9 h (P<0.05), and a 48-fold greater AUC of 84106.0±7616.8 μM. h AUC compared to free DOX (P<0.05). ABDN-CP-DOX micelles exhibited a plasma half-life of 30.8±2.0 h that was three-fold greater than that of CP-DOX (P<0.001), and an AUC of 509371.7±43095.2 μM. h that is six-fold larger than that of CP-DOX (P<0.001) (Table 5). Furthermore, despite a significant increase in the plasma half-life and AUC of ABDN-CP-DOX compared to CP-DOX and free DOX, no hematology or serum chemistry abnormalities were noted with ABDN-CP-DOX and CP-DOX groups one week after infusion (Table 6 and Table 7), suggesting that these micellar formulations do not cause dose-limiting adverse effects associated with free DOX.

TABLE 5

Canine pharmacokinetic parameters of ABDN-CP-DOX, CP-DOX, and free DOX at a dose of 27 DOX Equiv/m$^{-2}$ body surface area (BSA) for dogs weighing greater than 10 kg and 0.9 mg DOX Eqyuv/kg$^{-1}$ of body weight (BW) for dogs weighing less than 10 kg. Values ar eshown as mean ± SD (n = 2 for ABDN-CP-DOX, n = 3 for CP-DOX and DOX).

| | | DOX | CP-DOX | ABDN-CP-DOX |
|---|---|---|---|---|
| Elimination half-life | $\alpha\ t_{1/2}$ [h] | 2.9 ± 0.8 | 9.8 ± 1.9 | 30.8 ± 2.0 |
| Area under the curve | AUC [μM•h] | 1769.1 ± 498.0 | 84106.0 ± 7616.8 | 509371.7 ± 43095.2 |
| Distribution half-life | $\beta\ t_{1/2}$ [min] | 3.6 ± 0.5 | 6.6 ± 1.2 | 102.3 ± 49.3 |
| Apparent distribution volume | $V_D$ [mL g$^{-1}$] | 3.85 ± 0.26 | 0.27 ± 0.01 | 0.02 ± 0.00 |
| Plasma clearance | CL [mL h$^{-1}$ g$^{-1}$] | 0.7875 ± 0.0951 | 0.0194 ± 0.0004 | 0.0003 ± 0.0000 |
| Elimination rate constant | $k_g$ [h$^{-1}$] | 0.96 ± 0.13 | 0.15 ± 0.01 | 0.02 ± 0.00 |
| Tissue to plasma rate constant | $k_{tp}$ [h$^{-1}$] | 2.31 ± 0.42 | 2.85 ± 0.50 | 0.34 ± 0.17 |
| Plasma to tissue rate constant | $k_{pt}$ [h$^{-1}$] | 8.51 ± 1.20 | 3.37 ± 0.65 | 0.06 ± 0.03 |

TABLE 6

Canine hematology parameters one week after administration of CP-DOX and ABDN-CP-DOX micelles. No abnormalities in blood hematology were observed in any of the animals.

| | | CP-DOX | | | ABDN-CP-DOX | | |
|---|---|---|---|---|---|---|---|
| Test | Unit | Subject 1 | Subject 2 | Subject 3 | Subject 1 | Subject 2 | Normal range |
| WBC | X10^3/μL | 3.93 | 6.29 | 4.95 | 7.86 | 7.01 | 4.39-11.61 |
| RBC | X10^6/μL | 5.99 | 5.72 | 6.87 | 5.97 | 6.19 | 5.7-8.01 |
| Hemoglobin | g/dL | 13.9 | 13.6 | 16 | 14.7 | 14.6 | 13.8-20.3 |
| Hematocrit | % | 41.4 | 40.9 | 47.2 | 42.7 | 43.9 | 39.2-55.9 |
| MCV | fL | 69.1 | 71.6 | 68.7 | 71.7 | 71 | 61.8-75.1 |
| MCH | pg | 23.2 | 23.9 | 23.3 | 24.6 | 23.6 | 20.2-25.3 |
| MCHC | g/dL | 33.6 | 33.3 | 33.9 | 34.3 | 33.2 | 30.8-35.4 |
| RDW | % | 12.6 | 13.8 | 12.4 | 12.8 | 11.7 | 11.3-13.5 |
| Platelets | X10^3/μL | 369 | 617 | 342 | 228 | 208 | 190-468 |
| MPV | fL | 10.9 | 7.8 | 7.9 | 12.2 | 11.9 | 7.9-13.8 |
| PCT | % | 0.4 | 0.48 | 0.27 | 0.28 | 0.25 | 0.2-0.58 |
| Reticulocyte % | % | 0.44 | 2.74 | 0.59 | 0.43 | 0.23 | 0.11-1.26 |
| Reticulocyte # | X10^6/μL | 0.026 | 0.156 | 0.041 | 0.025 | 0.014 | |
| Reticulocyte Absolute | /μL | 26000 | 156000 | 41000 | 25000 | 14000 | 8040-93730 |
| Packed Cell-Volume | % | 41 | 40 | 44 | 42 | 42 | 39-58 |
| Plasma Protein | g/dL | 5.9 | 6 | 6 | 6.2 | 5.8 | 5.9-7.3 |
| Segmented Neutrophils | 10^3/μL | 3.105 | 4.969 | 3.861 | 5.502 | 4.276 | 2.841-9.112 |
| Lymphocytes | 10^3/μL | 0.393 | 0.252 | 3.396 | 1.572 | 1.122 | 0.594-3.305 |
| Abonormal Lymphs | 10^3/μL | 0.079 | 0.315 | 0.248 | 0.157 | 0.561 | 0.075-0.85 |
| Monocytes | 10^3/μL | 0.197 | 0.692 | 0.198 | 0.314 | 0.21 | 0.03-1.264 |

TABLE 7

Canine serum chemistry parameters one week after administration of CP-DOX and ABDN-CP-DOX micelles. No abnormalities in blood serum chemistry were observed in any of the animals.

| | | CP-DOX | | | ABDN-CP-DOX | | |
|---|---|---|---|---|---|---|---|
| Test | Unit | Subject 1 | Subject 2 | Subject 3 | Subject 1 | Subject 2 | Normal range |
| Glucose | mg/dL | 99 | 99 | 98 | 90 | 82 | 70-131 |
| Urea Nitrogen | mg/dL | 12 | 19 | 16 | 17 | 15 | 6-26 |
| Creatinine | mg/dL | 0.5 | 0.7 | 0.7 | 0.7 | 0.7 | 0.7-1.5 |
| Phosphorus | mg/dL | 3.2 | 4.7 | 4 | 4.1 | 4.7 | 2.5-5.6 |
| Calcium | mg/dL | 9.7 | 9.5 | 9.9 | 10.3 | 10.7 | 9.4-11.4 |
| Magnesium | mg/dL | 2 | 2.1 | 2 | 1.9 | 2.2 | 1.8-2.5 |
| Protein-Total | g/dL | 5.3 | 5.4 | 5.6 | 6 | 5.9 | 5.2-7.3 |
| Albumin | g/dL | 3.6 | 3.1 | 3.6 | 3.8 | 3.6 | 3-3.9 |
| Globulin | g/dL | 1.7 | 2.3 | 2 | 2.2 | 2.3 | 1.7-3.8 |
| Alb/Glob Ratio | | 2.12 | 1.35 | 1.8 | 1.73 | 1.57 | 0.9-1.8 |
| Cholesterol | mg/dL | 122 | 160 | 157 | 153 | 94 | 124-344 |
| Bilirubin-Total | mg/dL | <0.2 | <0.2 | <0.2 | <0.2 | <0.2 | 0-0.2 |
| Alkaline Phosphatase | IU/L | 29 | 45 | 59 | 26 | 31 | 16-140 |
| ALT | IU/L | 50 | 39 | 28 | 18 | 21 | 12-54 |
| AST | IU/L | 23 | 24 | 22 | 20 | 31 | 16-140 |
| GGT | IU/L | 6 | 3 | 3 | <3 | <3 | 0-6 |
| CK | IU/L | 121 | 152 | 134 | 141 | 296 | 43-234 |
| Sodium | mmol/L | 148 | 143 | 146 | 148 | 148 | 140-156 |
| Potassium | mmol/L | 4.3 | 4.8 | 4.2 | 4 | 4.4 | 4-5.3 |
| Chloride | mmol/L | 109 | 106 | 107 | 109 | 111 | 108-122 |
| Bicarbonate | mmol/L | 24 | 19 | 22 | 22 | 21 | 18-26 |
| Anion Gap | | 19.3 | 22.8 | 21.2 | 21 | 20.4 | 11.2-19.9 |
| Na/K Ratio | | 34.4 | 29.8 | 34.8 | 37 | 33.6 | 27.7-35.9 |
| Osomolality-Calc. | mOsm/kg | 293.1 | 287.2 | 290.5 | 293.8 | 293.4 | 278.7-311.6 |
| Amylase | IU/L | 563 | 1025 | 823 | 597 | 677 | 236-1337 |
| Lipase | IU/L | 51 | 208 | 31 | 57 | 57 | 12-147 |

Figure 10B:
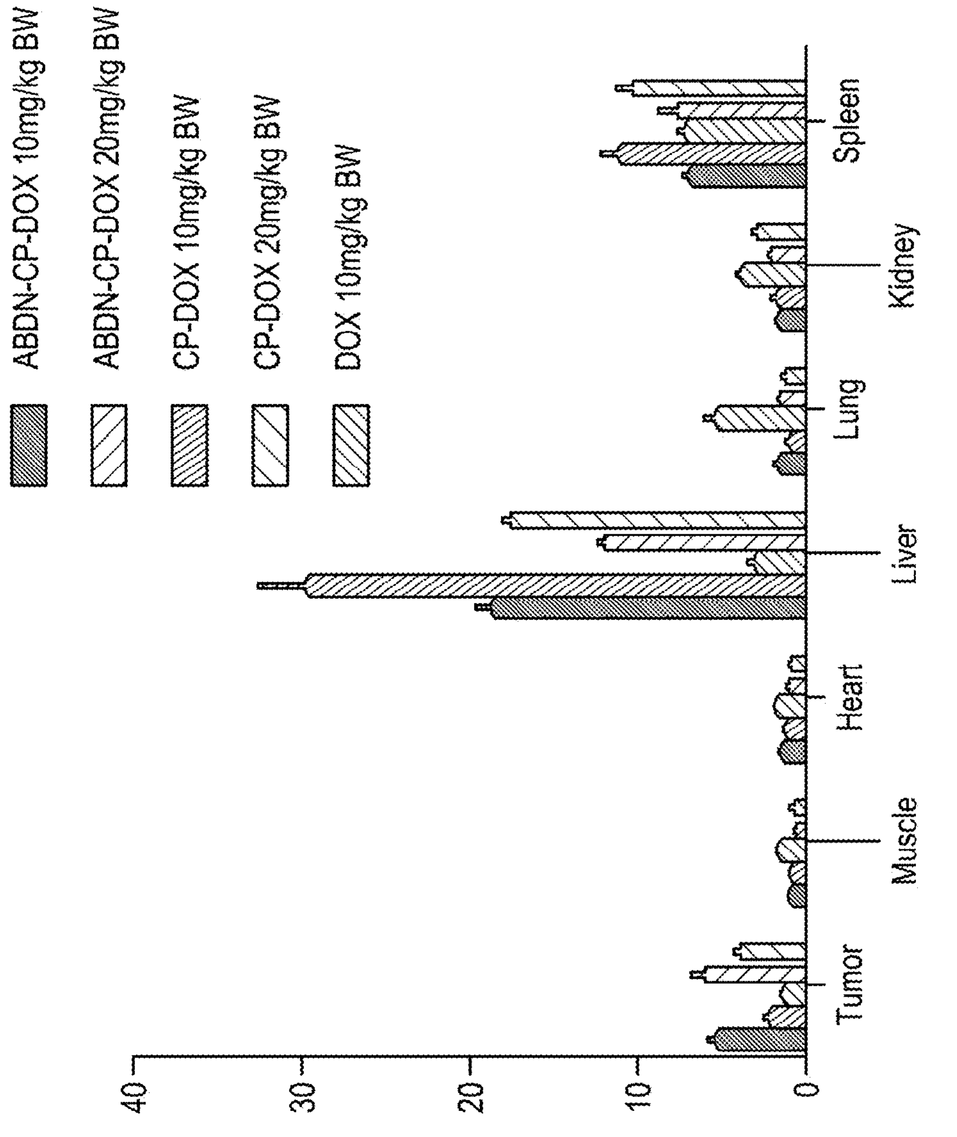
Figure 10C:
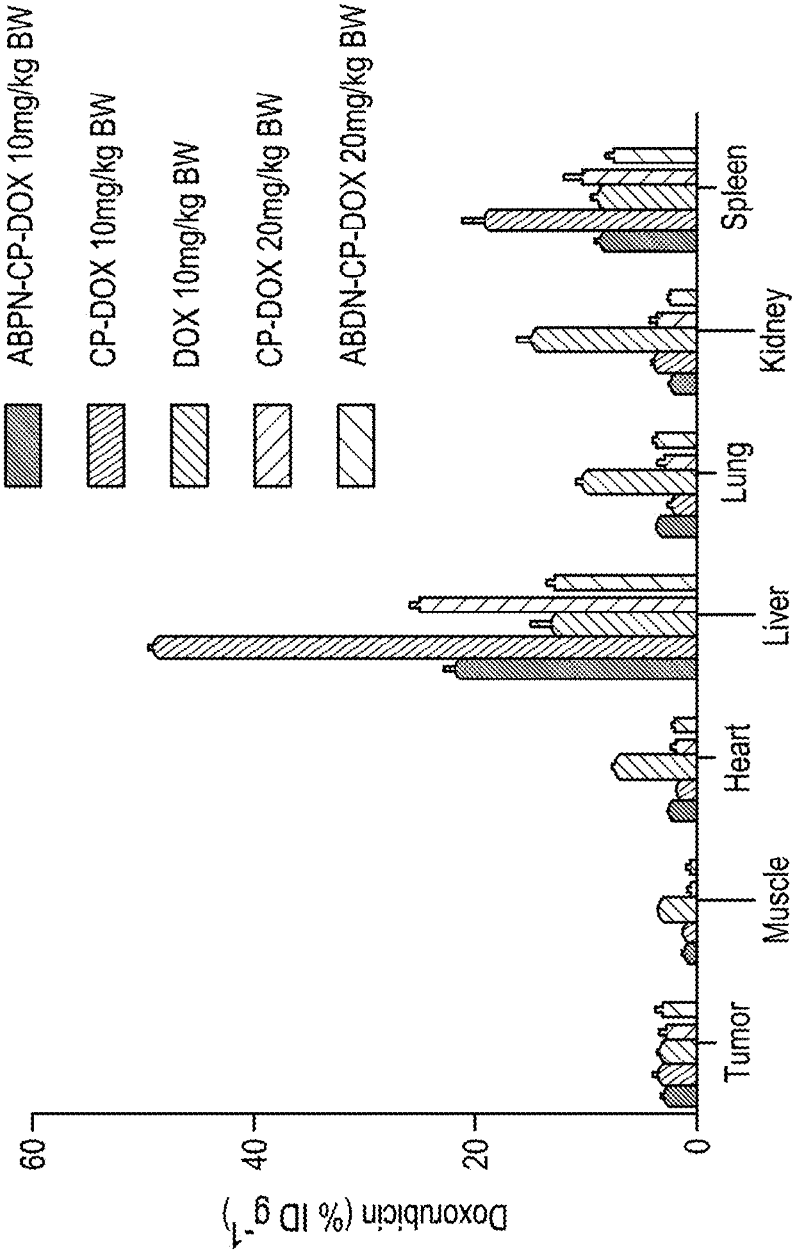

Example 7: Albumin Binding Improves Targeting and Biodistribution Profile of the Micelles The in vivo distribution of CP-DOX was evaluated after intravenous injection into tumor-bearing mice at a dose of 10 mg/kg and 20 mg/kg (FIG. 10B and FIG. 10C). It was observed that 24 h following injection, ABD-CP-DOX accumulated into tumor significantly more than CP-DOX and free DOX. CP-DOX micelles mainly distributed to the organs of the reticuloendothelial system i.e. liver and spleen (FIG. 10C). Furthermore, reticuloendothelial uptake of ABD-CP-DOX micelles was significantly smaller than that of CP-DOX micelles at both 2 h and 24 h time points. Free DOX showed smaller uptake than CP-DOX micelles in liver and spleen and ABD-CP-DOX in liver at both 2 h and 24 h time points. DOX however was distributed more to muscle, heart, lung, and kidney than CP-DOX and ABD-CP-DOX micelles.

Figure 12A:
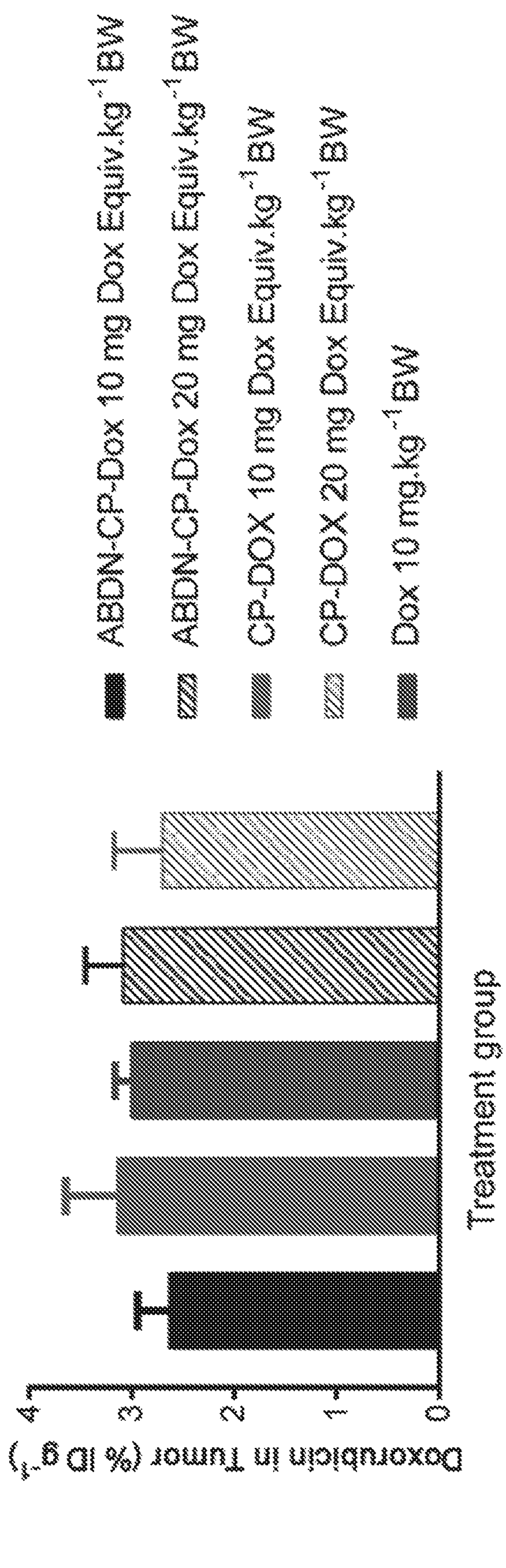
Figure 12B:
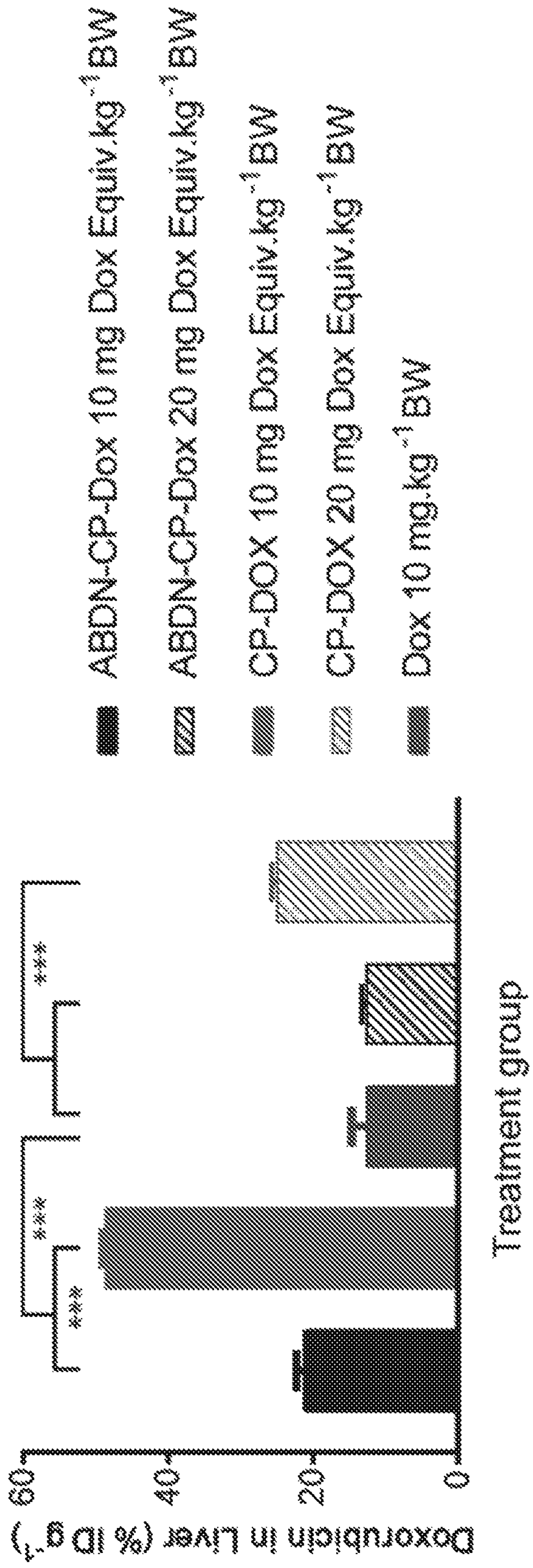
Figure 12C:
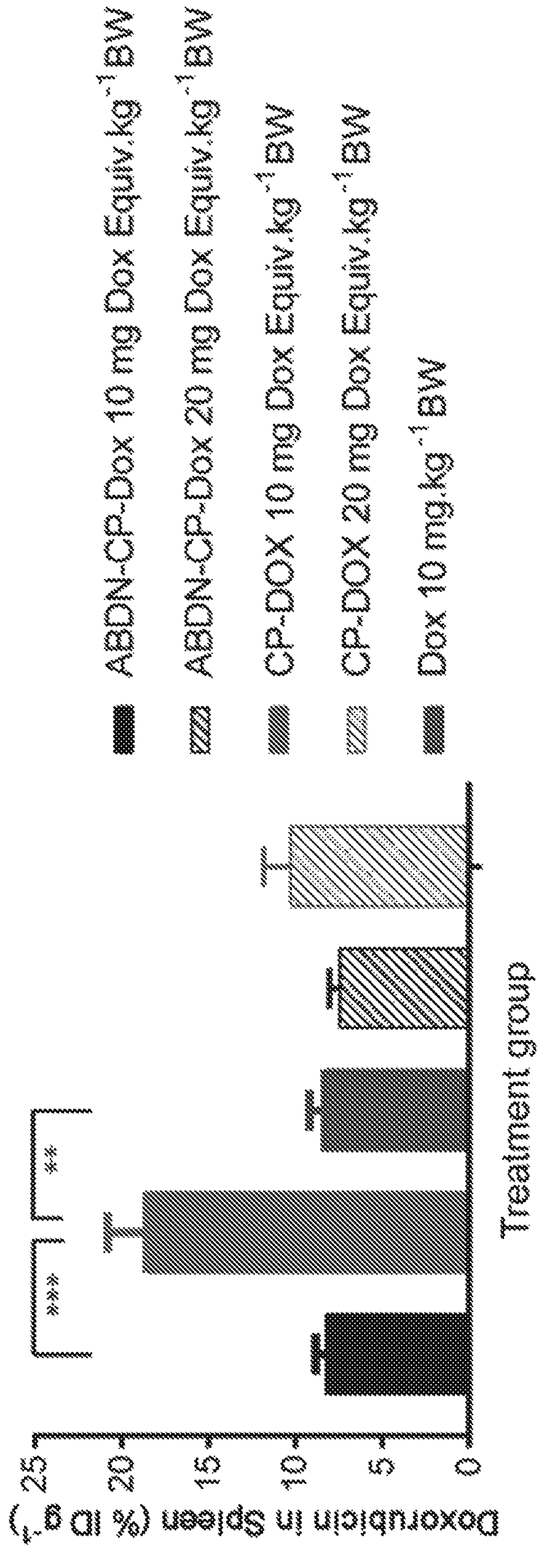
Figure 12D:
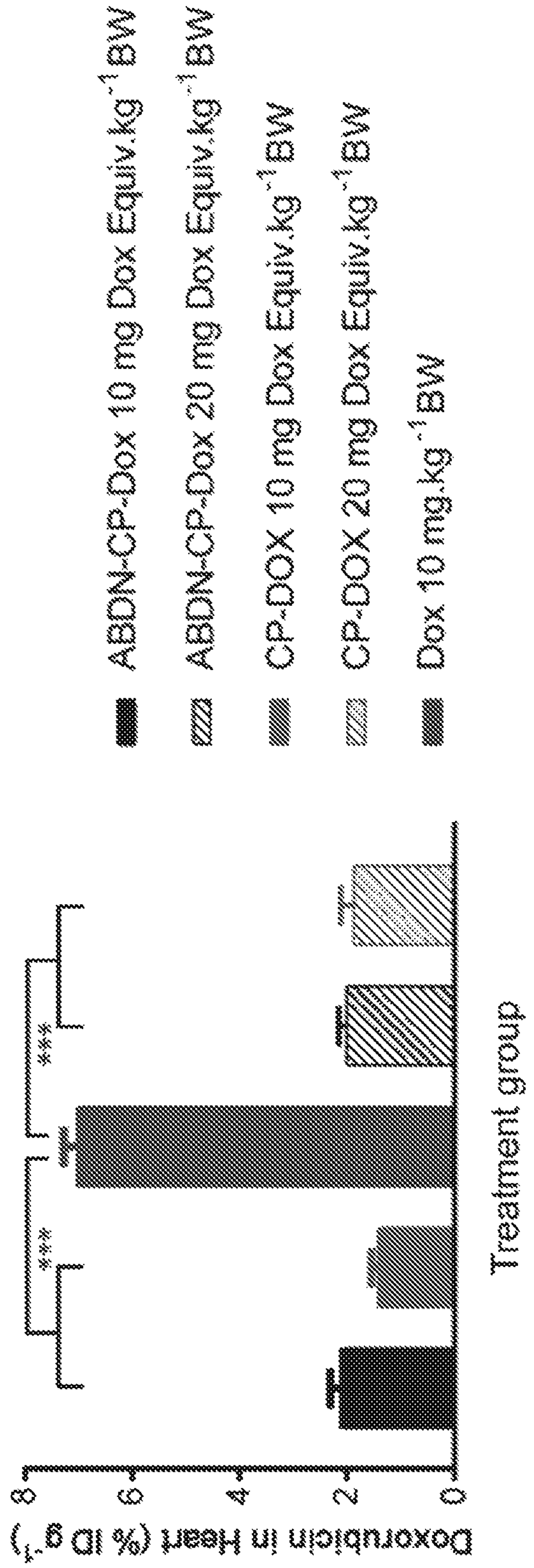
Figure 12E:
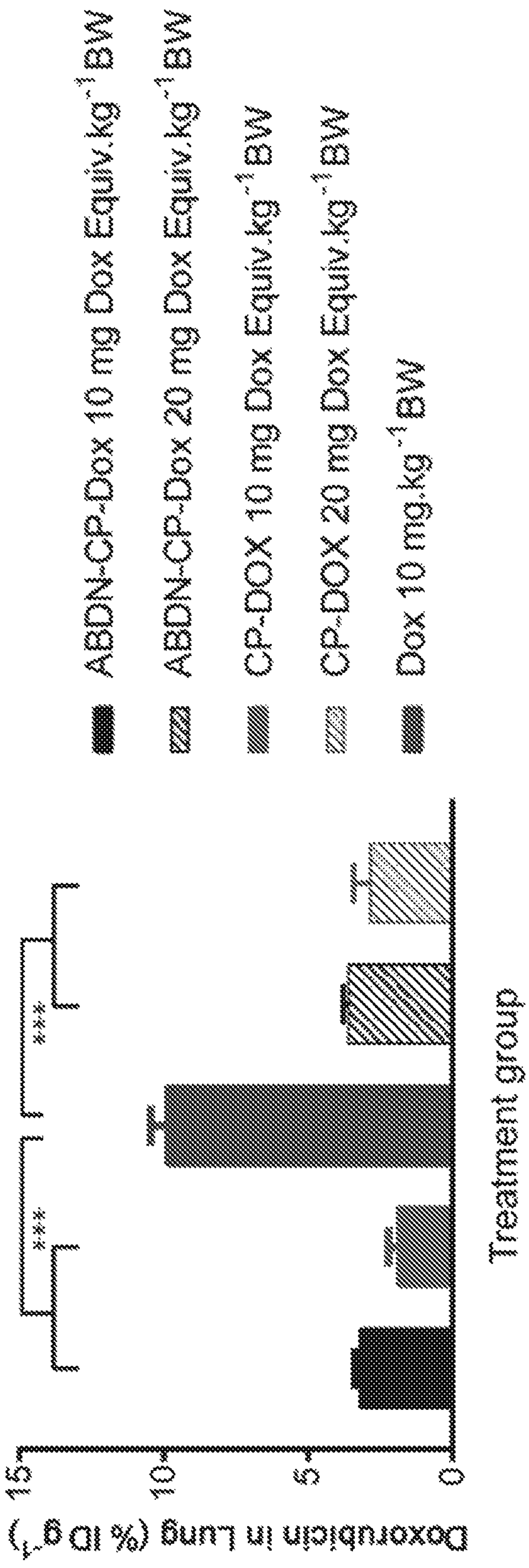
Figure 12F:
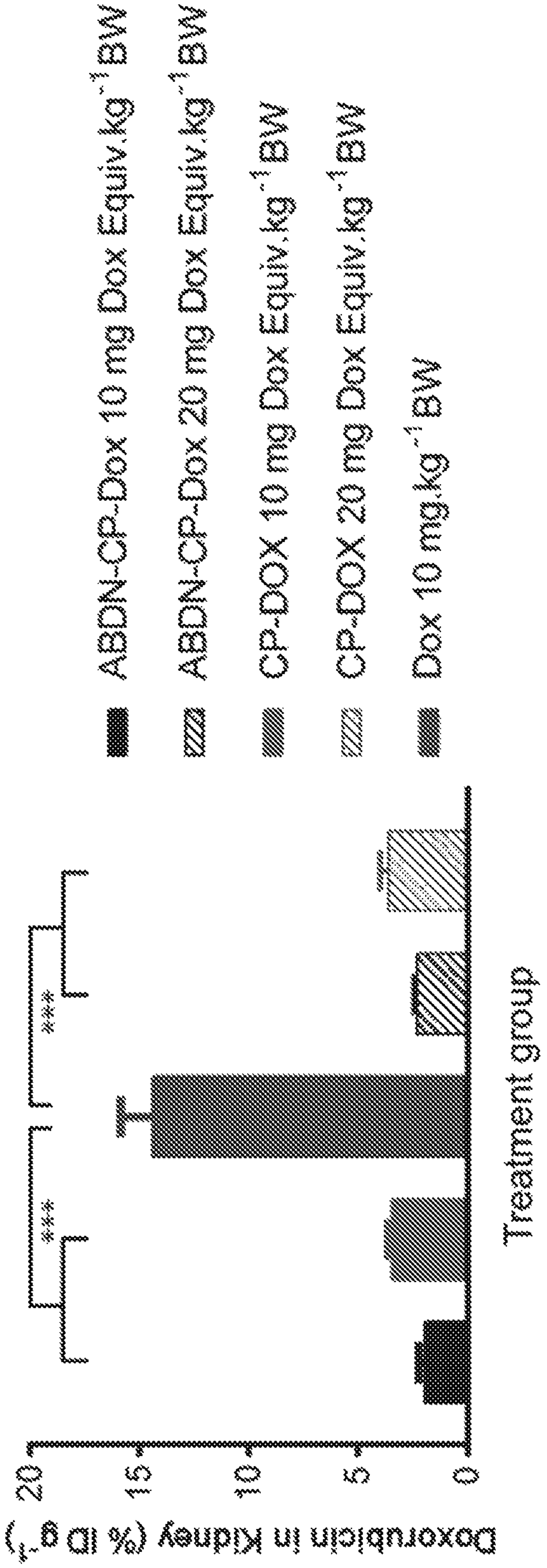
Figure 12G:
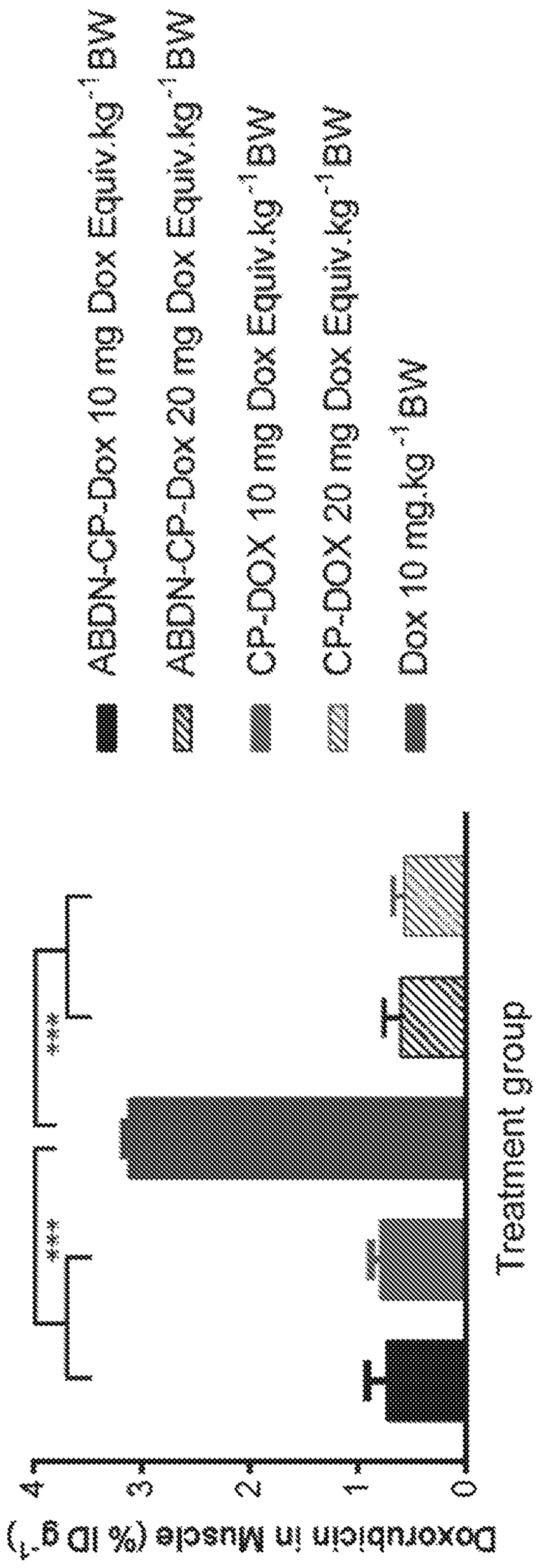
Figure 13A:
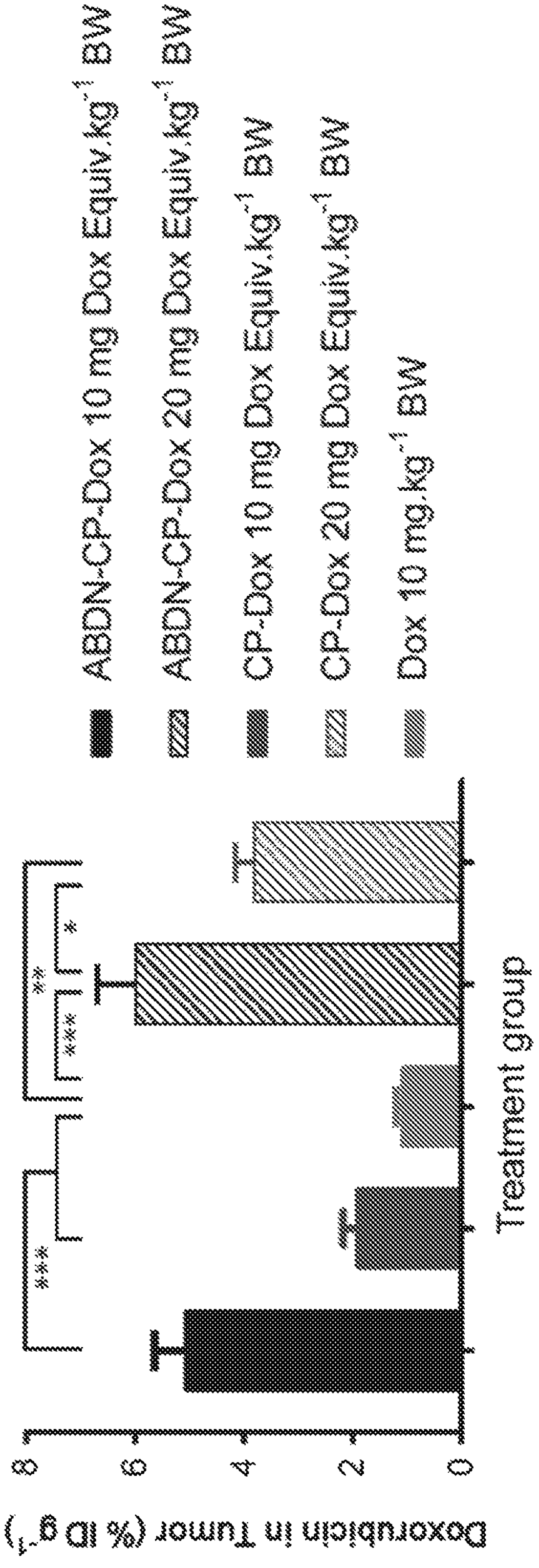
Figure 13B:
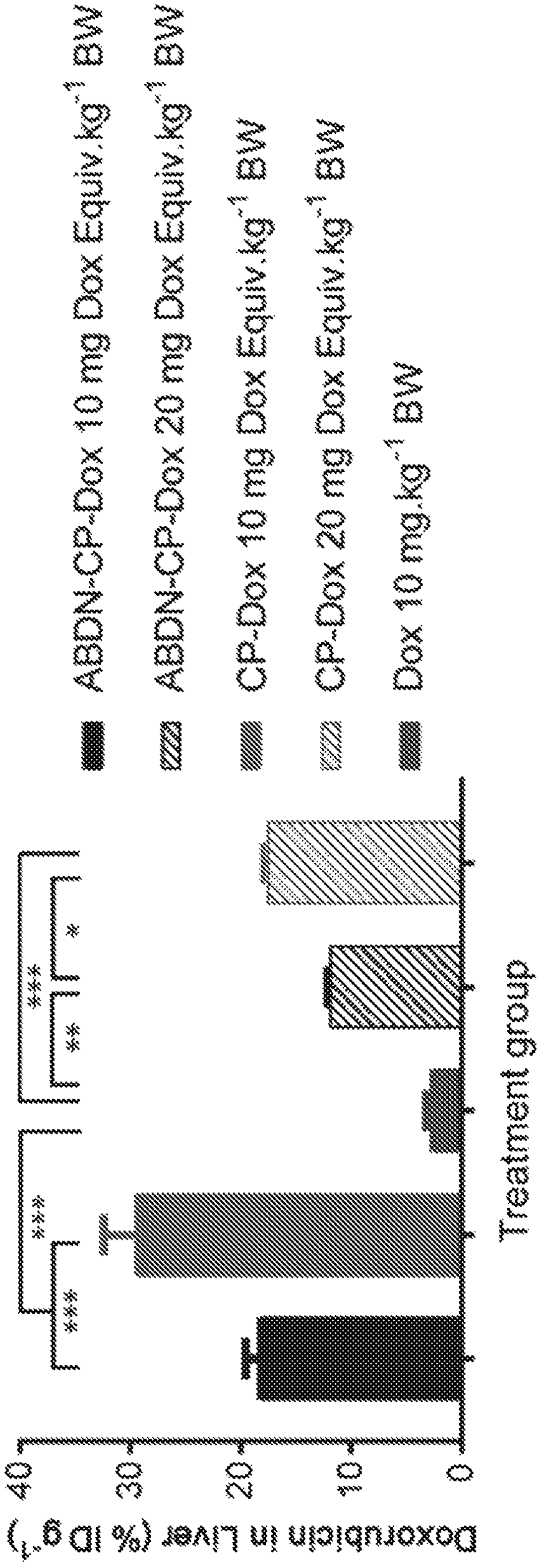

The in vivo tissue distribution of CP-DOX and ABDN-CP-DOX micelles was evaluated by i.v. injection of a dose of 10 and 20 mg DOX Equiv.$kg^{-1}$ into Balb/C mice bearing s.c. C26 tumors. Free DOX was injected at a dose of 10 mg DOX Equiv.$kg^{-1}$. The higher dose of 20 mg DOX Equiv.$kg^{-1}$ was not available for this study, as DOX is known to have a maximum tolerated dose that is <10 mg DOX Equiv.$kg^{-1}$. ABDN-CP-DOX micelles showed ~2 fold significantly greater accumulation in the tumor than CP-DOX micelles at 24 h post-injection at both 10 mg DOX Equiv.$kg^{+1}$ (P<0.001) and 20 mg DOX Equiv.$kg^{+1}$ (P<0.01) doses (FIG. 13A). Furthermore, compared with CP-DOX, ABDN-CP-DOX accumulated to a significantly lower extent in the liver and spleen at 2 h post-injection (FIGS. 12B-C) and had significantly lower accumulation in the liver at 24 h post-injection (FIG. 13B). Free DOX showed lower accumulation in the liver than both CP-DOX and ABDN-CP-DOX micelles (P<0.001), and lower accumulation in the spleen than CP-DOX micelles. No significant difference was observed between the spleen accumulation of free DOX and ABDN-CP-DOX. Free DOX however distributed to a greater extent to the heart, lung, kidneys, and muscle than CP-DOX and ABDN-CP-DOX micelles (FIG. 12D-G, FIG. 13D-G).

Figure 13C:
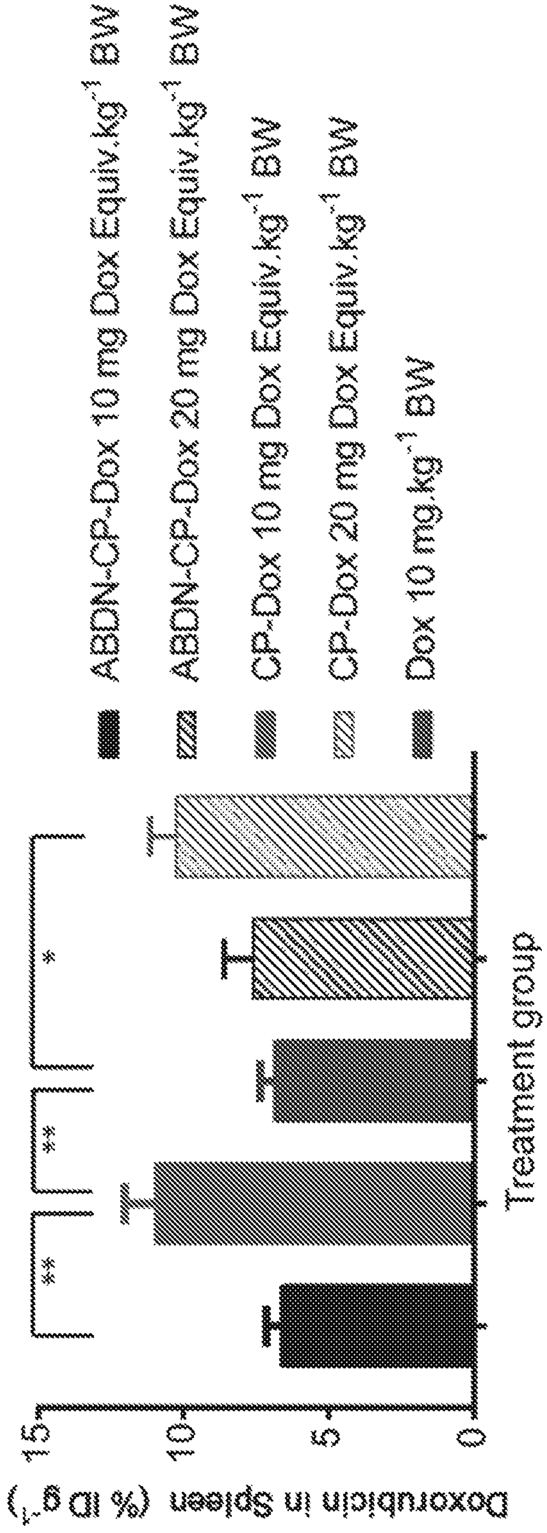
Figure 13D:
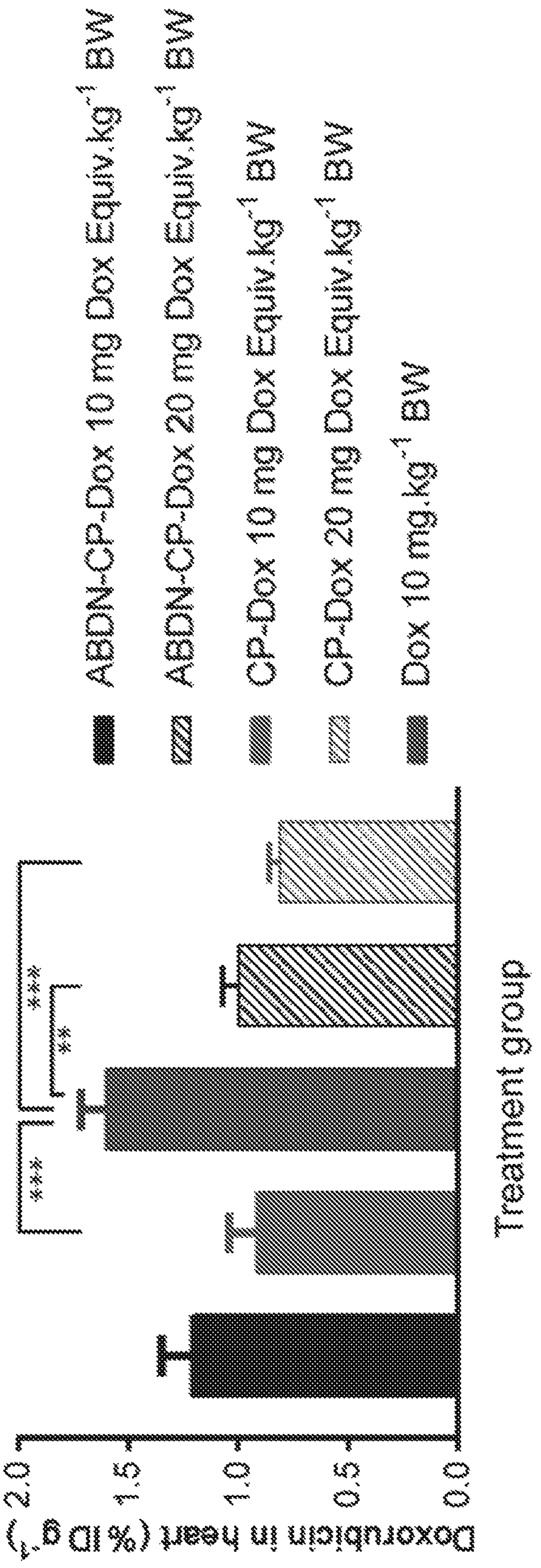
Figure 13E:
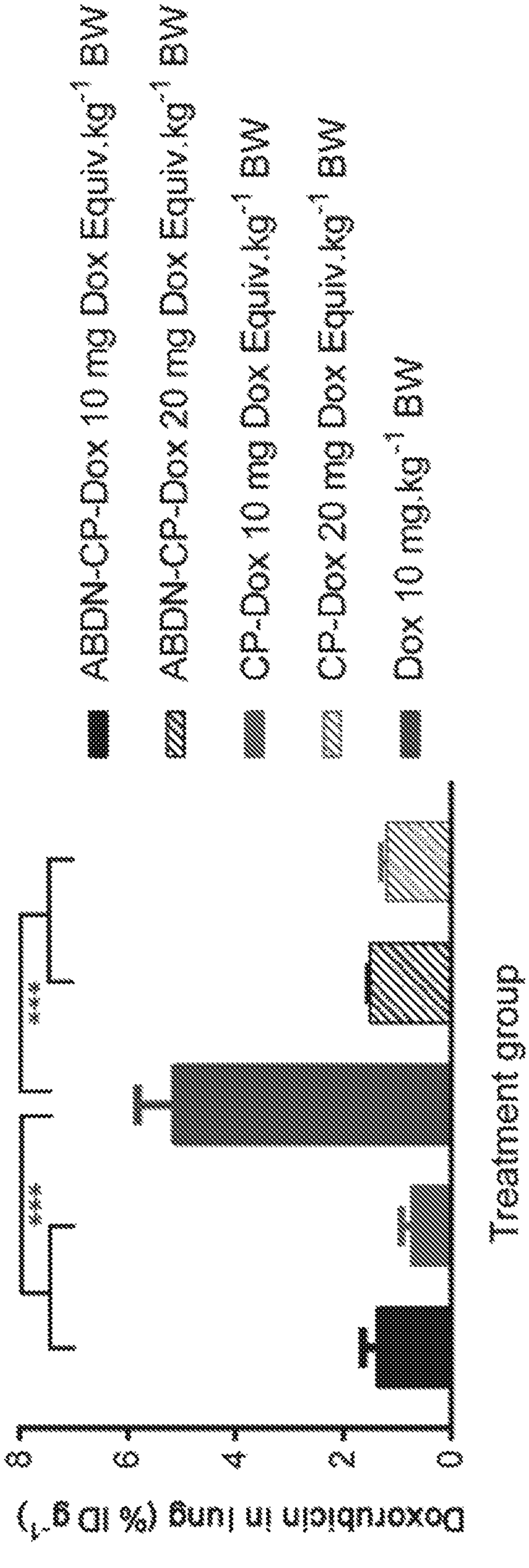
Figure 13F:
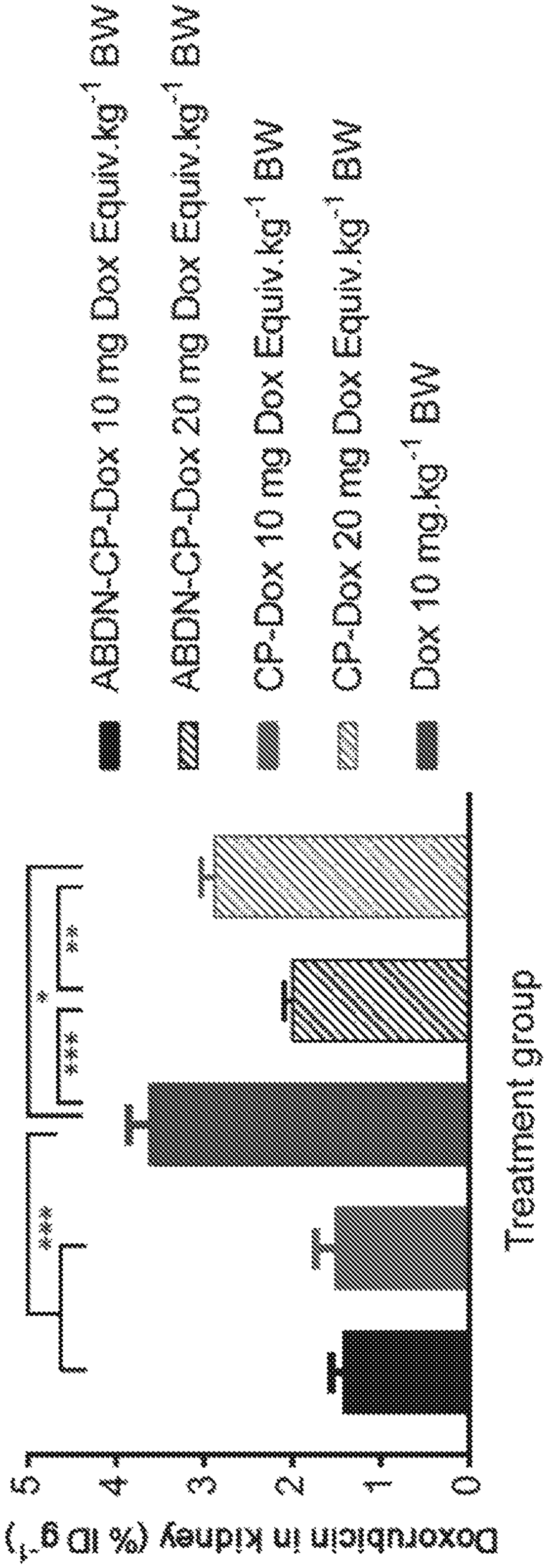
Figure 13G:
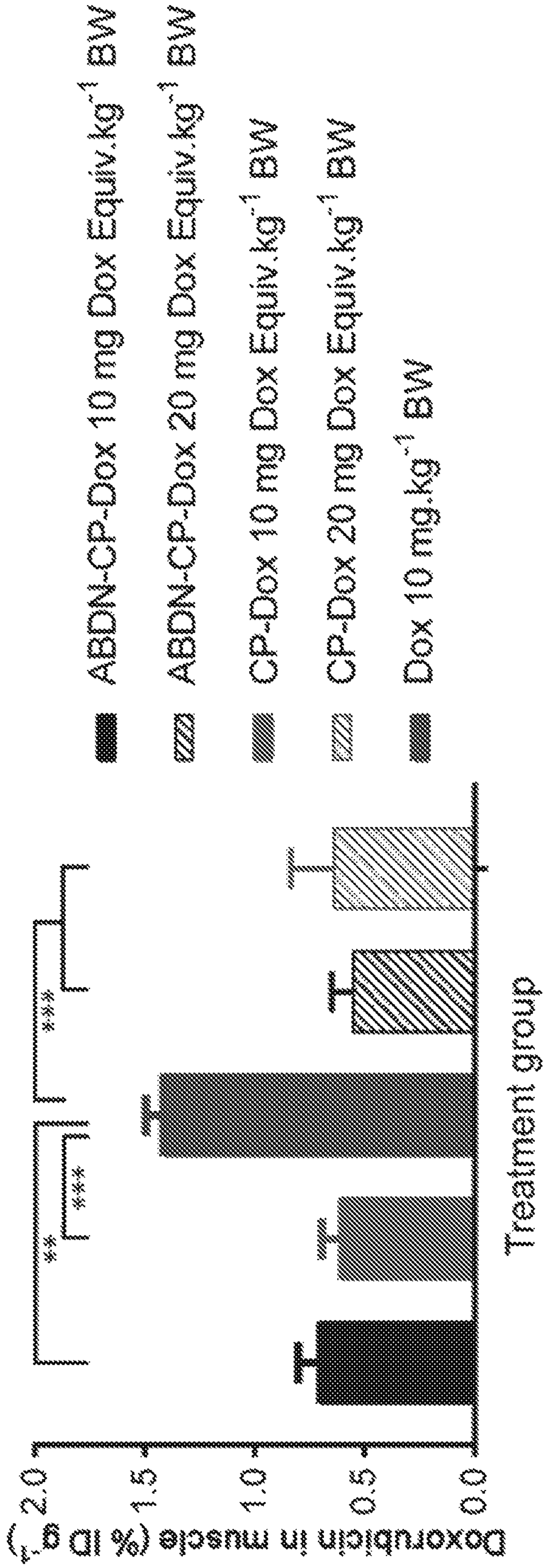
Figure 14A:
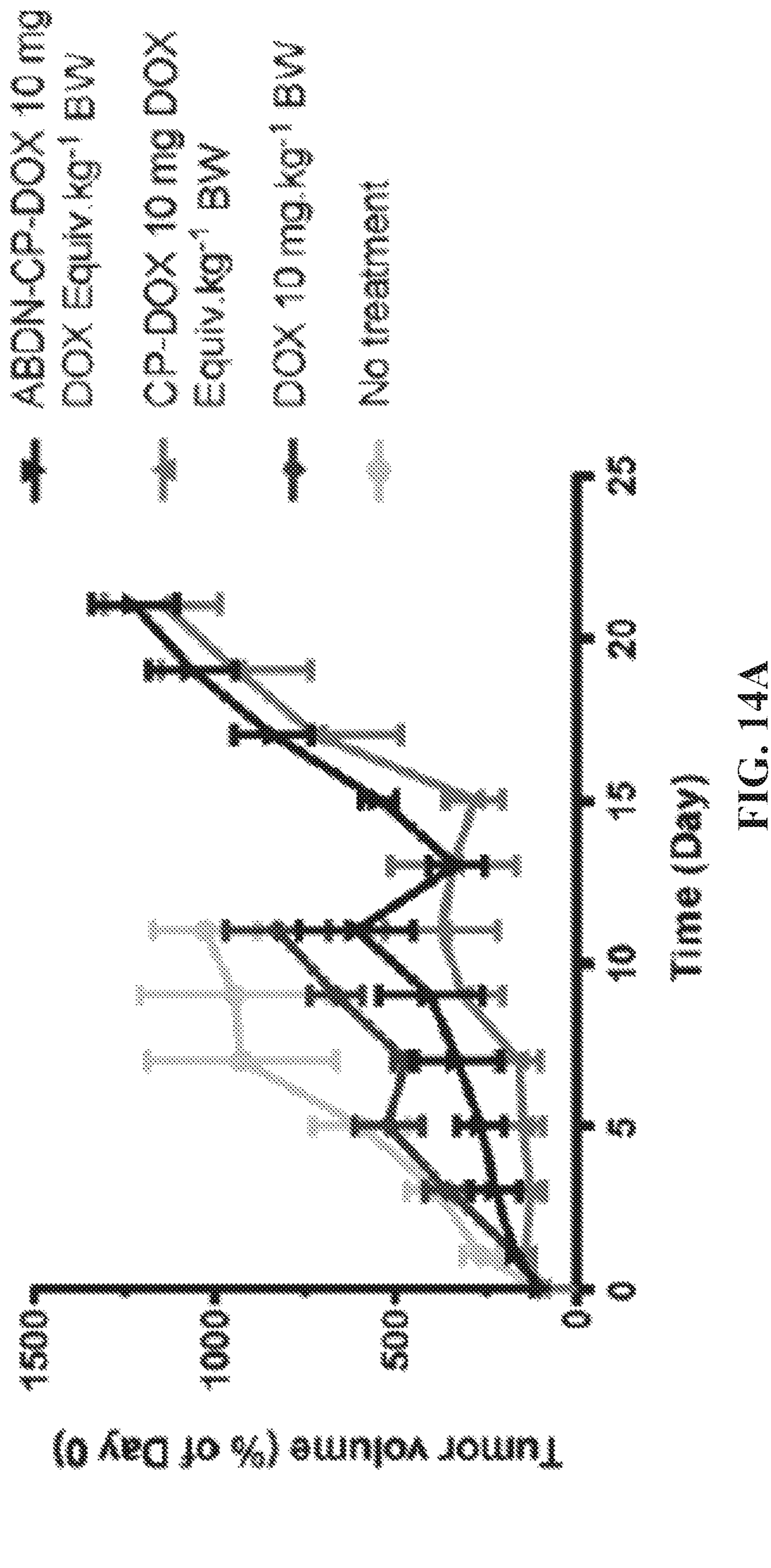
Figure 14B:
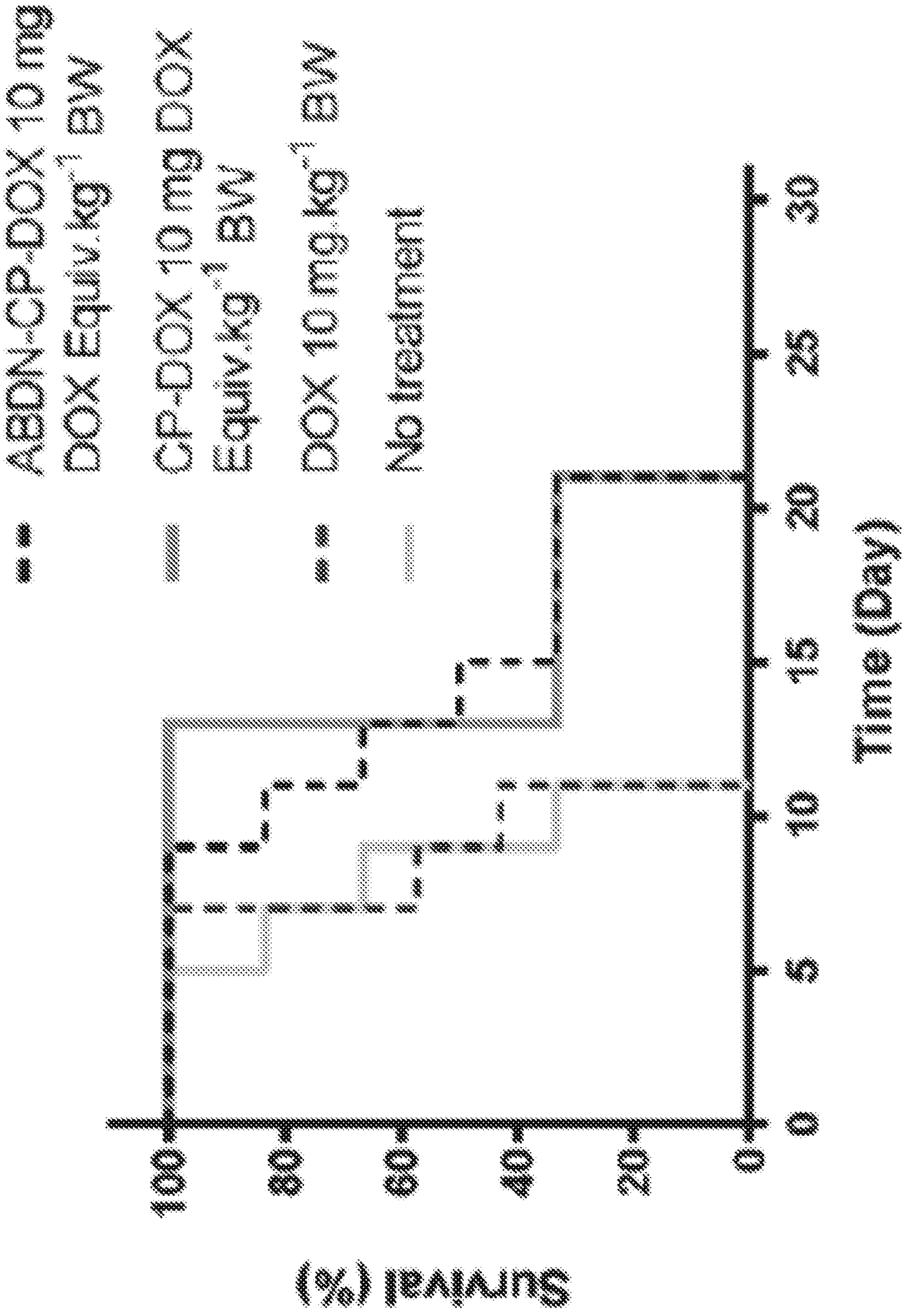
Figure 14C:
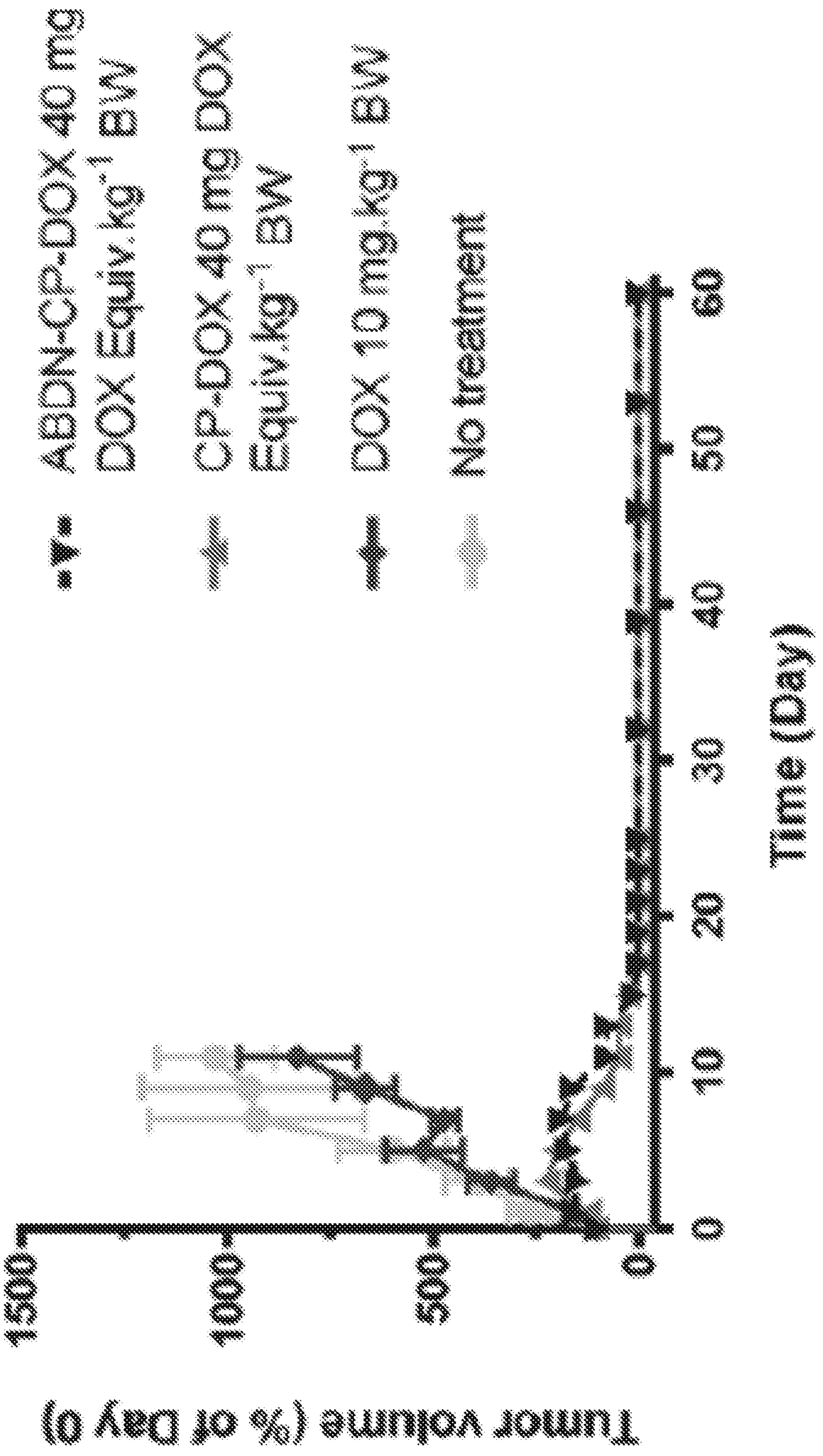
Figure 14D:
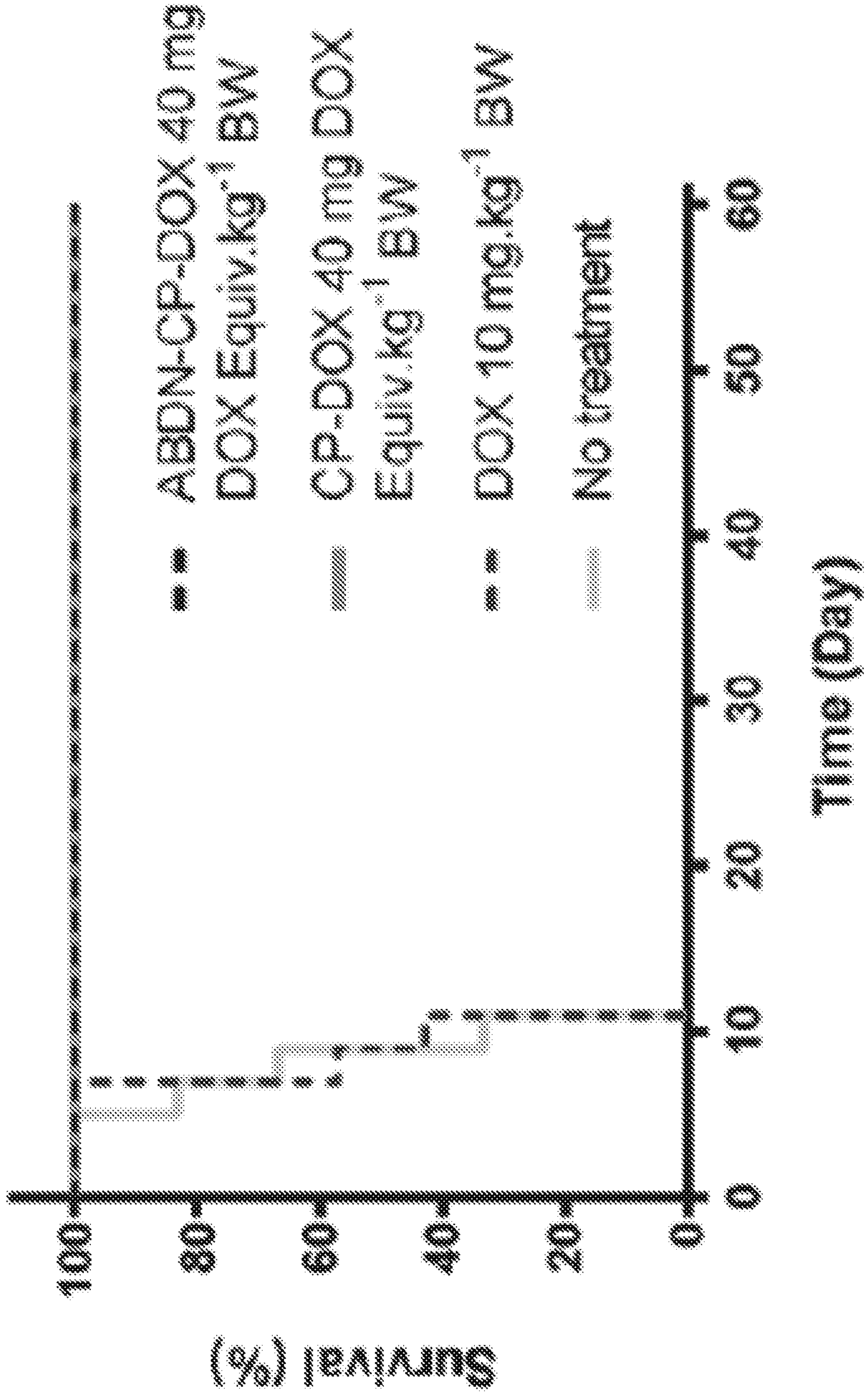
Figure 15A:
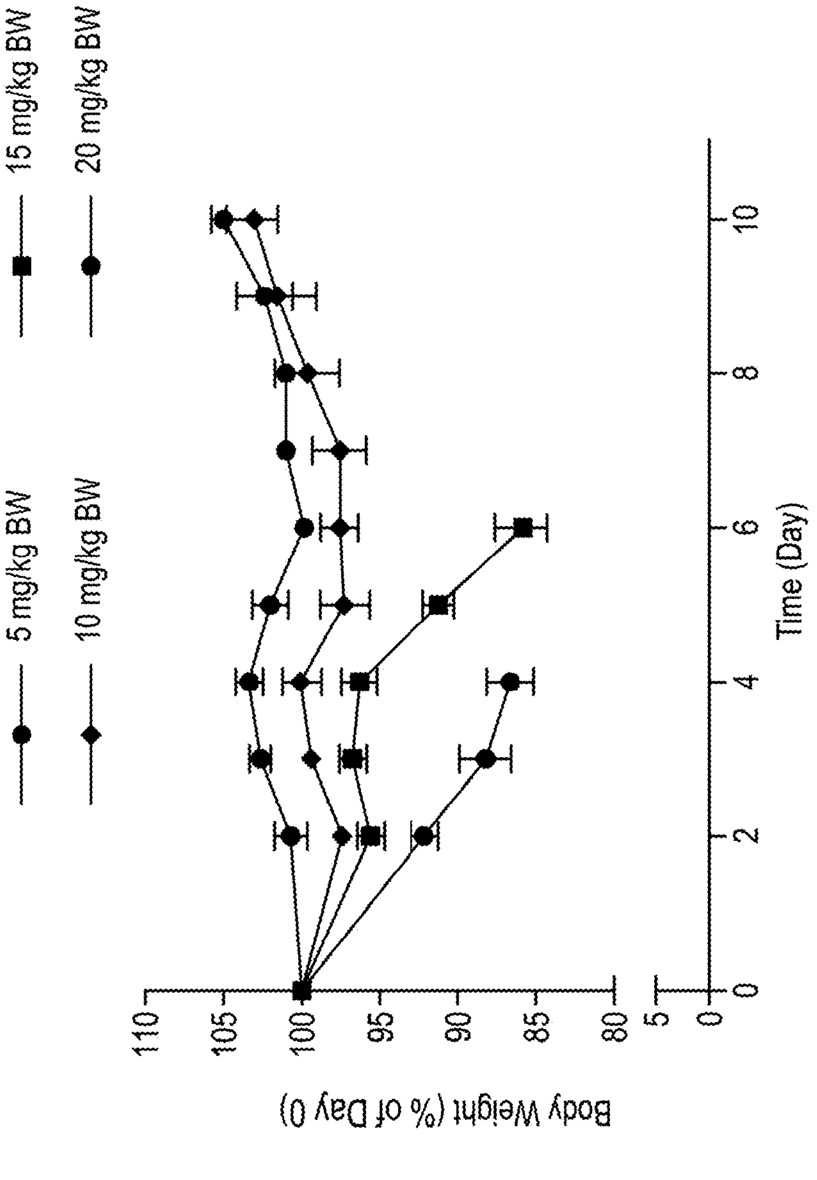
Figure 15B:
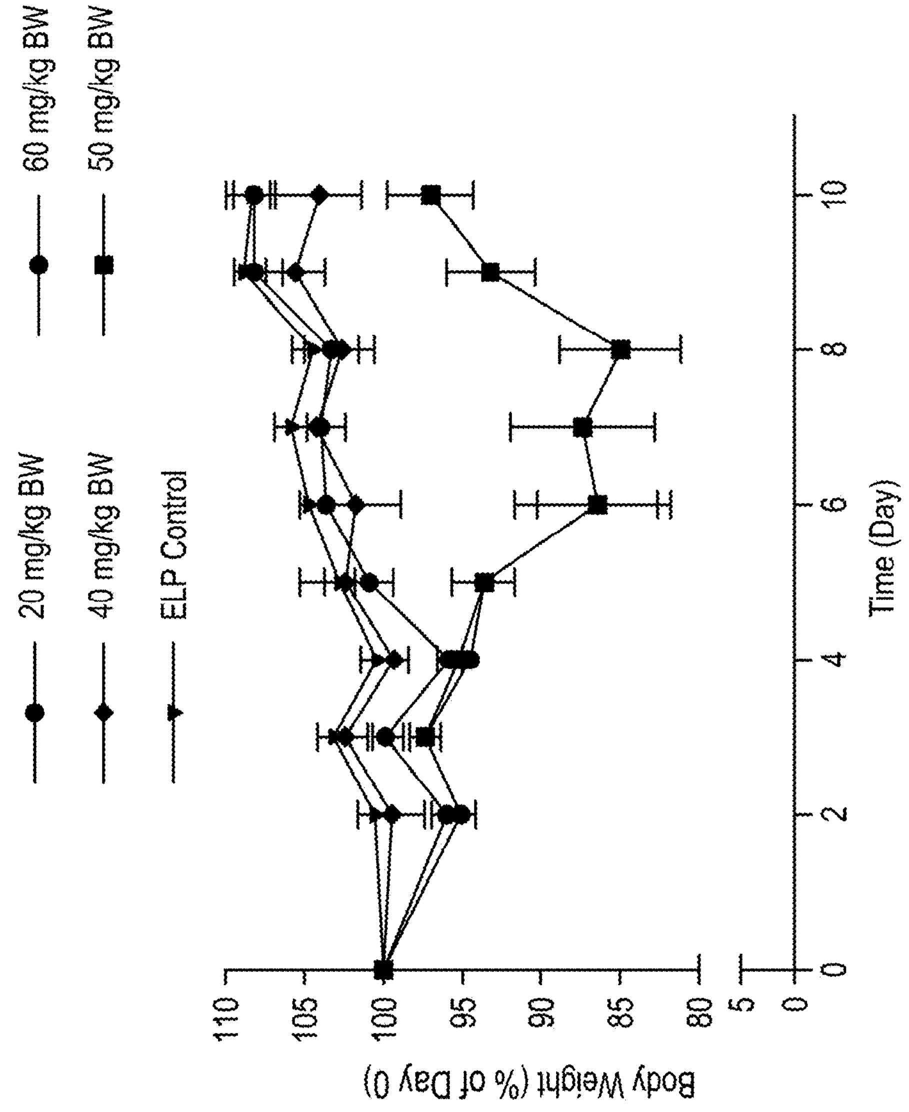
Figure 15C:
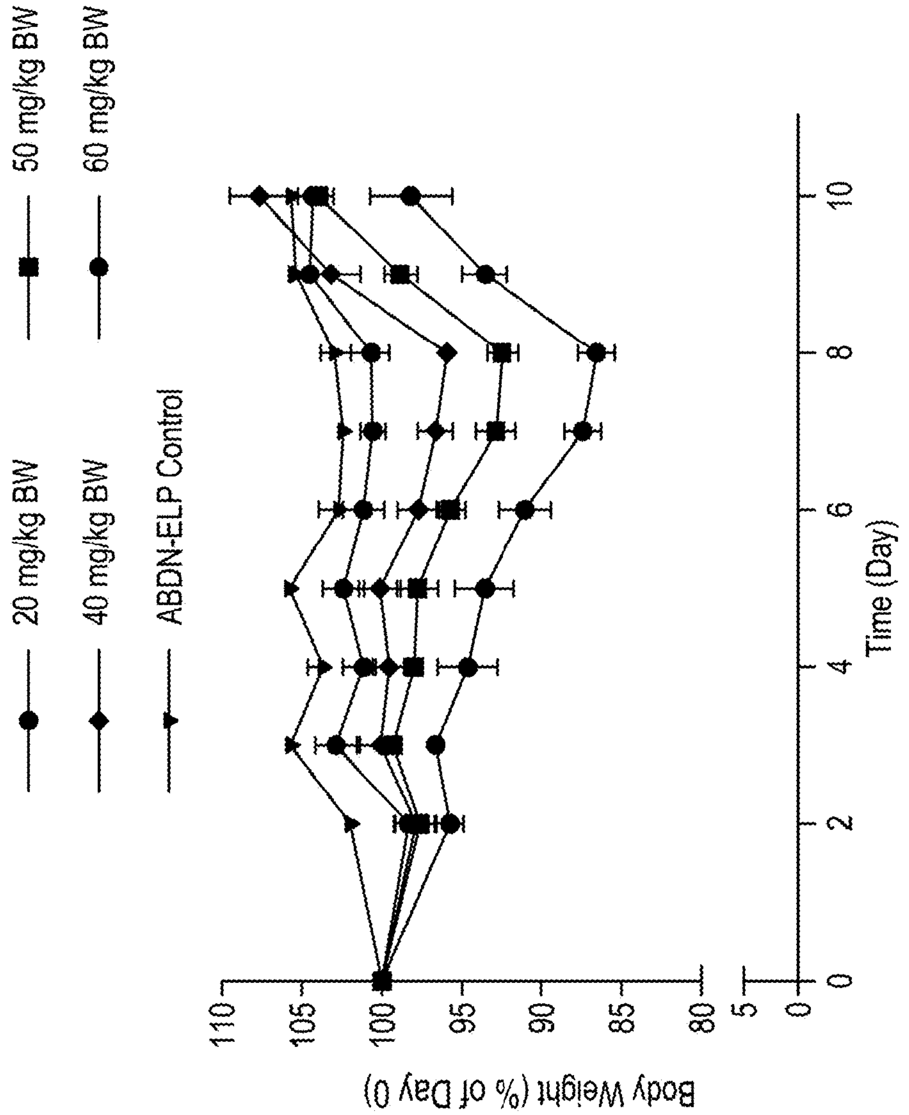

Biodistribution data in mice showed that albumin binding decreased the accumulation of micelles in RES organs i.e. liver and spleen. Micelles are colloidal nanoparticles and therefore are opsonized and sequestered into the RES organs i.e. the liver and spleen. Albumin coating prevents the adsorption of other serum proteins including opsonins and results in lower RES uptake, as reported in previous studies, and is consistent with an increase in plasma half-life at higher dose. The linear pharmacokinetics of ABD-CP-DOX micelle is significant from a clinical perspective, as dosing drugs with non-linear pharmacokinetics is difficult and infuses an element of unpredictability in terms of adverse reactions of the drug. Albumin binding nanoparticles showed lower accumulation in RES organs (liver and spleen) and therefore decrease the off-site toxicities of DOX (FIG. 13B and FIG. 13C). This is important from a clinical point view, as liver toxicity is a frontline concern in nanoparticulate drug development that accounts for the costly failure of many drugs late in the pipeline.

Consistent with the lower RES organ uptake, which are well known "sinks" for nanoparticles, the tumor accumulation of ABDN-CP-DOX micelles was approximately 2.5-fold greater than compared to CP-DOX micelles at a dose of 10, and was approximately 2-fold greater at a dose of 20 mg DOX Equiv.$kg^{-1}$ BW.

Example 8: ABD-CP-DOX Micelles Increase the Tumoricidal Effect

Figure 10D:
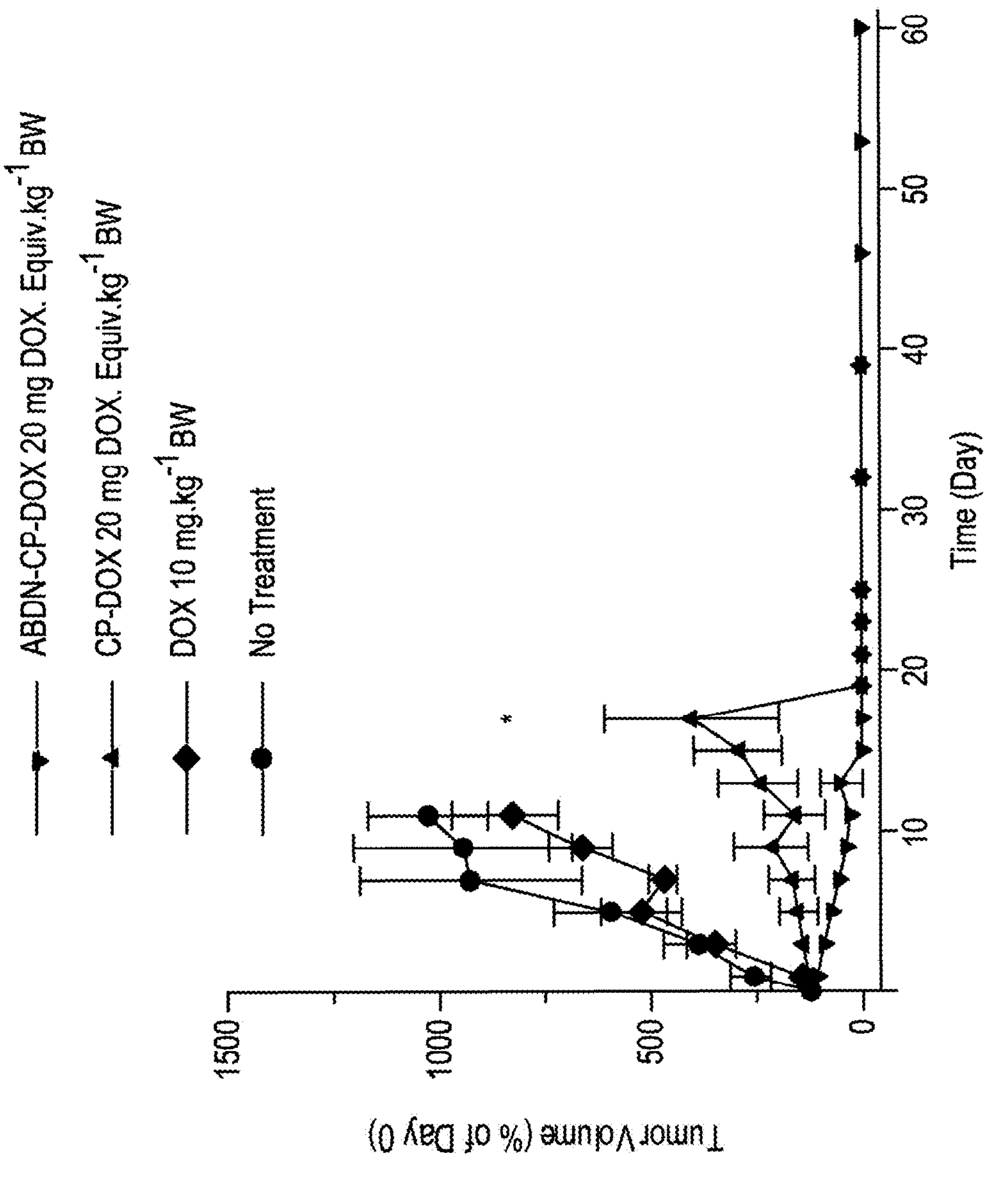
Figure 10E:
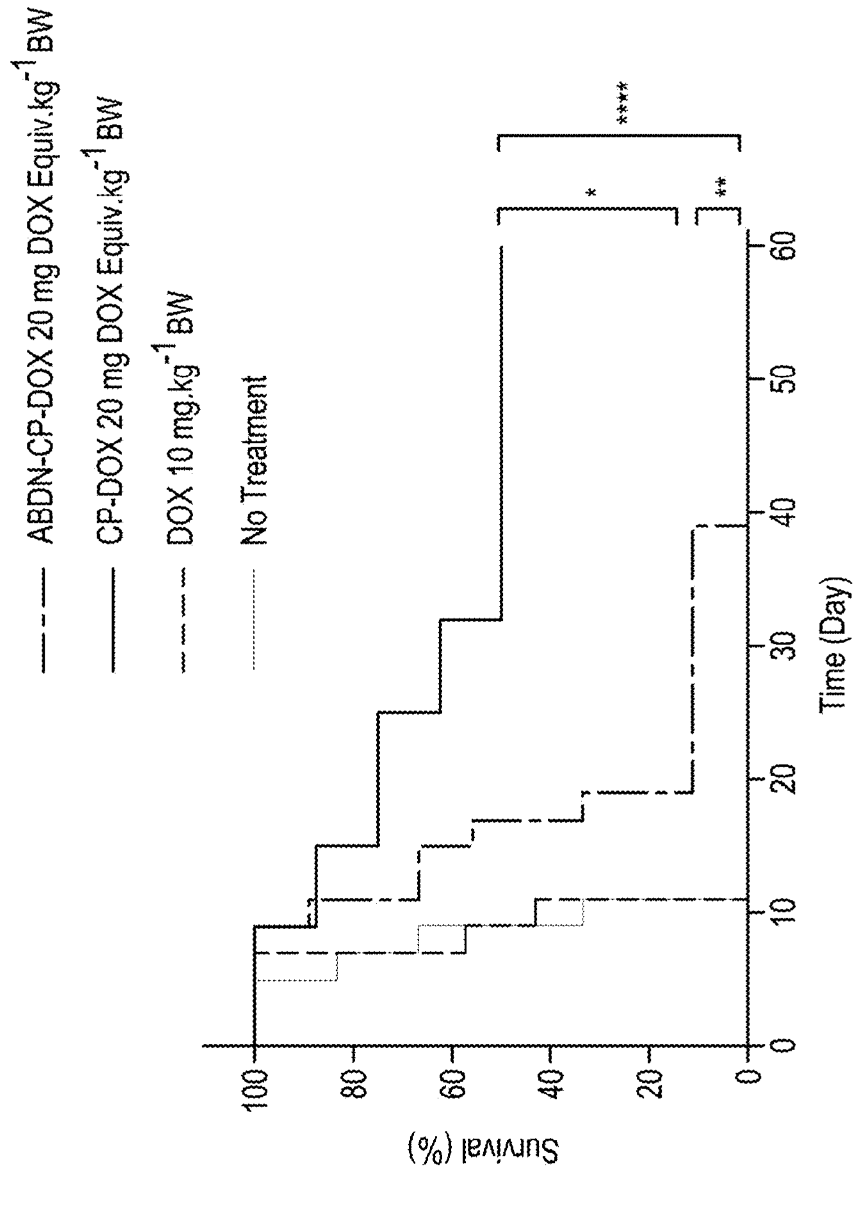

Anti-tumor efficacy of the ABD-CP-DOX micelles compared with CP-DOX micelles and free DOX was evaluated in a mouse C26 colon cancer model (FIG. 10D and FIG. 10F). Results of tumor measurements revealed that tumor growth was significantly slower in the ABD-CP-DOX administration group than that of CP-DOX and free DOX groups (FIG. 10D). Furthermore, at a DOX equivalent dose of 20 mg/kg BW, ABD-CP-DOX micelles prolonged the survival periods of tumor bearing mice as compared to CP-DOX micelles (FIG. 10E). 50% of tumor bearing mice treated with ABD-CP-DOX survived 60 days after treatment, whereas CP-DOX treated group showed a 39-day survival. Both micellar treatment groups showed slower tumor growth and longer survival than the free DOX treatment group.

Figure 16A:
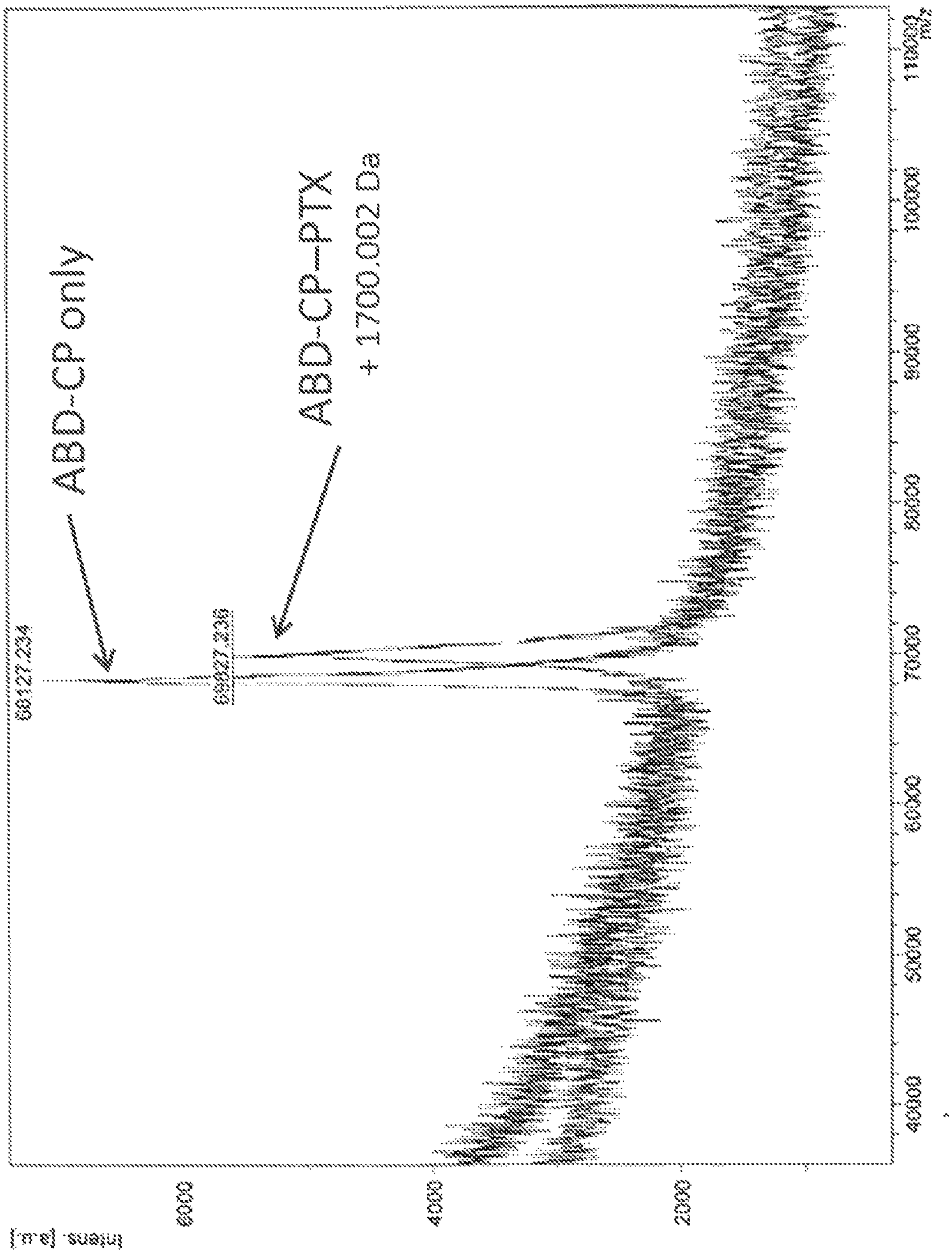
FIG. 16A and FIG. 16B show paclitaxel (PTX) loading of ABD-CP (FIG. 16A) and CP (FIG. 16B) by MALDI-TOF-MS.
Figure 16B:
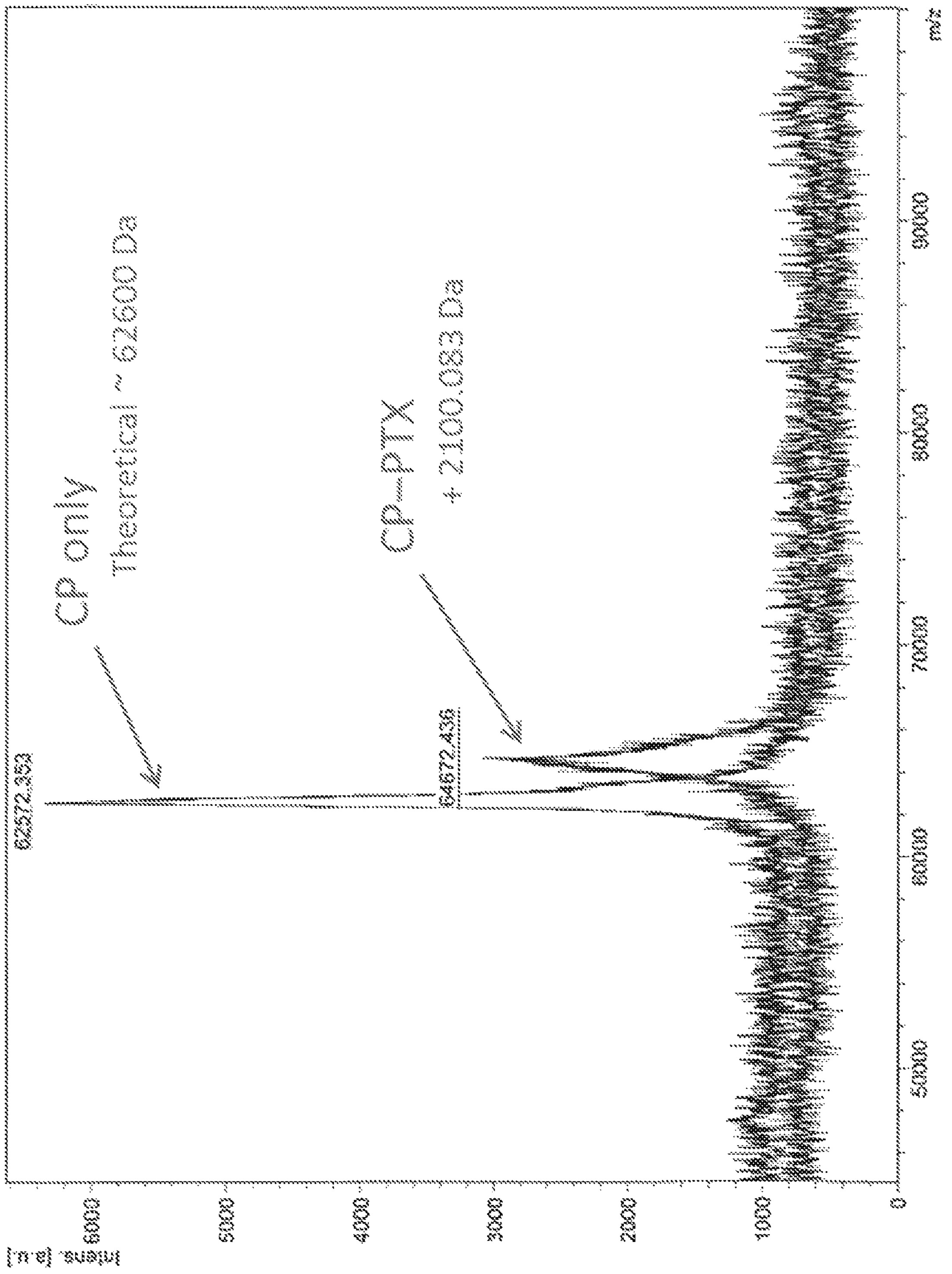
Figure 17A:
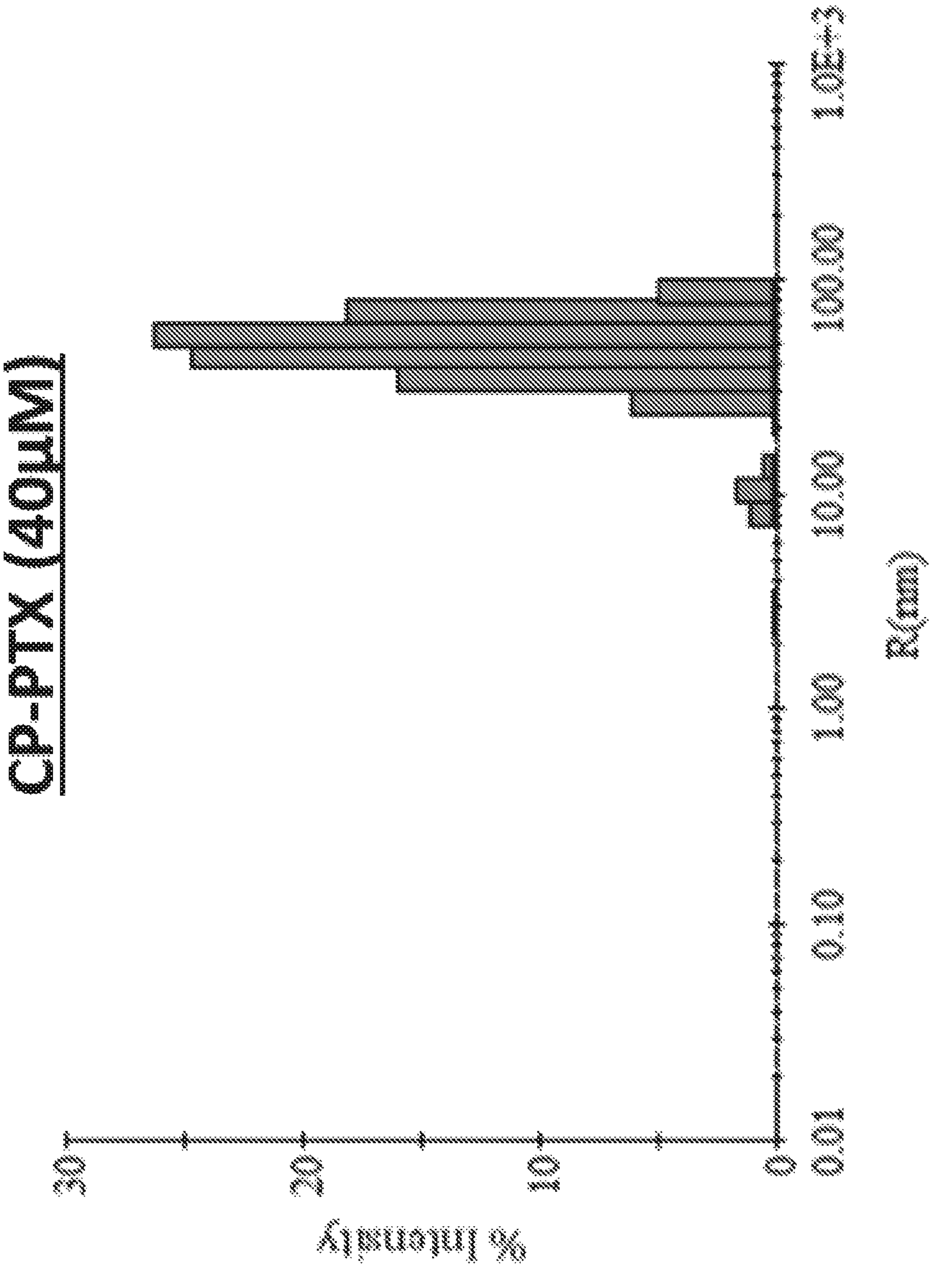
FIG. 17A and FIG. 17B show the dynamic light scattering graphs for CP-PTX (FIG. 17A) and ABD-CP-PTX (FIG. 17B).
Figure 17B:
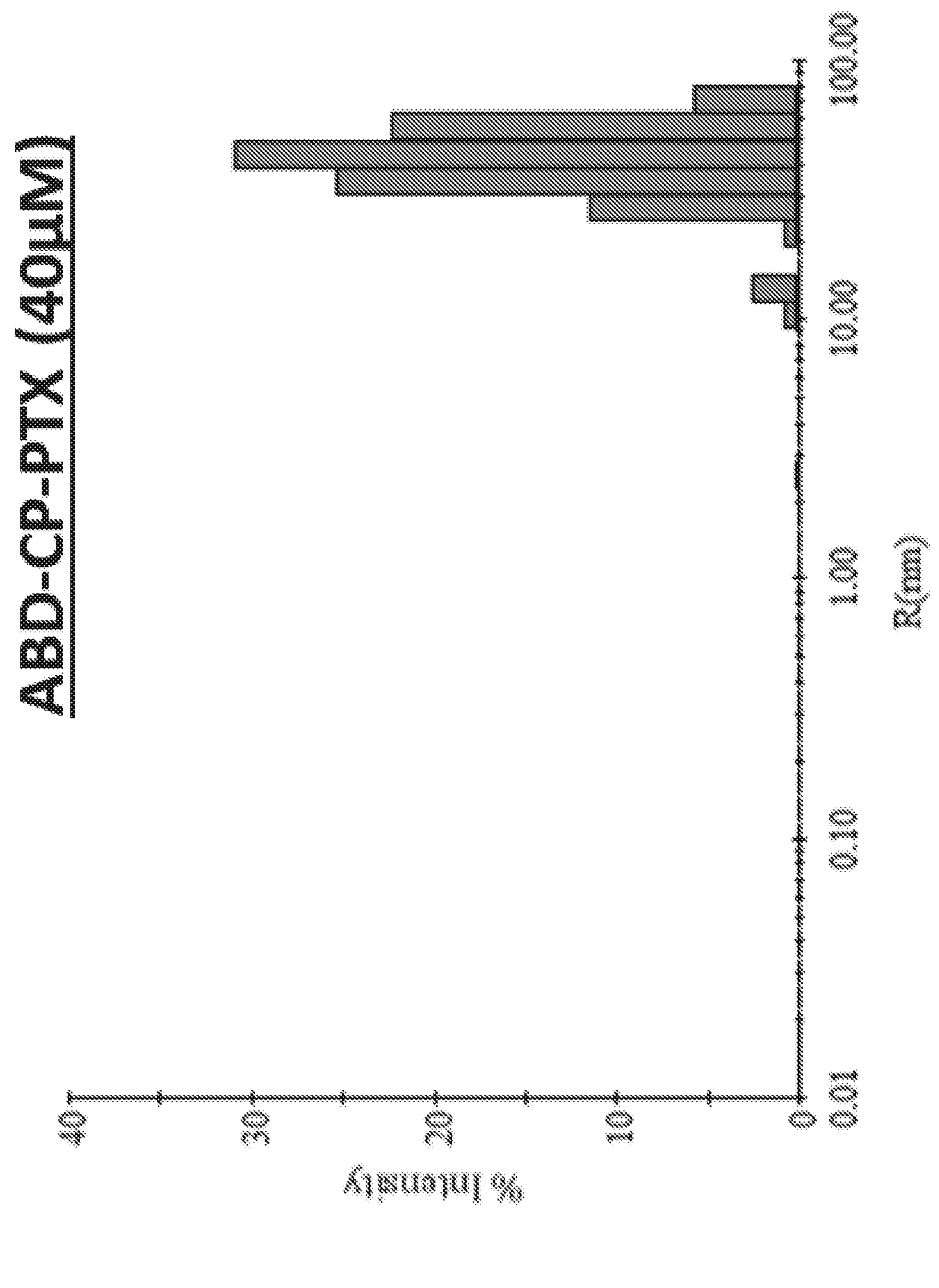

Example 9: Development of Albumin Binding Self-Assembling Micelles with Paclitaxel Paclitaxel was conjugated to cysteine residues at the C-terminus of CP and ABD-CP via a pH-sensitive linker, as described in Example 1. Paclitaxel conjugation was confirmed by MALDI-TOF-MS. Conjugation with ABD-CP resulted in a 1700 Dalton molecule weight difference indicating the presence of 2 drugs per ABD-CP (FIG. 16A). Conjugation with CP resulted in a 2100 Dalton molecule weight difference indicating the presence of on average 2.5 drugs per CP (FIG. 16B). Following conjugation to paclitaxel both CP-PTX and ABD-CP-PTX were evaluated by dynamic light scattering to verify their hydrodynamic radii (FIG. 17A and FIG. 17B). The results for two different concentrations are shown in Table 8.

TABLE 8

Dynamic light scattering data for ABDN-CP-PTX and CP-PTX

| Conjugate | Concentration (µM) | $R_h$ (nm) | % Intensity | Polydispersity |
|---|---|---|---|---|
| CP-PTX | 20 | 48.9 ± 2.3 | 99.3 | 40.8% |
| | 40 | 52.4 ± 2.9 | 96.4 | 30.5% |
| ABD-CP-PTX | 20 | 39.6 ± 2.2 | 95.4 | 24.6% |
| | 40 | 44.1 ± 4.7 | 96.6 | 26.6% |

Figure 18A:
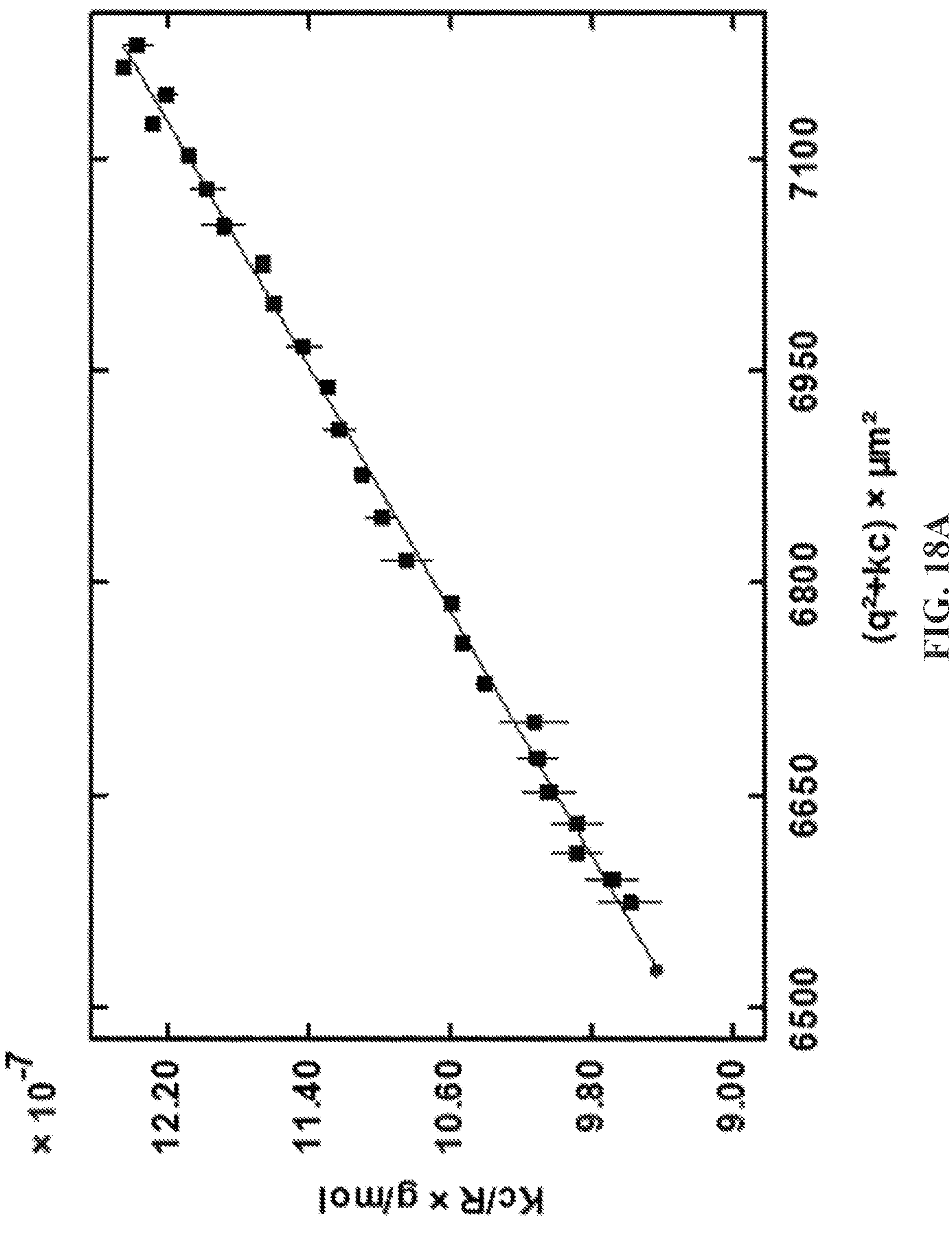
FIG. 18A and FIG. 18B show the static light scattering graphs for CP-PTX (FIG. 18A) and ABD-CP-PTX (FIG. 18B).
Figure 18B:
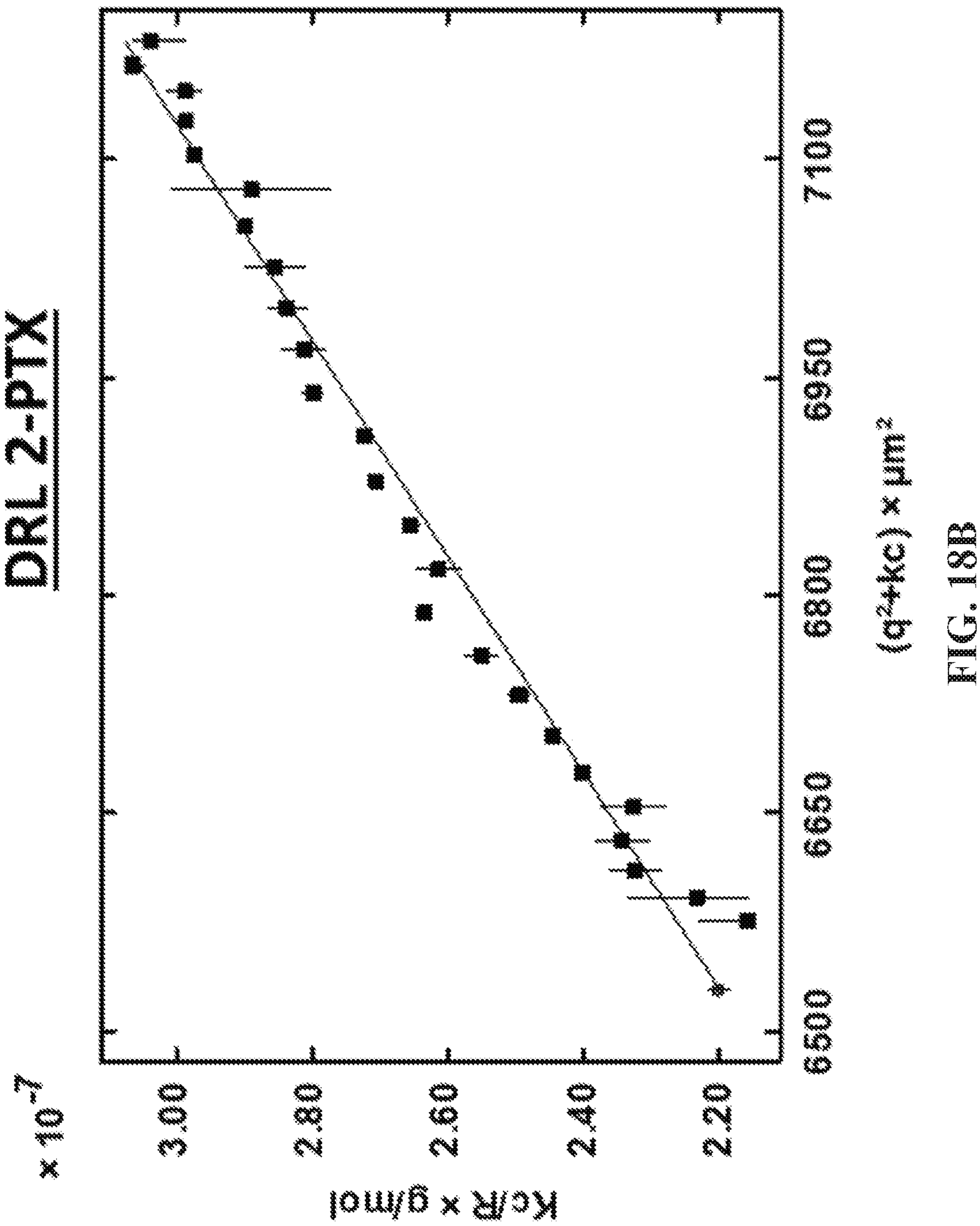
Figure 19A:
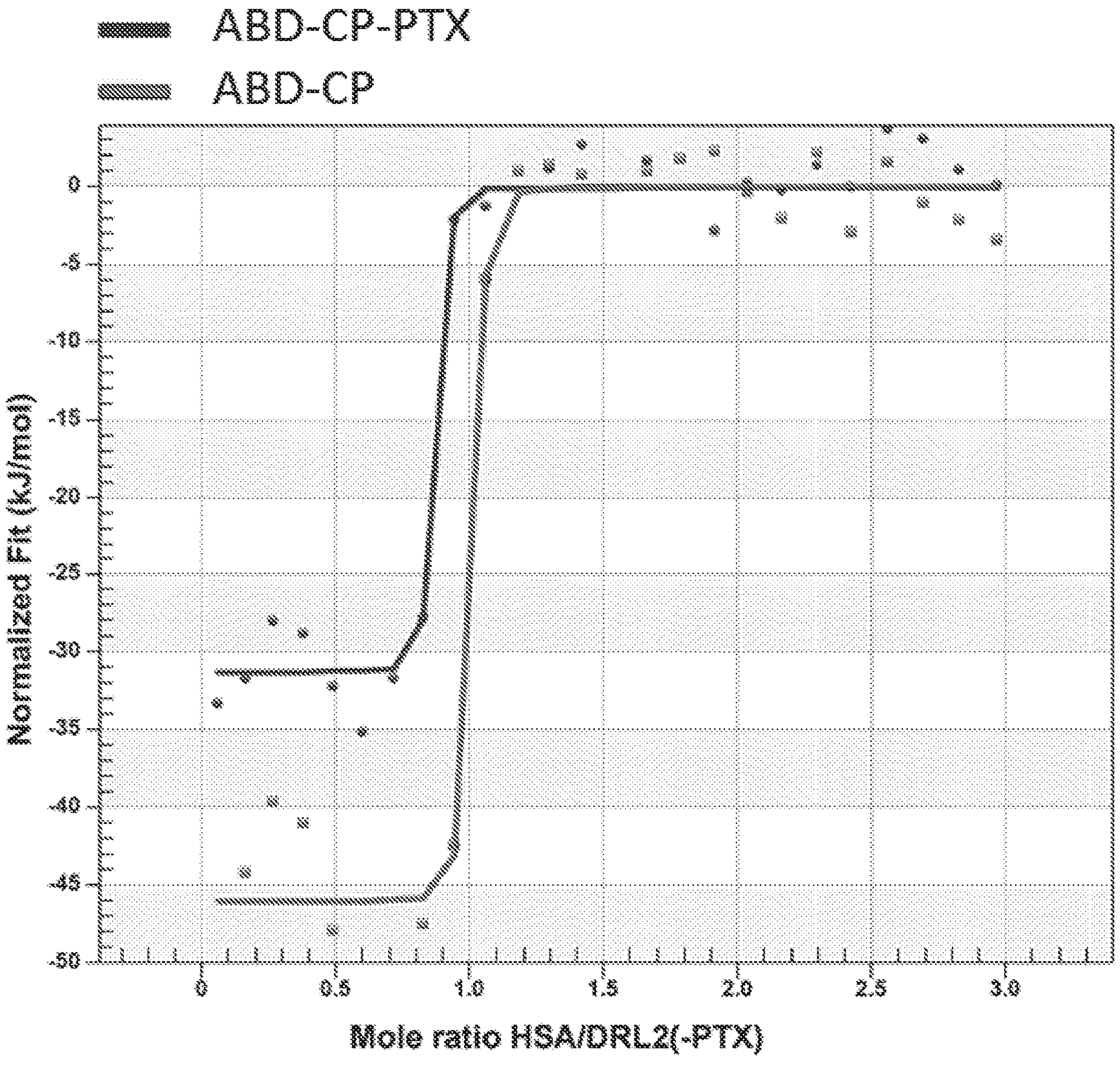
FIG. 19A and FIG. 19B show the calorimetric titration of HSA with ABD-CP-PTX and ABD-CP (FIG. 19A) and CP and CP-PTX (FIG. 19B).
Figure 19B:
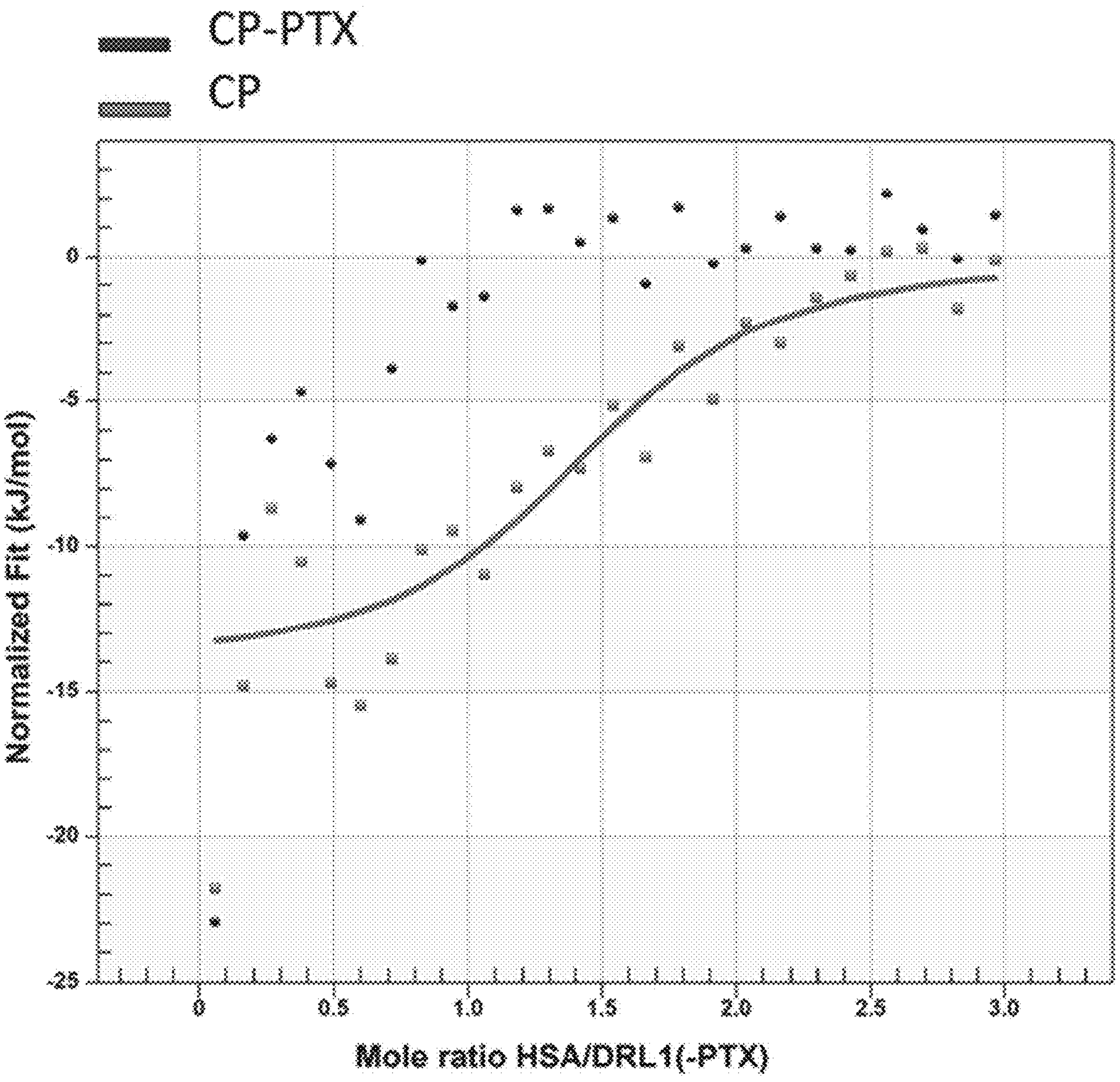
Figure 20A:
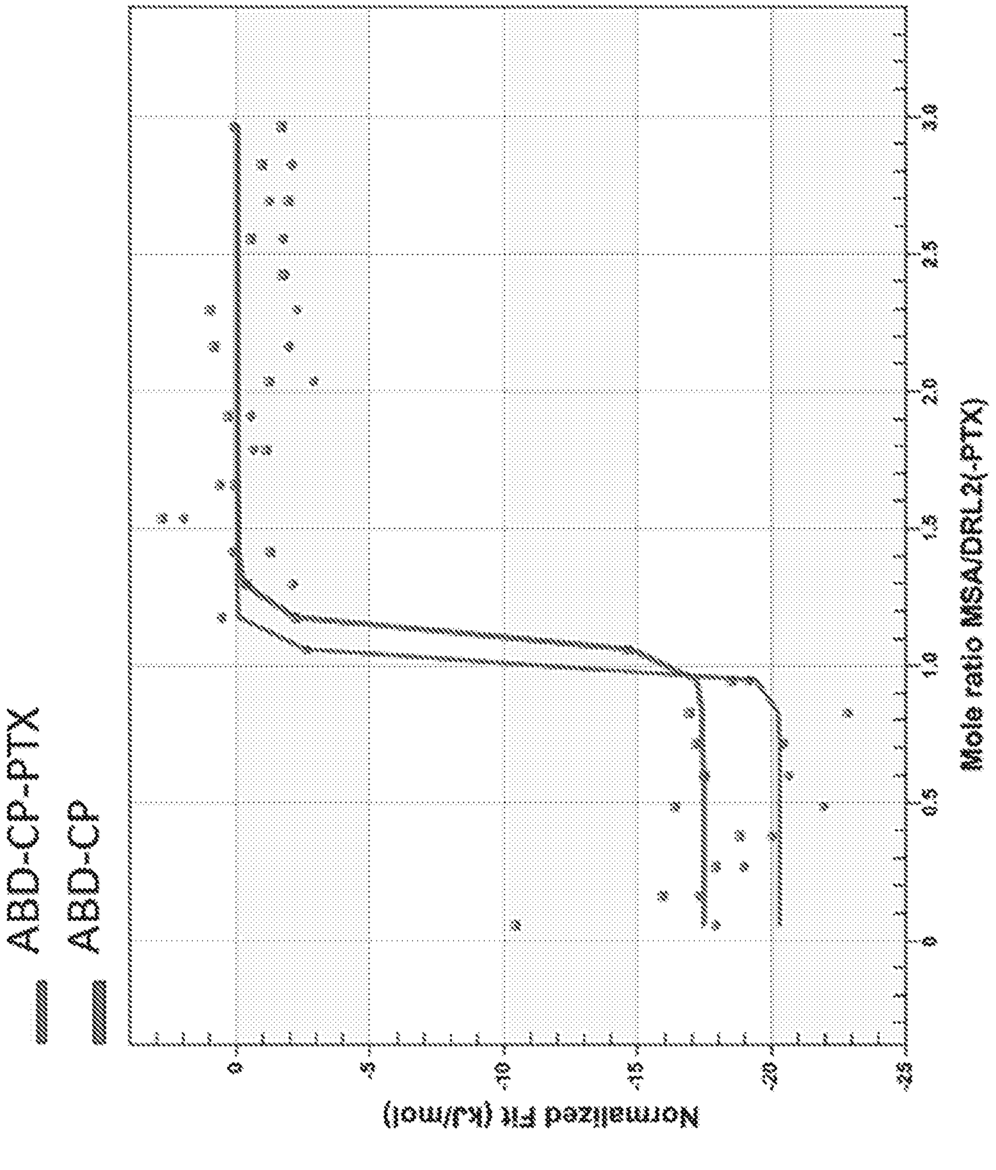
FIG. 20A and FIG. 20B show the calorimetric titration of MSA with ABD-CP-PTX and ABD-CP (FIG. 20A) and CP and CP-PTX (FIG. 20B).
Figure 20B:
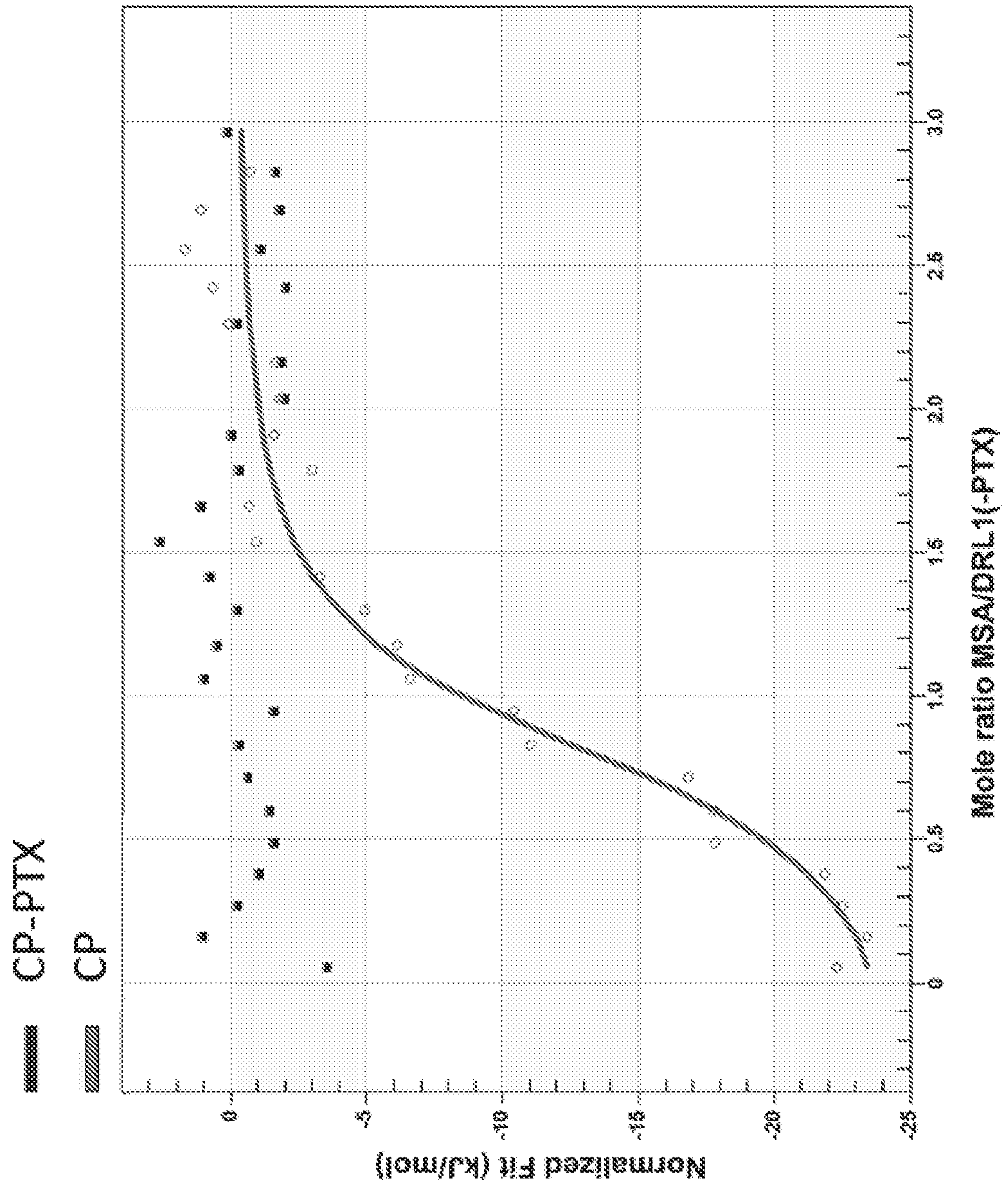

Static light scattering (FIG. 18A and FIG. 18B) was used to analyze the radius of gyration, $R_G$, a mass density size measurement and overall molecular weight of the conjugated nanoparticle. The dynamic and static light scattering results were combined to calculate a number of chains per nanoparticle ($n_{agg}$, Table 9).

TABLE 9

Light scattering data for ABDN-CP-PTX and CP-PTX at 20 µM concentration

| | DLS Analysis | | SLS Analysis | | |
|---|---|---|---|---|---|
| | $R_h$(nm) | Polydispersity | $R_G$ (nm) | $MW_{agg}$ | $N_{agg}$ |
| CP-PTX | 48.9 ± 2.3 | 40.8% | 38.35 | 1.060 MDa | 16.2 |
| ABD-CP-PTX | 39.6 ± 2.2 | 24.6% | 42.83 | 4.548 MDa | 64.5 |

As with the (ABD-)CP-DOX micelles, the binding affinity of ABD-CP and ABD-CP-PTX for human serum albumin (HSA) and mouse serum albumin (MSA) was analyzed quantitatively by ITC (FIGS. 19A, 19B, 20A, and 20B). It was observed that PTX conjugated ABD-CP still displayed strong sub-µM affinity for both mouse and human albumin (Table 10). The binding data showed that both ABD-CP monomers and ABD-CP-PTX micelles bind to human and mouse albumin with 1:1 stoichiometry and nanomolar affinity, whereas ELP and CP-PTX controls displayed no specific affinity.

TABLE 10

Albumin binding affinity for ABD-CP-PTX, ABD-CP and CP-PTX.

| Conjugate | Albumin | KD (nM) | n |
|---|---|---|---|
| ABD-CP | HSA | 6.47 | 0.95 |
| | MSA | 16.3 | 1.05 |
| ABD-CP-PTX | HSA | 5.58 | 0.92 |
| | MSA | 4.37 | 0.95 |
| CP | HSA | 4500 | 1.46 |
| | MSA | 3500 | 0.85 |
| CP-PTX | HSA | N/A | N/A |
| | MSA | N/A | N/A |

ABDN-CP fusions for conjugation with Paclitaxel showed that the $T_t$ decreased from 60° C. for CP to 48° C. for ABDN-CP. ABDN-CP-PTX nanoparticles, showed no aggregates at 37° C.

Example 10: In Vitro Cytotoxicity of ABDN-CP-PTX, CP-PTX, and Free PTX

Figure 21:
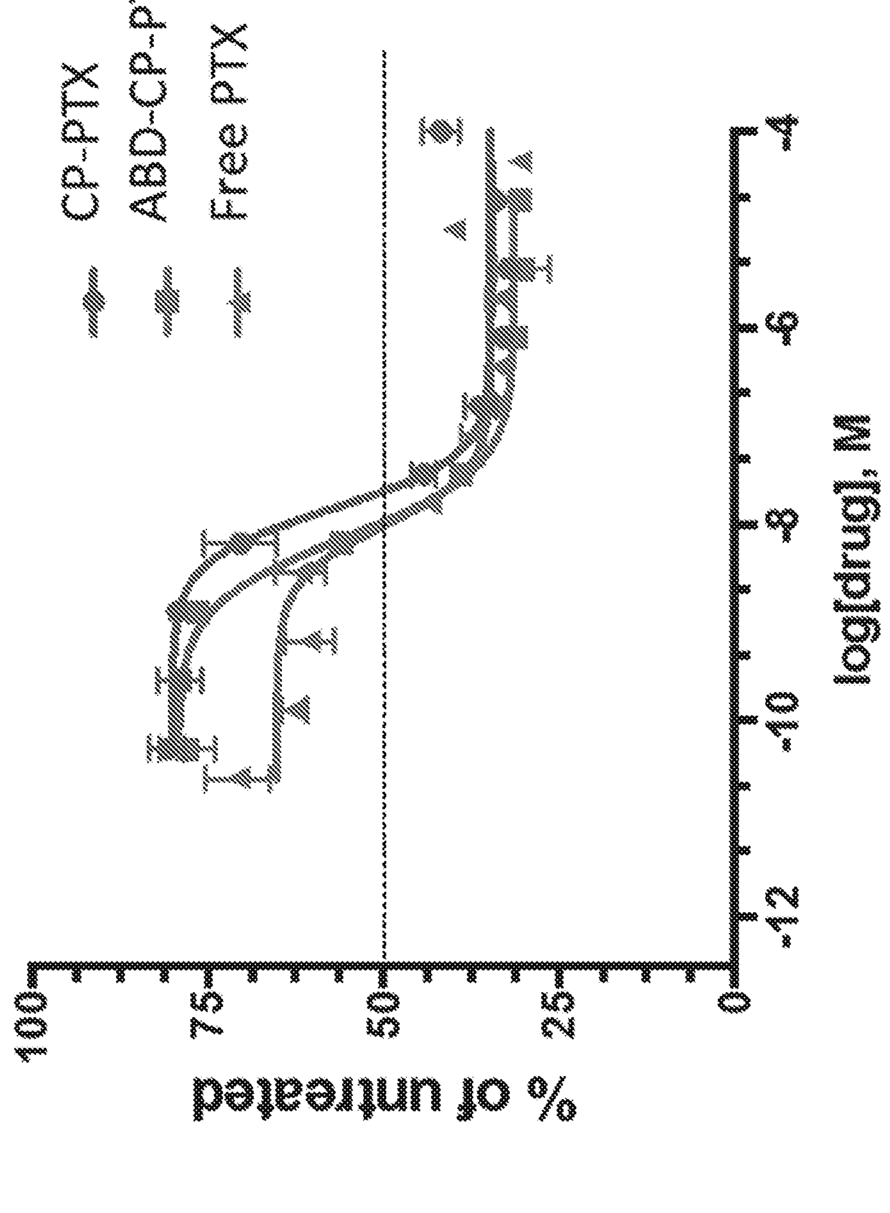
FIG. 21 shows in vitro cell line cytotoxicity of MDA-MB-231 human breast cancer cells treated with CP-PTX, ABD-CP-PTX and Free PTX. The $EC_{50}$ represents the relative 50% cell killing dose and $IC_{50}$ is the absolute 50% cell killing dose.
Figure 22:
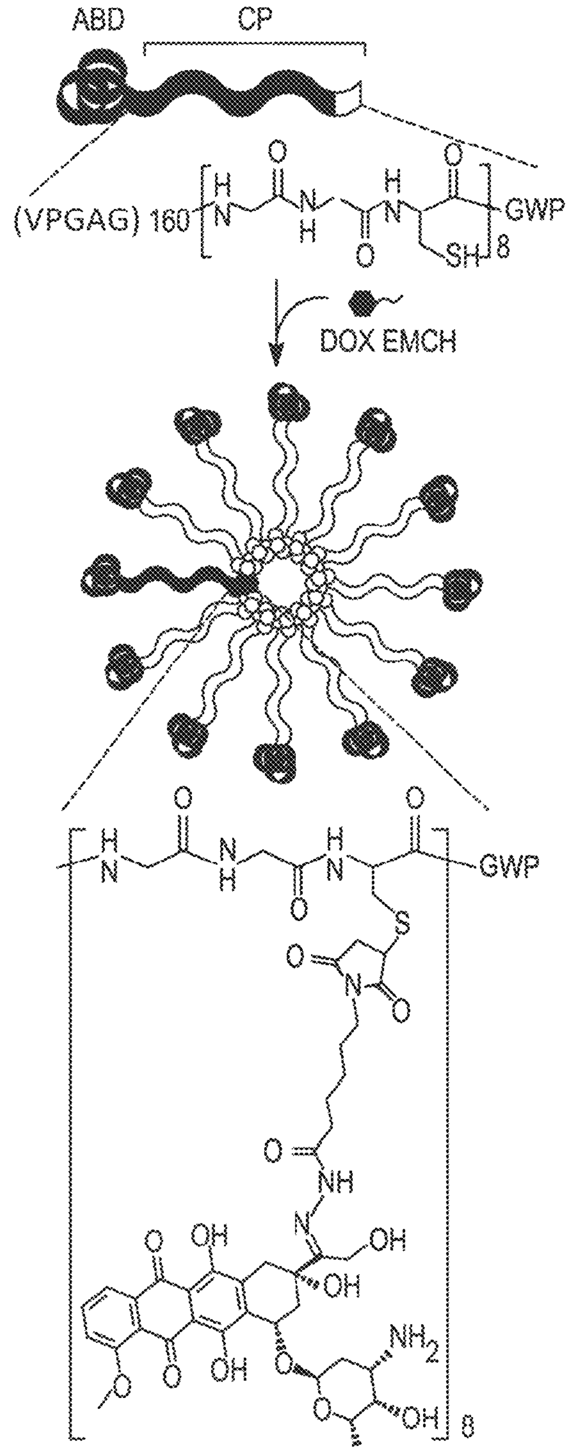
FIG. 22 shows a schematic of a self-assembling conjugate and assembly thereof.

In vitro cytotoxicity of the ABDN-CP-PTX versus that of naked CP-PTX and free PTX was determined using the calorimetric MTS assay in MDA-MB-213 human breast cancer cells (FIG. 21). This cell line was chosen because it demonstrates higher inherent resistance to Paclitaxel. The half-maximal inhibitory concentration (IC50), defined as the concentration of the drug required to cause 50% decrease in viable MDA-MB-213 cells in culture, was found to be 10.9, 22.4, and 9.8 nM for ABDN-CP-PTX, CP-PTX, and free PTX, respectively (FIG. 21). These $IC_{50}$ values are similar, confirming that the anticancer activity of PTX is not markedly reduced upon conjugation to ABDN-CP or the CP.

For reasons of completeness, various aspects of the invention are set out in the following numbered clauses:

Clause 1. A composition comprising: an assembly of self-assembling conjugates, each self-assembling conjugate comprising a polypeptide having a transition temperature ($T_t$) above 50° C. when the polypeptide is not attached to the conjugate; an albumin binding domain (ABD) attached to a first end of the polypeptide; and at least one molecule attached to a second end of the polypeptide through a cysteine group, wherein the molecule has an octanol-water distribution coefficient (log D) of greater than or equal to 1.5 at a pH of 7.4 when the molecule is not attached to the conjugate, wherein the conjugate has a $T_t$ above 40° C. at a concentration of 100 µM.

Clause 2. A composition comprising: an assembly of self-assembling conjugates, each self-assembling conjugate comprising a polypeptide having a transition temperature ($T_t$) above 50° C. when the polypeptide is not attached to the conjugate; an albumin binding domain (ABD) attached to a first end of the polypeptide, wherein the ABD attached to the polypeptide lowers the $T_t$ of the polypeptide no more than 5° C. relative to the polypeptide's $T_t$ when the polypeptide is not attached to the ABD or the conjugate; and at least one molecule attached to a second end of the polypeptide through a cysteine group, wherein the molecule has an octanol-water distribution coefficient (log D) of greater than or equal to 1.5 at a pH of 7.4 when the molecule is not attached to the conjugate.

Clause 3. The composition of clause 1 or clause 2, wherein the ABD comprises SEQ ID NO:6.

Clause 4. The composition of any one of clauses 1-3, wherein the polypeptide comprises an amino acid sequence of $(X^1GVPG)_x$ (SEQ ID NO:2), wherein $X^1$ is an amino acid or a combination of amino acids and x is 40 to 400.

Clause 5. The composition of any one of clauses 1-4, wherein the polypeptide comprises an amino acid sequence of $(X^1GVPG)_m$ (SEQ ID NO:3), wherein $X^1$ is A or V:A:G at a ratio of 1:7:8 and m is 160.

Clause 6. The composition of any one of clauses 1-3, wherein the polypeptide comprises an amino acid sequence of $(CGG)_z$ (SEQ ID NO:4) at its C-terminus, wherein z is greater than 1.

Clause 7. The composition of clause 6, wherein the polypeptide comprises an amino acid sequence of $(CGG)_8$ (SEQ ID NO:5) at its C-terminus.

Clause 8. The composition of any one of clauses 1-7, wherein the molecule is a chemotherapeutic or an imaging agent.

Clause 9. The composition of any one of clauses 1-8, wherein about 1 to about 15 molecules are attached to the polypeptide.

Clause 10. The composition of any one of clauses 1-9, wherein the molecule is attached to the polypeptide through a thiol group.

Clause 11. The composition of any one of clauses 1-10, wherein the assembly of self-assembling conjugates is a nanoparticle.

Clause 12. The composition of any one of clauses 1-11, wherein the molecule is located in a core of the nanoparticle.

Clause 13. The composition of any one of clauses 1-12, wherein the nanoparticle has an average hydrodynamic radius of about 10 nm to about 100 nm.

Clause 14. The composition of any one of clauses 1-13, wherein the nanoparticle is a micelle.

Clause 15. A method of killing multiple cancer cells comprising contacting multiple cancer cells with the composition of any of clauses 1-14.

Clause 16. A method of treating a disease or disorder in a subject comprising administering to the subject the composition of any of clauses 1-14.

Clause 17. The method of clause 16, wherein the disease or disorder is cancer.

Clause 18. A method of localizing a molecule to a tissue or organ in a subject, the method comprising administering to the subject the composition of any of clauses 1-14, wherein following administration of the composition the molecule is localized in the liver at less than 30% of the injected dose/gram of tissue or organ (ID/g).

Clause 19. A method of localizing a molecule to a tissue or organ in a subject, the method comprising administering to the subject the composition of any of clauses 1-14, wherein following administration of the composition the molecule is localized in the spleen at less than 10% of the injected dose/gram of tissue or organ (ID/g).

Clause 20. A method of localizing a molecule to a tissue or organ in a subject, the method comprising administering to the subject the composition of any of clauses 1-14, wherein following administration of the composition the amount of the molecule localized in the tissue or organ is decreased when compared to the molecule in a self-assembling conjugate without an albumin binding domain and wherein the tissue or organ is a kidney, liver, spleen or any combination thereof.

Clause 21. The method of clause 20, wherein the amount of the molecule localized in the tissue or organ is decreased at least two-fold.

Clause 22. A method of localizing a molecule to a tumor in a subject, the method comprising administering to the subject the composition of any of clauses 1-14, wherein following administration of the composition the amount of the molecule localized to the tumor is increased when compared to the molecule in a self-assembling conjugate without an albumin binding domain.

Clause 23. The method of clause 22, wherein the amount of the molecule localized to the tumor is increased at least two-fold.

Sequences $(VPGXG)_n$ wherein X is any amino acid except proline and n is an integer greater than or equal to 1 (SEQ ID NO:1)

$(X^1GVPG)_x$ wherein $X^1$ is an amino acid or a combination of amino acids and x is an integer from 40 to 400 (SEQ ID NO:2)

$(X^1GVPG)_m$ wherein $X^1$ is A or V:A:G at a ratio of 1:7:8 and m is 160 (SEQ ID NO:3)

$(CGG)_z$ wherein z is an integer greater than 1 (SEQ ID NO:4)

$(CGG)_8$ (SEQ ID NO:5)

LAEAKVLANRELDKYGVSDYYKNLINNAKTVEG-VKALIDEILAALP (SEQ ID NO:6)

LAEAKVLANRELDKYGVSDFYKRLINKAKTVEG-VEALKLHILAALP (SEQ ID NO:7)

KEKE (SEQ ID NO:8)

What is claimed is:

1. A composition comprising:

an assembly of self-assembling conjugates, each self-assembling conjugate comprising a polypeptide having a transition temperature ($T_t$) above 50° C. when the polypeptide is not attached to the conjugate, wherein the polypeptide comprises an amino acid sequence of $(X^1GVPG)_m$ (SEQ ID NO: 3), wherein $X^1$ is A or V: A: G at a ratio of 1:7:8 and m is 160 and wherein the polypeptide comprises an amino acid sequence of $(CGG)_z$ (SEQ ID NO:4) at its C-terminus, wherein z is 1 to 40;

an albumin binding domain (ABD) attached to a first end of the polypeptide's N-terminus, wherein the ABD comprises an amino acid sequence of SEQ ID NO: 6; and at least one molecule attached to a thiol group of an individual cysteine of SEQ ID NO:4 through a linker, wherein the molecule is a chemotherapeutic or an imaging agent, and wherein the molecule has an octanol-water distribution coefficient (logD) of greater than or equal to 1.5 at a pH of 7.4 when the molecule is not attached to the conjugate, wherein the conjugate has a $T_t$ above 40° C. at a concentration of 100 uM.

2. A composition comprising:

an assembly of self-assembling conjugates, each self-assembling conjugate comprising a polypeptide having a transition temperature ($T_t$) above 50° C. when the polypeptide is not attached to the conjugate, wherein the polypeptide comprises an amino acid sequence of $(X^1GVPG)_m$ (SEQ ID NO: 3), wherein $X^1$ is A or V: A: G at a ratio of 1:7:8 and m is 160 and wherein the polypeptide comprises an amino acid sequence of $(CGG)_z$ (SEQ ID NO:4) at its C-terminus, wherein z is 1 to 40;

an albumin binding domain (ABD) attached to the polypeptide's N-terminus, wherein the ABD attached to the polypeptide lowers the $T_t$ of the polypeptide no more than 5° C. relative to the polypeptide's $T_t$ when the polypeptide is not attached to the ABD or the conjugate, and wherein the ABD comprises an amino acid sequence of SEQ ID NO:6; and at least one molecule attached to a thiol group of an individual cysteine of SEQ ID NO:4 through a linker, wherein the molecule is a chemotherapeutic or an imaging agent, and wherein the molecule has an octanol-water distribution coefficient (logD) of greater than or equal to 1.5 at a pH of 7.4 when the molecule is not attached to the conjugate.

3. The composition of claim 1, wherein the polypeptide comprises an amino acid sequence of $(CGG)_8$ (SEQ ID NO:5) at its C-terminus.

4. The composition of claim 1, wherein about 1 to about 15 molecules are attached to the polypeptide.

5. The composition of claim 1, wherein the assembly of self-assembling conjugates is a nanoparticle.

6. The composition of claim 1, wherein the molecule is located in a core of the nanoparticle.

7. The composition of claim 5, wherein the nanoparticle has an average hydrodynamic radius of about 10 nm to about 100 nm.

8. The composition of claim 5, wherein the nanoparticle is a micelle.

9. A method of treating a cancer in a subject comprising administering to the subject the composition of claim 1 wherein the cancer is breast cancer, colon cancer or combination thereof.

10. A method of localizing a molecule to a tissue or organ in a subject, the method comprising administering to the subject the composition of claim 1, wherein following administration of the composition the amount of the molecule localized in the tissue or organ is decreased when compared to the molecule in a self-assembling conjugate without an albumin binding domain and wherein the tissue or organ is a kidney, liver, spleen or any combination thereof.

11. The method of claim 10, wherein the amount of the molecule localized in the tissue or organ is decreased at least two-fold.

12. A method of localizing a molecule to a tumor in a subject, the method comprising administering to the subject the composition of claim 1, wherein following administration of the composition the amount of the molecule localized to the tumor is increased when compared to the molecule in a self-assembling conjugate without an albumin binding domain.

13. The method of claim 12, wherein the amount of the molecule localized to the tumor is increased at least two-fold.

14. The composition of claim 1, wherein the linker comprises a haloacetyl, a maleimide, a hydrazide, an aziridines, an acryloyl, or a combination thereof.

15. The composition of claim 1, wherein the molecule is a chemotherapeutic and the linker is a pH dependent linker.

16. The composition of claim 15, wherein the chemotherapeutic is attached to the linker through a hydrazone linkage.

* * * * *